US012788979B2

(12) United States Patent
Månsson et al.

(10) Patent No.: US 12,788,979 B2
(45) **Date of Patent: *Nov. 10, 2026**

(54) COMBINATION THERAPY FOR THE TREATMENT OF DEPRESSION

(71) Applicant: Flow Neuroscience, Inc., Palo Alto, CA (US)

(72) Inventors: Daniel Månsson, Simrishamn (SE); Erik Rehn, Enebyberg (SE)

(73) Assignee: Flow Neuroscience, Inc., Palo Alto, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/890,300

(22) Filed: Sep. 19, 2024

(65) Prior Publication Data

US 2026/0077191 A1 Mar. 19, 2026

Related U.S. Application Data

(63) Continuation of application No. PCT/US2023/078112, filed on Oct. 27, 2023.

(60) Provisional application No. 63/515,823, filed on Jul. 26, 2023, provisional application No. 63/381,235, filed on Oct. 27, 2022.

(51) Int. Cl.

| | |
|---|---|
| ***A61N 1/36*** | (2006.01) |
| ***A61K 31/135*** | (2006.01) |
| ***A61K 31/136*** | (2006.01) |
| ***A61K 31/137*** | (2006.01) |
| ***A61K 31/138*** | (2006.01) |
| ***A61K 31/15*** | (2006.01) |
| ***A61K 31/343*** | (2006.01) |
| ***A61K 31/443*** | (2006.01) |
| ***A61K 31/495*** | (2006.01) |
| ***A61K 45/06*** | (2006.01) |
| ***A61P 25/24*** | (2006.01) |

(52) U.S. Cl.

CPC ........ *A61N 1/36025* (2013.01); *A61K 31/135* (2013.01); *A61K 31/136* (2013.01); *A61K 31/137* (2013.01); *A61K 31/138* (2013.01); *A61K 31/15* (2013.01); *A61K 31/343* (2013.01); *A61K 31/443* (2013.01); *A61K 31/495* (2013.01); *A61K 45/06* (2013.01); *A61P 25/24* (2018.01)

(58) Field of Classification Search

CPC ............. A61N 1/36025; A61K 31/135; A61K 31/138; A61K 31/343; A61K 45/06; A61K 31/443; A61K 31/136; A61K 31/137; A61K 31/15; A61K 31/495; A61P 25/24

See application file for complete search history.

(56) References Cited

U.S. PATENT DOCUMENTS

| | | | | |
|---|---|---|---|---|
| 9,101,766 | B2 * | 8/2015 | Nekhendzy | A61N 1/36034 |
| 9,486,618 | B2 | 11/2016 | Wingeier et al. | |
| 9,889,290 | B2 | 2/2018 | Wingeier et al. | |
| 10,188,342 | B2 | 1/2019 | Boyle et al. | |
| 10,525,255 | B2 | 1/2020 | Wingeier et al. | |
| 11,351,362 | B2 * | 6/2022 | Månsson | A61N 1/0456 |
| 11,364,383 | B2 | 6/2022 | Wingeier et al. | |
| 11,779,753 | B2 * | 10/2023 | Månsson | A61N 1/0484 607/45 |
| 12,017,062 | B2 * | 6/2024 | Månsson | A61N 1/3603 |
| 2013/0184779 | A1 | 7/2013 | Bikson et al. | |
| 2019/0329063 | A1 | 10/2019 | Hendler et al. | |
| 2020/0215321 | A1 | 7/2020 | Wingeier | |
| 2020/0215326 | A1 | 7/2020 | Wingeier et al. | |
| 2021/0275801 | A1 | 9/2021 | Månsson et al. | |
| 2021/0299434 | A1 | 9/2021 | Månsson et al. | |
| 2022/0257944 | A1 | 8/2022 | Shakour et al. | |

FOREIGN PATENT DOCUMENTS

| | | | |
|---|---|---|---|
| WO | WO-2018141830 | A1 | 8/2018 |
| WO | WO-2023172450 | A2 | 9/2023 |
| WO | WO-2024092251 | A1 | 5/2024 |

OTHER PUBLICATIONS

Dale et al., Biochem. Pharm., 2015, 95:81-97.*

Bastiaanssen et al., "Gutted! Unraveling the Role of the Microbiome in Major Depressive Disorder" Harvard Review of Psychiatry, 2020, 28(1), pp. 26-39.

Bikson et al., "Safety of Transcranial Direct Current Stimulation: Evidence Based Update 2016", Brain Stimul. Sep.-Oct. 2016; 9(5): 641-661. Epub Jun. 15, 2016.

Bikson et al., "Limited output transcranial electrical stimulation (LOTES—2017): Engineering principles, regulatory statutes, and industry standards for wellness, over-the-counter, or prescription devices with low risk", Brain Stimul. Jan.-Feb. 2018; 11(1): 134-157. Epub Oct. 17, 2017.

Borrione et al., "The Flow brain stimulation headset for the treatment of depression: overview of its safety, efficacy and portable design", Expert Review of Medical Devices (2020), vol. 17, No. 9, 867-878.

Borrione et al., "Use of app-based psychological interventions in combination with home-use transcranial direct current stimulation for the treatment of major depressive disorder: A case series", J Affect Disord. Jun. 1, 2021; 288: 189-190, Epub Apr. 17, 2021.

Brunoni et al., "The sertraline vs. electrical current therapy for treating depression clinical study: results from a factorial, randomized, controlled trial", JAMA Psychiatry. Apr. 2013; 70(4): 383-91.

Brunoni et al., "Trial of Electrical Direct-Current Therapy versus Escitalopram for Depression", N Engl J Med. Jun. 29, 2017; 376(26): 2523-2533.

Burkhardt et al., 2023. "Transcranial Direct Current Stimulation as an Additional Treatment to Selective Serotonin Reuptake Inhibitors in Adults with Major Depressive Disorder in Germany (DepressionDC): A Triple-Blind, Randomised, Sham-Controlled, Multicentre Trial." The Lancet 402 (10401): 545-554).

(Continued)

*Primary Examiner* — Olga N Chernyshev
(74) *Attorney, Agent, or Firm* — COOLEY LLP

(57) ABSTRACT

Provided are methods for treating depression and depression-related conditions by combining administration of pharmacologic agents and neuromodulation induced by transcranial electrical stimulation.

10 Claims, 13 Drawing Sheets

(56) References Cited

OTHER PUBLICATIONS

Carpena et al., "The effect of a six-week focused meditation training on depression and anxiety symptoms in Brazilian university students with 6 and 12 months of follow-up", Journal of Affective Disorders vol. 246, Mar. 1, 2019, pp. 401-407.
Chhabra et al., "Tolerance of transcranial direct current stimulation in psychiatric disorders: An analysis of 2000+ sessions", Psychiatry Res. Feb. 2020; 284: 112744. Epub Jan. 2, 2020, 8 pages.
clinicaltrials.gov "Empower: Transcranial Direct Current Stimulation in Major Depressive Disorder: a Double-blind, Placebo-controlled, Randomized, Superiority Trial", ID No. NCT05202119, located at https://www.clinicaltrials.gov/study/NCT05202119?term=NCT05202119&rank=1&tab=history&a=2#version-content-panel, retrieved on Apr. 5, 2022, v2, 12 total pages.
clinicaltrials.gov "Empower: Transcranial Direct Current Stimulation in Major Depressive Disorder: a Double-blind, Placebo-controlled, Randomized, Superiority Trial", ID No. NCT05202119, located at https://www.clinicaltrials.gov/study/NCT05202119?term=NCT05202119&rank=1&tab=history&a=3#version-content-panel, retrieved on May 13, 2022, v3, 12 total pages.
clinicaltrials.gov "Empower: Transcranial Direct Current Stimulation in Major Depressive Disorder: a Double-blind, Placebo-controlled, Randomized, Superiority Trial", ID No. NCT05202119, located at https://www.clinicaltrials.gov/study/NCT05202119?term=NCT05202119&rank=1&tab=history&a=4#version-content-panel, retrieved on May 18, 2022, v4, 11 total pages.
clinicaltrials.gov "Empower: Transcranial Direct Current Stimulation in Major Depressive Disorder: a Double-blind, Placebo-controlled, Randomized, Superiority Trial", ID No. NCT05202119, located at https://www.clinicaltrials.gov/study/NCT05202119?term=NCT05202119&rank=1&tab=history&a=5#version-content-panel, retrieved on Mar. 13, 2023, v5, 11 total pages.
clinicaltrials.gov "Empower: Transcranial Direct Current Stimulation in Major Depressive Disorder: a Double-blind, Placebo-controlled, Randomized, Superiority Trial", ID No. NCT05202119, located at https://www.clinicaltrials.gov/study/NCT05202119?term=NCT05202119&rank=1&tab=history&a=6#version-content-panell, retrieved on Apr. 18, 2023, v6, 12 total pages.
clinicaltrials.gov "Empower: Transcranial Direct Current Stimulation in Major Depressive Disorder: a Double-blind, Placebo-controlled, Randomized, Superiority Trial", ID No. NCT05202119, located at https://www.clinicaltrials.gov/study/NCT05202119?term=NCT05202119&rank=1&tab=history&a=7#version-content-panel, retrieved on Nov. 22, 2023, v7, 12 total pages.
clinicaltrials.gov "Empower: Transcranial Direct Current Stimulation in Major Depressive Disorder: a Double-blind, Placebo-controlled, Randomized, Superiority Trial", ID No. NCT05202119, located at https://www.clinicaltrials.gov/study/NCT05202119?term=NCT05202119&rank=1&tab=history&a=8#version-content-panel, retrieved on Sep. 6, 2024, v8, 12 total pages.
clinicaltrials.gov "Transcranial Direct Current Stimulation in Major Depressive Disorder: a Double-blind, Placebo-controlled, Randomized, Superiority Trial", ID No. NCT05202119, located at https://www.clinicaltrials.gov/study/NCT05202119?term=NCT05202119&rank=1&tab=history&a=1#version-content-panel, retrieved on Jan. 9, 2022, v1, 12 total pages.
Erb et al., "Antidepressants Accumulate in Lipid Rafts Independent of Monoamine Transporters to Modulate Redistribution of the G Protein", Gas. J Biol Chem. Sep. 16, 2016;291(38):19725-19733.
Fregni, et al., "Evidence-Based Guidelines and Secondary Meta-Analysis for the Use of Transcranial Direct Current Stimulation in Neurological and Psychiatric Disorders", International Journal of Neuropsychopharmacology, vol. 24, Issue 4, Apr. 2021, pp. 256-313.
Godos et al., "Adherence to the Mediterranean Diet is Associated with Better Sleep Quality in Italian Adults", Nutrients 2019, 11, 976, 15 pages.
Hallgren et al., "Associations of exercise frequency and cardiorespiratory fitness with symptoms of depression and anxiety—a cross-sectional study of 36,595 adults", Mental Health and Physical Activity, vol. 19, Oct. 2020, 100351, 13 pages.
International Search Report and Written Opinion for PCT Application No. PCT/US2023/078112 dated Jan. 24, 2024, 17 pages.
Keenan et al., (2014), "The Use of Fuzzy Promising Zones' to Mitigate Against Operational Bias in Adaptive Sample Size Re-estimation Designs," JSM 2014: 1493-1506.
Lachin et al., (2005), "A review of methods for futility stopping based on conditional power", Statist. Med., 24: 2747-2764.
Lane et al., "Biological and clinical insights from genetics of insomnia symptoms", Nat Genet. Mar. 2019; 51(3): 387-393. Epub Feb. 25, 2019.
Lassale et al., "Healthy dietary indices and risk of depressive outcomes: a systematic review and meta-analysis of observational studies", Mol Psychiatry. Jul. 2019; 24(7): 965-986. Epub Sep. 26, 2018.
Lederman et al., "Does exercise improve sleep quality in individuals with mental illness? A systematic review and meta-analysis", Journal of Psychiatric Research vol. 109, Feb. 2019, pp. 96-106.
Li et al., "Effects of mindfulness meditation on anxiety, depression, stress, and mindfulness in nursing students: a meta-analysis and trial sequential analysis of randomized controlled trials" Frontiers of Nursing, vol. 7, No. 1, 2020, pp. 59-69.
Loo et al., "Transcranial direct current stimulation for depression: 3-week, randomised, sham-controlled trial", Br J Psychiatry. Jan. 2012; 200(1): 52-9.
Lookene M, et al., "Reduction of symptoms in patients with major depressive disorder after transcranial direct current stimulation treatment: A real-world study", Journal of Affective Disorders Reports, 2022, vol. 8, 100347, 5 pages.
Meena, et al., "Transcranial Direct Current Stimulation as an Augmenting Intervention in Depression", International Medical Journal, vol. 28, No. 2, Apr. 2021, pp. 153-155.
Mehta et al., "Adaptive increase in sample size when interim results are promising: a practical guide with examples." Stat Med. Dec. 10, 2011;30(28): 3267-84. doi: 10.1002/sim.4102. Epub Nov. 30, 2010. 18 pages.
Mutz et al., "Comparative efficacy and acceptability of non-surgical brain stimulation for the acute treatment of major depressive episodes in adults: systematic review and network meta-analysis", BMJ. Mar. 27, 2019; 364: 1079, 13 pages.
Nikolin et al., "Time-course of the tDCS antidepressant effect: An individual participant data meta-analysis", Prog Neuropsychopharmacol Biol Psychiatry. 2023, 125:110752. Epub Mar. 16, 2023, 8 pages.
Non-Final Office Action for U.S. Appl. No. 18/890,394 mailed Feb. 18, 2025, 12 pages.
Oh et al., "Effect of Self-administered Transcranial Direct Stimulation in Patients with Major Depressive Disorder: A Randomized, Single-blinded Clinical Trial", Clinical Psychopharmacology and Neuroscience, Feb. 2022, vol. 20(1), pp. 87-96.
Pavlova et al., "Transcranial direct current stimulation of 20- and 30-minutes combined with sertraline for the treatment of depression", Prog Neuropsychopharmacol Biol Psychiatry. Mar. 2, 2018; 82: 31-38. Epub Dec. 9, 2017.
Razza et al., "A systematic review and meta-analysis on the effects of transcranial direct current stimulation in depressive episodes", Depress Anxiety. Jul. 2020; 37(7): 594-608. Epub Feb. 26, 2020.
Reangsing et al., "Effects of mindfulness meditation interventions on depression in older adults: A meta-analysis", (2021), Aging & Mental Health, 25:7, 1181-1190.
Riemann et al., "Sleep, insomnia, and depression", Neuropsychopharmacol. 45, pp. 74-89 (2019).
Rimmer et al., "Acceptability of community-based transcranial direct current stimulation (tDCS) in major depression: mixed methods analysis of individual experiences", 2022, 26 pages.
Rush et al., "Acute and longer-term outcomes in depressed outpatients requiring one or several treatment steps: a STAR*D report," Am J Psychiatry, 2006; 163:1905-1917.
Schuch et al., "The Role of Exercise in Preventing and Treating Depression", Current Sports Medicine Reports, Aug. 2019, 18(8): pp. 299-304.

(56) References Cited

OTHER PUBLICATIONS

Sharafi et al., "Transcranial Direct Current Stimulation for Treatment-Resistant Major Depression: A Double-Blind Randomized Sham-Controlled Trial", Clin EEG Neurosci. Nov. 2019; 50(6): 375-382.
Sobral et al., "Home-based transcranial direct current stimulation in dual active treatments for symptoms of depression and anxiety: A case series", Front. Psychiatry, Oct. 6, 2022 Sec. Neuroimaging, vol. 13, 11 pages.
Uzer et al., "The effect of circadian preferences on insomnia severity and depressive symptoms via sleep hygiene in older adults with depression and healthy controls", Psychogeriatrics, The Official Journal of the Japanese Psychogeriatric Society, vol. 20, Issue 6, Nov. 2020, pp. 871-879.
Valiengo et al., "The sertraline versus electrical current therapy for treating depression clinical study (select-TDCS): results of the crossover and follow-up phases", Depress Anxiety. Jul. 2013; 30(7): 646-53. Epub Apr. 26, 2013.
Wang et al., "Is transcranial direct current stimulation, alone or in combination with antidepressant medications or psychotherapies, effective in treating major depressive disorder? A systematic review and meta-analysis", BMC Medicine, Dec. 2021, vol. 19(1), 14 pages.
Waye et al., "Antidepressant action of transcranial direct current stimulation in olfactory bulbectomised adolescent rats", Journal of psychopharmacology, Aug. 2021, vol. 35(8), 14 pages.
Woodham et al., Adjunctive home-based transcranial direct current stimulation treatment for major depression with real-time remote supervision: An open-label, single-arm feasibility study with long term outcomes, Journal of Psychiatric Research, vol. 153, Sep. 2022, pp. 197-205.
Woodham et al., "Home-based transcranial direct current stimulation RCT in major depression", medRxiv 2023.11.27.23299059, 22 pages.
Zhdanava et al., "The Prevalence and National Burden of Treatment-Resistant Depression and Major Depressive Disorder in the United States", J Clin Psychiatry. Mar. 16, 2021; 82(2): 10 pages.
Zugliani et al., "Clinical effectiveness of non-TMS neurostimulation in depression: Clinical trials from 2010 to 2020", Progress in neuro-psychopharmacology& biological psychiatry, Aug. 2021, vol. 110, 110287, 14 pages.
Ferrucci et al., "Transcranial direct current stimulation in severe, drug-resistant major depression", Journal of Affective Disorders vol. 118, Issues 1-3, Nov. 2009, pp. 215-219.
Final Office Action for U.S. Appl. No. 18/890,394 mailed Jun. 4, 2025, 12 pages.
International Preliminary Report on Patentability for PCT Application No. PCT/US2023/078112 dated Apr. 29, 2025, 8 pages.
Bennabi, D., et al., "Pilot study of feasibility of the effect of treatment with tDCS in patients suffering from treatment-resistant depression treated with escitalopram", Clinical Neurophysiology. (Jun. 2015). 126(6):1185-1189.
U.S. Appl. No. 18/890,394, Notice of Allowance mailed Mar. 3, 2026; Inventor Månsson, Daniel et al.; 12 pages.
Wang et al., "Supplemental Dataset for 'Is transcranial direct current stimulation, alone or in combination with antidepressant medications or psychotherapies, effective in treating major depressive disorder A systematic review and meta-analysis'," (original article published 2021; publication date of the supplement dataset is unknown), S1 and S2; 7 pages.

* cited by examiner

COMBINATION THERAPY FOR THE TREATMENT OF DEPRESSION

CROSS-REFERENCE TO RELATED APPLICATIONS

This application is a continuation of International Application No. PCT/US2023/078112, filed Oct. 27, 2023, which claims priority to, and the benefit of, U.S. Provisional Application No. 63/381,235, filed Oct. 27, 2022, and U.S. Provisional Application No. 63/515,823, filed Jul. 26, 2023.

TECHNICAL FIELD

Described herein are systems, devices, and methods of combining neuromodulation and pharmacologic treatment of depression by delivering transcranial electrical stimulation and administering a pharmacologic antidepressant agent to a subject.

BACKGROUND

Depressive disorders are common in populations, recurrent in individuals suffering from them, may be chronic conditions, and require treatment. Transcranial electrical stimulation (tES) is a form a non-invasive electrical brain stimulation shown to operate as a versatile tool for modulating neuronal function in subjects that are in healthy and pathological conditions, including subjects with a depressive disorder. Neuronal function may be modulated by tES to alter neuroplasticity, to induce behavioral effects in part by enhancing or decreasing neuronal excitability, to improve cognitive function, or to tune network connectivity within the brain. tES utilizes low intensity electrical stimulation of selected areas of the brain and has been demonstrated as a safe, efficient, and cost-effective means of inducing neuromodulation. As such, tES has been put forward as a means to potentially rehabilitate functional deficits within neuronal systems and improve symptoms of various mood disorders. Pharmacological intervention of depressive disorders through the administration of antidepressant agents can be therapeutically effective for treating depression in some patients and many drugs are well tolerated. Numerous antidepressant agents can operate to modulate neurotransmitter levels or modulate efficacy of neurotransmission throughout the brain. These modulations induced by antidepressant agents may have an effect to improve neuronal function and enhance network connectivity deficits within subjects having a depressive disorder. However, prolonged treatment with antidepressant drugs carries an elevated risk of adverse drug reactions, unwanted side effects, and a difficulty in maintaining patient compliance with ongoing treatments.

SUMMARY

Provided herein are methods for combining means of neuromodulation with administration of pharmacological antidepressant agents for the treatment of depression. Transcranial electrical stimulation (tES) is a safe and effective means of stimulating the brain to induce neuromodulation and sustain neuromodulatory effects. Due to its non-invasive nature, paucity of side effects, and cost-effectiveness, tES has been investigated for efficacy in treatment of various depressive disorders. tES may be delivered to a subject through several different formats of electrical stimulation including transcranial direct current stimulation (tDCS), transcranial alternating current stimulation (tACS), or transcranial random noise stimulation (tRNS).

The methods disclosed herein describe administering of a pharmacologic antidepressant to a subject in need thereof to treat depression and delivering to the subject a tES. Existing methods using pharmacologic antidepressants to treat depression have several shortcomings. One of these shortcomings is achieving a desired treatment outcome in a large enough number of subjects. In some previous methods of treating depression by administering an antidepressant to a subject, many individuals do not show significant improvement in depressive symptoms. In other previous methods of treating depression by administering antidepressants to a subject, many patients never reach remission of one or more depressive symptoms. In some previous methods, a pharmacological treatment regimen must be maintained for an extended period of time to evaluate effectiveness or treatment regimens must be modified by changing dosages, frequency of administration, or type of pharmacologic antidepressant agent. These modifications to existing methods can prolong the suffering a person endures and/or increase a risk of occurrence or severity of an adverse drug reaction. By combining administering of a pharmacologic antidepressant to the subject with delivering to the subject a tES in the methods described herein, many of the shortcomings of previous treatment methods are lessened, ultimately resulting in improved depression treatments. The methods described herein can result in more extensive improvement in depression symptoms than existing treatment methods. The methods described herein can result in a greater occurrence of remission in one or more depression symptoms than existing treatment methods. The methods described herein can improve depressive symptoms in subjects more rapidly than previous methods and also maintain those improvements for an extended period of time. This can ease the burden of suffering of individuals enduring a depressive episode. This also can allow for a treatment effective dosage or frequency of administration of a pharmacologic antidepressant agent to be decreased and still yield a desired treatment outcome for the subject. In some methods described herein, certain classes of antidepressant show increased treatment efficacy when combined with tES. In some methods described herein, combining tES with administering of a particular pharmacologic antidepressant agent to a subject surprisingly yields significantly improved results in depression treatment compared with combining tES and administering of a different pharmacologic antidepressant agent of the same drug class. The unexpected synergy of tES with certain antidepressants between and within drug classes provides improved treatment options for individuals with depression. Subjects with a particular co-morbidity to depression show significant improvement in one or more depressive symptoms by use of the methods of treatment described herein. In addition, particular co-morbidities to depression show significant improvement in components of their symptomatology by use of the methods of treatment described herein.

In one aspect, disclosed herein are methods of treatment for depression in a subject, the methods comprising: (a) administering to the subject a pharmacologic antidepressant agent; and (b) delivering to the subject a transcranial electrical stimulation (tES). In some embodiments, the pharmacologic antidepressant agent comprises one or more pharmacologic antidepressant agents. In some embodiments, the pharmacologic antidepressant agent is administered as part of a treatment regimen. In some embodiments, the pharmacologic antidepressant agent is administered in a treatment effective amount. In some embodiments, the delivering to the subject the tES comprises a delivery of tES prior to the administering, a delivery of tES concurrently to the administering as part of a treatment regimen, a delivery of tES subsequent to the administering, a delivery of tES concurrently with or following a change in a dosage of the pharmacologic antidepressant agent of the administering, or a delivery of tES following a completion of a schedule of the administering. In some embodiments, the delivery comprises one or more of non-invasive brain stimulation sessions. In some embodiments, the delivering in (b) comprises delivering tES via a tES device. In some embodiments, delivering tES via the tES device elicits neuromodulation in the subject. In some embodiments, the methods further comprise assessing a response of the subject to the treatment regimen. In some embodiments, the methods further comprise assessing a response of the subject to the one or more of non-invasive brain stimulation sessions. In some embodiments, the assessing the response of the subject comprises determining a treatment effectiveness. In some embodiments, the methods further comprise adjusting parameters in (a) and (b) to achieve to a desired treatment outcome.

In one aspect, disclosed herein are methods of treatment for depression in a subject, the methods comprising: (a) administering to the subject a pharmacologic antidepressant agent in a treatment effective amount as part of a treatment regimen; (b) delivering concurrently to the subject one or more of non-invasive brain stimulation sessions via a transcranial electrical stimulation (tES) device to elicit neuromodulation; (c) assessing a response of the subject to the treatment regimen and to the one or more of non-invasive brain stimulation sessions in order to determine treatment effectiveness; and (d) adjusting parameters in (a) and (b) to achieve to a desired treatment outcome. In some embodiments, the pharmacologic antidepressant agent comprises a selective serotonin reuptake inhibitor (SSRI), a serotonin-norepinephrine reuptake inhibitor (SNRI), a noradrenergic and specific serotonergic antidepressant (NaSSA), a serotonin modulator and stimulator (SMS), a serotonin antagonist and reuptake inhibitor (SARI), a serotonin-norepinephrine-dopamine reuptake inhibitor (SNDRI), a norepinephrine reuptake inhibitor (NRI), a norepinephrine-dopamine reuptake inhibitor (NDRI), a norepinephrine-dopamine releasing agent (NDRA), a serotonin-norepinephrine-dopamine releasing agent (SNDRA), a tricyclic antidepressant (TCA), a tetracyclic antidepressant (TeCA), a monoamine oxidase inhibitor (MAOI), an NMDA receptor modulator, an atypical antipsychotic, an atypical antidepressant, a benzodiazepine, or any combination thereof. In some embodiments, the SSRI comprises fluoxetine, citalopram, escitalopram, paroxetine, sertraline, dapoxetine, fluvoxamine, or vortioxetine. In some embodiments, the SNRI comprises desvenlafaxine, duloxetine, levomilnacipran, milnacipran, venlafaxine immediate release (venlafaxine IR), or venlafaxine extended release (venlafaxine XR). In some embodiments, the NaSSA comprises aptazapine, esmirtazapine, mianserin, mirtazapine, or setiptiline. In some embodiments, the SMS comprises vilazodone or vortioxetine. In some embodiments, the SARI comprises nefazodone or trazodone. In some embodiments, the SNDRI comprises toludesvenlafaxine, OPC-64005, or ansofaxine. In some embodiments, the NRI comprises atomoxetine, reboxetine, teniloxazine, or viloxazine. In some embodiments, the NDRI comprises bupropion, amineptine, methylphenidate, or AXS-05. In some embodiments, the NDRA comprises lisdexamfetamine, phenethylamine, tyramine, amphetamine, methamphetamine, cathinone, methcathinone, propylhexedrine, phenmetrazine, pemoline, 4-methylaminorex, or benzylpiperazine. In some embodiments, the SNDRA comprises midomafetamine, 3,4-Methylenedioxymethamphetamine, 3,4-Methylenedioxyamphetamine, naphthylisopropylamine, mephedrone, methylone, α-methyltryptamine, or α-ethyltryptamine. In some embodiments, the TCA comprises amitriptyline, clomipramine, desipramine, dosulepin, doxepin, imipramine, lofepramine, nortriptyline, protriptyline, or trimipramine. In some embodiments, the TeCA comprises amoxapine, maprotiline, mianserin, mirtazapine, or setiptiline. In some embodiments, the MAOI comprises selegiline, tranylcypromine, phenelzine, or isocarboxazid. In some embodiments, the NMDA receptor modulator comprises 4-cholorokynurenine, apimostinel, arketamine, esketamine, esmethadone, ketamine, rislenemdaz, or rapastinel. In some embodiments, the atypical antipsychotic comprises brilaroxazine, cariprazine, lumateperone, lurasidone, pimavanserin, aripiprazole, brexpiprazole, olanzapine, quetiapine, ziprasidone, SEP-4199, or NRX-101. In some embodiments, the atypical antidepressant comprises allopregnanolone, agomelatine, trazodone, mirtazapine, vortioxetine, vilazodone, psilocybin, DMT, zuranolone, seltorexant, XEN1101, erteberel, NV-5138, TS-121, or ALKS 5461. In some embodiments, the benzodiazepine comprises diazepam, alprazolam, triazolam, clonazepam, chlordiazepoxide, nitrazepam, or loprazolam. In some embodiments, the pharmacologic antidepressant agent is administered in a formulation comprising a tablet, a capsule, a delayed-release capsule, or a liquid. In some embodiments, the pharmacologic antidepressant agent is administered orally, sublingually, buccally, nasally, rectally, vaginally, intravenously, intramuscularly, subcutaneously, or through inhalation. In some embodiments, the treatment effective amount comprises a dose of the pharmacologic antidepressant agent of at least about 0.01 mg, 0.02 mg, 0.03 mg, 0.04 mg, 0.05 mg, 0.06 mg, 0.07 mg, 0.08 mg, 0.09 mg, 0.1 mg, 0.15 mg, 0.2 mg, 0.25 mg, 0.30 mg, 0.35 mg, 0.4 mg, 0.45 mg, 0.50 mg, 0.55 mg, 0.6 mg, 0.7 mg, 0.8 mg, 0.9 mg, 1 mg, 1.25 mg, 1.5 mg, 1.75 mg, 2 mg, 2.5 mg, 3 mg, 3.5 mg, 4 mg, 4.5 mg, 5 mg, 5.5 mg, 6 mg, 6.5 mg, 7 mg, 7.5 mg, 8 mg, 8.5 mg, 9 mg, 9.5 mg, 10 mg, 11 mg, 12 mg, 13 mg, 14 mg, 15 mg, 16 mg, 17 mg, 18 mg, 19 mg, 20 mg, 21 mg, 22 mg, 23 mg, 24 mg, 25 mg, 26 mg, 27 mg, 28 mg, 29 mg, 30 mg, 32 mg, 34 mg, 35 mg, 36 mg, 37.5 mg, 38 mg, 40 mg, 42 mg, 44 mg, 46 mg, 48 mg, 50 mg, 52 mg, 54 mg, 56 mg, 58 mg, 60 mg, 65 mg, 70 mg, 75 mg, 80 mg, 85 mg, 90 mg, 95 mg, 100 mg, 105 mg, 110 mg, 115 mg, 120 mg, 125 mg, 130 mg, 140 mg, 150 mg, 160 mg, 170 mg, 180 mg, 190 mg, 200 mg, 250 mg, 300 mg, 400 mg, or 600 mg. In some embodiments, the treatment effective amount comprises a dose of the pharmacologic antidepressant agent of less than about 0.01 mg, 0.02 mg, 0.03 mg, 0.04 mg, 0.05 mg, 0.06 mg, 0.07 mg, 0.08 mg, 0.09 mg, 0.1 mg, 0.15 mg, 0.2 mg, 0.25 mg, 0.30 mg, 0.35 mg, 0.4 mg, 0.45 mg, 0.50 mg, 0.55 mg, 0.6 mg, 0.7 mg, 0.8 mg, 0.9 mg, 1 mg, 1.25 mg, 1.5 mg, 1.75 mg, 2 mg, 2.5 mg, 3 mg, 3.5 mg, 4 mg, 4.5 mg, 5 mg, 5.5 mg, 6 mg, 6.5 mg, 7 mg, 7.5 mg, 8 mg, 8.5 mg, 9 mg, 9.5 mg, 10 mg, 11 mg, 12 mg, 13 mg, 14 mg, 15 mg, 16 mg, 17 mg, 18 mg, 19 mg, 20 mg, 21 mg, 22 mg, 23 mg, 24 mg, 25 mg, 26 mg, 27 mg, 28 mg, 29 mg, 30 mg, 32 mg, 34 mg, 35 mg, 36 mg, 37.5 mg, 38 mg, 40 mg, 42 mg, 44 mg, 46 mg, 48 mg, 50 mg, 52 mg, 54 mg, 56 mg, 58 mg, 60 mg, 65 mg, 70 mg, 75 mg, 80 mg, 85 mg, 90 mg, 95 mg, 100 mg, 105 mg, 110 mg, 115 mg, 120 mg, 125 mg, 130 mg, 140 mg, 150 mg, 160 mg, 170 mg, 180 mg, 190 mg, 200 mg, 250 mg, 300 mg, or 400 mg. In some embodiments, the treatment regimen comprises a drug administration regime wherein the dose of the pharmacologic antidepressant agent is administered at most about every 1 hour, every 2 hours, every 3 hours, every 4 hours, every 5 hours, every 6 hours, every 7 hours, every 8 hours, every 9 hours, every 10 hours, every 11 hours, every 12 hours, every 13 hours, every 14 hours, every 15 hours, every 16 hours, every 17 hours, every 18 hours, every 19 hours, every 20 hours, every 21 hours, every 22 hours, every 23 hours, every 24 hours, every 28 hours, every 32 hours, every 36 hours, every 40 hours, every 44 hours, every 2 days, every 3 days, every 4 days, every 5 days, every 6 days, every 7 days, every 10 days, every 14 days, every 21 days, or every 28 days. In some embodiments, the treatment regimen comprises a drug administration regime wherein the dose of the pharmacologic antidepressant agent is administered about once a month, once every three weeks, once every two weeks, once every 10 days, once every week, once every 6 days, once every 5 days, once every 4 days, once every 3 days, once every 2 days, once every day, twice every day, three times every day, four times every day, five times every day, six times every day, seven times every day, eight times every day, nine times every day, ten times every day, eleven times every day, or twelve times every day. In some embodiments, the drug administration regime continues for a period of time of at least 1 week, 2 weeks, 3 weeks, 4 weeks, 5 weeks, 6 weeks, 7 weeks, 8 weeks, 9 weeks, 10 weeks, 11 weeks, 12 weeks, 13 weeks, 14 weeks, 15 weeks, 16 weeks, 17 weeks, 18 weeks, 19 weeks, 20 weeks, 21 weeks, 22 weeks, 23 weeks, 24 weeks, 25 weeks, 26 weeks, 7 months, 8 months, 9 months, 10 months, 11 months, 12 months, 13 months, 14 months, 15 months, 16 months, 17 months, 18 months, or 2 years. In some embodiments, the treatment regimen comprises a multi-dose drug administration regime. In some embodiments, the tES device comprises a transcranial direct current stimulation (tDCS) device, a transcranial alternating current stimulation (tACS) device, or a transcranial random noise stimulation (tRNS) device. In some embodiments, the tES device comprises a transcranial direct current stimulation (tDCS) device. In some embodiments, the tES device is configurated as a headset comprising a circuit comprising a first electrode, a second electrode, and a power source configured to provide power to the circuit. In some embodiments, the tES device further comprises a wireless transceiver configured to wirelessly communicate with an electronic device having processing capabilities and a controller being configured to control powering of the circuit according to a control signal for the headset such that transcranial brain stimulation is performed according to a schedule for performing the transcranial brain stimulation. In some embodiments, the headset further comprises a memory configured to store the schedule for performing the transcranial brain stimulation. In some embodiments, the electronic device having processing capabilities comprises a non-transitory computer-readable recording medium having recorded thereon a program which is executable on the electronic device wherein the program comprises program code portions which when executed on the electronic device is configured to: store, in a computer memory, a schedule for performing the transcranial brain stimulation, generate and maintain the control signal according to the schedule for performing the transcranial brain stimulation, and display information on a display of the electronic device in accordance with a schedule for displaying information, wherein the schedule for displaying information is related to the schedule for performing the transcranial brain stimulation. In some embodiments, the headset further comprises a forehead frame, the forehead frame defining an elongated arch; the first electrode arranged at a first end portion of the elongated arched forehead frame; the second electrode arranged at a second end portion of the elongated arched forehead frame; and a bracket fixedly fastened at a center portion of the elongated arched forehead frame, the elongated arched forehead frame is configured to support the bracket. In some embodiments, the method further comprises wherein upon use of the headset in delivering concurrently to the subject one or more of non-invasive brain stimulation sessions, the elongated arched forehead frame is configured such that the first electrode is located at a left side of a forehead of the subject, and such that the second electrode is located at a right side of the forehead of the subject, and the bracket is configured to extend from the elongated arched forehead frame over the skull of the subject towards a neck portion of the subject. In some embodiments, the program further comprises program code portions which when executed on the electronic device is configured to prompt the subject to input information pertaining to status of the subject wherein the information pertaining to status of the subject comprises information pertaining to information about the subject's current health. In some embodiments, the program further comprises program code portions which when executed on the electronic device is configured to store information pertaining to performed transcranial brain stimulation on a computer memory. In some embodiments, the program further comprises program code portions which when executed on the electronic device is configured to remind the subject to use the headset according to the schedule for performing the transcranial brain stimulation. In some embodiments, the program further comprises program code portions which when executed on the electronic device is configured to update the schedule for performing the transcranial brain stimulation. In some embodiments, the headset further comprises the first and second electrodes being pivotable such that they can adapt to a shape of the forehead of the subject. In some embodiments, the headset further comprises the first and second electrodes having an adhesive layer configured such that the adhesive layer adheres to the forehead of the subject. In some embodiments, the bracket has a longitudinal extension which, when the headset is used, extends from the forehead of the subject towards the back of the subject's head and wherein the bracket has a variable extension from the forehead frame. In some embodiments, the bracket further comprises a support cushion arranged at an end portion of the bracket being opposite to where the bracket is fastened at the forehead frame and wherein the forehead frame is a single member shaped as an elongated arch. In some embodiments, the subject has been diagnosed with one or more conditions or disorders selected from the group consisting of: depression, mild depression, moderate depression, severe depression, major depression, major depressive disorder, anxious distress, melancholy, melancholic depression, agitation, persistent depressive disorder, bipolar disorder type 1, bipolar disorder type 2, bipolar disorder not otherwise specified, cyclothymia, season affective disorder, psychotic depression, psychotic major depression, postpartum depression, premenstrual dysphoric disorder, situational depression, breakthrough depression, atypical depression, treatment resistant depression, catatonic depression, dysthymia, double depression, unspecified depressive disorder, depressive personality disorder, recurrent brief depression, minor depressive disorder, alcohol-induced depression, substance-induced depression, benzodiazepine-induced depression, and mixed anxiety-depressive disorder. In some embodiments, the subject is at risk for developing a condition or disorder selected from the group consisting of: depression, mild depression, moderate depression, severe depression, major depression, major depressive disorder, anxious distress, melancholy, melancholic depression, agitation, persistent depressive disorder, bipolar disorder type 1, bipolar disorder type 2, bipolar disorder not otherwise specified, cyclothymia, season affective disorder, psychotic depression, psychotic major depression, postpartum depression, premenstrual dysphoric disorder, situational depression, breakthrough depression, atypical depression, treatment resistant depression, catatonic depression, dysthymia, double depression, unspecified depressive disorder, depressive personality disorder, recurrent brief depression, minor depressive disorder, alcohol-induced depression, substance-induced depression, benzodiazepine-induced depression, and mixed anxiety-depressive disorder. In some embodiments, the subject has achieved remission from symptoms related to a condition or disorder selected from the group consisting of: depression, mild depression, moderate depression, severe depression, major depression, major depressive disorder, anxious distress, melancholy, melancholic depression, agitation, persistent depressive disorder, bipolar disorder type 1, bipolar disorder type 2, bipolar disorder not otherwise specified, cyclothymia, season affective disorder, psychotic depression, psychotic major depression, postpartum depression, premenstrual dysphoric disorder, situational depression, breakthrough depression, atypical depression, treatment resistant depression, catatonic depression, dysthymia, double depression, unspecified depressive disorder, depressive personality disorder, recurrent brief depression, minor depressive disorder, alcohol-induced depression, substance-induced depression, benzodiazepine-induced depression, and mixed anxiety-depressive disorder. In some embodiments, the subject has demonstrated improvement of one or more symptoms related to a condition or disorder selected from the group consisting of: depression, mild depression, moderate depression, severe depression, major depression, major depressive disorder, anxious distress, melancholy, melancholic depression, agitation, persistent depressive disorder, bipolar disorder type 1, bipolar disorder type 2, bipolar disorder not otherwise specified, cyclothymia, season affective disorder, psychotic depression, psychotic major depression, postpartum depression, premenstrual dysphoric disorder, situational depression, breakthrough depression, atypical depression, treatment resistant depression, catatonic depression, dysthymia, double depression, unspecified depressive disorder, depressive personality disorder, recurrent brief depression, minor depressive disorder, alcohol-induced depression, substance-induced depression, benzodiazepine-induced depression, and mixed anxiety-depressive disorder. In some embodiments, the subject has been diagnosed with one or more conditions or disorders that carry a risk of depression as a co-morbidity selected from the group consisting of: Alzheimer's disease, a cancer, coronary heart disease, acute coronary syndrome, diabetes, epilepsy, HIV/AIDS, hypothyroidism, multiple sclerosis, Parkinson's disease, stroke, systemic lupus erythematosus, rheumatoid arthritis, psoriasis, panic disorder, generalized anxiety disorder, obsessive-compulsive disorder, post-traumatic stress disorder, dementia, substance-abuse disorder, a psychotic disorder, anorexia nervosa, bulimia nervosa, muscle dysmorphia, binge eating disorder, compulsive over eating, polycystic ovary syndrome, Prader Willi syndrome, diabulimia, an autoimmune disorder, and an inflammatory disorder. In some embodiments, the one or more of non-invasive brain stimulation sessions comprises using the tES device with the first electrode and the second in close proximity to or touching the forehead of the subject. In some embodiments, the frontal lobes of the brain of the subject are stimulated to elicit neuromodulation. In some embodiments, the parietal lobes of the brain of the subject are stimulated to elicit neuromodulation. In some embodiments, the temporal lobes of the brain of the subject are stimulated to elicit neuromodulation. In some embodiments, the prefrontal cortex of the subject is stimulated to elicit neuromodulation. In some embodiments, the dorsolateral prefrontal cortex (DLPFC) of the subject is stimulated to elicit neuromodulation. The DLPFC is an area of the brain that assists in regulating mood, focus, and can impact sleep and appetite. When lower activity is associated with this area of the brain, these functions can be affected. In some embodiments, the left dorsolateral prefrontal cortex of the subject is stimulated to elicit neuromodulation. In some embodiments, the methods further comprise pyramidal cells of the cerebral cortex exhibiting cell bodies and axons which become depolarized. In some embodiments, the methods further comprise pyramidal cells of the cerebral cortex exhibiting cell bodies and axons which become hyper-polarized. In some embodiments, the methods further comprise pyramidal cells of the cerebral cortex exhibiting apical dendrites which become depolarized. In some embodiments, the methods further comprise pyramidal cells of the cerebral cortex exhibiting apical dendrites which become hyper-polarized. In some embodiments, the methods further comprise interneurons of the cerebral cortex becoming depolarized. In some embodiments, the methods further comprise interneurons of the cerebral cortex becoming hyper-polarized. In some embodiments, the methods further comprise neural activity in the DLPFC increasing at a time point following the one or more of non-invasive brain stimulation sessions. In some embodiments, the methods further comprise functional connectivity increasing between the DLPFC and the orbitofrontal cortex, the thalamus, the dorsal caudate nucleus, the hippocampus, one or more primary association areas of the neocortex, or one or more secondary association areas of the neocortex, or any combination thereof. In some embodiments, the methods further comprise neuroplasticity in the brain of the subject increasing. In some embodiments, the methods further comprise cognitive function significantly improving in the subject. In some embodiments, the methods further comprise one or more executive functions of the brain significantly improving in the subject. In some embodiments, the methods further comprise attention significantly improved in the subject. In some embodiments, cognitive inhibition significantly improving in the subject. In some embodiments, the methods further comprise inhibitory control significantly improving in the subject. In some embodiments, the methods further comprise cognitive planning significantly improving in the subject. In some embodiments, the methods further comprise working memory significantly improving in the subject. In some embodiments, the methods further comprise depressive mood significantly improving in the subject. In some embodiments, the methods further comprise one or more symptoms of depressive significantly improving in the subject. In some embodiments, the methods further comprise a feeling of wellness being significantly restored in the subject. In some embodiments, each of the one or more of non-invasive brain stimulation sessions deliver tES to the subject for a duration of at least about 1 minute, 2 minutes, 3 minutes, 4 minutes, 5 minutes, 6 minutes, 7 minutes, 8 minutes, 9 minutes, 10 minutes, 11 minutes, 12 minutes, 13 minutes, 14 minutes, 15 minutes, 16 minutes, 17 minutes, 18 minutes, 19 minutes, 20 minutes, 21 minutes, 22 minutes, 23 minutes, 24 minutes, 25 minutes, 26 minutes, 28 minutes, 29 minutes, 30 minutes, 31 minutes, 32 minutes, 33 minutes, 34 minutes, 35 minutes, 40 minutes, 45 minutes, or 50 minutes. In some embodiments, each of the one or more of non-invasive brain stimulation sessions deliver tES to the subject for a duration of less than about 1 minute, 2 minutes, 3 minutes, 4 minutes, 5 minutes, 6 minutes, 7 minutes, 8 minutes, 9 minutes, 10 minutes, 11 minutes, 12 minutes, 13 minutes, 14 minutes, 15 minutes, 16 minutes, 17 minutes, 18 minutes, 19 minutes, 20 minutes, 21 minutes, 22 minutes, 23 minutes, 24 minutes, 25 minutes, 26 minutes, 28 minutes, 29 minutes, 30 minutes, 31 minutes, 32 minutes, 33 minutes, 34 minutes, 35 minutes, 40 minutes, 45 minutes, or 50 minutes. In some embodiments, the subject undergoes the one or more of non-invasive brain stimulation sessions with a frequency of about twice every day, once every 18 hours, once every day, once every 36 hours, once every other day, 6 times per week, 5 times per week, 4 times per week, 3 times per week, 2 times per week, 1 time per week, or 1 time every two weeks. In some embodiments, the subject undergoes the one or more of non-invasive brain stimulation sessions according to a schedule of an initial activation phase with a frequency of about twice every day, once every 18 hours, once every day, once every 36 hours, once every other day, 6 times per week, 5 times per week, 4 times per week, 3 times per week, 2 times per week, 1 time per week, or 1 time every two weeks. In some embodiments, the subject undergoes the one or more of non-invasive brain stimulation sessions according to a schedule of a secondary strengthening phase with a frequency of about twice every day, once every 18 hours, once every day, once every 36 hours, once every other day, 6 times per week, 5 times per week, 4 times per week, 3 times per week, 2 times per week, 1 time per week, or 1 time every two weeks. In some embodiments, the initial activation phase lasts for a period of time about 3 days, 4 days, 5 days, 6 days, 7 days, 8 days, 9 days, 10 days, 11 days, 12 days, 13 days, 2 weeks, 3 weeks, 4 weeks, 5 weeks, 6 weeks, 7 weeks, 8 weeks, 9 weeks, 10 weeks, 11 weeks, 12 weeks, 13 weeks, 14 weeks, 15 weeks, 16 weeks, 17 weeks, 18 weeks, 19 weeks, or 20 weeks. In some embodiments, the secondary strengthen phase begins a period of time about 3 days, 4 days, 5 days, 6 days, 7 days, 8 days, 9 days, 10 days, 11 days, 12 days, 13 days, 2 weeks, 3 weeks, 4 weeks, 5 weeks, 6 weeks, 7 weeks, 8 weeks, 9 weeks, 10 weeks, 11 weeks, 12 weeks, 13 weeks, 14 weeks, 15 weeks, 16 weeks, 17 weeks, 18 weeks, 19 weeks, 20 weeks, 21 weeks, 22 weeks, 23 weeks, 24 weeks, or 25 weeks after completion of the initial activation phase. In some embodiments, tDCS delivers a current of about +/−0.5 mA, +/−0.6 mA, +/−0.7 mA, +/−0.8 mA, +/−0.9 mA, +/−1.0 mA, +/−1.1 mA, +/−1.2 mA, +/−1.3 mA, +/−1.4 mA, +/−1.5 mA, +/−1.6 mA, +/−1.7 mA, +/−1.8 mA, +/−1.9 mA, +/−2.0 mA, +/−2.1 mA, +/−2.2 mA, +/−2.3 mA, +/−2.4 mA, +/−2.5 mA, +/−2.6 mA, +/−2.7 mA, +/−2.8 mA, +/−2.9 mA, +/−3.0 mA, +/−3.1 mA, +/−3.2 mA, +/−3.3 mA, +/−3.4 mA, +/−3.5 mA, +/−3.6 mA, +/−3.7 mA, +/−3.8 mA, +/−3.9 mA, +/−4.0 mA, +/−4.5 mA, or +/−5.0 mA to the subject during the one or more of non-invasive brain stimulation sessions. In some embodiments, the current is delivered continuously during a duration of the one or more of non-invasive brain stimulation sessions. In some embodiments, the subject completes at least 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, or 70 of the one or more of non-invasive brain stimulation sessions. In some embodiments, the subject shows an decrease in Montgomery-Åsberg Depression Rating Scale Score (MADRS-S) during treatment or after treatment completion compared to a MADRS-S taken prior to treatment initiation or taken at an earlier time point in treatment of at least 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, or 54 points. In some embodiments, one or more MADRS-S measurements are determined via a self-assessment questionnaire. In some embodiments, MADRS-S measurements are used in part for assessing the response of the subject to the treatment regimen and to the one or more stimulation sessions in order to determine treatment effectiveness in (c). In some embodiments, the prompt of the subject to input information pertaining to information about the subject's current health comprises displaying a self-assessment MADRS-S questionnaire to the subject and the subject completing the questionnaire and having results from the completed questionnaire stored in a computer memory of the electronic device. In some embodiments, the electronic device is a handheld device. In some embodiments, the desired treatment outcome is an improvement in a symptom of the subject. In some embodiments, the symptom of the subject is a symptom of depression. In some embodiments, the improvement comprises decrease in MADRS-S of the subject. In some embodiments, the decrease in MADRS-S of the subject is sustained for a period of at least 1 week, 2 weeks, 3 weeks, 4 weeks, 5 weeks, 6 weeks, 7 weeks, 8 weeks, 9 weeks, 10 weeks, 11 weeks, 12 weeks, 13 weeks, 14 weeks, 15 weeks, 16 weeks, 17 weeks, 18 weeks, 19 weeks, 20 weeks, 21 weeks, 22 weeks, 23 weeks, 24 weeks, or 25 weeks. In some embodiments, the methods further comprise a subject having moderate depression showing a significant decrease in MADRS-S following at least 6 weeks of tES treatment comprising at least 21 of the non-invasive brain stimulation sessions. In some embodiments, the methods further comprise a subject having moderate depression showing a significant decrease in MADRS-S following at least 10 weeks of tES treatment comprising at least 21 of the non-invasive brain stimulation sessions. In some embodiments, the methods further comprise a subject having severe depression showing a significant decrease in MADRS-S following at least 6 weeks of tES treatment comprising at least 21 of the non-invasive brain stimulation sessions. In some embodiments, the methods further comprise a subject having severe depression showing a significant decrease in MADRS-S following at least 10 weeks of tES treatment comprising at least 21 of the non-invasive brain stimulation sessions. In some embodiments, the methods further comprise a subject having depression being administered sertraline as part of a treatment regimen and following at least 6 weeks of tES treatment comprising at least 21 of the non-invasive brain stimulation sessions showing a significant decrease in MADRS-S. In some embodiments, the significant decrease in MADRS-S is greater than a decrease in MADRS-S in a second subject being administered fluoxetine as part of a treatment regimen and following at least 6 weeks of tES treatment comprising at least 21 of the non-invasive brain stimulation sessions. In some embodiments, the adjusting parameters in (a) and (b) to achieve to a desired treatment outcome comprises decreasing an ongoing dosage of the administered pharmacologic antidepressant agent to the subject necessary to maintain an improvement in one of more symptoms of depression. In some embodiments, the adjusting parameters in (a) and (b) to achieve to a desired treatment outcome comprises decreasing an ongoing administration frequency of the pharmacologic antidepressant agent to the subject necessary to maintain an improvement in one of more symptoms of depression. In some embodiments, the adjusting parameters in (a) and (b) to achieve to a desired treatment outcome comprises decreasing a frequency of tES sessions the subject requires to maintain an improvement in one of more symptoms of depression. In some embodiments, the adjusting parameters in (a) and (b) to achieve to a desired treatment outcome comprises decreasing a duration of tES sessions the subject requires to maintain an improvement in one of more symptoms of depression. In some embodiments, the adjusting parameters in (a) and (b) to achieve to a desired treatment outcome comprises decreasing a current administered to the subject in ongoing tES sessions required to maintain an improvement in one of more symptoms of depression. In some embodiments, the methods further comprise the subject undergoing a focused meditation exercise or a focused relaxation exercise during the one or more of non-invasive brain stimulation sessions.

In one aspect, disclosed herein are methods of neuromodulatory intervention in a subject, the methods comprising: (a) administering to the subject a pharmacological antidepressant agent in a treatment effective amount as part of a treatment regimen; (b) delivering concurrently to the subject one or more of non-invasive brain stimulation sessions via a transcranial electrical stimulation (tES) device; (c) assessing a response of the subject to the treatment regimen and the one or more of non-invasive brain stimulation sessions in order to determine treatment effectiveness; and (d) adjusting parameters in (a) and (b) to achieve to a desired treatment outcome.

In one aspect, disclosed herein are methods of preventing breakthrough depression in a subject, the methods comprising: (a) administering to the subject a pharmacological antidepressant agent in a treatment effective amount as part of a treatment regimen; (b) delivering concurrently to the subject one or more of non-invasive brain stimulation sessions via a transcranial electrical stimulation (tES) device; (c) assessing a response of the subject to the treatment regimen and the one or more of non-invasive brain stimulation sessions in order to determine treatment effectiveness; and (d) adjusting parameters in (a) and (b) to achieve to a desired treatment outcome.

In one aspect, disclosed herein are methods of maintaining depression remission in a subject, the methods comprising: (a) administering to the subject a pharmacological antidepressant agent in a treatment effective amount as part of a treatment regimen; (b) delivering concurrently to the subject one or more of non-invasive brain stimulation sessions via a transcranial electrical stimulation (tES) device; (c) assessing a response of the subject to the treatment regimen and the one or more of non-invasive brain stimulation sessions in order to determine treatment effectiveness; and (d) adjusting parameters in (a) and (b) to achieve to a desired treatment outcome.

In one aspect, disclosed herein are uses of a pharmaceutical composition comprising a pharmacologic antidepressant agent, for manufacture of a medicament for treating depression in subject in need thereof, wherein the pharmaceutical composition is administered to the subject and wherein a transcranial electrical stimulation (tES) is administered to the subject.

INCORPORATION BY REFERENCE

All publications, patents, and patent applications mentioned in this specification are herein incorporated by reference to the same extent as if each individual publication, patent, or patent application was specifically and individually indicated to be incorporated by reference. To the extent publications and patents or patent applications incorporated by reference contradict the disclosure contained in the specification, the specification is intended to supersede and/or take precedence over any such contradictory material.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings of which:

FIG. 12A depicts the absolute number of patients in each adherence group, with numbers showing, from top to bottom in each group, the number of patients with severe, moderate, and mild depression, respectively. FIG. 12B depicts disease severity for each adherence group as a percentage of the total, showing, from top to bottom in each group, the percentage of patients, relative to the total number of patients in that adherence group with severe, moderate, and mild depression, respectively.

DETAILED DESCRIPTION

Figure 1:
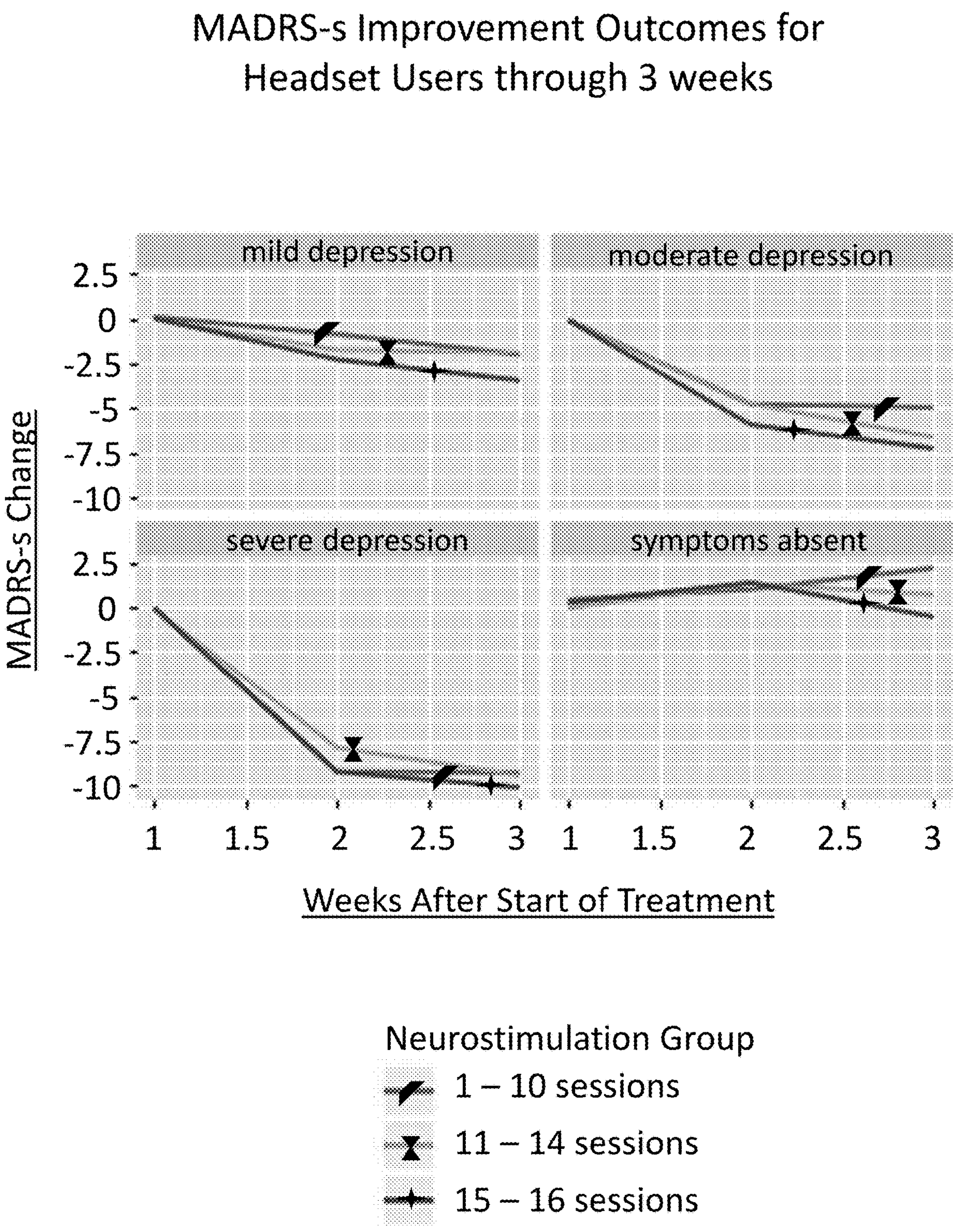
FIG. 1 shows graphs of depression score improvement outcomes through three weeks following initiation of neurostimulation. Subjects were grouped by symptom severity and graphed according to number of neurostimulation sessions.

Many potential benefits relating to the use of transcranial electrical stimulation (tES) for neuromodulation to treat depressive disorders have been contemplated. Additionally, pharmacological intervention and treatment by way of administration of a pharmacologic antidepressant agent remains an effective means of treatment for many individuals affected by a depressive disorder. Numerous neurological conditions, including those either categorized as a depressive disorder or those containing a depressive behavioral component, are resistant to current treatments in a significant segment of the population and present widespread socioeconomic burden and personal suffering. Several problems have persisted in adapting tES procedures into effective therapies for depression. Among these problems is a lack of a thorough understanding of how variables relating to delivery of tES (e.g., format, intensity of stimulation, duration, repetition, location) induce and maintain an extent of neuromodulation within a given population. tES has been demonstrated to be neuromodulatory in healthy subjects and in subject having a pathological condition. Types and extents of neuromodulation that may be therapeutic can vary according to the particular neurological state and condition of a given subject. As a non-limiting example, an individual diagnosed with mild depression may benefit from a more modest extent of neuromodulation than an individual diagnosed with more severe form of major depressive disorder (MDD). As another non-limiting example, an individual with depression showing improvement in one or more depression symptoms, may benefit from a more modest extent of neuromodulation than an individual with an intractable or chronic form of depression. As another non-limiting example, an individual with a severe form of depression such as catatonic depression may benefit from a more robust extent of neuromodulation than an individual diagnosed a mild form of depression such as minor depressive disorder. Pharmacological intervention and treatment of depression, despite being effective in many cases, does suffer from some of the same type problems of efficacy as tES in improvement of depressive symptoms in certain individuals. As a non-limiting example, the estimated 12-month prevalence of treatment resistant depression (TRD) amongst those with medication-treated MDD was recently calculated as 30.9% of this population of individuals (Zhdanava M. et al. *The Prevalence and National Burden of Treatment-Resistant Depression and Major Depressive Disorder in the United States*. J Clin Psychiatry. 2021 Mar. 16; 82(2):20m13699). Due the prevalence of depression, the deep-reaching effects on the health and well-being of individuals suffering from depression, the extent of an unmanageable or untreatable depression, and the burdens of side effects and patient non-adherence to depression treatment protocols, clearly the need exists to develop more effective treatments for depressive disorders.

Provided herein are methods for treating depression that combine neuromodulation with administration of pharmacologic antidepressants. tES provides a safe and effective means of inducing neuromodulation in a subject. By varying the parameters of a tES delivery protocol, neurostimulation may be delivered to an extent that is tailored to a given subject based on numerous subject criteria. These subject criteria can include a particular depressive disorder diagnosis, a medical history, a rating of depressive symptoms, a modulation of depressive symptoms, a length of time affected by depressive symptoms. tES also provides a safe and effective means of maintaining neuromodulation in a subject. Varying the parameters of a tES delivery protocol, including format, intensity of stimulation, duration, repetition, and location of stimulation all contribute to induction (activation) and maintenance or strengthening of neuromodulation.

I. METHODS

In an aspect, disclosed herein are methods of treatment for depression in a subject comprising administering to the subject a pharmacologic antidepressant agent and delivering to the subject a transcranial electrical stimulation (tES). In some embodiments, the method comprises administering a pharmacologic antidepressant agent further comprising one or more pharmacologic antidepressant agents. In some embodiments, the method comprises administering the pharmacologic antidepressant agent as part of a treatment regimen. In some embodiments, the method comprises administering the pharmacologic antidepressant agent in a treatment effective amount. In some embodiments, the method comprises the delivering to the subject the tES at a particular time point relative to the administration of the pharmacologic antidepressant agent. In some embodiments, the methods comprises delivery of tES through one or more of non-invasive brain stimulation sessions. In some embodiments, the methods comprises delivery of tES via a tES device. In some embodiments, the method comprises assessing a response of the subject to the treatment regimen of administering the pharmacologic antidepressant agent. In some embodiments, the method comprises assessing a response of the subject to the one or more of non-invasive brain stimulation sessions. In some embodiments, assessing the response of the subject comprises determining a treatment effectiveness. In some embodiments, the method comprises adjusting parameters of administering to the subject the pharmacologic antidepressant agent to achieve to a desired treatment outcome. In some embodiments, the method comprises adjusting parameters of delivering to the subject the tES to achieve to a desired treatment outcome.

Pharmacologic Antidepressant Agents

In some embodiments, the methods disclosed herein further comprise administering to the subject a pharmacologic antidepressant agent known to modulate neurotransmission. In some embodiments, the pharmacologic antidepressant agent known to modulate neurotransmission comprises a selective serotonin reuptake inhibitor (SSRI). In some embodiments, the pharmacologic antidepressant agent known to modulate neurotransmission comprises a serotonin-norepinephrine reuptake inhibitor (SNRI). In some embodiments, the pharmacologic antidepressant agent known to modulate neurotransmission comprises a noradrenergic and specific serotonergic antidepressant (NaSSA). In some embodiments, the pharmacologic antidepressant agent known to modulate neurotransmission comprises a serotonin modulator and stimulator (SMS). In some embodiments, the pharmacologic antidepressant agent known to modulate neurotransmission comprises a serotonin antagonist and reuptake inhibitor (SARI). In some embodiments, the pharmacologic antidepressant agent known to modulate neurotransmission comprises a serotonin-norepinephrine-dopamine reuptake inhibitor (SNDRI). In some embodiments, the pharmacologic antidepressant agent known to modulate neurotransmission comprises a norepinephrine reuptake inhibitor (NRI). In some embodiments, the pharmacologic antidepressant agent known to modulate neurotransmission comprises a norepinephrine-dopamine reuptake inhibitor (NDRI). In some embodiments, the pharmacologic antidepressant agent known to modulate neurotransmission comprises a norepinephrine-dopamine releasing agent (NDRA). In some embodiments, the pharmacologic antidepressant agent known to modulate neurotransmission comprises a serotonin-norepinephrine-dopamine releasing agent (SNDRA). In some embodiments, the pharmacologic antidepressant agent known to modulate neurotransmission comprises a tricyclic antidepressant (TCA). In some embodiments, the pharmacologic antidepressant agent known to modulate neurotransmission comprises a tetracyclic antidepressant (TeCA). In some embodiments, the pharmacologic antidepressant agent known to modulate neurotransmission comprises a monoamine oxidase inhibitor (MAOI). In some embodiments, the pharmacologic antidepressant agent known to modulate neurotransmission comprises a NMDA receptor modulator. In some embodiments, the pharmacologic antidepressant agent known to modulate neurotransmission comprises an atypical antipsychotic. In some embodiments, the pharmacologic antidepressant agent known to modulate neurotransmission comprises an atypical antidepressant. In some embodiments, the pharmacologic antidepressant agent known to modulate neurotransmission comprises a benzodiazepine. In some embodiments, the pharmacologic antidepressant agent known to modulate neurotransmission comprises one or more pharmacologic antidepressant agents. In some embodiments, the pharmacologic antidepressant agent known to modulate neurotransmission comprises two pharmacologic antidepressant agents. In some embodiments, the pharmacologic antidepressant agent known to modulate neurotransmission comprises three pharmacologic antidepressant agents. In some embodiments, the one or more pharmacologic antidepressant agents comprise a combination of one or more agents categorized as an SSRI, an SNRI, a NaSSA, an SMS, an SARI, an SNDRI, a NRI, a NDRI, a NDRA, an SNDRA, a TCA, a TeCA, an MAOI, an NMDA receptor modulator, an atypical antipsychotic, an atypical antidepressant, or a benzodiazepine, or any combination thereof.

SSRIs are a class of drugs commonly prescribed to function as antidepressants to subjects in need thereof. SSRIs have been demonstrated to function to increase an extracellular level of the neurotransmitter serotonin (5-HT) by limiting its reuptake into a presynaptic cell. Neurotransmission in the brain occurs via signaling from one neuron to another through chemical synapses. A chemical synapse physically comprises a small gap between neurons. A presynaptic cell involved in propagating a neuronal signal releases neurotransmitters into the space near a chemical synapse. Following the process of presynaptic release of neurotransmitters and postsynaptic binding of released neurotransmitters to postsynaptic receptors resulting in initiation of neuronal signal propagation, about 90% of the neurotransmitters initially released from the presynaptic neuron's synapse either remain in the synaptic space or are then released from receptors back into the synaptic space. These free neurotransmitters can then be taken up by monoamine transporters into the presynaptic cells in a process termed reuptake and subsequently recycled for use again in neurotransmission. In serotonergic neurons, an action potential stimulates a calcium-dependent release of 5-HT from presynaptic vesicles into the synaptic space, where the 5-HT interacts with both presynaptic and postsynaptic receptors. A feedback loop regulates the 5-HT concentration in the synaptic space and therefore also regulates an extent of stimulation of various serotonin receptors at a postsynaptic membrane. By selectively inhibiting reuptake of 5-HT in presynaptic cells, SSRI treatment results in an increase in extracellular 5-HT levels near chemical synapses involved in serotonergic neurotransmission. This has an acute net effect of lowering a threshold of presynaptic 5-HT release required to initiate serotonin-mediated neuronal signal propagation in postsynaptic neurons connected through these affected chemical synapses. This effect of 5-HT molecules remaining in synaptic gaps longer in SSRI-treating subjects compared to untreated subjects can also translate into repeated stimulation of postsynaptic serotonergic receptors to elicit neurotransmission. Thus, acute SSRI treatment tends to increase neurotransmission from nerve cells utilizing 5-HT as a neurotransmitter. This acute response to SSRI treatment can be seen in elevated synaptic 5-HT levels within one hour from administering a dose of the SSRI medication. Decreased serotonergic activity has been implicated in a variety of depressive disorders and hence increasing serotonergic neurotransmission is believed to be beneficial in the treatment of depressive disorders. Upon chronic dosing with an SSRI, increased occupancy of postsynaptic serotonin receptors signals a presynaptic neuron to produce and release less 5-HT. This ultimately leads to a desensitized 5-HT and serotonin receptor feedback loop and downregulation of postsynaptic serotonin receptors.

Despite the above-mentioned acute effects SSRIs render on presynaptic and postsynaptic serotonergic neurons, subjects that respond to SSRI therapy often take a period of time much greater than that of the acute effects of SSRI therapy at the synapse in order to manifest as an improvement in one or more depression symptoms. Continued SSRI treatment as a monotherapy may take a period of time of 2-4 weeks before a subject experiences an improvement in one or more depression symptoms. Continued SSRI treatment as a monotherapy may take a period of time up to 12 weeks before a maximal benefit of the subject manifested as an improvement in one or more depression symptoms can be achieved. Although the nature of the delay from initiation of SSRI therapy to measurable improvements in depression symptoms in SSRI-responsive subjects is unclear, the proportion of subjects experiencing symptom improvements with SSRI treatment remains significant. Approximately 50% of depressed subjects respond to an initial SSRI treatment regimen with a noticeable improvement in depressive symptoms. Approximately 35-40% of depressed subjects on an initial SSRI treatment regimen achieve a period of remission, wherein remission is defined as a resolution of depressive symptoms (Rush A J et al., *Acute and longer-term outcomes in depressed outpatients requiring one or several treatment steps: a STAR*D report*. Am J Psychiatry. 2006 November; 163(11):1905-17.). Due to the prevalence of depressive disorders and the widely held view within the clinical community of SSRI therapy as a viable first line treatment strategy, several issues emerge following initiation of SSRI therapy in subjects with a depressive disorder. One such issue is that a significant percentage of the subjects will not respond to SSRI therapy and achieve any noticeable improvement in depressive symptoms. In line with this issue, a common therapeutic strategy when a subject is not responsive to an initial SSRI treatment regimen is to either alter the SSRI dosage being administered, alter the frequency of SSRI dosage administration, change to administering a different antidepressant medication, or any combination thereof. As the effects of SSRI and other antidepressant medication therapy can take weeks to manifest, these types of changes to a treatment regimen and the need to prolong an assessment of effectiveness of a newly enacted treatment regimen can result in prolonged symptomology and suffering in an affected subject. Accordingly, many subjects will go through several different prolonged treatment regimens using administration of an SSRI or another antidepressant medication only to realize no measurable improvement in depressive symptoms. Even in subjects that do experience a marked improvement in a depressive symptom, those subjects may still have impaired mood, psychosocial, and work functions if they have failed to achieve remission. Methods that yield a greater proportion of affected subjects achieving improvement in a depressive symptom, a greater extent of improvement in a depressive symptom, a greater proportion of affected subjects achieving remission of depression, an increase in the speed in which improvement in a depressive symptom is achievement, or allow a decrease in effective dosage and/or effective administration frequency of a pharmacologic antidepressant agent would substantial lessen the extent of suffering for those subjects having depression and also improve the overall burden produced as a result of depression.

As indicated, the nature of the delay from initiation of SSRI therapy to measurable improvements in depression symptoms in SSRI-responsive subjects is unclear. The length of time required for alterations in functional neural networks and network connectivity following prolonged SSRI therapy may contribute to this delay in improvement in depression symptoms. Additionally, and/or alternatively, widespread changes within the nervous system including alterations in gene expression, alterations in protein synthesis, and alterations in cellular protein localization may contribute to this delayed drug response. As a non-limiting example, it has been observed that subjects with depression often possess a higher percentage of G proteins in neurons and glial cells associated with lipid raft features of the cell membrane which as microdomains present in the plasma membrane tend not to aggregate near chemical synapses. SSRI treatment of glial cells resulted in eventual SSRI accumulation within lipid rafts and a concurrent redistribution of G proteins from lipid rafts into cellular regions away from lipid rafts which may be more conducive to eliciting functional G protein signaling events within a timeframe that could contribute to the delayed drug response of SSRI treatment (Erb S J et al. *Antidepressants Accumulate in Lipid Rafts Independent of Monoamine Transporters to Modulate Redistribution of the G Protein, Gas*. J Biol Chem. 2016 Sep. 16; 291(38):19725-19733.). SSRIs have also been noted to produce other effects on cells including anti-inflammatory effects. As described herein, methods for treating depression by combining tES with administration of pharmacological antidepressant agents, including SSRIs as non-limiting examples, results in improvement in one or more symptoms of depression to an extent greater than either method on its own. In some embodiments described herein, combining tES with administration of a pharmacological antidepressant agent produces a synergistic effect in the alteration of functional neural networks and network connectivity in the brain of a subject with depression. In some embodiments described herein, combining tES with administration of a pharmacological antidepressant agent produces a synergistic effect in an alteration of gene expression in the brain of a subject with depression. In some embodiments described herein, combining tES with administration of a pharmacological antidepressant agent produces a synergistic effect in an alteration of protein synthesis in the brain of a subject with depression. In some embodiments described herein, combining tES with administration of a pharmacological antidepressant agent produces a synergistic effect in an alteration of protein localization in the brain of a subject with depression. In some embodiments described herein, combining tES with administration of a pharmacological antidepressant agent produces a synergistic effect in reducing inflammation in the brain of a subject with depression.

Individual members of the class of drugs categorized as SSRIs may have differential effects on subjects being treated for a depressive disorder due to differences in chemical structure or composition of the particular SSRI. SSRIs of distinct chemical composition each have particular pharmacokinetic properties. Some SSRIs are able to be distinguished from each other on the basis of their particular pharmacokinetic properties. In some instances, a certain SSRI may have particular pharmacokinetic properties more conducive to effective treatment for a particular type of depressive disorder, or a distinct symptom indicative of a particular type of depressive disorder. SSRIs have been demonstrated to vary in their selectivity for different monoamine transporters. There are three main classes of monoamine transporters: serotonin transporters (SERT), dopamine transporters (DAT), and norepinephrine transporters (NET). SERT is responsible for the reuptake of extracellular 5-HT in a $Na+/Cl-$-dependent process. DAT is responsible for the reuptake of extracellular dopamine (DA) in a $Na+/Cl-$-dependent process. NET is responsible for the $Na+/Cl-$-dependent reuptake of extracellular norepinephrine (NE). It has been noted that DAT can also transport extracellular NE and that NET can also transport extracellular DA. As mentioned above, SSRI-monoamine transporter selectivity varies for each SSRI drug, but all drugs categorized as SSRIs exhibit a robust pharmacokinetic effect to inhibit pre-synaptic 5-HT reuptake, with inhibiting pre-synaptic reuptake of other monoamines to a lesser extent. In addition to influencing 5-HT reuptake, various SSRIs have been observed to function as ligands for sigma receptors. The SSRIs fluvoxamine, fluoxetine, escitalopram, and citalopram each can function as agonist for the Sigma-1 receptor. The SSRI sertraline can function as an antagonist for the Sigma-1 receptor. In some embodiments described herein, combining tES with administration of a pharmacological antidepressant agent that functions as an agonist of the Sigma-1 receptor leads to a synergistic effect on improvement of a cognitive deficit that is a symptom of a depressive disorder.

Treatment with SSRIs has been known to carry a risk of occurrence of potential unwanted side effects. In general, SSRIs may be tolerated better than many other types of pharmacologic antidepressants with a majority of subjects taking SSRIs only experiencing mild side effects. Treatment with an SSRI may induce an unwanted side effects including indigestion, diarrhea, constipation, weight loss, loss of appetite, blurred vision, dizziness, dry mouse, excessive sweating, insomnia, headache, excessive drowsiness, headache, sexual dysfunction, anxious feelings, anxiety, abnormal thinking, behavioral agitation, shakiness, increased risk of bleeding adverse events, confusion, urinary retention, hallucinations, hypoglycemia, low sodium, nausea, rash, serotonin syndrome. Occurrences of these unpleasant potential side effects can discourage a subject from maintaining a treatment regimen of prolonged administration of a given SSRI. An ability to reduce a dosage of an SSRI taken by a subject while maintaining a therapeutic benefit in one or more symptoms of depression would be beneficial in mitigating a risk of unwanted side effects.

Described herein, in some embodiments, are method of treatment for depression comprising administering to a subject an SSRI and delivering to the subject a tES. In some embodiments, administering the SSRI and delivering to the subject the tES eases a symptom of mild depression. In some embodiments, administering the SSRI and delivering to the subject the tES eases a symptom of moderate depression. In some embodiments, administering the SSRI and delivering to the subject the tES eases a symptom of severe depression. In some embodiments, the administering the SSRI comprises administering two or more SSRIs. In some embodiments, the administering the SSRI comprises administering an SSRI and a second pharmacologic antidepressant agent belonging to a drug category of SNRI, NaSSA, SMS, SARI, SNDRI, NRI, NDRI, NDRA, SNDRA, TCA, TeCA, MAOI, an NMDA receptor modulator, an atypical antipsychotic, an atypical antidepressant, or a benzodiazepine. In some embodiments, the SSRI is fluoxetine. In some embodiments, the SSRI is citalopram. In some embodiments, the SSRI is escitalopram. In some embodiments, the SSRI is paroxetine. In some embodiments, the SSRI is sertraline. In some embodiments, the SSRI is dapoxetine. In some embodiments, the SSRI is fluvoxamine. In some embodiments, the SSRI is vortioxetine.

SNRIs are a class of drugs commonly prescribed to function as antidepressants to subjects in need thereof. SNRIs are a class of monoamine inhibitors and have been demonstrated to function to increase an extracellular level of the neurotransmitters 5-HT and norepinephrine by limiting reuptake into a presynaptic cell. SNRIs do not have as selective as a role in 5-HT uptake as do SSRIs, which act primarily on 5-HT levels. SNRIs are defined as having shared features of inhibiting reuptake of 5-HT and norepinephrine but each member of the class has a distinct chemical structure and distinct pharmacological properties. As a non-limiting example, duloxetine and desvenlafaxine demonstrate a 10-fold higher selectivity for serotonin reuptake inhibition than norepinephrine reuptake inhibition. Venlafaxine has an even higher relative selectivity for serotonin reuptake inhibition as it has been shown to exhibit 30-fold higher selectivity for serotonin reuptake inhibition than norepinephrine reuptake inhibition. Venlafaxine and duloxetine inhibit serotonin and norepinephrine reuptake in a sequential manner, such that serotonin reuptake is initially inhibited, and followed later by norepinephrine reuptake inhibition. Levomilnacipran demonstrates a 2-fold greater potency for norepinephrine reuptake inhibition than serotonin reuptake inhibition. Milnacipran demonstrates a 3-fold greater potency for norepinephrine reuptake inhibition than serotonin reuptake inhibition. Unlike venlafaxine and duloxetine, milnacipran exerts simultaneous effects on reuptake of both 5-TH and norepinephrine.

Treatment with SNRIs has been known to carry a risk of occurrence of potential unwanted side effects. All SNRIs inhibit κ-HT uptake in human platelets, which has been associated with an increased risk of bleeding adverse events. Duloxetine and venlafaxine at high doses weakly inhibit the reuptake of dopamine, which may contribute to effects on blood pressure. Treatment with venlafaxine can lead to an increased risk of unwanted side effects including hypoglycemia, low sodium, rash, constipation, diarrhea, weight loss, sweating, headaches, nausea, fatigue, sexual dysfunction, activation effects (including disinhibition, impulsivity, insomnia, restlessness, hyperactivity, irritability, and abnormal thinking), dry mouth, and night sweats. These are non-limited examples of potential unwanted side effects of SNRI usage. The sequential effects on reuptake inhibition of duloxetine and venlafaxine can also results in a sequential side effect profile, with serotonergic side effects onset initially, followed by noradrenergic side effects. Occurrences of these unpleasant potential side effects can discourage a subject from maintaining a treatment regimen of prolonged administration of a given SNRI. An ability to reduce a dosage of an SNRI taken by a subject while maintaining a therapeutic benefit in one or more symptoms of depression would be beneficial in mitigating a risk of unwanted side effects such as increased risk of abnormal bleeding, increased risk of a coagulation disorder, elevated blood pressure, or other side effects described herein.

Described herein, in some embodiments, are method of treatment for depression comprising administering to a subject an SNRI and delivering to the subject a tES. In some embodiments, administering the SNRI and delivering to the subject the tES eases a symptom of mild depression. In some embodiments, administering the SNRI and delivering to the subject the tES eases a symptom of moderate depression. In some embodiments, administering the SNRI and delivering to the subject the tES eases a symptom of severe depression. In some embodiments, the administering the SNRI comprises administering two or more SNRIs. In some embodiments, the administering the SNRI comprises administering an SNRI and a second pharmacologic antidepressant agent belonging to a drug category of SSRI, NaSSA, SMS, SARI, SNDRI, NRI, NDRI, NDRA, SNDRA, TCA, TeCA, MAOI, an NMDA receptor modulator, an atypical antipsychotic, an atypical antidepressant, or a benzodiazepine. In some embodiments, the SNRI is desvenlafaxine. In some embodiments, the SNRI is duloxetine. In some embodiments, the SNRI is levomilnacipran. In some embodiments, the SNRI is milnacipran. In some embodiments, the SNRI is venlafaxine IR. In some embodiments, the SNRI is venlafaxine XR.

NaSSAs are a class of drugs commonly prescribed to function as antidepressants to subjects in need thereof. NaSSAs act by antagonizing the α2-adrenergic receptor and particular 5-HT receptors thereby causing noradrenaline and 5-HT to increase in concentration at the synapse. NaSSAs bind to and inhibit α2-adrenergic autoreceptors and α2-adrenergic heteroreceptors. This has an effect of preventing a negative feedback loop of synaptic noradrenaline on 5-HT and noradrenaline neurotransmission thereby sustaining neurotransmission through these synapses. Blockage of 5-HT2 and 5-HT3 receptors on postsynaptic membranes by NaSSAs can also cause enhances 5-HT1 receptor mediated neurotransmission.

Treatment with NaSSAs has been known to carry a risk of occurrence of potential unwanted side effects. Many of the side effects associated with NaSSAs overlap with those of SSRIs. Some non-limiting examples of unwanted side effects shared between use of SSRIs and NaSSAs are dizziness, drowsiness, dry mouth, constipation, shaking, confusion, fainting, agitation, nausea, diarrhea, blurred vision, and serotonin syndrome. However, differences in rates of incidences and extents of unwanted side effects between NaSSAs and SSRIs have also been demonstrated. As non-limiting examples, treatment with NaSSAs has a lower occurrence of sexual dysfunction side effects than treatment with SSRIs and treatment with NaSSAs may lead to more incidences and a stronger extent of drowsiness than treatment with SSRIs. This drowsiness side effect is particularly evident in many subjects during an initial phase of treatment using an NaSSA. NaSSA treatment has also been associated with weight gain, increased appetite, swelling of the hands and/or feet, eye pain, widening pupils, loss of coordination, and twitching muscles. Occurrences of these unpleasant potential side effects can discourage a subject from maintaining a treatment regimen of prolonged administration of a given NaSSA. An ability to reduce a dosage of an NaSSA taken by a subject while maintaining a therapeutic benefit in one or more symptoms of depression would be beneficial in mitigating a risk of unwanted side effects.

Described herein, in some embodiments, are method of treatment for depression comprising administering to a subject an NaSSA and delivering to the subject a tES. In some embodiments, administering the NaSSA and delivering to the subject the tES eases a symptom of mild depression. In some embodiments, administering the NaSSA and delivering to the subject the tES eases a symptom of moderate depression. In some embodiments, administering the NaSSA and delivering to the subject the tES eases a symptom of severe depression. In some embodiments, the administering the NaSSA comprises administering two or more SNRIs. In some embodiments, the administering the NaSSA comprises administering an NaSSA and a second pharmacologic antidepressant agent belonging to a drug category of SSRI, SNRI, SMS, SARI, SNDRI, NRI, NDRI, NDRA, SNDRA, TCA, TeCA, MAOI, an NMDA receptor modulator, an atypical antipsychotic, an atypical antidepressant, or a benzodiazepine. In some embodiments, the NaSSA is aptazapine. In some embodiments, the NaSSA is esmirtazapine. In some embodiments, the NaSSA is mianserin. In some embodiments, the NaSSA is mirtazapine. In some embodiments, the NaSSA is setiptiline. Treatment with NaSSAs has been known to carry a risk of occurrence of potential unwanted side effects. Treatment with NaSSAs can lead to an increased risk of unwanted side effects including constipation, dry mouth, weight gain, drowsiness, sedation, blurred vision, and dizziness. More serious adverse reactions to NaSSAs include seizures, white blood cell reduction, fainting, and allergic reactions. An ability to reduce a dosage of an NaSSA taken by a subject while maintaining a therapeutic benefit in one or more symptoms of depression would be beneficial in mitigating a risk of unwanted side effects.

SMSs are a class of drugs prescribed to function as antidepressants to subjects in need thereof. SMSs act by simultaneously modulating one or more serotonin receptors and inhibit the reuptake of serotonin. Described herein, in some embodiments, are method of treatment for depression comprising administering to a subject an SMS and delivering to the subject a tES. In some embodiments, administering the SMS and delivering to the subject the tES eases a symptom of mild depression. In some embodiments, administering the SMS and delivering to the subject the tES eases a symptom of moderate depression. In some embodiments, administering the SMS and delivering to the subject the tES eases a symptom of severe depression. In some embodiments, the administering the SMS comprises administering two or more SMSs. In some embodiments, the administering the SMS comprises administering an SMS and a second pharmacologic antidepressant agent belonging to a drug category of SSRI, SNRI, NaSSA, SARI, SNDRI, NRI, NDRI, NDRA, SNDRA, TCA, TeCA, MAOI, an NMDA receptor modulator, an atypical antipsychotic, an atypical antidepressant, or a benzodiazepine. In some embodiments, the SMS is vilazodone. Vilazodone is known to function as a serotonin reuptake inhibitor and a partial agonist of serotonin receptors. In some embodiments, the SMS is vortioxetine. Vortioxetine is known to function as a serotonin reuptake inhibitor, a partial agonist of the 5-$HT_{1A}$ receptor, and antagonist of the 5-$HT_3$ and 5-$HT_7$ receptors.

SARIs are a class of drugs prescribed to function as antidepressants to subjects in need thereof. SARIs act by antagonizing serotonin receptors such as the 5-$HT_{2A}$ receptor and by inhibiting the postsynaptic reuptake of serotonin, norepinephrine, and/or dopamine. Several members of the SARI class of drugs also function as α1-adrenergic receptor antagonists. Described herein, in some embodiments, are method of treatment for depression comprising administering to a subject an SARI and delivering to the subject a tES. In some embodiments, administering the SARI and delivering to the subject the tES eases a symptom of mild depression. In some embodiments, administering the SARI and delivering to the subject the tES eases a symptom of moderate depression. In some embodiments, administering the SARI and delivering to the subject the tES eases a symptom of severe depression. In some embodiments, the administering the SARI comprises administering two or more SARIs. In some embodiments, the administering the SARI comprises administering an SARI and a second pharmacologic antidepressant agent belonging to a drug category of SSRI, SNRI, NaSSA, SMS, SNDRI, NRI, NDRI, NDRA, SNDRA, TCA, TeCA, MAOI, an NMDA receptor modulator, an atypical antipsychotic, an atypical antidepressant, or a benzodiazepine. In some embodiments, the SARI is nefazodone. In some embodiments, the SARI is trazodone.

SNDRIs are a class of drugs prescribed to function as antidepressants to subjects in need thereof. SNDRIs are known as triple reuptake inhibitors as they act as combined reuptake inhibitor of serotonin, norepinephrine, and dopamine. SNDRIs function by concomitantly inhibiting the serotonin transporter (SERT), the norepinephrine transporter (NET), and the dopamine transporter (DAT). Inhibition of the reuptake of these neurotransmitters increases extracellular concentration near synapses and, therefore, results in an increase in serotonergic, adrenergic, and dopaminergic neurotransmission. SNDRIs share a similar result of their activity following administration compared with MAOIs in that each class of drugs increases the action of serotonin, norepinephrine, and dopamine in neurotransmission. Described herein, in some embodiments, are method of treatment for depression comprising administering to a subject an SNDRI and delivering to the subject a tES. In some embodiments, administering the SNDRI and delivering to the subject the tES eases a symptom of mild depression. In some embodiments, administering the SNDRI and delivering to the subject the tES eases a symptom of moderate depression. In some embodiments, administering the SNDRI and delivering to the subject the tES eases a symptom of severe depression. In some embodiments, the administering the SNDRI comprises administering two or more SNDRIs. In some embodiments, the administering the SNDRI comprises administering an SNDRI and a second pharmacologic antidepressant agent belonging to a drug category of SSRI, SNRI, NaSSA, SMS, SARI, NRI, NDRI, NDRA, SNDRA, TCA, TeCA, MAOI, an NMDA receptor modulator, an atypical antipsychotic, an atypical antidepressant, or a benzodiazepine. In some embodiments, the SNDRI is toludesvenlafaxine. In some embodiments, the SNDRI is OPC-64005. In some embodiments, the SNDRI is ansofaxine.

NRIs are a class of drugs prescribed to function as antidepressants to subjects in need thereof. NRIs are known to function as reuptake inhibitors of the neurotransmitters norepinephrine and epinephrine by inhibiting the action of the norepinephrine transporter leading to increased extracellular concentrations of norepinephrine and epinephrine that may thereby increase adrenergic neurotransmission. Described herein, in some embodiments, are method of treatment for depression comprising administering to a subject an NRI and delivering to the subject a tES. In some embodiments, administering the NRI and delivering to the subject the tES eases a symptom of mild depression. In some embodiments, administering the NRI and delivering to the subject the tES eases a symptom of moderate depression. In some embodiments, administering the NRI and delivering to the subject the tES eases a symptom of severe depression. In some embodiments, the administering the NRI comprises administering two or more NRIs. In some embodiments, the administering the NRI comprises administering an NRI and a second pharmacologic antidepressant agent belonging to a drug category of SSRI, SNRI, NaSSA, SMS, SARI, SNDRI, NDRI, NDRA, SNDRA, TCA, TeCA, MAOI, an NMDA receptor modulator, an atypical antipsychotic, an atypical antidepressant, or a benzodiazepine. In some embodiments, the NRI is atomoxetine. In some embodiments, the NRI is reboxetine. In some embodiments, the NRI is teniloxazine. In some embodiments, the NRI is viloxazine.

NDRIs are a class of drugs prescribed to function as antidepressants to subjects in need thereof. NDRIs are known to function as reuptake inhibitors of the neurotransmitters norepinephrine and dopamine by inhibiting the function of NET and DAT leading to increased extracellular concentrations of norepinephrine and dopamine that may thereby increase adrenergic and dopaminergic neurotransmission. Described herein, in some embodiments, are method of treatment for depression comprising administering to a subject an NDRI and delivering to the subject a tES. In some embodiments, administering the NDRI and delivering to the subject the tES eases a symptom of mild depression. In some embodiments, administering the NDRI and delivering to the subject the tES eases a symptom of moderate depression. In some embodiments, administering the NDRI and delivering to the subject the tES eases a symptom of severe depression. In some embodiments, the administering the NDRI comprises administering two or more NDRIs. In some embodiments, the administering the NDRI comprises administering an NDRI and a second pharmacologic antidepressant agent belonging to a drug category of SSRI, SNRI, NaSSA, SMS, SARI, SNDRI, NRI, NDRA, SNDRA, TCA, TeCA, MAOI, an NMDA receptor modulator, an atypical antipsychotic, an atypical antidepressant, or a benzodiazepine. In some embodiments, an NDRI is combined with dextromethorphan. In some embodiments, bupropion is combined with dextromethorphan. The dextromethorphan component of AXS-05 is an antagonist of the NMDA receptor, an ionotropic glutamate receptor, and a sigma-1 receptor agonist, all of which are believed to function in modulating glutamatergic neurotransmission. The bupropion component of AXS-05 functions as a norepinephrine and dopamine reuptake inhibitor and increases the bioavailability of dextromethorphan. In some embodiments, the NDRI is bupropion. In some embodiments, the NDRI is amineptine. In some embodiments, the NDRI is methylphenidate. In some embodiments, the NDRI is AXS-05. AXS-05 is a pharmaceutical formulation comprising dextromethorphan and bupropion.

NDRAs are a class of drugs prescribed to function as antidepressants to subjects in need thereof. NDRAs are known to function to induce a release of norepinephrine and dopamine. Described herein, in some embodiments, are method of treatment for depression comprising administering to a subject an NDRA and delivering to the subject a tES. In some embodiments, administering the NDRA and delivering to the subject the tES eases a symptom of mild depression. In some embodiments, administering the NDRA and delivering to the subject the tES eases a symptom of moderate depression. In some embodiments, administering the NDRA and delivering to the subject the tES eases a symptom of severe depression. In some embodiments, the administering the NDRA comprises administering two or more NDRAs. In some embodiments, the administering the NDRA comprises administering an NDRA and a second pharmacologic antidepressant agent belonging to a drug category of SSRI, SNRI, NaSSA, SMS, SARI, SNDRI, NRI, NDRI, SNDRA, TCA, TeCA, MAOI, an NMDA receptor modulator, an atypical antipsychotic, an atypical antidepressant, or a benzodiazepine. In some embodiments, the NDRA is lisdexamfetamine. In some embodiments, the NDRA is phenethylamine. In some embodiments, the NDRA is tyramine. In some embodiments, the NDRA is amphetamine. In some embodiments, the NDRA is methamphetamine. In some embodiments, the NDRA is cathinone. In some embodiments, the NDRA is methcathinone. In some embodiments, the NDRA is propylhexedrine. In some embodiments, the NDRA is phenmetrazine. In some embodiments, the NDRA is pemoline. In some embodiments, the NDRA is 4-methylaminorex. In some embodiments, the NDRA is benzylpiperazine.

SNDRAs are a class of drugs prescribed to function as antidepressants to subjects in need thereof. SNDRAs are known to function to induce a release of serotonin, norepinephrine, and dopamine. Described herein, in some embodiments, are method of treatment for depression comprising administering to a subject an SNDRA and delivering to the subject a tES. In some embodiments, administering the SNDRA and delivering to the subject the tES eases a symptom of mild depression. In some embodiments, administering the SNDRA and delivering to the subject the tES eases a symptom of moderate depression. In some embodiments, administering the SNDRA and delivering to the subject the tES eases a symptom of severe depression. In some embodiments, the administering the SNDRA comprises administering two or more SNDRAs. In some embodiments, the administering the SNDRA comprises administering an SNDRA and a second pharmacologic antidepressant agent belonging to a drug category of SSRI, SNRI, NaSSA, SMS, SARI, SNDRI, NRI, NDRI, NDRA, TCA, TeCA, MAOI, an NMDA receptor modulator, an atypical antipsychotic, an atypical antidepressant, or a benzodiazepine. In some embodiments, the SNDRA is midomafetamine. In some embodiments, the SNDRA is 3,4-Methylenedioxymethamphetamine. In some embodiments, the SNDRA is 3,4-Methylenedioxyamphetamine. In some embodiments, the SNDRA is naphthylisopropylamine. In some embodiments, the SNDRA is mephedrone. In some embodiments, the SNDRA is methylone. In some embodiments, the SNDRA is α-methyltryptamine. In some embodiments, the SNDRA is α-ethyltryptamine.

TCAs are a class of drugs prescribed to function as antidepressants to subjects in need thereof. TCAs are known to act on at least four different neurotransmitter pathways. TCAs have been shown to block the reuptake of serotonin and norepinephrine in presynaptic terminals, which leads to increased concentration of these neurotransmitters in the extracellular synaptic cleft. TCAs also act as competitive antagonists on postsynaptic alpha cholinergic, muscarinic, and histaminergic receptors. By these means, TCAs affect extracellular levels of serotonin, norepinephrine, acetylcholine, and histamine. Described herein, in some embodiments, are method of treatment for depression comprising administering to a subject a TCA and delivering to the subject a tES. In some embodiments, administering the TCA and delivering to the subject the tES eases a symptom of mild depression. In some embodiments, administering the TCA and delivering to the subject the tES eases a symptom of moderate depression. In some embodiments, administering the TCA and delivering to the subject the tES eases a symptom of severe depression. In some embodiments, the administering the TCA comprises administering two or more TCAs. In some embodiments, the administering the TCA comprises administering a TCA and a second pharmacologic antidepressant agent belonging to a drug category of SSRI, SNRI, NaSSA, SMS, SARI, SNDRI, NRI, NDRI, NDRA, SNDRA, TeCA, MAOI, an NMDA receptor modulator, an atypical antipsychotic, an atypical antidepressant, or a benzodiazepine. In some embodiments, the TCA is amitriptyline. In some embodiments, the TCA is clomipramine. In some embodiments, the TCA is desipramine. In some embodiments, the TCA is dosulepin. In some embodiments, the TCA is doxepin. In some embodiments, the TCA is imipramine. In some embodiments, the TCA is lofepramine. In some embodiments, the TCA is nortriptyline. In some embodiments, the TCA is protriptyline. In some embodiments, the TCA is trimipramine.

Treatment with TCAs has been known to carry a risk of occurrence of potential unwanted side effects. Treatment with TCAs can lead to an increased risk of unwanted side effects including seizures, insomnia, anxiety, arrhythmia, hypertension, rash, nausea, vomiting, abdominal cramps, weight loss, constipation, urinary retention, increase in eye pressure, and sexual dysfunction. An ability to reduce a dosage of a TCA taken by a subject while maintaining a therapeutic benefit in one or more symptoms of depression would be beneficial in mitigating a risk of unwanted side effects.

TeCAs are a class of drugs prescribed to function as antidepressants to subjects in need thereof. TeCAs do not inhibit the reuptake of 5-HT, with amoxapine being a noticeable exception. TeCAs, apart from mirtazapine, do inhibit reuptake of norepinephrine. TeCAs have been demonstrated to block 5-$HT_2$ receptors similarly to TCAs. TeCAs also function to block the action of α1-adrenergic receptors and the histamine $H_1$ receptor. TeCAs have a low affinity for muscarinic acetylcholine receptors and as such are associated with few or very mild anticholinergic side effects unlike TCAs. Described herein, in some embodiments, are method of treatment for depression comprising administering to a subject a TeCA and delivering to the subject a tES. In some embodiments, administering the TeCA and delivering to the subject the tES eases a symptom of mild depression. In some embodiments, administering the TeCA and delivering to the subject the tES eases a symptom of moderate depression. In some embodiments, administering the TeCA and delivering to the subject the tES eases a symptom of severe depression. In some embodiments, the administering the TeCA comprises administering two or more TeCAs. In some embodiments, the administering the TeCA comprises administering a TeCA and a second pharmacologic antidepressant agent belonging to a drug category of SSRI, SNRI, NaSSA, SMS, SARI, SNDRI, NRI, NDRI, NDRA, SNDRA, TCA, MAOI, an NMDA receptor modulator, an atypical antipsychotic, an atypical antidepressant, or a benzodiazepine. In some embodiments, the TeCA is amoxapine. In some embodiments, the TeCA is maprotiline. In some embodiments, the TeCA is mianserin. In some embodiments, the TeCA is mirtazapine. In some embodiments, the TeCA is setiptiline.

MAOIs are a class of drugs prescribed to function as antidepressants to subjects in need thereof. MAOIs are known to inhibit activity of one or both monoamine oxidase enzymes (MAO-A and MAO-B). A subset of MAIOs are known as Reversible inhibitors of monoamine oxidase A (RIMAs) which selectively and reversibly inhibit MAO-A. By inhibiting the activity of monoamine oxidase enzymes, the breakdown of monoamine neurotransmitters is reduced which has an effect of increasing availability of these neurotransmitters (e.g., 5-HT, norepinephrine, and dopamine). Described herein, in some embodiments, are method of treatment for depression comprising administering to a subject an MAOI and delivering to the subject a tES. In some embodiments, administering the MAOI and delivering to the subject the tES eases a symptom of mild depression. In some embodiments, administering the MAOI and delivering to the subject the tES eases a symptom of moderate depression. In some embodiments, administering the MAOI and delivering to the subject the tES eases a symptom of severe depression. In some embodiments, the administering the MAOI comprises administering two or more MAOIs. In some embodiments, the administering the MAOI comprises administering an MAOI and a second pharmacologic antidepressant agent belonging to a drug category of SSRI, SNRI, NaSSA, SMS, SARI, SNDRI, NRI, NDRI, NDRA, SNDRA, TCA, TeCA, an NMDA receptor modulator, an atypical antipsychotic, an atypical antidepressant, or a benzodiazepine. In some embodiments, the MAOI is selegiline. In some embodiments, the MAOI is tranylcypromine. In some embodiments, the MAOI is phenelzine. In some embodiments, the MAOI is isocarboxazid. Treatment with MAOIs has been known to carry a risk of occurrence of potential unwanted side effects. Treatment with MAOs can lead to an increased risk of unwanted side effects including blurred vision, rash, seizures, edema, weight disturbances, sexual dysfunction, diarrhea, nausea, constipation, anxiety, insomnia, drowsiness, headache, dizziness, arrhythmia, fainting, and hypertension. An ability to reduce a dosage of an MAOI taken by a subject while maintaining a therapeutic benefit in one or more symptoms of depression would be beneficial in mitigating a risk of unwanted side effects.

NMDA receptor modulators are a class of drugs prescribed to function as antidepressants to subjects in need thereof. NMDA receptor modulators are known to effect NMDA receptor function by either inhibiting or potentiating NMDA receptor activation. As such, NMDA receptor modulators influence the relative effect of glutamate on neurotransmission. In some embodiments, an NMDA receptor modulators may also function as an agonist to a glycine receptor. Described herein, in some embodiments, are method of treatment for depression comprising administering to a subject an NMDA receptor modulator and delivering to the subject a tES. In some embodiments, administering the NMDA receptor modulator and delivering to the subject the tES eases a symptom of mild depression. In some embodiments, administering the NMDA receptor modulator and delivering to the subject the tES eases a symptom of moderate depression. In some embodiments, administering the NMDA receptor modulator and delivering to the subject the tES eases a symptom of severe depression. In some embodiments, the administering the NMDA receptor modulator comprises administering two or more NMDA receptor modulators. In some embodiments, the administering the NMDA receptor modulator comprises administering an NMDA receptor modulator and a second pharmacologic antidepressant agent belonging to a drug category of SSRI, SNRI, NaSSA, SMS, SARI, SNDRI, NRI, NDRI, NDRA, SNDRA, TCA, TeCA, MAOI, an atypical antipsychotic, an atypical antidepressant, or a benzodiazepine. In some embodiments, the NMDA receptor modulator is 4-cholorokynurenine. In some embodiments, the NMDA receptor modulator is apimostinel. In some embodiments, the NMDA receptor modulator is a ketamine-containing drug for treating depression. In some embodiments, the NMDA receptor modulator is arketamine. In some embodiments, the NMDA receptor modulator is esketamine. In some embodiments, the NMDA receptor modulator is esmethadone. In some embodiments, the NMDA receptor modulator is ketamine. In some embodiments, the NMDA receptor modulator is rislenemdaz. In some embodiments, the NMDA receptor modulator is rapastinel.

Atypical antipsychotics, also known as second generation antipsychotics (SGAs) and serotonin-dopamine antagonists (SDAs) are a class of drugs prescribed to function as antidepressants to subjects in need thereof. Typical antipsychotics function almost exclusively by modulating the dopamine system. Atypical antipsychotics generally function as neuroleptics and most members of this class of drug do block receptors in the dopamine pathway. In some embodiments, an atypical antipsychotic selectively binds to and blocks the function of dopamine D2 and D3 receptors, with little or no affinity for dopamine D1, D4, or D5 receptors. Additionally, various representatives of atypical antipsychotic can modulate 5-HT, norepinephrine, and/or histamine neurotransmission in addition to effects registered in the dopaminergic system. In some embodiments, an atypical antipsychotic that modulates $5\text{-HT}_{2A}$ receptors is combined with an NMDA receptor antagonist. Described herein, in some embodiments, are method of treatment for depression comprising administering to a subject an atypical antipsychotic and delivering to the subject a tES. In some embodiments, administering the atypical antipsychotic and delivering to the subject the tES eases a symptom of mild depression. In some embodiments, administering the atypical antipsychotic and delivering to the subject the tES eases a symptom of moderate depression. In some embodiments, administering the atypical antipsychotic and delivering to the subject the tES eases a symptom of severe depression. In some embodiments, the administering the atypical antipsychotic comprises administering two or more atypical antipsychotics. In some embodiments, the administering the atypical antipsychotic comprises administering an atypical antipsychotic and a second pharmacologic antidepressant agent belonging to a drug category of SSRI, SNRI, NaSSA, SMS, SARI, SNDRI, NRI, NDRI, NDRA, SNDRA, TCA, TeCA, MAOI, an NMDA receptor modulator, an atypical antidepressant, or a benzodiazepine. In some embodiments, the atypical antipsychotic is brilaroxazine. In some embodiments, the atypical antipsychotic is cariprazine. In some embodiments, the atypical antipsychotic is lumateperone. In some embodiments, the atypical antipsychotic is lurasidone. In some embodiments, the atypical antipsychotic is pimavanserin. In some embodiments, the atypical antipsychotic is aripiprazole. In some embodiments, the atypical antipsychotic is brexpiprazole. In some embodiments, the atypical antipsychotic is olanzapine. In some embodiments, the atypical antipsychotic is quetiapine. In some embodiments, the atypical antipsychotic is ziprasidone. In some embodiments, the atypical antipsychotic is SEP-4199. In some embodiments, SEP-4199 comprises a non-racemic ratio of amisulpride enantiomers with increased potency for $5\text{-HT}_7$ receptors relative to dopamine D2 receptors. SEP-4199 comprises an 85-15 ratio of R-amisulpride to S-amisulpride. In some embodiments, the atypical antipsychotic is NRX-101. NRX-101 is a pharmaceutical formulation of lurasidone and D-cycloserine. In some embodiments, NRX-101 functions as a modulator of $5\text{-HT}_{2A}$ receptor function and an NMDA receptor antagonist. In some embodiments, olanzapine may be combined with an SSRI as an adjunct treatment for MDD. In some embodiments, olanzapine may be combined with fluoxetine as an adjunct treatment for MDD. In some embodiments, aripiprazole may be combined with an SSRI as an adjunct treatment for MDD. In some embodiments, brexpiprazole may be combined with an SSRI as an adjunct treatment for MDD. In some embodiments, quetiapine may be administered as part of a pharmacologic monotherapy or quetiapine may be combined with an SSRI as an adjunct treatment for MDD.

Treatment with atypical antipsychotics has been known to carry a risk of occurrence of potential unwanted side effects. Treatment with atypical antipsychotics can lead to an increased risk of unwanted side effects including weight gain, movement disorders, dizziness, feeling tired, constipation, dry mouth, allergic reactions, low blood pressure, neuroleptic malignant syndrome, hyperglycemia, seizures, tardive dyskinesia, vomiting, excessive sleepiness, nasopharyngitis, and/or upper respiratory tract infection. These are non-limited examples of potential unwanted side effects of atypical antipsychotic usage. Occurrences of these unpleasant potential side effects can discourage a subject from maintaining a treatment regimen of prolonged administration of a given atypical antipsychotic. An ability to reduce a dosage or frequency of administration of an atypical antipsychotic taken by a subject while maintaining a therapeutic benefit in one or more symptoms of depression would be beneficial in mitigating a risk of unwanted side effects described herein.

Atypical antidepressants are a class of drugs prescribed to function as antidepressants to subjects in need thereof. Atypical antidepressants are often grouped as such in that their biochemical mechanism of action falls outside of the known mechanisms of actions of typical antidepressants such as SSRIs, SNRIs, MAOIs, and TCAs all of which typically induce an increase in extracellular postsynaptic levels of serotonin and/or norepinephrine. In some embodiments, atypical antidepressants may function as agonists for 5-HT receptors. In some embodiments, atypical antidepressants may function as agonists for $5\text{-HT}_1$ receptor subtypes. In some embodiments, atypical a antidepressants may function as agonists for $5\text{-HT}_{1A}$ receptors. In some embodiments, atypical antidepressants may function as agonists for 5-$HT_2$ receptor subtypes. In some embodiments, atypical antidepressants may function as agonists for 5-$HT_{2A}$ receptors. In some embodiments, atypical antidepressants may function as a selective estrogen receptor beta (NR3A2) agonist. In some embodiments, atypical antidepressants may function as a partial opioid receptor modulator. In some embodiments, atypical antidepressants may function as a partial opioid receptor antagonist. In some embodiments, atypical antidepressants may function as a peripherally selective aromatic L-amino acid decarboxylase inhibitor and may be combined with a serotonin precursor. In some embodiments, atypical antidepressants may function as sigma1 receptor agonists, NMDA receptor antagonists, serotonin and norepinephrine reuptake inhibitors, and CYP2D6 inhibitors. Described herein, in some embodiments, are method of treatment for depression comprising administering to a subject an atypical antidepressant and delivering to the subject a tES. In some embodiments, administering the atypical antidepressant and delivering to the subject the tES eases a symptom of mild depression. In some embodiments, administering the atypical antidepressant and delivering to the subject the tES eases a symptom of moderate depression. In some embodiments, administering the atypical antidepressant and delivering to the subject the tES eases a symptom of severe depression. In some embodiments, the administering the atypical antidepressant comprises administering two or more atypical antidepressants. In some embodiments, the administering the atypical antidepressant comprises administering an atypical antidepressant and a second pharmacologic antidepressant agent belonging to a drug category of SSRI, SNRI, NaSSA, SMS, SARI, SNDRI, NRI, NDRI, NDRA, SNDRA, TCA, TeCA, MAOI, an NMDA receptor modulator, an atypical antipsychotic, or a benzodiazepine. In some embodiments, the atypical antidepressant is allopregnanolone. In some embodiments, the atypical antidepressant is agomelatine. In some embodiments, the atypical antidepressant is trazodone. In some embodiments, the atypical antidepressant is mirtazapine. In some embodiments, the atypical antidepressant is vortioxetine. In some embodiments, the atypical antidepressant is vilazodone. In some embodiments, the atypical antidepressant is psilocybin. In some embodiments, the atypical antidepressant is a psilocybin-containing drug for treating depression. In some embodiments, the atypical antidepressant is DMT. In some embodiments, the atypical antidepressant is zuranolone. In some embodiments, the atypical antidepressant is seltorexant. In some embodiments, the atypical antidepressant is XEN1101. In some embodiments, the atypical antidepressant is erteberel. In some embodiments, the atypical antidepressant is NV-5138. In some embodiments, the atypical antidepressant is TS-121. In some embodiments, the atypical antidepressant is ALKS 5461. ALKS 5461 is a pharmaceutical formulation comprising buprenorphine and samidorphan. In some embodiments, the atypical antidepressant is a pharmaceutical formulation comprising carbidopa and oxitriptan. In some embodiments, the atypical antidepressant is a pharmaceutical formulation comprising deudextromethorphan and quinidine. In some embodiments, the pharmaceutical formulation comprising deudextromethorphan and quinidine functions as a sigma1 receptor agonist, an NMDA receptor antagonist, a serotonin and norepinephrine reuptake inhibitor, and antiarrhythmic agent, and a CYP2D6 inhibitor.

Allopregnanolone is known to function as a positive allosteric modulator of the action of γ-aminobutyric acid (GABA) at $GABA_A$ receptors. Agometaline is known to function as an agonist of both melatonin $MT_1$ and $MT_2$ receptors. Trazodone is known to inhibit the reuptake of serotonin and block both histamine receptors and α1-adrenergic receptors. Mirtazapine has been classified as an NaSSA, as a TeCA, and as an atypical antidepressant and although the mechanism of action of mirtazapine is not fully understand, it is known that both noradrenergic and serotonergic activity increase following mirtazapine administration. Mirtazapine is also a strong antagonist of serotonin 5-$HT_2$ and 5-$HT_3$ receptors. mirtazapine is a peripheral α1-adrenergic antagonist and as a potent histamine (H1) receptor antagonist. Vortioxetine has been shown to possess dual mechanisms of action towards the serotonin neurotransmitter system whereby it simultaneously modulates one or more serotonin receptors and also inhibits 5-HT reuptake. Vortioxetine also functions as a partial agonist of the 5-$HT_{1B}$ receptor, an agonist of 5-$HT_{1A}$, and antagonist of the 5-$HT_3$, 5-$HT_{1D}$, and 5-$HT_7$ receptors. Vilazodone acts to selectively inhibit 5-HT reuptake and also acts as a partial agonist of $5HT_{1A}$ receptors. Psilocybin and DMT are both known to function as agonists for various 5-HT receptors. Zuranolone is known to act as a positive allosteric modulator of the $GABA_A$ receptor. Seltorexant is known to function as an orexin antagonist. In some embodiments, seltorexant is a selective agonist of the orexin OX2 receptor (2-SORA). XEN1101 is known to function as an modulator of voltage-gated potassium channels. XEN1101 is known to function as an modulator of Kv7 potassium channels. XEN1101 is known to function as an agonist of KCNQ2/3 channels. Erteberel is a nonsteroidal estrogen drug which is known to act as a selective estrogen receptor beta agonist. In some embodiments, erteberel may function as an agonist for estrogen receptor alpha. NV-5138 is a small molecule drug known to directly and selectively activate the mTORC1 signaling pathway by binding to and modulating the activity of sestrin2. TS-121 is known to function as a vasopressin V1B receptor antagonist.

Benzodiazepines are a class of drugs prescribed to function as antidepressants to subjects in need thereof. Benzodiazepines may be used to treat one or more depression symptoms. Benzodiazepines may be used to treat one or more symptoms co-occurring with depression symptoms. In some embodiments, the one or more symptoms co-occurring with depression symptoms comprise anxiety symptoms, insomnia, parasomnia, muscle stiffness, muscle spasticity, seizures, and/or alcohol withdrawal. Benzodiazepines are known to function as allosteric modulators of the gamma amino butyric acid $(GABA)\text{-}_A$ receptor.

Benzodiazepines are known to potentiate the function of the inhibitory neurotransmitter GABA. Certain benzodiazepines are known to have interactions with additional neurotransmitter systems. As a non-limiting example, clonazepam functions both as a $GABA\text{-}_A$ receptor agonist in a highly-potent, long lasting manner but also as a serotonin agonist. Benzodiazepines tend to be fast-acting and thus a subject taking a benzodiazepines may experience rapid relief of a symptom. Benzodiazepines are generally not considered safe for continuous use as this has a potential to increase a risk of physical dependence. Benzodiazepines, as part of a treatment regimen, may reduce the intensity of physiological symptoms of Generalized Anxiety Disorder such as panic attacks, sweating, headache, muscle tension, insomnia, and restlessness. Benzodiazepines, as part of a treatment regimen, may reduce cognitive symptoms of an anxiety disorder, such as excessive worry or rumination. Possible side effects associated with benzodiazepine use include excessive drowsiness, confusion, dizziness, depression, impaired motor coordination, and visual disturbances. Benzodiazepine use may not be indicated in a subject exhibiting suicidal thoughts or suicidal ideation, or having addictive tendencies or a family history of addiction. Described herein, in some embodiments, are method of treatment for depression comprising administering to a subject a benzodiazepine and delivering to the subject a tES.

In some embodiments, the administering the benzodiazepine comprises administering a benzodiazepine and a second pharmacologic antidepressant agent belonging to a drug category of SSRI, SNRI, NaSSA, SMS, SARI, SNDRI, NRI, NDRI, NDRA, SNDRA, TCA, TeCA, MAOI, an NMDA receptor modulator, an atypical antipsychotic, or an atypical antidepressant. In some embodiments, the benzodiazepine is diazepam. In some embodiments, the benzodiazepine is alprazolam. In some embodiments, the benzodiazepine is triazolam. In some embodiments, the benzodiazepine is lorazepam. In some embodiments, the benzodiazepine is clonazepam. In some embodiments, the benzodiazepine is chlordiazepoxide. In some embodiments, the benzodiazepine is nitrazepam. In some embodiments, the benzodiazepine is loprazolam.

Administration of Pharmacologic Antidepressant Agents

In some aspects, the methods of treatment for depression comprise administering to a subject a pharmacologic antidepressant agent and delivering to the subject a tES. In some embodiments the pharmacologic antidepressant agent is administered orally. In some embodiments the pharmacologic antidepressant agent is administered sublingually. In some embodiments the pharmacologic antidepressant agent is administered buccally. In some embodiments the pharmacologic antidepressant agent is administered nasally. In some embodiments the pharmacologic antidepressant agent is administered rectally. In some embodiments the pharmacologic antidepressant agent is administered vaginally. In some embodiments the pharmacologic antidepressant agent is administered intravenously. In some embodiments the pharmacologic antidepressant agent is administered intramuscularly. In some embodiments the pharmacologic antidepressant agent is administered subcutaneously. In some embodiments the pharmacologic antidepressant agent is administered transdermally. In some embodiments the pharmacologic antidepressant agent is administered through inhalation. In some preferred embodiments, the pharmacologic antidepressant agent is administered orally or intravenously. In some embodiments, the pharmacologic antidepressant agent may be administered orally and intravenously.

Solid dosage forms for oral administration of the pharmacologic antidepressant agent can include capsules, tablets, caplets, pills, troches, lozenges, powders, and granules. A capsule can comprise a core material comprising a nutritive protein or composition and a shell wall that encapsulates a core material. In some embodiments a core material can comprise at least one of a solid, a liquid, and an emulsion. In some embodiments a shell wall material can comprise at least one of a soft gelatin, a hard gelatin, and a polymer. Suitable polymers can include but not limited to: cellulosic polymers such as hydroxypropyl cellulose, hydroxyethyl cellulose, hydroxypropyl methyl cellulose (HPMC), methyl cellulose, ethyl cellulose, cellulose acetate, cellulose acetate phthalate, cellulose acetate trimellitate, hydroxypropylmethyl cellulose phthalate, hydroxypropylmethyl cellulose succinate and carboxymethylcellulose sodium; vinyl polymers and copolymers such as polyvinyl pyrrolidone, polyvinyl acetate, polyvinylacetate phthalate, vinylacetate crotonic acid copolymer, and ethylene-vinyl acetate copolymers; and shellac (purified lac). In some embodiments at least one polymer can function as taste-masking agents. In some embodiments, the pharmacologic antidepressant agent may be formulated as a gel. In some embodiments, the pharmacologic antidepressant agent may be formulated as a cream. In some embodiments, the pharmacologic antidepressant agent may be formulated as an ointment. In some embodiments, the pharmacologic antidepressant agent may be formulated as a solution. In some embodiments, the pharmacologic antidepressant agent may be formulated as a powder. In some embodiments, the pharmacologic antidepressant agent may be formulated as a paste. In some embodiments, the pharmacologic antidepressant agent may be formulated as a foam. In some embodiments, the pharmacologic antidepressant agent may be formulated as an emulsion.

Tablets, pills, and the like can be compressed, multiply compressed, multiply layered, and/or coated. A coating can be single or multiple. In some embodiments, a coating material can comprise at least one of a saccharide, a polysaccharide, and glycoproteins extracted from at least one of a plant, a fungus, and a microbe. Non-limiting examples can include corn starch, wheat starch, potato starch, tapioca starch, cellulose, hemicellulose, dextrans, maltodextrin, cyclodextrins, inulins, pectin, mannans, gum arabic, locust bean gum, mesquite gum, guar gum, gum karaya, tragacanth gum, funori, carrageenans, agar, alginates, chitosans, or gellan gum. In some embodiments a coating material can comprise a protein. In some embodiments, a coating material can comprise at least one of a fat and/or an oil. In some embodiments the at least one of a fat and/or an oil can be high temperature melting. In some embodiments the at least one of a fat and/or an oil can be hydrogenated or partially hydrogenated. In some embodiments the at least one of a fat and/or an oil can be derived from a plant. In some embodiments the at least one of a fat and/or an oil can comprise at least one of glycerides, free fatty acids, and fatty acid esters. In some embodiments a coating material can comprise at least one edible wax. An edible wax can be derived from animals, insects, or plants. Non-limiting examples can include beeswax, lanolin, bayberry wax, carnauba wax, and rice bran wax. Tablets and pills can additionally be prepared with enteric coatings.

Liquid formulations can include a syrup (for example, an oral formulation), an intravenous formulation, an intranasal formulation, an ointment, a cream, an aerosol, and the like. In some embodiments, a combination of various formulations can be administered. In some embodiments, the pharmacologic antidepressant agent may be administered orally with a solid formulation and intravenously with a liquid formulation.

In some embodiments, a tablet, a pill, a capsule, and the like can be formulated for an extended-release profile. In some embodiments, a tablet, a pill, a capsule, and the like can be formulated for a delayed-release profile. In some embodiments, a tablet, a pill, a capsule, and the like can be formulated for a sustained-release profile. In some embodiments, a tablet, a pill, a capsule, and the like can be formulated for a prolonged-release profile. In some embodiments, a tablet, a pill, a capsule, and the like can be formulated for a slow-release profile. In some embodiments, a tablet, a pill, a capsule, and the like can be formulated so that the pharmacologic antidepressant agent In some embodiments, a tablet, a pill, a capsule, and the like can be formulated to comprises two or more pharmacologic antidepressant agents. In some embodiments, the two or more pharmacologic antidepressant agents may be formulated to be released in the subject according to different release profiles. In some embodiments, a first pharmacologic antidepressant agent may be formulated for immediate or rapid release and a second pharmacologic antidepressant agent may be formulated for extended release. In some embodiments, a first pharmacologic antidepressant agent may be formulated for immediate or rapid release and a second pharmacologic antidepressant agent may be formulated for delayed release. In some embodiments, the pharmacologic antidepressant agent formulation comprises a liposome. In some embodiments, the pharmacologic antidepressant agent formulation comprises a liposome. In some embodiments, the pharmacologic antidepressant agent loaded into a liposome leads to a superior pharmacokinetic profile following the administering due to low solubility of the pharmacologic antidepressant agent in aqueous solution. In some embodiments, the pharmacologic antidepressant agent formulation comprises a nanoparticle. In some embodiments, the pharmacologic antidepressant agent formulation comprises a nanoparticle. In some embodiments, the nanoparticle comprises a magnetic nanoparticle, a zinc oxide nanoparticle, a selenium-coated nanoparticle, a solid lipid nanoparticle, a nanostructured lipid carrier, a chitosan-coated nanoparticle, polymeric micelles, a cyclodextrin, or a dendrimer. In some embodiments, the formulation comprises a slower release of the pharmacologic antidepressant agent than a conventional oral formulation. In some embodiments, the formulation comprises a slower release of the pharmacologic antidepressant agent than a conventional liquid formulation. In some embodiments, the pharmacologic antidepressant agent formulation comprises a matrix. In some embodiments, the matrix comprises a bioresorbable polymer. In some embodiments, the bioresorbable polymer is poly (lactic-co-glycolic acid) (PLGA), poly (ethylene glycol) (PEG), poly (vinyl alcohol) (PVA), or poly (glycolic acid) (PGA). In some embodiments, the matrix comprises a bioinert polymer. In some embodiments, the bioinert polymer is ethylene vinyl acetate, cellulose acetate or low density polyethylene (LDPE). In some aspects, the matrix may release one active ingredient comprising a pharmacologic antidepressant agent. In some aspects, the matrix may release two or more active ingredients comprising a pharmacologic antidepressant agent. In some aspects, the matrix may release two or more active ingredients comprising a plurality of pharmacologic antidepressant agents. In some aspects, the matrix may allow for a delayed release of the pharmacologic antidepressant agent. In some aspects, the matrix may allow for a sustained release of the pharmacologic antidepressant agent. In some aspects, the matrix may allow for a prolonged release of the pharmacologic antidepressant agent. In some aspects, the matrix may allow for a slow release of the pharmacologic antidepressant agent. In some aspects, the matrix may allow for an extended release of the pharmacologic antidepressant agent. In some aspects, the matrix is contained within and formulated for administration by a patch. In some embodiments, the pharmacologic antidepressant agent is administered via a patch. In some embodiments, the pharmacologic antidepressant agent administered via a patch is administered transdermally.

Described herein are methods to administer a pharmacologic antidepressant agent. In some embodiments, the pharmacologic antidepressant agent is administered to a subject in need thereof according to a treatment regimen. In some embodiments, the pharmacologic antidepressant agent is administered to a subject in a therapeutically effective amount of the pharmacologic antidepressant agent. In some embodiments, the therapeutically effective amount of the pharmacologic antidepressant agent is sufficient to produce an improvement in a symptom of depression. In some embodiments, the therapeutically effective amount of the pharmacologic antidepressant agent is sufficient to produce an improvement two or more symptoms of depression. In some embodiments, the therapeutically effective amount of the pharmacologic antidepressant agent is sufficient to produce an improvement in a symptom of mild depression. In some embodiments, the therapeutically effective amount of the pharmacologic antidepressant agent is sufficient to produce an improvement in a symptom of moderate depression. In some embodiments, the therapeutically effective amount of the pharmacologic antidepressant agent is sufficient to produce an improvement in a symptom of severe depression.

In some embodiments, the treatment regimen comprises a single administration of an amount of the pharmacologic antidepressant agent. In some embodiments, the treatment regimen comprises at least one administration of an amount of the pharmacologic antidepressant agent. In some embodiments, the treatment regimen comprises 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 42, 43, 44, 45, 46, 47, 48, 49, 50, 51, 52, 53, 54, 55, 56, 57, 58, 59, 60 or more administrations of an amount of the pharmacologic antidepressant agent. In some embodiments, the administrations of the amount of the pharmacologic antidepressant agent comprise administrations of a therapeutically effective amount of the pharmacologic antidepressant agent. In some embodiments, the amount contained within one administration is an effective amount for at least 2 hours, 3 hours, 4 hours, 5 hours, 6 hours, 7 hours, 8 hours, 9 hours, 10 hours, 11 hours, 12 hours, 14 hours, 16 hours, 18 hours, 20 hours, 22 hours, 24 hours, 30 hours, 36 hours, 40 hours, 44 hours, or 48 hours. In some embodiments, the amount contained within one administration is an effective amount for at least 0.5, 1, 1.5, 2, 2.5, 3, 3.5, 4, 4.5, 5, 6, 7, 8, 9, 10, 11, 12, 13, 14, 15, 16, 17, 18, 19, 20, 21, 22, 23, 24, 25, 26, 27, 28, 29, 30, 31, 35, 42, 49, 56, 60, 61, 62, or 90 days. In some embodiments, one administration comprises an effective amount for at least 1 week, at least 2 weeks, at least 4 week, at least 2 months, or at least 6 months. In some embodiments, the therapeutically effective amount of the pharmacologic antidepressant agent is sufficient to improve a symptom of depression. In some embodiments, the therapeutically effective amount of the pharmacologic antidepressant agent is sufficient to improve two or more symptoms of depression. In some embodiments, the therapeutically effective amount of the pharmacologic antidepressant agent remains consistent throughout a time period of the treatment regimen.

In some embodiments, the consistent amount of therapeutically effective pharmacologic antidepressant agent is sufficient to maintain a measurement of one or more depression symptoms. In some embodiments, the consistent amount of therapeutically effective pharmacologic antidepressant agent is sufficient to improve a measurement of one or more depression symptoms. In some embodiments, the consistent amount of therapeutically effective pharmacologic antidepressant agent is sufficient to prevent relapse of one or more depression symptoms. In some embodiments, the therapeutically effective amount of the pharmacologic antidepressant agent can be reduced throughout a time period of the treatment regimen. In some embodiments, the reduced therapeutically effective amount of the pharmacologic antidepressant agent is sufficient to maintain a measurement of one or more depression symptoms. In some embodiments, the reduced therapeutically effective amount of the pharmacologic antidepressant agent is sufficient to improve a measurement of one or more depression symptoms. In some embodiments, the reduced therapeutically effective amount of the pharmacologic antidepressant agent is sufficient to prevent relapse of one or more depression symptoms. In some embodiments, improvement in the measurement of one or more depression symptoms comprises a reduction in one or more depression symptoms. In some embodiments, improvement in the measurement of one or more depression symptoms comprises a reduction in a MADRS score. In some embodiments, improvement in the measurement of one or more depression symptoms comprises a reduction in a MADRS-s score. In some embodiments, maintenance of the measurement of one or more depression symptoms comprises preventing an increase in a MADRS score. In some embodiments, maintenance of the measurement of one or more depression symptoms comprises preventing an increase in a MADRS-s score. In some embodiments, prevention of relapse of one or more depression symptoms comprises preventing an increase in a MADRS score of the subject compared with a MADRS score of the subject taken at an earlier time point. In some embodiments, prevention of relapse of one or more depression symptoms comprises preventing an increase in a MADRS-s score of the subject compared with a MADRS-s score of the subject taken at an earlier time point.

In some embodiments, the treatment regimen comprises administration of the pharmacologic antidepressant agent according to a recommendation. In some embodiments, the recommendation comprises a recommendation of administration frequency. In some embodiments, the recommendation comprises a recommendation of administration dosage. In some embodiments, the recommendation comprises an assessment of one or more symptoms of depression. In some embodiments, the recommendation comprises a reduction in frequency of administration following a certain number of administrations of the pharmacologic antidepressant agent. In some embodiments, the recommendation comprises a reduction in a dosage of pharmacologic antidepressant agent administered following a certain number of administrations. In some embodiments, the recommendation is provided by a physician or medical practitioner. In some embodiments, the recommendation is a medical prescription for treatment of depression. In some embodiments, the recommendation is provided by a system that analyzes one or more symptoms of depression in the subject. In some embodiments, the treatment regimen comprises daily administration of the pharmacologic antidepressant agent. In some embodiments, the treatment regimen comprises twice daily administration of the pharmacologic antidepressant agent. In some embodiments, the treatment regimen comprises three times daily administration of the pharmacologic antidepressant agent. In some embodiments, the treatment regimen comprises four times daily administration of the pharmacologic antidepressant agent. In some embodiments, the treatment regimen comprises administration every other day of the pharmacologic antidepressant agent. In some embodiments, the treatment regimen comprises administration every third day of the pharmacologic antidepressant agent. In some embodiments, the treatment regimen comprises administration every fourth day of the pharmacologic antidepressant agent. In some embodiments, the treatment regimen comprises administration every fifth day of the pharmacologic antidepressant agent. In some embodiments, the treatment regimen comprises administration every sixth day of the pharmacologic antidepressant agent. In some embodiments, the treatment regimen comprises administration every seventh day of the pharmacologic antidepressant agent. In some embodiments, the treatment regimen comprises administration of the pharmacologic antidepressant agent until a period of time in which an improvement in a symptom of depression is indicated by the subject. In some embodiments, the treatment regimen comprises administration of the pharmacologic antidepressant agent until a period of time in which an improvement in a symptom of depression is recorded by the subject in a survey. In some embodiments, the treatment regimen comprises administration of the pharmacologic antidepressant agent until a period of time in which an improvement in a symptom of depression in the subject is indicated by a physician or medical practitioner. In some embodiments, the treatment regimen comprises administration of the pharmacologic antidepressant agent for a period of time following after improvement in a symptom of depression is indicated by the subject. In some embodiments, the treatment regimen comprises administration of the pharmacologic antidepressant agent for a period of time following after improvement in a symptom of depression is recorded by the subject in a survey. In some embodiments, the survey is completed by the subject. In some embodiments, the survey is completed by a physician or medical practitioner providing health care to the subject. In some embodiments, the treatment regimen comprises administration of the pharmacologic antidepressant agent for a period of time following after improvement in a symptom of depression in the subject is indicated by a physician or medical practitioner.

In some embodiments described herein are methods wherein the pharmacologic antidepressant agent is administered to the subject in a treatment effective amount. In some embodiments, the treatment effective amount increases during a period of time of treatment. In some embodiments, the treatment effective amount is maintained at a same amount during a period of time of treatment. In some embodiments, the treatment effective amount decreases during a period of time of treatment. In some embodiments, an increase in a treatment effective amount prevents a need to substitute a pharmacologic antidepressant agent of the same drug class with the currently administered pharmacologic antidepressant agent. In some embodiments, an increase in a treatment effective amount prevents a need to substitute a pharmacologic antidepressant agent of a different antidepressant drug class with the currently administered pharmacologic antidepressant agent. In some embodiments, a maintenance of the treatment effective amount prevents a need to substitute a pharmacologic antidepressant agent of the same drug class with the currently administered pharmacologic antidepressant agent. In some embodiments, a maintenance of the treatment effective amount prevents a need to substitute a pharmacologic antidepressant agent of a different antidepressant drug class with the currently administered pharmacologic antidepressant agent. In some embodiments, a decrease in a treatment effective amount prevents a need to substitute a pharmacologic antidepressant agent of the same drug class with the currently administered pharmacologic antidepressant agent. In some embodiments, a decrease in a treatment effective amount prevents a need to substitute a pharmacologic antidepressant agent of a different antidepressant drug class with the currently administered pharmacologic antidepressant agent. In some embodiments, the increase in the treatment effective amount comprises an increase in a dosage of the pharmacologic antidepressant agent. In some embodiments, the increase in the treatment effective amount comprises an increase in a frequency of administration of the pharmacologic antidepressant agent. In some embodiments, the increase in the treatment effective amount comprises an increase in the dosage of the pharmacologic antidepressant agent and an increase in the frequency of administration of the pharmacologic antidepressant agent. In some embodiments, the maintenance of the treatment effective amount comprises an increase in a dosage of the pharmacologic antidepressant agent and a decrease in a frequency of administration. In some embodiments, the maintenance of the treatment effective amount comprises an decrease in a dosage of the pharmacologic antidepressant agent and an increase in a frequency of administration. In some embodiments, the decrease in the treatment effective amount comprises a decrease in a frequency of administration of the pharmacologic antidepressant agent. In some embodiments, the decrease in the treatment effective amount comprises a decrease in a dosage of the pharmacologic antidepressant agent. In some embodiments, the decrease in the treatment effective amount comprises a decrease in a dosage of the pharmacologic antidepressant agent and a decrease in a frequency of administration of the pharmacologic antidepressant agent. In some embodiments, the treatment effective amount of the pharmacologic antidepressant agent is tapered down and an assessment of one or more symptoms of depression is taken. In some embodiments, the tapered down treatment effective amount comprises a reduction in dosage administered of the pharmacologic antidepressant agent. In some embodiments, the tapered down treatment effective amount comprises a reduction in frequency of administration of the pharmacologic antidepressant agent. In some embodiments the assessment of one or more symptoms of depression is completed a successive time points to determine treatment effectiveness.

In some embodiments the treatment effective amount comprises a dose of the pharmacologic antidepressant agent. In some embodiments, the dose of the pharmacologic antidepressant agent is between 0.01 mg and 150 mg. In some embodiments, the dose of the pharmacologic antidepressant agent is at least about 0.01 mg, 0.02 mg, 0.03 mg, 0.04 mg, 0.05 mg, 0.06 mg, 0.07 mg, 0.08 mg, 0.09 mg, 0.1 mg, 0.15 mg, 0.2 mg, 0.25 mg, 0.30 mg, 0.35 mg, 0.4 mg, 0.45 mg, 0.50 mg, 0.55 mg, 0.6 mg, 0.7 mg, 0.8 mg, 0.9 mg, 1 mg, 1.25 mg, 1.5 mg, 1.75 mg, 2 mg, 2.5 mg, 3 mg, 3.5 mg, 4 mg, 4.5 mg, 5 mg, 5.5 mg, 6 mg, 6.5 mg, 7 mg, 7.5 mg, 8 mg, 8.5 mg, 9 mg, 9.5 mg, 10 mg, 11 mg, 12 mg, 13 mg, 14 mg, 15 mg, 16 mg, 17 mg, 18 mg, 19 mg, 20 mg, 21 mg, 22 mg, 23 mg, 24 mg, 25 mg, 26 mg, 27 mg, 28 mg, 29 mg, 30 mg, 32 mg, 34 mg, 35 mg, 36 mg, 37.5 mg, 38 mg, 40 mg, 42 mg, 44 mg, 46 mg, 48 mg, 50 mg, 52 mg, 54 mg, 56 mg, 58 mg, 60 mg, 65 mg, 70 mg, 75 mg, 80 mg, 85 mg, 90 mg, 95 mg, 100 mg, 105 mg, 110 mg, 115 mg, 120 mg, 125 mg, 130 mg, 140 mg, 150 mg, 160 mg, 170 mg, 180 mg, 190 mg, 200 mg, 250 mg, 300 mg, or 400 mg. In some embodiments, the dose of the pharmacologic antidepressant agent is less than about 0.01 mg, 0.02 mg, 0.03 mg, 0.04 mg, 0.05 mg, 0.06 mg, 0.07 mg, 0.08 mg, 0.09 mg, 0.1 mg, 0.15 mg, 0.2 mg, 0.25 mg, 0.30 mg, 0.35 mg, 0.4 mg, 0.45 mg, 0.50 mg, 0.55 mg, 0.6 mg, 0.7 mg, 0.8 mg, 0.9 mg, 1 mg, 1.25 mg, 1.5 mg, 1.75 mg, 2 mg, 2.5 mg, 3 mg, 3.5 mg, 4 mg, 4.5 mg, 5 mg, 5.5 mg, 6 mg, 6.5 mg, 7 mg, 7.5 mg, 8 mg, 8.5 mg, 9 mg, 9.5 mg, 10 mg, 11 mg, 12 mg, 13 mg, 14 mg, 15 mg, 16 mg, 17 mg, 18 mg, 19 mg, 20 mg, 21 mg, 22 mg, 23 mg, 24 mg, 25 mg, 26 mg, 27 mg, 28 mg, 29 mg, 30 mg, 32 mg, 34 mg, 35 mg, 36 mg, 37.5 mg, 38 mg, 40 mg, 42 mg, 44 mg, 46 mg, 48 mg, 50 mg, 52 mg, 54 mg, 56 mg, 58 mg, 60 mg, 65 mg, 70 mg, 75 mg, 80 mg, 85 mg, 90 mg, 95 mg, 100 mg, 105 mg, 110 mg, 115 mg, 120 mg, 125 mg, 130 mg, 140 mg, 150 mg, 160 mg, 170 mg, 180 mg, 190 mg, 200 mg, 250 mg, 300 mg, or 400 mg. In some embodiments, the dose of the pharmacologic antidepressant agent is about 0.1 mg. In some embodiments, the dose of the pharmacologic antidepressant agent is about 0.25 mg. In some embodiments, the dose of the pharmacologic antidepressant agent is about 0.50 mg. In some embodiments, the dose of the pharmacologic antidepressant agent is about 0.75 mg. In some embodiments, the dose of the pharmacologic antidepressant agent is about 1 mg. In some embodiments, the dose of the pharmacologic antidepressant agent is about 1.5 mg. In some embodiments, the dose of the pharmacologic antidepressant agent is about 2 mg. In some embodiments, the dose of the pharmacologic antidepressant agent is about 2.5 mg. In some embodiments, the dose of the pharmacologic antidepressant agent is about 5 mg. In some embodiments, the dose of the pharmacologic antidepressant agent is about 7.5 mg. In some embodiments, the dose of the pharmacologic antidepressant agent is about 10 mg. In some embodiments, the dose of the pharmacologic antidepressant agent is about 12.5 mg. In some embodiments, the dose of the pharmacologic antidepressant agent is about 15 mg. In some embodiments, the dose of the pharmacologic antidepressant agent is about 20 mg. In some embodiments, the dose of the pharmacologic antidepressant agent is about 25 mg. In some embodiments, the dose of the pharmacologic antidepressant agent is about 30 mg. In some embodiments, the dose of the pharmacologic antidepressant agent is about 35 mg. In some embodiments, the dose of the pharmacologic antidepressant agent is about 37.5 mg. In some embodiments, the dose of the pharmacologic antidepressant agent is about 40 mg. In some embodiments, the dose of the pharmacologic antidepressant agent is about 45 mg. In some embodiments, the dose of the pharmacologic antidepressant agent is about 50 mg. In some embodiments, the dose of the pharmacologic antidepressant agent is about 60 mg. In some embodiments, the dose of the pharmacologic antidepressant agent is about 70 mg. In some embodiments, the dose of the pharmacologic antidepressant agent is about 75 mg. In some embodiments, the dose of the pharmacologic antidepressant agent is about 80 mg. In some embodiments, the dose of the pharmacologic antidepressant agent is about 100 mg. In some embodiments, the dose of the pharmacologic antidepressant agent is about 125 mg. In some embodiments, the dose of the pharmacologic antidepressant agent is about 150 mg. In some embodiments, the dose of the pharmacologic antidepressant agent is about 200 mg. In some embodiments, the dose of the pharmacologic antidepressant agent is about 250 mg. In some embodiments, the dose of the pharmacologic antidepressant agent is about 300 mg. In some embodiments, the dose of the pharmacologic antidepressant agent is about 400 mg. In some embodiments, the dose of the pharmacologic antidepressant agent is about 500 mg. In some embodiments, the dose of the pharmacologic antidepressant agent is about 600 mg. In some embodiments, the dose of fluoxetine is about 10 mg. In some embodiments, the dose of fluoxetine is about 20 mg. In some embodiments, the dose of fluoxetine is about 20 mg taken once a day. In some embodiments, the dose of fluoxetine is about 20 mg taken once a day in the morning. In some embodiments, the dose of fluoxetine is about 20 mg taken once a day in the evening. In some embodiments, the dose of fluoxetine is about 40 mg. In some embodiments, the dose of fluoxetine is about 40 mg in the morning. In some embodiments, the dose of fluoxetine is about 50 mg. In some embodiments, the dose of fluoxetine is about 50 mg taken once a day in the evening. In some embodiments, the dose of fluoxetine is about 60 mg. In some embodiments, the dose of fluoxetine is about 60 mg once a day in the morning. In some embodiments, the dose of fluoxetine is about 80 mg once a day. In some embodiments, the dose of citalopram is about 10 mg. In some embodiments, the dose of citalopram is about 20 mg. In some embodiments, the dose of citalopram is about 30 mg. In some embodiments, the dose of citalopram is about 40 mg. In some embodiments, the dose of escitalopram is about 5 mg. In some embodiments, the dose of escitalopram is about 10 mg. In some embodiments, the dose of escitalopram is about 20 mg. In some embodiments, the dose of paroxetine is about 10 mg. In some embodiments, the dose of paroxetine is about 20 mg. In some embodiments, the dose of sertraline is about 25 mg taken once a day. In some embodiments, the dose of sertraline is about 50 mg taken once a day. In some embodiments, the dose of sertraline is about 75 mg taken once a day. In some embodiments, the dose of sertraline is about 100 mg taken once a day. In some embodiments, the dose of sertraline is about 125 mg taken once a day. In some embodiments, the dose of sertraline is about 150 mg taken once a day. In some embodiments, the dose of sertraline is about 175 mg taken once a day. In some embodiments, the dose of sertraline is about 200 mg taken once a day. In some embodiments, the dose of dapoxetine is about 30 mg taken once a day. In some embodiments, the dose of dapoxetine is about 60 mg. In some embodiments, the dose of fluvoxamine is about 25 mg. In some embodiments, the dose of fluvoxamine is about 25 mg taken once a day in the evening. In some embodiments, the dose of fluvoxamine is about 50 mg. In some embodiments, the dose of fluvoxamine is about 50 mg taken once a day in the evening. In some embodiments, the dose of fluvoxamine is about 50 mg taken once a day at bedtime. In some embodiments, the dose of fluvoxamine is about 100 mg. In some embodiments, the dose of fluvoxamine is about 150 mg. In some embodiments, the dose of fluvoxamine is about 200 mg. In some embodiments, the dose of fluvoxamine is about 250 mg. In some embodiments, the dose of fluvoxamine is about 300 mg. In some embodiments, the dose of vortioxetine is about 5 mg. In some embodiments, the dose of vortioxetine is about 10 mg. In some embodiments, the dose of vortioxetine is about 10 mg once a day without regard to meals. In some embodiments, the dose of vortioxetine is about 15 mg. In some embodiments, the dose of vortioxetine is about 20 mg. In some embodiments, the dose of desvenlafaxine is about 10 mg once a day. In some embodiments, the dose of desvenlafaxine is about 20 mg once a day. In some embodiments, the dose of desvenlafaxine is about 25 mg once a day. In some embodiments, the dose of desvenlafaxine is about 50 mg once a day. In some embodiments, the dose of desvenlafaxine is about 100 mg once a day. In some embodiments, the dose of desvenlafaxine is about 200 mg once a day. In some embodiments, the dose of desvenlafaxine is about 300 mg once a day. In some embodiments, the dose of desvenlafaxine is about 400 mg once a day. In some embodiments, the dose of duloxetine is about 20 mg once a day. In some embodiments, the dose of duloxetine is about 30 mg once a day. In some embodiments, the dose of duloxetine is about 40 mg once a day. In some embodiments, the dose of duloxetine is about 50 mg once a day. In some embodiments, the dose of duloxetine is about 60 mg once a day. In some embodiments, the dose of levomilnacipran is about 20 mg once a day. In some embodiments, the dose of levomilnacipran is about 40 mg. In some embodiments, the dose of levomilnacipran is about 60 mg. In some embodiments, the dose of levomilnacipran is about 80 mg. In some embodiments, the dose of milnacipran is about 12.5 mg. In some embodiments, the dose of milnacipran is about 25 mg. In some embodiments, the dose of milnacipran is about 37.5 mg. In some embodiments, the dose of milnacipran is about 50 mg. In some embodiments, the dose of milnacipran is about 50 mg twice a day. In some embodiments, the dose of milnacipran is about 75 mg. In some embodiments, the dose of milnacipran is about 100 mg. In some embodiments, the dose of venlafaxine IR is about 37.5 mg. In some embodiments, the dose of venlafaxine IR is about 37.5 mg once a day. In some embodiments, the dose of venlafaxine IR is about 75 mg. In some embodiments, the dose of venlafaxine IR is about 75 mg once a day. In some embodiments, the dose of venlafaxine IR is about 150 mg. In some embodiments, the dose of venlafaxine IR is about 225 mg. In some embodiments, the dose of venlafaxine XR is about 37.5 mg once a day. In some embodiments, the dose of venlafaxine XR is about 37.5 mg twice a day. In some embodiments, the dose of venlafaxine XR is about 75 mg. In some embodiments, the dose of venlafaxine XR is about 75 mg once a day. In some embodiments, the dose of venlafaxine XR is about 150 mg. In some embodiments, the dose of aptazapine is about 15 mg. In some embodiments, the dose of aptazapine is about 30 mg. In some embodiments, the dose of aptazapine is about 45 mg. In some embodiments, the dose of esmirtazapine is about 1.5 mg. In some embodiments, the dose of esmirtazapine is about 3 mg. In some embodiments, the dose of esmirtazapine is about 4.5 mg. In some embodiments, the dose of mianserin is about 30 mg. In some embodiments, the dose of mianserin is about 40 mg. In some embodiments, the dose of mianserin is about 60 mg. In some embodiments, the dose of mianserin is about 80 mg. In some embodiments, the dose of mianserin is about 90 mg. In some embodiments, the dose of mirtazapine is about 15 mg. In some embodiments, the dose of mirtazapine is about 30 mg. In some embodiments, the dose of mirtazapine is about 45 mg. In some embodiments, the dose of setiptiline is about 30 mg. In some embodiments, the dose of vilazodone is about 10 mg. In some embodiments, the dose of vilazodone is about 20 mg. In some embodiments, the dose of vortioxetine is about 5 mg. In some embodiments, the dose of vortioxetine is about 10 mg. In some embodiments, the dose of vortioxetine is about 15 mg. In some embodiments, the dose of vortioxetine is about 20 mg. In some embodiments, the dose of nefazodone is about 100 mg. In some embodiments, the dose of nefazodone is about 200 mg. In some embodiments, the dose of trazodone is about 50 mg. In some embodiments, the dose of trazodone is about 100 mg. In some embodiments, the dose of trazodone is about 150 mg. In some embodiments, the dose of trazodone is about 200 mg. In some embodiments, the dose of trazodone is about 250 mg. In some embodiments, the dose of trazodone is about 300 mg. In some embodiments, the dose of toludesvenlafaxine is about 50 mg. In some embodiments, the dose of toludesvenlafaxine is about 75 mg. In some embodiments, the dose of toludesvenlafaxine is about 100 mg. In some embodiments, the dose of OPC-64005 is about 20 mg. In some embodiments, the dose of ansofaxine is 40 mg. In some embodiments, the dose of ansofaxine is 80 mg. In some embodiments, the dose of ansofaxine is 120 mg. In some embodiments, the dose of ansofaxine is 160 mg. In some embodiments, the dose of atomoxetine is about 40 mg. In some embodiments, the dose of atomoxetine is about 80 mg. In some embodiments, the dose of reboxetine is about 4 mg. In some embodiments, the dose of reboxetine is about 8 mg. In some embodiments, the dose of reboxetine is about 10 mg. In some embodiments, the dose of teniloxazine is about 80 mg. In some embodiments, the dose of viloxazine is about 100 mg. In some embodiments, the dose of viloxazine is about 200 mg. In some embodiments, the dose of bupropion is about 100 mg. In some embodiments, the dose of bupropion is about 150 mg. In some embodiments, the dose of bupropion is about 200 mg. In some embodiments, the dose of bupropion is about 300 mg. In some embodiments, the dose of bupropion is about 400 mg. In some embodiments, the dose of bupropion is about 450 mg. In some embodiments, the dose of amineptine is about 100 mg. In some embodiments, the dose of amineptine is about 200 mg. In some embodiments, the dose of methylphenidate is about 5 mg. In some embodiments, the dose of methylphenidate is about 10 mg. In some embodiments, the dose of methylphenidate is about 15 mg. In some embodiments, the dose of methylphenidate is about 20 mg. In some embodiments, the dose of methylphenidate is about 25 mg. In some embodiments, the dose of methylphenidate is about 30 mg. In some embodiments, the dose of AXS-05 is about 45 mg dextromethorphan and about 105 mg bupropion. In some embodiments, the dose of AXS-05 is about 90 mg dextromethorphan and about 210 mg bupropion. In some embodiments, the dose of lisdexamfetamine is about 30 mg once a day in the morning. In some embodiments, the dose of lisdexamfetamine is about 40 mg once a day in the morning. In some embodiments, the dose of lisdexamfetamine is about 50 mg once a day in the morning. In some embodiments, the dose of lisdexamfetamine is about 60 mg once a day in the morning. In some embodiments, the dose of phenethylamine is about 10 mg. In some embodiments, the dose of phenethylamine is about 20 mg. In some embodiments, the dose of phenethylamine is about 30 mg. In some embodiments, the dose of phenethylamine is about 40 mg. In some embodiments, the dose of phenethylamine is about 50 mg. In some embodiments, the dose of phenethylamine is about 60 mg. In some embodiments, the dose of pemoline is about 37.5 mg. In some embodiments, the dose of pemoline is about 75 mg. In some embodiments, the dose of mephedrone is about 100 mg. In some embodiments, the dose of mephedrone is about 200 mg. In some embodiments, the dose of mephedrone is about 300 mg. In some embodiments, the dose of amitriptyline is about 25 mg. In some embodiments, the dose of amitriptyline is about 50 mg. In some embodiments, the dose of amitriptyline is about 75 mg. In some embodiments, the dose of amitriptyline is about 100 mg. In some embodiments, the dose of amitriptyline is about 125 mg. In some embodiments, the dose of amitriptyline is about 150 mg. In some embodiments, the dose of clomipramine is about 25 mg. In some embodiments, the dose of clomipramine is about 50 mg. In some embodiments, the dose of clomipramine is about 75 mg. In some embodiments, the dose of clomipramine is about 100 mg. In some embodiments, the dose of desipramine is about 100 mg. In some embodiments, the dose of desipramine is about 200 mg. In some embodiments, the dose of desipramine is about 300 mg. In some embodiments, the dose of dosulepin is about 75 mg. In some embodiments, the dose of dosulepin is about 150 mg. In some embodiments, the dose of dosulepin is about 225 mg. In some embodiments, the dose of doxepin is about 25 mg. In some embodiments, the dose of doxepin is about 50 mg. In some embodiments, the dose of doxepin is about 75 mg. In some embodiments, the dose of doxepin is about 100 mg. In some embodiments, the dose of doxepin is about 125 mg. In some embodiments, the dose of doxepin is about 150 mg. In some embodiments, the dose of imipramine is about 75 mg. In some embodiments, the dose of imipramine is about 100 mg. In some embodiments, the dose of imipramine is about 150 mg. In some embodiments, the dose of lofepramine is about 70 mg. In some embodiments, the dose of lofepramine is about 140 mg. In some embodiments, the dose of lofepramine is about 210 mg. In some embodiments, the dose of nortriptyline is about 25 mg 3 to 4 times a day. In some embodiments, the dose of nortriptyline is about 50 mg. In some embodiments, the dose of nortriptyline is about 75 mg. In some embodiments, the dose of nortriptyline is about 75 mg once a day. In some embodiments, the dose of nortriptyline is about 100 mg. In some embodiments, the dose of protriptyline is about 10 mg. In some embodiments, the dose of protriptyline is about 15 mg. In some embodiments, the dose of protriptyline is about 20 mg. In some embodiments, the dose of protriptyline is about 30 mg. In some embodiments, the dose of protriptyline is about 45 mg. In some embodiments, the dose of protriptyline is about 60 mg. In some embodiments, the dose of trimipramine is about 50 mg. In some embodiments, the dose of trimipramine is about 50 mg once a day. In some embodiments, the dose of trimipramine is about 75 mg. In some embodiments, the dose of trimipramine is about 100 mg. In some embodiments, the dose of trimipramine is about 150 mg. In some embodiments, the dose of amoxapine is about 25 mg 2 to 3 times a day. In some embodiments, the dose of amoxapine is about 50 mg 2 to 3 times a day. In some embodiments, the dose of amoxapine is about 75 mg 2 to 3 times a day. In some embodiments, the dose of maprotiline is about 25 mg 2 to 3 times a day. In some embodiments, the dose of maprotiline is about 50 mg 2 to 3 times a day. In some embodiments, the dose of maprotiline is about 75 mg 2 to 3 times a day. In some embodiments, the dose of mianserin is about 30 mg 1 to 3 times a day. In some embodiments, the dose of mirtazapine is about 15 mg 1 to 3 times a day. In some embodiments, the dose of selegiline is about 1.25 mg. In some embodiments, the dose of selegiline is about 2.5 mg. In some embodiments, the dose of selegiline is about 3.75 mg. In some embodiments, the dose of selegiline is about 5 mg. In some embodiments, the dose of selegiline is about 6.25 mg. In some embodiments, the dose of selegiline is about 7.5 mg. In some embodiments, the dose of selegiline is about 10 mg. In some embodiments, the dose of selegiline is about 12 mg. In some embodiments, the dose of tranylcypromine is about 10 mg 1 to 3 times a day. In some embodiments, the dose of tranylcypromine is about 15 mg 1 to 3 times a day. In some embodiments, the dose of tranylcypromine is about 20 mg 1 to 3 times a day. In some embodiments, the dose of phenelzine is about 10 mg. In some embodiments, the dose of phenelzine is about 10 mg 3 times a day. In some embodiments, the dose of phenelzine is about 15 mg. In some embodiments, the dose of phenelzine is about 15 mg 3 times a day. In some embodiments, the dose of phenelzine is about 20 mg. In some embodiments, the dose of phenelzine is about 20 mg 3 times a day. In some embodiments, the dose of phenelzine is about 25 mg 3 times a day. In some embodiments, the dose of phenelzine is about 30 mg 3 times a day. In some embodiments, the dose of isocarboxazid is about 10 mg. In some embodiments, the dose of isocarboxazid is about 10 mg 2 times a day. In some embodiments, the dose of isocarboxazid is about 15 mg 2 times a day. In some embodiments, the dose of isocarboxazid is about 20 mg 2 times a day. In some embodiments, the dose of isocarboxazid is about 25 mg 2 times a day. In some embodiments, the dose of apimostinel is about 50 mg. In some embodiments, the dose of apimostinel is about 100 mg. In some embodiments, the dose of apimostinel is about 150 mg. In some embodiments, the dose of apimostinel is about 200 mg. In some embodiments, the dose of apimostinel is about 250 mg. In some embodiments, the dose of apimostinel is about 375 mg. In some embodiments, the dose of apimostinel is about 500 mg. In some embodiments, the dose of arketamine is about 25 mg. In some embodiments, the dose of arketamine is about 50 mg. In some embodiments, the dose of arketamine is about 75 mg. In some embodiments, the dose of arketamine is about 100 mg. In some embodiments, the dose of arketamine is about 150 mg. In some embodiments, the dose of esketamine is about 25 mg. In some embodiments, the dose of esketamine is about 50 mg. In some embodiments, the dose of esketamine is about 75 mg. In some embodiments, the dose of esketamine is about 100 mg. In some embodiments, the dose of esketamine is about 150 mg. In some embodiments, the dose of esketamine is about 28 mg. In some embodiments, the dose of esketamine is about 56 mg. In some embodiments, the dose of esketamine is about 84 mg. In some embodiments, the dose of esketamine is about 56 mg administered intranasally once a week. In some embodiments, the dose of esketamine is about 56 mg administered intranasally twice a week. In some embodiments, the dose of esketamine is about 84 mg once a week. In some embodiments, the dose of esketamine is about 84 mg twice a week. In some embodiments, the dose of esmethadone is about 25 mg. In some embodiments, the dose of rislenemdaz is about 8 mg. In some embodiments, the dose of rislenemdaz is about 12 mg. In some embodiments, the dose of rislenemdaz is about 20 mg. In some embodiments, rapastinel is administered as an intravenous infusion. In some embodiments, rapastinel is administered as an intravenous infusion at a dosage of 1 mg/kg. In some embodiments, rapastinel is administered as an intravenous infusion at a dosage of 3 mg/kg. In some embodiments, rapastinel is administered as an intravenous infusion at a dosage of 5 mg/kg. In some embodiments, rapastinel is administered as an intravenous infusion at a dosage of 10 mg/kg. In some embodiments, rapastinel is administered as an intravenous infusion at a dosage of 30 mg/kg. In some embodiments, the dose of brilaroxazine is about 15 mg. In some embodiments, the dose of brilaroxazine is about 25 mg. In some embodiments, the dose of brilaroxazine is about 50 mg. In some embodiments, the dose of cariprazine is about 1 mg. In some embodiments, the dose of cariprazine is about 1.5 mg. In some embodiments, the dose of cariprazine is about 2 mg. In some embodiments, the dose of cariprazine is about 2.5 mg. In some embodiments, the dose of cariprazine is about 3 mg. In some embodiments, the dose of lumateperone is about 42 mg. In some embodiments, the dose of lurasidone is about 20 mg. In some embodiments, the dose of lurasidone is about 40 mg. In some embodiments, the dose of pimavanserin is about 17 mg. In some embodiments, the dose of pimavanserin is about 34 mg. In some embodiments, the dose of aripiprazole is about 2 mg once a day. In some embodiments, the dose of aripiprazole is about 3.5 mg once a day. In some embodiments, the dose of aripiprazole is about 5 mg once a day. In some embodiments, the dose of brexpiprazole is about 0.5 mg once a day. In some embodiments, the dose of brexpiprazole is about 1 mg once a day. In some embodiments, the dose of olanzapine is about 2.5 mg once a day. In some embodiments, the dose of olanzapine is about 5 mg once a day. In some embodiments, the dose of olanzapine is about 10 mg once a day. In some embodiments, the dose of quetiapine is about 50 mg once a day. In some embodiments, the dose of quetiapine is about 75 mg once a day. In some embodiments, the dose of quetiapine is about 100 mg once a day. In some embodiments, the dose of quetiapine is about 125 mg once a day. In some embodiments, the dose of quetiapine is about 150 mg once a day. In some embodiments, the dose of ziprasidone is about 40 mg 2 times a day. In some embodiments, the dose of ziprasidone is about 60 mg 2 times a day. In some embodiments, the dose of SEP-4199 is about 50 mg/day In some embodiments, the dose of SEP-4199 is about 100 mg/day. In some embodiments, the dose of SEP-4199 is about 200 mg/day. In some embodiments, the dose of SEP-4199 is about 400 mg/day. In some embodiments, the dose of NRX-101 comprises about 66 mg lurasidone and about 950 mg of D-cycloserine. In some embodiments, the dose of allopregnanolone is about 30 mg once a day. In some embodiments, the dose of allopregnanolone is administered as a continuous intravenous infusion. In some embodiments, the dose of allopregnanolone is administered as a continuous intravenous infusion over a period of about 60 hours. In some embodiments, the dose of allopregnanolone is administered as a continuous intravenous infusion starting with a dose of about 30 mcg/kg/hour. In some embodiments, the dose of allopregnanolone is administered as a continuous intravenous infusion increasing to a dose of 60 mcg/kg/hour. In some embodiments, the dose of allopregnanolone is administered as a continuous intravenous infusion increasing to a dose of 90 mcg/kg/hour. In some embodiments, the dose of allopregnanolone is administered as a continuous intravenous infusion decreasing to a dose of 60 mcg/kg/hour. In some embodiments, the dose of allopregnanolone is administered as a continuous intravenous infusion decreasing to a dose of 30 mcg/kg/hour. In some embodiments, the dose of agomelatine is about 12.5 mg once a day at bedtime. In some embodiments, the dose of agomelatine is about 25 mg once a day at bedtime. In some embodiments, the dose of trazodone is about 150 mg. In some embodiments, the dose of mirtazapine is about 15 mg 1 to 3 times a day. In some embodiments, the dose of vortioxetine is about 2.5 mg. In some embodiments, the dose of vortioxetine is about 5 mg. In some embodiments, the dose of vortioxetine is about 10 mg. In some embodiments, the dose of vilazodone is about 10 mg. In some embodiments, the dose of vilazodone is about 20 mg. In some embodiments, the dose of vilazodone is about 40 mg. In some embodiments, the dose of psilocybin is about 10 mg. In some embodiments, the dose of psilocybin is about 20 mg. In some embodiments, the dose of psilocybin is about 25 mg. In some embodiments, the dose of psilocybin is about 35 mg. In some embodiments, the dose of psilocybin is about 40 mg. In some embodiments, the dose of psilocybin is about 50 mg. In some embodiments, the dose of DMT is about 6 mg. In some embodiments, the dose of DMT is about 8 mg. In some embodiments, the dose of DMT is about 18 mg. In some embodiments, the dose of DMT is about 24 mg. In some embodiments, the dose of DMT is about 30 mg. In some embodiments, the dose of zuranolone is about 20 mg. In some embodiments, the dose of zuranolone is about 30 mg. In some embodiments, the dose of zuranolone is about 50 mg. In some embodiments, the dose of seltorexant is 10 mg. In some embodiments, the dose of seltorexant is 20 mg. In some embodiments, the dose of seltorexant is 40 mg. In some embodiments, the dose of XEN1101 is 10 mg. In some embodiments, the dose of XEN1101 is 20 mg. In some embodiments, the dose of erteberel is 25 mg. In some embodiments, the dose of erteberel is 50 mg. In some embodiments, the dose of erteberel is 75 mg. In some embodiments, the dose of NV-5138 is 200 mg. In some embodiments, the dose of NV-5138 is 400 mg. In some embodiments, the dose of NV-5138 is 800 mg. In some embodiments, the dose of NV-5138 is 1200 mg. In some embodiments, the dose of NV-5138 is 1600 mg. In some embodiments, the dose of TS-121 is 10 mg. In some embodiments, the dose of TS-121 is 25 mg. In some embodiments, the dose of TS-121 is 50 mg. In some embodiments, the dose of ALKS 5461 comprises about 2 mg buprenorphine and about 2 mg samidorphan. In some embodiments, the dose of ALKS 5461 comprises about 8 mg buprenorphine and about 8 mg samidorphan. In some embodiments, the dose of the pharmaceutical formulation comprising carbidopa and oxitriptan comprises about 25 mg carbidopa and about 50 mg oxitriptan. In some embodiments, the dose of the pharmaceutical formulation comprising carbidopa and oxitriptan comprises about 25 mg carbidopa and about 75 mg oxitriptan. In some embodiments, the dose of the pharmaceutical formulation comprising carbidopa and oxitriptan comprises about 10 mg carbidopa and about 50 mg oxitriptan. In some embodiments, the dose of the pharmaceutical formulation comprising deudextromethorphan hydrobromide (d6-DM) and quinidine comprise about 18 mg d6-DM and about 4.9 mg quinidine. In some embodiments, the dose of the pharmaceutical formulation comprising d6-DM and quinidine comprise about 28 mg d6-DM and about 4.9 mg quinidine. In some embodiments, the dose of diazepam is about 2 mg. In some embodiments, the dose of diazepam is about 2.5 mg. In some embodiments, the dose of diazepam is about 2 mg 1 to 4 times a day. In some embodiments, the dose of diazepam is about 2.5 mg 1 to 4 times a day. In some embodiments, the dose of alprazolam is about 0.25 mg. In some embodiments, the dose of alprazolam is about 0.25 mg 1 to 3 times a day. In some embodiments, the dose of alprazolam is about 0.5 mg. In some embodiments, the dose of alprazolam is about 0.5 mg 1 to 3 times a day. In some embodiments, the dose of triazolam is about 0.125 mg. In some embodiments, the dose of triazolam is about 0.125 mg taken at bedtime. In some embodiments, the dose of triazolam is about 0.25 mg. In some embodiments, the dose of triazolam is about 0.25 mg taken at bedtime. In some embodiments, the dose of lorazepam is about 0.5 mg. In some embodiments, the dose of lorazepam is about 1 mg. In some embodiments, the dose of lorazepam is about 1 mg 1 to 4 times a day. In some embodiments, the dose of lorazepam is about 2.5 mg. In some embodiments, the dose of lorazepam is about 2.5 mg 1 to 4 times a day. In some embodiments, the dose of clonazepam is about 0.25 mg. In some embodiments, the dose of clonazepam is about 0.25 mg 2 times a day. In some embodiments, the dose of clonazepam is about 0.5 mg. In some embodiments, the dose of clonazepam is about 1 mg. In some embodiments, the dose of clonazepam is about 2 mg. In some embodiments, the dose of clonazepam is about 2.5 mg. In some embodiments, the dose of chlordiazepoxide is about 5 mg. In some embodiments, the dose of chlordiazepoxide is about 5 mg 3 to 4 times a day. In some embodiments, the dose of chlordiazepoxide is about 10 mg. In some embodiments, the dose of chlordiazepoxide is about 10 mg 3 to 4 times a day. In some embodiments, the dose of nitrazepam is about 5 mg. In some embodiments, the dose of nitrazepam is about 5 mg taken at bedtime. In some embodiments, the dose of nitrazepam is about 10 mg. In some embodiments, the dose of nitrazepam is about 10 mg taken at bedtime. In some embodiments, the dose of loprazolam is about 1 mg. In some embodiments, the dose of loprazolam is about 1 mg taken at bedtime. In some embodiments, the dose of loprazolam is about 1.5 mg. In some embodiments, the dose of loprazolam is about 1.5 mg take at bedtime. In some embodiments, the dose of loprazolam is about 2 mg. In some embodiments, the dose of loprazolam is about 2 mg taken at bedtime. In some embodiments, the dose of the pharmacologic antidepressant agent is titrated upward until a desired improvement in one or more depression symptoms is achieved. In some embodiments, the dose of the pharmacologic antidepressant agent is titrated downward to determine a lowest effective dosage. In some embodiments, the dose of the pharmacologic antidepressant agent is titrated downward to determine a lowest effective dosage demonstrating a desired improvement in one or more depression symptoms in the subject. In some embodiments, the dose of the pharmacologic antidepressant agent is titrated downward to determine a lowest effective dosage and reducing a severity or an occurrence of an unwanted drug side effect. In some embodiments, the dose of the pharmacologic antidepressant agent is titrated downward to determine a lowest effective dosage demonstrating a desired improvement in one or more depression symptoms in the subject and reducing a severity or an occurrence of an unwanted drug side effect in the subject. In some embodiments, the dose of the pharmacologic antidepressant agent is titrated downward to alleviate two or more unwanted drug side effects in the subject. In some embodiments, the dose of the pharmacologic antidepressant agent is titrated upwards in increments of 0.25 mg, 0.50 mg, 0.75 mg, 1 mg, 1.25 mg, 1.5 mg, 1.75 mg, 2 mg, 2.5 mg, 3 mg, 3.5 mg, 4 mg, 5 mg, 6 mg, 7 mg, 8 mg, 9 mg, 10 mg, 11 mg, 12 mg, 13 mg, 14 mg, 15 mg, 16 mg, 17 mg, 18 mg, 19 mg, 20 mg, 21 mg, 22 mg, 23 mg, 24 mg, 25 mg, 26 mg, 27 mg, 28 mg, 29 mg, 30 mg, 32 mg, 34 mg, 35 mg, 36 mg, 37.5 mg, 38 mg, 40 mg, 42 mg, 45 mg, 50 mg, 55 mg, 60 mg, 65 mg, 70 mg, 75 mg, 80 mg, 85 mg, 90 mg, 95 mg, 100 mg, 105 mg, 110 mg, 115 mg, 120 mg, 125 mg, 130 mg, 140 mg, 150 mg, 175 mg, 200 mg, 225 mg, or 250 mg. In some embodiments, the dose of the pharmacologic antidepressant agent is titrated downwards in increments of 0.25 mg, 0.50 mg, 0.75 mg, 1 mg, 1.25 mg, 1.5 mg, 1.75 mg, 2 mg, 2.5 mg, 3 mg, 3.5 mg, 4 mg, 5 mg, 6 mg, 7 mg, 8 mg, 9 mg, 10 mg, 11 mg, 12 mg, 13 mg, 14 mg, 15 mg, 16 mg, 17 mg, 18 mg, 19 mg, 20 mg, 21 mg, 22 mg, 23 mg, 24 mg, 25 mg, 26 mg, 27 mg, 28 mg, 29 mg, 30 mg, 32 mg, 34 mg, 35 mg, 36 mg, 37.5 mg, 38 mg, 40 mg, 42 mg, 45 mg, 50 mg, 55 mg, 60 mg, 65 mg, 70 mg, 75 mg, 80 mg, 85 mg, 90 mg, 95 mg, 100 mg, 105 mg, 110 mg, 115 mg, 120 mg, 125 mg, 130 mg, 140 mg, 150 mg, 175 mg, 200 mg, 225 mg, or 250 mg. In some embodiments, an administration frequency and a dosage per administration of the pharmacologic antidepressant agent is selected to treat a subject wherein the subject is an adult. In some embodiments, an administration frequency and a dosage per administration of the pharmacologic antidepressant agent is selected to treat a subject wherein the subject is elderly. In some embodiments, an administration frequency and a dosage per administration of the pharmacologic antidepressant agent is selected to treat a subject wherein the subject is an adolescent. In some embodiments, an administration frequency and a dosage per administration of the pharmacologic antidepressant agent is selected to treat a subject wherein the subject is a child. In some embodiments, the child or the adolescent is undergoing treatment for depression during puberty. In some embodiments, an administration frequency and a dosage per administration of the pharmacologic antidepressant agent is selected to provide a therapeutic benefit for the treatment of depression that is partially responsive to a separate antidepressant therapy. In some embodiments, the an administration frequency and a dosage per administration of the pharmacologic antidepressant agent is selected to provide an adjunctive treatment for depression.

In some embodiments, the treatment regimen comprises a drug administration regime. In some embodiments the drug administration regime specifies a frequency of administration of the dose of the pharmacologic antidepressant agent. In some embodiments, the frequency of administration is at most about every 1 hour, every 2 hours, every 3 hours, every 4 hours, every 5 hours, every 6 hours, every 7 hours, every 8 hours, every 9 hours, every 10 hours, every 11 hours, every 12 hours, every 13 hours, every 14 hours, every 15 hours, every 16 hours, every 17 hours, every 18 hours, every 19 hours, every 20 hours, every 21 hours, every 22 hours, every 23 hours, every 24 hours, every 28 hours, every 32 hours, every 36 hours, every 40 hours, every 44 hours, every 2 days, every 3 days, every 4 days, every 5 days, every 6 days, every 7 days, every 10 days, every 14 days, every 21 days, or every 28 days. In some embodiments, the frequency of administration is about once a month, once every three weeks, once every two weeks, once every 10 days, once every week, once every 6 days, once every 5 days, once every 4 days, once every 3 days, once every 2 days, once every day, twice every day, three times every day, four times every day, five times every day, six times every day, seven times every day, eight times every day, nine times every day, ten times every day, eleven times every day, or twelve times every day. In some embodiments, the frequency of administration is about every 8 hours. In some embodiments, the frequency of administration is 3 times a day. In some embodiments, the frequency of administration is about every 12 hours. In some embodiments, the frequency of administration is 2 times a day. In some embodiments, the frequency of administration is about every 24 hours. In some embodiments, the frequency of administration is once daily. In some embodiments, the frequency of administration is once daily in the morning. In some embodiments, the frequency of administration is once daily in the evening. In some embodiments, the frequency of administration is once daily at bedtime. In some embodiments, the frequency of administration is once daily irrespective of food intake. In some embodiments, the frequency of administration is once daily coinciding with food intake. In some embodiments, the frequency of administration is about every 36 hours. In some embodiments, the frequency of administration is about every other day. In some embodiments, the frequency of administration is about once every three days. In some embodiments, the frequency of administration is about once every 4 days. In some embodiments, the frequency of administration is about two times per week. In some embodiments, the frequency of administration is about once a week. In some embodiments, the pharmacologic antidepressant agent administered to the subject is a pharmaceutically acceptable salt of a pharmacologic antidepressant agent named herein.

In some embodiments, the drug administration regime continues for a period of time. In some embodiments, the period of time is determined prior to the initiation of treatment. In some embodiments, the period of time is determined about at the initiation of treatment. In some embodiments, the period of time is determined after treatment has begun. In some embodiments, the period of time is determined after treatment has begun according to results from a measurement of one or more symptoms of depression. In some embodiments, the period of time is determined by the subject. In some embodiments, the period of time is determined by a physician or medical practitioner providing medical treatment to the subject. In some embodiments, the period of time is determined according to the subject achieving a desired treatment outcome. In some embodiments, the desired treatment outcome is a reduction in one or more symptoms of depression. In some embodiments, the desired treatment outcome is a significant change in a MADRS score. In some embodiments, the desired treatment outcome is a significant change in a MADRS-s score. In some embodiments, the desired treatment outcome is a remission of one or more symptoms of depression. In some embodiments, the desired treatment outcome is a full remission of depression symptoms. In some embodiments, the drug administration regime continues for a period of time, stops for a second period of time, and resumes for a third period of time. In some embodiments, the drug administration regime continues for a period of time, stops for a second period of time during which the subject maintains a desired treatment outcome, and resumes for a third period of time during which the subject seeks to improve one or more symptoms of depression. In some embodiments, the drug administration regime continues for a period of time, stops for a second period of time during which the subject maintains a desired treatment outcome, and resumes for a third period of time during which the subject seeks to improve one or more symptoms of depression as measured by achieving an significant reduction in a MADRS or MADRS-s score. In some embodiments, the drug administration regime continues for a period of time of at least 1 week, 2 weeks, 3 weeks, 4 weeks, 5 weeks, 6 weeks, 7 weeks, 8 weeks, 9 weeks, 10 weeks, 11 weeks, 12 weeks, 13 weeks, 14 weeks, 15 weeks, 16 weeks, 17 weeks, 18 weeks, 19 weeks, 20 weeks, 21 weeks, 22 weeks, 23 weeks, 24 weeks, 25 weeks, 26 weeks, 7 months, 8 months, 9 months, 10 months, 11 months, 12 months, 13 months, 14 months, 15 months, 16 months, 17 months, 18 months, or 2 years. In some embodiments, the drug administration regime continues for a period of time of 6 weeks. In some embodiments, the drug administration regime continues for a period of time of 10 weeks. In some embodiments, the drug administration regime continues for a period of time of 12 weeks. In some embodiments, the drug administration regime continues for a period of time of 16 weeks. In some embodiments, the drug administration regime continues for a period of time of 20 weeks. In some embodiments, the drug administration regime continues for a period of time of 25 weeks. In some embodiments, the drug administration regime continues for a period of time of 52 weeks. In some embodiments, the treatment regimen comprises a multi-dose drug administration regime. In some embodiments, the dosages in the multi-dose drug administration regime are adjusted during period of time of treatment comprising administration of the pharmacologic antidepressant agent.

Conditions Treated

In another aspect, provided herein are methods of treating a disease, a disorder, or a condition in a subject in need thereof, the method comprising administering to the subject a pharmacologic antidepressant agent and delivering to the subject a tES. In some embodiments, the disease, the disorder, or the condition is depression or a disease, a disorder, or a condition related to depression. In some embodiments, the depression is mild depression, moderate depression, severe depression, major depression, MDD, melancholic depression, persistent depressive disorder, psychotic depression, psychotic major depression, postpartum depression, situational depression, breakthrough depression, atypical depression, treatment resistant depression, catatonic depression, double depression, unspecified depressive disorder, recurrent brief depression, minor depressive disorder, alcohol-induced depression, substance-induced depression, benzodiazepine-induced depression. In some embodiments, the disease, the disorder, or the condition related to depression is anxiety. In some embodiments, the disease, the disorder, or the condition related to depression is anxious distress, melancholy, agitation, bipolar disorder type 1, bipolar disorder type 2, bipolar disorder not otherwise specified, cyclothymia, season affective disorder, premenstrual dysphoric disorder, dysthymia, depressive personality disorder, or mixed anxiety-depressive disorder. In some embodiments, methods of treating depression or a disease, a disorder, or a condition related to depression comprise treating the symptoms associated with the depression or the disease, the disorder, or the condition related to depression. In some embodiments, a subject has been diagnosed with MDD based on the diagnostic criteria in the Diagnostic and statistical manual of mental disorders-5th edition (DSM-V). In some embodiments, the subject diagnosed with MDD has also received a thorough diagnostic assessment in order to identify other psychiatric or general medical conditions that may require attention. In some embodiments, a psychiatrist develops a comprehensive plan for treatment of MDD of the subject and conducts an evaluation including a history of the present illness and current symptoms that may trigger or exacerbate depressive symptoms. In some embodiments, the psychiatrist makes use of one of several clinically validated standard scales available for the assessment of the severity of depressive symptoms and based on the cut-offs from these scales, classifies the severity of MDD of the subject as mild depression, moderate depression, or severe depression.

The methods described herein may be used to treat depression or depression-related conditions in a variety of subjects. In some embodiments, the subject is an adult. In some embodiments, the subject is elderly. In some embodiments, the subject is an adolescent. In some embodiments, the subject is a child. In some embodiments, the adolescent or the child has depression or a depression-related condition during puberty. In some embodiments, the subject has had a prior depressive episode. In some embodiments, the prior depressive episode was partially responsive to treatment. In some embodiments, the prior depressive episode was partially responsive to treatment with an SSRI. In some embodiments, the prior depressive episode was partially responsive to treatment with an SNRI. In some embodiments, the prior depressive episode was partially responsive to treatment with an NaSSA. In some embodiments, the prior depressive episode was partially responsive to treatment with an SMS. In some embodiments, the prior depressive episode was partially responsive to treatment with an SARI. In some embodiments, the prior depressive episode was partially responsive to treatment with an SNDRI. In some embodiments, the prior depressive episode was partially responsive to treatment with an NRI. In some embodiments, the prior depressive episode was partially responsive to treatment with an NDRI. In some embodiments, the prior depressive episode was partially responsive to treatment with an NDRA. In some embodiments, the prior depressive episode was partially responsive to treatment with an SNDRA. In some embodiments, the prior depressive episode was partially responsive to treatment with a TCA. In some embodiments, the prior depressive episode was partially responsive to treatment with a TeCA. In some embodiments, the prior depressive episode was partially responsive to treatment with an MAOI. In some embodiments, the prior depressive episode was partially responsive to treatment with an NMDA receptor modulator, In some embodiments, the prior depressive episode was partially responsive to treatment with an atypical antipsychotic. In some embodiments, the prior depressive episode was partially responsive to treatment with an atypical antidepressant. In some embodiments, the prior depressive episode was partially responsive to treatment with a benzodiazepine. In some embodiments, a subject having undergone a prior treatment for depression that was determined to be partially responsive to treatment may be defined as the subject having achieved a decrease in an assessment of depression of less than 50% symptom improvement. In some embodiments, a subject having undergone a prior treatment for depression that was determined to be partially responsive to treatment may be defined as the subject having achieved a decrease in MADRS score than is less than 50%, 45%, 40%, 35%, 30%, 25%, 20%, 15%, 10%, or 5% of a baseline MADRS score. In some embodiments, a subject having undergone a prior treatment for depression that was determined to be partially responsive to treatment may be defined as the subject having achieved a decrease in MADRS-s score than is less than 50%, 45%, 40%, 35%, 30%, 25%, 20%, 15%, 10%, or 5% of a baseline MADRS-s score. In some embodiments, a desired treatment outcome of the subject being treated with a method described herein is an improvement in one or more symptoms of the subject. In some embodiments, a desired treatment outcome of the subject being treated with a method described herein is a remission of one or more symptoms of the subject. In some embodiments, the one or more symptoms are symptoms of depression or a depression-related condition. In some embodiments, the one or more symptoms are symptoms of a co-morbidity of the subject. In some embodiments, the desired treatment outcome of the subject may be a reduction of a MADRS-s score of 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, or 54 points compared to a baseline MADRS-s score of the subject. In some embodiments, the desired treatment outcome of the subject may be maintenance of an improvement of a MADRS-s score of 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, or 54 points compared to a baseline MADRS-s score of the subject for a period of time. In some embodiments, the period of time is at least 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, or 52 weeks.

Symptoms

Described herein are methods of treatment for depression in a subject wherein one or more symptoms of a mood disorder are modulated. In some embodiments, one or more symptoms indicative of depression or a depression-related disorder or condition are modulated. In some embodiments, one or more symptoms not indicative of depression or a depression-related disorder or condition are modulated. In some embodiments, the mood disorder is selected from the group consisting of: Depression, clinical depression, a depression-related condition, MDD, MDD with suicidal risk, Bipolar I disorder, Bipolar II disorder, Seasonal affective disorder (SAD), Cyclothymic disorder, Premenstrual dysphoric disorder, perimenopausal depression, Persistent depressive disorder (dysthymia), Disruptive mood dysregulation disorder, Depression related to a medical illness, post-traumatic stress disorders, Depression induced by substance use or medication, Postpartum depression, perinatal depression, atypical depression, melancholic depression, psychotic major depression, catatonic depression, double depression, depressive personality disorder, recurrent brief depression, minor depressive disorder, treatment-resistant depression, depression with anxiety, refractory depression, suicidality, and suicidal behavior. In some embodiments, one or more symptoms of depression improve in the subject. In some embodiments, one or more symptoms not indicative of depression or a depression-related disorder or condition improve in the subject. In some embodiments, the one or more symptoms of depression decrease in the subject. In some embodiments, the one or more symptoms not indicative of depression or a depression-related disorder or condition decrease in the subject. In some embodiments, the one or more symptoms of depression increase in the subject. In some embodiments, the one or more symptoms not indicative of depression or a depression-related disorder or condition increase in the subject. In some embodiments, the one or more symptoms of depression are maintained in the subject. In some embodiments, the one or more symptoms not indicative of depression or a depression-related disorder are maintained in the subject. In some embodiments, the one or more symptoms of depression are assessed by the subject. In some embodiments, the one or more symptoms of depression are assessed by a physician or a medical practitioner. In some embodiments, the one or more symptoms of depression are recorded in a questionnaire. In some embodiments, the one or more symptoms not indicative of depression or a depression-related disorder or condition are assessed by the subject. In some embodiments, the one or more symptoms not indicative of depression or a depression-related disorder or condition are assessed by a physician or a medical practitioner. In some embodiments, the one or more symptoms not indicative of depression or a depression-related disorder or condition are recorded in a questionnaire. In some embodiments, the one or more symptoms of depression are assessed by the subject. some embodiments, the one or more not indicative of depression or a depression-related disorder or condition. In some embodiments, an administration frequency and a dosage per administration of the pharmacologic antidepressant agent are selected to provide therapeutic benefits for the treatment of a depression selected from Depression, clinical depression, a depression-related condition, MDD, MDD with suicidal risk, Bipolar I disorder, Bipolar II disorder, SAD, Cyclothymic disorder, Premenstrual dysphoric disorder, perimenopausal depression, dysthymia, Disruptive mood dysregulation disorder, Depression related to a medical illness, post-traumatic stress disorders, Depression induced by substance use or medication, Postpartum depression, perinatal depression, atypical depression, melancholic depression, psychotic major depression, catatonic depression, double depression, depressive personality disorder, recurrent brief depression, minor depressive disorder, treatment-resistant depression, depression with anxiety, refractory depression, suicidality, or suicidal behavior.

In some embodiments, the methods described herein modulate one or more symptoms of a subject. In some embodiments, the one or more modulated symptoms are symptoms of depression. In some embodiments, the one or more modulated symptoms are symptoms related to depression. In some embodiments, the one or more modulated symptoms are symptoms indicative of depression. In some embodiments, the one or more modulated symptoms are symptoms diagnostic for depression. In some embodiments, the one or more modulated symptoms of depression are selected from the group consisting of: depressed mood, irritability, instability of mood, changes in mood, mood swings, hormonal-related mood swings, impaired short term memory, impaired abstract thinking, impaired judgement, impaired language skills, persistent anxious feelings, persistent sad feelings, feelings of helplessness, feelings of hopelessness, pessimism, feelings of worthlessness, lack of energy, restlessness, insomnia, disturbed sleep, irritability, excessive fatigue, motor function impairment, loss of interest in pleasurable activities, loss of ability to concentrate, poor self-esteem, lack of positive thoughts, lack of positive plans, excessive sleeping, overeating, loss of appetite, self-harm, suicidal ideation, suicidal thoughts, suicide attempts, anxiety, apathy, general discontent, feelings of guilt, sadness, agitation, excessive crying, social isolation, early awakening, restless sleep, excessive hunger, slowness in activity, lethargy, weight gain, weight loss, poor appetite, rumination, changes in daily behavior, angry outbursts, slowed speech, slowed body movements, fixation on past failures, self-blame, difficulty thinking, difficulty making decisions, frequent or recurrent thoughts of death, headache, back pain, excessive worry, clinginess, excessive anger, avoidance of social interactions, personality changes, loss of libido, and persistent feelings of emptiness. In some embodiments, the one or more modulated symptoms are symptoms not indicative of depression or a depression-related disorder or condition. In some embodiments, the symptoms not indicative of depression or a depression-related disorder or condition may be derived from long-term stress, long-term exhaustion, an anxiety syndrome, Borderline personality disorder, chronic pain, insomnia, Attention-deficit/hyperactivity disorder (ADHD), Bipolar disorder, an eating disorder, Posttraumatic Stress Disorder (PTSD), Obsessive-compulsive Disorders (OCD), an Autism-spectrum Disorder, alcohol addiction, drug addiction, pregnancy, or a hormonal imbalance.

Improvement and Assessment of Symptoms Related to Depression

Changes in symptoms related to depression in a subject with a depressive condition can be determined by a number of methods and these changes can inform a treatment plan for the subject. In some embodiments, the treatment plan for the subject is modified according to an assessment of the subject. In some embodiments, the modification of the treatment plan may include a reduction in a dosage of pharmacologic antidepressant agent the subject is receiving, a reduction in a frequency of administration of the pharmacologic antidepressant agent the subject is receiving, a reduction in a number of tES sessions being delivered to the subject, a reduction in a duration of tES sessions being delivered to the subject, and/or a reduction in an intensity of tES in the sessions being delivered to the subject. In some embodiments, the modification of the treatment plan may include an increase in a dosage of pharmacologic antidepressant agent the subject is receiving, an increase in a frequency of administration of the pharmacologic antidepressant agent the subject is receiving, a change in a number of tES sessions being delivered to the subject that may be either an increase or a decrease in number of tES sessions, a change in a duration of tES sessions being delivered to the subject that may be either an increase or a duration of tES sessions, and/or a change in an intensity of tES in the sessions being delivered to the subject that may be either an increase or a duration in the intensity of the tES in the sessions. In some embodiments, an assessment can be made to determine a change in symptoms related to depression. In some embodiments, the assessment can be used to determine an improvement in symptoms related to depression. In some embodiments, the assessment can be used to determine a persistence of symptoms related to depression. In some embodiments, the assessment can be used to determine a worsening of symptoms related to depression. In some embodiments, the assessment can be used to determine a development of new symptoms related to depression. In some embodiments, the assessment can be used to determine a reduction in symptoms related to depression. In some embodiment, the reduction in symptoms related to depression comprises a reduction in an extent or severity of one or more symptoms related to depression. In some embodiment, the reduction in symptoms related to depression comprises a reduction in a number of categories of symptoms related to depression. In some embodiment, the reduction in symptoms related to depression comprises a remission of one of more symptoms related to depression. In some embodiments, the reduction in symptoms related to depression is maintained for a period of time. In some embodiments, the reduction in symptoms related to depression is maintained for a period of time and the subject continues to improve in terms of an extent of one of more symptoms related to depression. In some embodiments, the period of time in which the subject experiences a reduction in one or more symptoms related to depression is any period of time between 1 week and 1 year. In some embodiments, the period of time in which the subject experiences a remission in one or more symptoms related to depression is any period of time between 1 week and 1 year. In some embodiments, a reduction in one or more symptoms related to depression improves a self-reported quality of life assessment of the subject. In some embodiments, a remission in one or more symptoms related to depression improves a self-reported quality of life assessment of the subject. In some embodiments, a reduction in one or more symptoms related to depression allows the subject to regain an ability to successfully complete one or more activities of daily living (ADLs). In some embodiments, a remission in one or more symptoms related to depression allows the subject to regain an ability to successfully complete one or more activities of daily living (ADLs). In some embodiments, a reduction in one or more symptoms related to depression allows a dosage of a pharmacologic antidepressant agent taken by the subject to be reduced. In some embodiments, a reduction in one or more symptoms related to depression allows a frequency of administration of a pharmacologic antidepressant agent taken by the subject to be reduced. In some embodiments, a reduction in one or more symptoms related to depression prevents a need to switch a medication being administered to the subject to a different pharmacologic antidepressant agent as part of an attempt to improve a treatment outcome. In some embodiments, a remission in one or more symptoms related to depression allows a dosage of a pharmacologic antidepressant agent taken by the subject to be reduced. In some embodiments, a remission in one or more symptoms related to depression allows a frequency of administration of a pharmacologic antidepressant agent taken by the subject to be reduced. In some embodiments, a remission in one or more symptoms related to depression prevents a need to switch a medication being administered to the subject to a different pharmacologic antidepressant agent as part of an attempt to improve a treatment outcome. In some embodiments, a remission in one or more symptoms related to depression allows the subject to taper down a dose or a frequency of administration of a pharmacologic antidepressant agent and maintain the remission of the one or more symptoms related to depression. In some embodiments, a remission in one or more symptoms related to depression allows the subject to taper down a dose or a frequency of administration of a pharmacologic antidepressant agent and eventually cease the administration of the pharmacologic antidepressant agent and maintain the remission of the one or more symptoms related to depression. In some embodiments, a reduction in one or more symptoms related to depression allows the subject to change a frequency of delivery to the subject of a tES. In some embodiments, a remission in one or more symptoms related to depression allows the subject to change a frequency of delivery to the subject of a tES. In some embodiments, a reduction in one or more symptoms related to depression allows the subject to reduce a frequency of delivery to the subject of a tES. In some embodiments, a remission in one or more symptoms related to depression allows the subject to reduce a frequency of delivery to the subject of a tES. In some embodiments, a reduction in one or more symptoms related to depression allows for a reduction in intensity of a tES delivered to the subject. In some embodiments, a remission in one or more symptoms related to depression allows for a reduction in intensity of a tES delivered to the subject. In some embodiments, a reduction in one or more symptoms related to depression following an initiation phase of delivering a tES to the subject allows for a reduction in a dosage of the pharmacologic antidepressant agent, a reduction in a frequency of administration of the pharmacologic antidepressant agent, and/or a reduction in the number of tES sessions required to maintain the improvement in depression in the subject. In some embodiments, a remission of one or more symptoms related to depression following an initiation phase of delivering a tES to the subject allows for a reduction in a dosage of the pharmacologic antidepressant agent, a reduction in a frequency of administration of the pharmacologic antidepressant agent, and/or a reduction in the number of tES sessions required to maintain the improvement in depression in the subject.

Changes in symptoms related to depression in a subject with a depressive condition can be determined by a number of methods. In some embodiments, an assessment can be made to determine a change in symptoms related to depression. In some embodiments, the assessment can be a self-assessment made by the subject. In some embodiments, the assessment can be an assessment made by a physician or medical practitioner providing treatment to the subject. In some embodiments, the assessment can be made by the subject completing a questionnaire. In some embodiments, the questionnaire is a diagnostic questionnaire. In some embodiments, the assessment can be made by a physical examination of the subject. In some embodiments, the assessment can be made to determine a baseline score. In some embodiments, additional assessments can be made following the baseline score to determine ongoing treatment effectiveness. In some embodiments, additional assessments can be made at intervals of about 1, 2, 3, 4, 5, 6, 7, 8, 9, 10, 11, 12, 13, 14, 15, 16, 17, 18, 19, 20, 21, 22, 23, 24, 25, 26, 27, 28, 29 or 30 days. In some embodiments, additional assessments can be made at intervals of about 1, 2, 3, 4, 5, 6, 7, 8, 9, 10, 11, 12, 13, 14, 15, 16, 17, 18, 19, 20, 21, 22, 23, 24, 25, 26, 27, 28, 29 or 30 weeks. In some embodiments, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 35, 40, 45, 50, 55, 60, 65, 70, 75, 80, 85, 90, 95 or 100 additional assessments can be made.

One method that may be used as a measure of severity of a depressive episode in a subject is an assessment by completion of a Montgomery-Åsberg Depression Rating Scale (MADRS) questionnaire. In some embodiments, the assessment is made by an individual completing a MADRS questionnaire which assesses symptoms of the subject. In some embodiment, a physician or medical practitioner completed the MADRS questionnaire. In some embodiments, the physician is a psychiatrist. MADRS scores can be calculated and provide an overall assessment of a number and an extent of depression or depression symptoms in a subject at the time of the assessment. In some embodiments, a MADRS score measures overall severity of depression or depression-related symptoms in a subject with a mood disorder. In some embodiments, a MADRS score measures overall severity of depression or depression-related symptoms in a subject with MDD. In some embodiments, MADRS scores are calculated on a scale of 0-60 points. In some embodiments, MADRS scores indicate a presence and an extent of symptoms related to a number of aspects of depression. In some aspects, the number of aspects of depression include apparent sadness, reported sadness, inner tension, reduced sleep, reduced appetite, concentration difficulties, lassitude, inability to feel, pessimistic thoughts, and suicidal thoughts. In some embodiments, each item assessed with MADRS is scored on a scale of 0 to 6 points. In some embodiments, a score of 0 indicates an absence of one or more symptoms of depression related to the item. In some embodiments, a score of 6 indicates a maximum extent of one or more symptoms of depression related to the item. In some embodiments, a score ranging between 1 to 5 indicates an increasing severity of an extent of one or more symptoms of depression related to the item. In some embodiments, a total point score for a subject is calculated by summing the point values for each item together. In some embodiments, the subject is determined to have a measurement of a severity in a depressive episode at the time the assessment is taken by categorizing the subject according to normal/symptom absent, mild depression, moderate depression, and severe depression. In some embodiments, normal/symptom absent is the determination of the severity in a depressive episode of the subject following a summed MADRS score of 0 to 6. In some embodiments, mild depression is the determination of the severity in a depressive episode of the subject following a summed MADRS score of 7 to 19. In some embodiments, moderate depression is the determination of the severity in a depressive episode of the subject following a summed MADRS score of 20 to 34. In some embodiments, severe depression is the determination of the severity in a depressive episode of the subject following a summed MADRS score of 34 or above. In some embodiments, a change of at least between 6 to 9 points from baseline MADRS score to MADRS score at a later time point has been shown to correspond to a clinically meaningful change in depression in the subject. In some embodiments, a change of at least 6 points from baseline MADRS score to MADRS score at a later time point has been shown to correspond to a clinically meaningful change in depression in the subject. In some embodiments, depression is more severe at baseline and a clinically meaningful change in MADRS may be more than 6 points. In some embodiments, depression has improved compared to baseline and further clinically meaningful improvement may be represented by an additional decrease of 6 points or an additional decrease of less than 6 points. In some embodiments, an increase in MADRS score indicates an increase in the severity and/or extent of depression in the subject. In some embodiments, a decrease in MADRS score indicates a decrease in the severity and/or extent of depression in the subject. In some embodiments, a decrease in MADRS score indicates an improvement in depression in the subject. In some embodiments, when distinct treatment groups comprising multiple subjects are compared, a 2-point or more difference in MADRS between groups has been found to be clinically meaningful. In some embodiments, when distinct treatment groups comprising multiple subjects are compared, a 2-point or more difference in MADRS between groups has been found to be a statistically significant difference. In some embodiments, when distinct treatment groups comprising multiple subjects are compared, a 2-point or more difference in MADRS between groups has been found to represent a significantly different rate of remission of depressive symptoms in matched subjects. In some embodiments, when distinct treatment groups comprising multiple subjects are compared, a 2-point or more difference in MADRS between groups favoring a particular distinct treatment group may be clinically relevant and represent significant clinical effects (including a change in MADRS of 6 points or more since baseline assessment) among a subgroup of depressed subjects within the distinct treatment group who benefited from the treatment.

One method that may be used as a measure of severity of a depressive episode in a subject is an assessment by completion of a Montgomery-Åsberg Depression Rating Scale Self-assessment (MADRS-s) questionnaire. In some embodiments, the assessment is made by the subject completing a MADRS-s questionnaire which assesses their own symptoms. MADRS-s scores can be calculated and provide an overall assessment of a number and an extent of depression or depression symptoms in a subject at the time of the assessment. In some embodiments, a MADRS-s score measures overall severity of depression or depression-related symptoms in a subject with a mood disorder. In some embodiments, a MADRS-s score measures overall severity of depression or depression-related symptoms in a subject with MDD. In some embodiments, MADRS-s scores are calculated on a scale of 0-54 points. In some embodiments, to obtain a total MADRS-s score, the score of a scale of 0-6 for each item is summed to obtain the total MADRS-s score. In some embodiments, MADRS-s scores indicate a presence and an extent of symptoms related to a number of aspects of depression. In some aspects, the number of aspects of depression include reported sadness or reported mood, inner tension or feelings of unease, sleep, appetite, concentration difficulties or ability to concentrate, lassitude or initiative, inability to feel or emotional involvement, pessimistic thoughts or pessimism, and suicidal thoughts or zest for life. In some embodiments, each item assessed with MADRS-s is scored on a scale of 0 to 6 points. In some embodiments, a score of 0 indicates an absence of one or more symptoms of depression related to the item. In some embodiments, a score of 6 indicates a maximum extent of one or more symptoms of depression related to the item. In some embodiments, a score ranging between 1 to 5 indicates an increasing severity of an extent of one or more symptoms of depression related to the item. In some embodiments, a total point score for a subject is calculated by summing the point values for each item together. In some embodiments, the subject is determined to have a measurement of a severity in a depressive episode at the time the assessment is taken by categorizing the subject according to normal/symptom absent, mild depression, moderate depression, and severe depression. In some embodiments, normal/symptom absent or very mild depression is the determination of the severity in a depressive episode of the subject following a summed MADRS-s score of 0 to 12. In some embodiments, mild depression is the determination of the severity in a depressive episode of the subject following a summed MADRS-s score of 13 to 19. In some embodiments, moderate depression is the determination of the severity in a depressive episode of the subject following a summed MADRS-s score of 20 to 34. In some embodiments, severe depression is the determination of the severity in a depressive episode of the subject following a summed MADRS-s score of 35 or above. In some embodiments, a change of at least between 6 to 9 points from baseline MADRS-s score to MADRS-s score at a later time point has been shown to correspond to a clinically meaningful change in depression in the subject. In some embodiments, a change of at least 6 points from baseline MADRS-s score to MADRS-s score at a later time point has been shown to correspond to a clinically meaningful change in depression in the subject. In some embodiments, depression is more severe at baseline and a clinically meaningful change in MADRS-s may be more than 6 points. In some embodiments, depression has improved compared to baseline and further clinically meaningful improvement may be represented by an additional decrease of 6 points or an additional decrease of less than 6 points. In some embodiments, an increase in MADRS-s score indicates an increase in the severity and/or extent of depression in the subject. In some embodiments, a decrease in MADRS-s score indicates a decrease in the severity and/or extent of depression in the subject. In some embodiments, a decrease in MADRS-s score indicates an improvement in depression in the subject. In some embodiments, when distinct treatment groups comprising multiple subjects are compared, a 2-point or more difference in MADRS-s between groups has been found to be clinically meaningful. In some embodiments, when distinct treatment groups comprising multiple subjects are compared, a 2-point or more difference in MADRS-s between groups has been found to be a statistically significant difference. In some embodiments, when distinct treatment groups comprising multiple subjects are compared, a 2-point or more difference in MADRS-s between groups has been found to represent a significantly different rate of remission of depressive symptoms in matched subjects. In some embodiments, when distinct treatment groups comprising multiple subjects are compared, a 2-point or more difference in MADRS-s between groups favoring a particular distinct treatment group may be clinically relevant and represent significant clinical effects (including a change in MADRS-s of 6 points or more since baseline assessment) among a subgroup of depressed subjects within the distinct treatment group who benefited from the treatment. In some embodiments, the subject shows a decrease in MADRS-s score during treatment or after treatment completion compared to a baseline score of at least 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, or 54 points. In some embodiments, MADRS-S measurements are used in part for assessing the response of the subject to the treatment regimen and to the one or more stimulation sessions in order to determine treatment effectiveness. In some embodiments, MADRS-S measurements are used in part for assessing the response of the subject to the treatment regimen and to the one or more stimulation sessions in order to determine treatment effectiveness of an activation phase of neurostimulation. In some embodiments, MADRS-S measurements are used in part for assessing the response of the subject to the treatment regimen and to the one or more stimulation sessions in order to determine treatment effectiveness of a strengthening phase of neurostimulation.

Additional methods or alternative methods, apart from MADRS or MADRS-s, may be used as a measure of severity of a depressive episode in a subject. In some embodiments, the subject may be evaluated via the Hamilton Depression Rating Scale (HAM-D). The HAM-D assessment is a widely used clinician-administered depression assessment scale. In some embodiments, the HAM-D assessment contains 17 items pertaining to symptoms of depression experienced over the past week. The HAM-D questionnaire is designed to be used by clinicians to rate the severity of depressive symptoms in adults by probing mood, feelings of guilt, suicidal ideation, insomnia, agitation or retardation, anxiety, weight loss, and somatic symptoms. In some embodiments, the subject may be evaluated via the Hamilton Rating Scale for anxiety (HAM-A). The HAM-A assessment is a scale to measure the severity of anxiety symptoms and in some embodiments is made of 14 items, each defined by a series of symptoms, and measures both psychic anxiety such as mental agitation and psychological distress and somatic anxiety including physical complaints related to anxiety. In some embodiments, the subject may be evaluated via a Mini International Neuropsychiatric Interview (MINI). MINI is a short structured diagnostic interview for DSM-IV and ICD-10 psychiatric disorders. In some embodiments, the subject may be evaluated via the Young Mania Rating Scale (YMRS). YMRS is a scale to assess manic symptoms. The YMRS scale has 11 items and is based on a patient's subjective report of their clinical condition over the previous 48 hours. In some embodiments, the subject may be evaluated via Rey Auditory Verbal Learning Test (RAVLT). RAVLT is a neuropsychological assessment designed to evaluate verbal memory in patients 16 years of age or older. The RAVLT can be used to evaluate the nature and severity of memory dysfunction and to track changes in memory function over time. In some embodiments, the subject may be evaluated in terms of Clinical Global Impressions (CGI). In some embodiments, subscale scores of CGI may be determined. In some embodiments, a subscale score of CGI may be a severity of illness subscale (CGI-S). In some embodiments, a subscale score of CGI may be an improvement of illness subscale (CGI-I). In some embodiments, a CGI-S score is referred to on an Efficacy Index Subscale. In some embodiments, the subject may be evaluated via a Symptoms of Depression Questionnaire (SDQ). In some embodiments, the subject may be evaluated via a determination using the Pittsburgh Sleep Quality Index (PSQI). In some embodiments, clinician reported outcomes comprise HAM-D, MADRS, MINI, HAM-A, YMRS, RAVLT, CGI-S, CGI-I, SDQ, PSQI, or any combination thereof. In some embodiments, the subject may be tested using MADRS, MADRS-s, HAM-D, HAM-A, CGI-S, CGI-I, SDQ, or PSQI, or any combination thereof to produce a baseline score. In some embodiments, the subject may be tested using MADRS, MADRS-s, HAM-D, HAM-A, CGI-S, CGI-I, SDQ, or PSQI, or any combination thereof to compare a score during treatment to a baseline score. In some embodiments, effectiveness of a dosage regimen can be determined by evaluation via MADRS as a primary efficacy endpoint. In some embodiments, effectiveness of a dosage regimen can be determined by evaluation via MADRS-s as a primary efficacy endpoint. In some embodiments, effectiveness of a dosage regimen can be determined by evaluation via MADRS as a primary efficacy endpoint in association with secondary efficacy endpoints such as MADRS-s, HAM-D, HAM-A, CGI-S, CGI-I, SDQ, PSQI, or any combination thereof. In some embodiments, effectiveness of a dosage regimen can be determined by evaluation via MADRS-s as a primary efficacy endpoint in association with secondary efficacy endpoints such as MADRS, HAM-D, HAM-A, CGI-S, CGI-I, SDQ, PSQI, or any combination thereof. In some embodiments, an administration frequency and a dosage per administration of the pharmacologic antidepressant agent are selected to provide treatment of severe depression in a subject having a MADRS-s score of 34 or higher. In some embodiments, an administration frequency and a dosage per administration of the pharmacologic antidepressant agent are selected to provide treatment of moderate depression in a subject having a MADRS-s score of between 20-33. In some embodiments, an administration frequency and a dosage per administration of the pharmacologic antidepressant agent are selected to provide treatment of mild depression in a subject having a MADRS-s score of between 13-19. In some embodiments, the subject completes a patient reported outcome questionnaire. In some embodiments, the patient reported outcome questionnaire is a MADRS-s. In some embodiments, the patient reported outcome questionnaire is a EuroQol-5 Dimensionas-3 Level (EQ-5D-3L) score, a Symbol-Digit Modalities Test (SDMT), a Treatment Acceptability Questionnaire (TAQ), a tDCS Adverse Events Questionnaire (AEQ), a Columbia Suicide Severity Rating Scale (C-SSRS), or a combination thereof. C-SSRS is a rating scale to evaluate suicide risk. The C-SSRS scale identifies specific behaviors which may be indicative of a subject's intent to kill themselves. The SDMT assessment detects cognitive impairment. SDMT enables clinicians to screen for organic cerebral dysfunction in both children (8 years of age and older) and in adults. The SDMT is brief, easy to administer, and has demonstrated sensitivity in detecting the presence of brain damage and also in detecting cognitive functioning over time in response to treatment. TAQ is a questionnaire for probing how acceptable participants of a tDCS clinical trial think the treatment is. At baseline, TAQ measures a participant's expectations about the trial (e.g., expected treatment outcome(s), effort needed by the subject, ethics, etc.) and then follows up on these expectations during and/or at the end of the trial. AEQ is a specialized questionnaire developed to capture adverse events encountered by subjects during trials involving tDCS. The EQ-5D-3L assessment is a standardized measure of health-related quality of life.

In some embodiments, an administration frequency and a dosage per administration of the pharmacologic antidepressant agent are selected to improve an aspect of depression or a depression-related condition in the subject. In some embodiments, the aspect of depression or a depression-related condition is reported sadness or reported mood. In some embodiments, the aspect of depression or a depression-related condition is inner tension or feelings of unease. In some embodiments, the aspect of depression or a depression-related condition is sleep. In some embodiments, the aspect of depression or a depression-related condition is appetite. In some embodiments, the aspect of depression or a depression-related condition is concentration difficulty or ability to concentrate. In some embodiments, the aspect of depression or a depression-related condition is lassitude or initiative. In some embodiments, the aspect of depression or a depression-related condition is inability to feel or emotional involvement. In some embodiments, the aspect of depression or a depression-related condition is pessimistic thoughts or pessimism. In some embodiments, the aspect of depression or a depression-related condition is suicidal thoughts or zest for life. In some embodiments, depressive mood is significantly improved in the subject. In some embodiments, a feeling of wellness is significantly restored in the subject. In some embodiments, sleep-related aspect of depression or depression-related condition in the subject is insomnia. In some embodiments, an extent of insomnia may be measured as a latency to persistent sleep (LPS) compared to an LPS score during a prior treatment. In some embodiments, an extent of insomnia may be measured as a decline in wake time after sleep onset (WASO) compared to a WASO score during a prior treatment. In some embodiments, an extent of insomnia may be measured as average of total sleep time per sleep episode as compared to a previous measurement of average of total sleep time per sleep episode. In some embodiments, an extent of insomnia may be measured as a function of sleep efficiency compared to a previous measurement of sleep efficiency of the subject prior to treatment. In some embodiments, total sleep time is the amount of actual sleep time in a sleep episode. In some embodiments, sleep efficiency is the percentage of total time in bed actually spent in a state of sleep. In some embodiments, latency to persistent sleep is the length of time that it takes the subject to accomplish a transition from full wakefulness to a state of sleep. In some embodiments, the improvement in the sleep-related condition in the subject is defined as an increase in WASO of at least 25%, 37.5%, 50%, 62.5%, 75%, 87.5%, or 100% as compared to a previous WASO measurement of the subject. In some embodiments, the improvement in the sleep-related condition in the subject is defined as an decrease in LPS of at least 25%, 37.5%, 50%, 62.5%, 75%, 87.5%, or 100% as compared to a previous LPS measurement of the subject. In some embodiments, the improvement in the sleep-related condition in the subject is defined as an increase in sleep efficiency of at least 25%, 37.5%, 50%, 62.5%, 75%, 87.5%, or 100% as compared to a previous sleep efficiency measurement of the subject. In some embodiments, the improvement in the sleep-related condition in the subject is defined as an increase in total sleep time of at least 25%, 37.5%, 50%, 62.5%, 75%, 87.5%, or 100% as compared to a previous total sleep time measurement of the subject. In some embodiments, the improvement in the sleep-related condition in the subject is measure by assessment via the Pittsburgh Sleep Quality Index (PSQI), the Epworth Sleepiness Scale (ESS), the Insomnia Severity Scale (ISI), the Athens Insomnia Scale (AIS), the Sleep Quality Index (SQI), or any combination thereof.

Improvement of a cognitive aspect of a subject may be achieved by the methods described herein. In some embodiments, neurostimulation via delivery of tES to the subject creates an improvement in cognition. In some embodiments, administration of the pharmacologic antidepressant agent and neurostimulation via delivery of tES to the subject creates a significant improvement in cognition. In some embodiments, depression or a depression-related condition in the subject has led to an impairment in an aspect of cognition in the subject. In some embodiments, a co-morbid condition of the subject carries with it an impairment in an aspect of cognition in the subject. In some embodiments, the co-morbid condition of the subject carries with it an impairment in an aspect of cognition is Alzheimer's disease, a cancer, coronary heart disease, acute coronary syndrome, diabetes, epilepsy, HIV/AIDS, hypothyroidism, multiple sclerosis, Parkinson's disease, stroke, systemic lupus erythematosus, rheumatoid arthritis, psoriasis, panic disorder, generalized anxiety disorder, obsessive-compulsive disorder, post-traumatic stress disorder, dementia, substance-abuse disorder, a psychotic disorder, anorexia nervosa, bulimia nervosa, muscle dysmorphia, binge eating disorder, compulsive over eating, polycystic ovary syndrome, Prader Willi syndrome, diabulimia, an autoimmune disorder, an inflammatory disorder, or a combination thereof. In some embodiments, cognitive function is improved in the subject during treatment. In some embodiments, cognitive function is improved in the subject following a period treatment. In some embodiments, cognitive function is significantly improved in the subject during treatment. In some embodiments, cognitive function is significantly improved in the subject following a period treatment. In some embodiments, one or more executive functions of the brain is improved in the subject. Executive functions refer to higher-level cognitive skills used to coordinate and control various other cognitive behaviors and abilities. Executive functions can refer to organization skills for gathering information and structuring said information for evaluation. Additionally, executive functions can refer to regulation skills that involve evaluating available information and modulating a response to a given environment. Organization skills falling under executive functions include attention, planning, sequencing, problem-solving, working memory, cognitive flexibility, abstract thinking, acquisition of rules, and selecting relevant sensory information. Regulation skills falling under executive functions include initiation of action, self-control, emotional regulation, monitoring internal stimuli, monitoring external stimuli, initiating and inhibiting context-specific behavior, moral and ethical reasoning, and decision-making. In some embodiments, attention is improved in the subject. In some embodiments, cognitive inhibition is improved in the subject. In some embodiments, inhibitory control is improved in the subject. In some embodiments, cognitive planning is improved in the subject. In some embodiments, working memory is improved in the subject. In some embodiments, emotional regulation is improved in the subject. In some embodiments, planning is improved in the subject. In some embodiments, sequencing is improved in the subject. In some embodiments, problem-solving is improved in the subject. In some embodiments, cognitive flexibility is improved in the subject. In some embodiments, abstract thinking is improved in the subject. In some embodiments, rule acquisition is improved in the subject. In some embodiments, initiation of action is improved in the subject. In some embodiments, self-control is improved in the subject. In some embodiments, initiating and inhibiting context-specific behavior is improved in the subject. In some embodiments, moral and ethical reasoning is improved in the subject. In some embodiments, decision-making is improved in the subject.

Co-Morbidities

A subject using a method of treatment described herein may have been diagnosed with a condition which carries a risk of depression as a co-morbidity. In some embodiments, the condition which carries a risk of depression as a co-morbidity may be an acute condition. In some embodiments, the condition which carries a risk of depression as a co-morbidity may be a chronic condition. In some embodiments, the condition which carries a risk of depression as a co-morbidity may be a neurological condition. In some embodiments, the condition which carries a risk of depression as a co-morbidity may be a personality disorder. In some embodiments, the condition which carries a risk of depression as a co-morbidity may be a metabolic condition. In some embodiments, the condition which carries a risk of depression as a co-morbidity may be an immune condition. In some embodiments, the condition which carries a risk of depression as a co-morbidity may be an inflammatory condition. In some embodiments, the condition which carries a risk of depression as a co-morbidity may be a genetic condition. In some embodiments, the condition which carries a risk of depression as a co-morbidity may be an environmentally-induced condition. In some embodiments, the condition which carries a risk of depression as a co-morbidity is one or more of Alzheimer's disease, a cancer, coronary heart disease, acute coronary syndrome, diabetes, epilepsy, HIV/AIDS, hypothyroidism, multiple sclerosis, Parkinson's disease, stroke, systemic lupus erythematosus, rheumatoid arthritis, psoriasis, chronic pain, neuropathic pain, panic disorder, generalized anxiety disorder, obsessive-compulsive disorder, post-traumatic stress disorder, dementia, substance-abuse disorder, a psychotic disorder, anorexia nervosa, bulimia nervosa, muscle dysmorphia, binge eating disorder, compulsive over eating, polycystic ovary syndrome, Prader Willi syndrome, diabulimia, an autoimmune disorder, or an inflammatory disorder. In some embodiments, the methods described herein allow for a therapeutic benefit of depression or a depression-related condition without a treatment-induced worsening of a co-morbid condition. In some embodiments, the methods described herein allow for a therapeutic benefit of depression or a depression-related condition without an interference of a treatment of a co-morbid condition. In some embodiments, the methods described herein allow for a therapeutic benefit of depression or a depression-related condition using a lower dosage of a pharmacologic antidepressant agent that may worsen a symptom of a co-morbid condition. In some embodiments, the methods described herein allow for a therapeutic benefit of depression or a depression-related condition using a lower dosage of a pharmacologic antidepressant agent that may interfere with a treatment of a co-morbid condition.

A subject using a method of treatment described herein may have one or more co-morbid conditions that are modulated by the method of treatment. In some embodiments, the one or more co-morbid conditions of the subject may be worsened by a method of treatment described herein. In some embodiments, the one or more co-morbid conditions of the subject may be improved by a method of treatment described herein. In some embodiments, the one or more co-morbid conditions of the subject may not be affected by a method of treatment described herein. In some embodiments, the improvement in the one or more co-morbid conditions by using the method of treatment may comprise an improvement in one or more symptoms of the co-morbid condition. In some embodiments, the one or more co-morbid conditions of the subject that may be improved by the method of treatment is selected from an anxiety disorder, a post-traumatic stress disorder, schizophrenia, chronic pain, neuropathic pain, an eating disorder, a conduct-dissocial disorder, a sleep disorder, a neurodevelopmental disorder, a personality disorder, a traumatic brain injury, a stroke, or an autoimmune disorder.

In some embodiments, the co-morbid sleep disorder improved by the method of treatment described herein is bruxism, central sleep apnea, chronic fatigue syndrome, a circadian rhythm sleep disorder, excessive sleepiness, hypersomnia, insomnia, narcolepsy, night terrors, non-24-hour sleep wake disorder, obstructive sleep apnea, parasomnia, periodic limb movements disorder, REM sleep behavior disorder, delayed sleep phase disorder, nocturia, rapid eye movement sleep behavior disorder, somniphobia, restless leg syndrome, shift work disorder, sleepwalking, sleep apnea, a sleep-related breathing disorder, a sleep-related movement disorder, sleep paralysis, or any combination thereof.

In some embodiments, the co-morbid personality disorder improved by the method of treatment described herein is paranoid personality disorder, schizoid personality disorder, schizotypal personality disorder, antisocial personality disorder, borderline personality disorder, histrionic personality disorder, narcissistic personality disorder, or avoidant personality disorder.

In some embodiments, the co-morbid eating disorder improved by the method of treatment described herein is anorexia nervosa, bulimia nervosa, muscle dysmorphia, binge eating disorder, compulsive overeating, diabulimia, orthorexia nervosa, selective eating disorder, drunkorexia, or pregorexia.

In some embodiments, the co-morbid neurodevelopmental disorder improved by the method of treatment described herein is attention-deficit/hyperactivity disorder (ADHD), a learning disability (e.g., dyslexia, dyspraxia, dyscalculia, or dysgraphia), an autism spectrum disorder, a communication disorder, cerebral palsy, a neurodevelopmental motor disorder, a developmental language disorder, a traumatic brain injury during a neurodevelopmental period, or a fetal alcohol spectrum disorder.

In some embodiments, the co-morbid autoimmune disorder improved by the method of treatment described herein is Addison disease, celiac disease, dermatomyositis, Graves' disease, multiple sclerosis, myasthenia gravis, pernicious anemia, reactive arthritis, rheumatoid arthritis, Sjogren syndrome, or systemic lupus erythematosus.

Transcranial Electrical Stimulation

Several methods of stimulation activity in the brain have been investigated which deliver either electrical or chemical stimuli to the brain. One such technique is termed transcranial magnetic stimulation (TMS) which in a non-invasive technique that involves placing a purpose-made electromagnetic coil against the scalp of a subject in order to induce electric currents in the brain using repetitive magnetic pulses. This treatment requires specialist equipment and medical supervision and is therefore not suitable for home use.

Electroconvulsive therapy (ECT) is a technique in which a strong electrical current (generally around 800 mA) is passed through the brain of the subject to produce a convulsion or seizure. To minimize discomfort, ECT is administered under general anesthesia. Immediately after treatment, many subjects receiving ECT experience headache, muscle aches, and temporary amnesia about the period just prior to the ECT. Confusion may also occur following ECT treatment, mostly in elderly subjects, and may last for user to 3 days. Long-term memory dysfunction has also been reported in subjects undergoing ECT. Because of its procedures and requirements for medical supervision, ECT is an expensive, labor-intensive treatment, which requires the care of medical practitioners and the use of medical facilities by the subject. Deep brain stimulation (DBS) is another technique used to stimulate the brain of subjects. DBS involves a neurosurgical procedure for placement of a device called a neurostimulator, which sends electrical impulses, through implanted electrodes, to specific targets deep in the brain. DBS has been used to target particular brain nuclei in order to provide a means to treat disorders such as dystonia, Parkinson's disease, essential tremor, and epilepsy. As it involves a surgical procedure, DBS carries with it the risks of major surgery and surgical complications such as hemorrhage and infection. Other potential risk of DBS treatments include neuropsychiatric side effects such as apathy, hallucinations, hypersexuality, cognitive dysfunction, depression, and euphoria. In contract to TMS, ECT, and DBS, transcranial electrical stimulation (tES) offers an alternative form of neurostimulation that is non-invasive, cost-effective, can be conducted by the subject at home, and carries with it a minimal risk profile of potential side effects.

tES is a non-invasive brain stimulation technique which passes an electrical current through the brain in order to alter brain function. tES works by inducing neuromodulation that alters neural activity through the targeted delivery of an electrical stimulus. Electrical current is applied to a subject's scalp usually via two or more electrodes, and whilst a large amount of the current applied is conducted between electrodes through outer layers of soft tissue and the skull, a portion of the current has been shown to penetrate the scalp and skull and be conducted through the brain tissue. Through this means of conducting small electrical current through the brain, neuronal excitability of the subject can be altered. Placement of the two or more electrodes used for tES can affect nearby brain tissue by neuromodulatory intervention which alters neural activity by targeted delivery of a stimulus. In contract to some other brain stimulation techniques, the current delivered in tES is not powerful enough to elicit action potentials and is maintained at subthreshold levels to effect neuronal excitability only. tES may alter neuronal oscillations in neural networks and regulate functional connectivity between brain regions. Examples of tES include transcranial direct current stimulation (tDCS), transcranial alternating current stimulation (tACS) and transcranial random noise stimulation (tRNS).

tDCS utilizes a direct current that is delivered at low intensities through one or more active electrodes (anode). In some embodiments, the electrical intensities used in tDCS are between 0.5-4 mA. In some embodiments, the electrical intensities used in tDCS are between 0.5-2 mA. In some embodiments, the electrical intensities used in tDCS are between 0.8-2 mA. In some embodiments, the electrical intensities used in tDCS are between 1.0-2.0 mA. In some embodiments, the electrical intensity output used in tDCS is about 0.5 mA. In some embodiments, the electrical intensity output used in tDCS is about 0.6 mA. In some embodiments, the electrical intensity output used in tDCS is about 0.7 mA. In some embodiments, the electrical intensity output used in tDCS is about 0.8 mA. In some embodiments, the electrical intensity output used in tDCS is about 0.9 mA. In some embodiments, the electrical intensity output used in tDCS is about 1.0 mA. In some embodiments, the electrical intensity output used in tDCS is about 1.1 mA. In some embodiments, the electrical intensity output used in tDCS is about 1.2 mA. In some embodiments, the electrical intensity output used in tDCS is about 1.3 mA. In some embodiments, the electrical intensity output used in tDCS is about 1.4 mA. In some embodiments, the electrical intensity output used in tDCS is about 1.5 mA. In some embodiments, the electrical intensity output used in tDCS is about 1.6 mA. In some embodiments, the electrical intensity output used in tDCS is about 1.7 mA. In some embodiments, the electrical intensity output used in tDCS is about 1.8 mA. In some embodiments, the electrical intensity output used in tDCS is about 1.9 mA. In some embodiments, the electrical intensity output used in tDCS is about 2.0 mA. In some embodiments, the electrical intensity output used in tDCS is about 2.1 mA. In some embodiments, the electrical intensity output used in tDCS is about 2.2 mA. In some embodiments, the electrical intensity output used in tDCS is about 2.3 mA. In some embodiments, the electrical intensity output used in tDCS is about 2.4 mA. In some embodiments, the electrical intensity output used in tDCS is about 2.5 mA. When applying a current in tDCS, the direction of current flow is from a positive voltage (anode) to a negative voltage (cathode). This net one-way flow of electrical stimulus in tDCS modulates neuronal excitability by usually increasing excitability in neurons closer to the anodal electrode and usually decreasing excitability in neurons closer to the cathodal electrode. Since the electrical field utilized in tDCS is subthreshold, it is capable of modifying neuronal transmembrane potentials and modulating neuronal excitability, thereby bringing certain neurons closer to or farther away from their firing potential without initiating action potentials. In some embodiments, tDCS delivers a current of about +/−0.5 mA, +/−0.6 mA, +/−0.7 mA, +/−0.8 mA, +/−0.9 mA, +/−1.0 mA, +/−1.1 mA, +/−1.2 mA, +/−1.3 mA, +/−1.4 mA, +/−1.5 mA, +/−1.6 mA, +/−1.7 mA, +/−1.8 mA, +/−1.9 mA, +/−2.0 mA, +/−2.1 mA, +/−2.2 mA, +/−2.3 mA, +/−2.4 mA, +/−2.5 mA, +/−2.6 mA, +/−2.7 mA, +/−2.8 mA, +/−2.9 mA, +/−3.0 mA, +/−3.1 mA, +/−3.2 mA, +/−3.3 mA, +/−3.4 mA, +/−3.5 mA, +/−3.6 mA, +/−3.7 mA, +/−3.8 mA, +/−3.9 mA, +/−4.0 mA, +/−4.5 mA, or +/−5.0 mA to the subject during the one or more of non-invasive brain stimulation sessions. In some embodiments, the level of current delivered in a strengthening phase is less than a level of current delivered in an activation phase. In some embodiments, the level of current delivered in a strengthening phase is about 0.1 mA, 0.2 mA, 0.3 mA, 0.4 mA, 0.5 mA, 0.6 mA, 0.7 mA, 0.8 mA, 0.9 mA, 1 mA, 1.1 mA, 1.2 mA, 1.3 mA, 1.4 mA, 1.5 mA, 1.6 mA, 1.7 mA, 1.8 mA, 1.9 mA, 2 mA, 2.1 mA, 2.2 mA, 2.3 mA, 2.4 mA, or 2.5 mA less than a level of current delivered in an activation phase.

tDCS electrodes can be placed anywhere on the scalp of the subject. In most scalp locations, the closest brain tissue will be an area of cerebral cortex. In some embodiments, tES device with the first electrode and the second in close proximity to or touching the forehead of the subject may be used. tDCS has been put forward as a technique for targeted neuromodulation of the cerebral cortex. Changes in the tDCS electrode placement, also called montage, change the distribution of the induced electrical fields in the brain. Different montages may be used depending on the indication to be targeted in the subject. In some embodiments, the frontal lobes of the brain of the subject are stimulated to elicit neuromodulation. In some embodiments, the parietal lobes of the brain of the subject are stimulated to elicit neuromodulation. In some embodiments, the temporal lobes of the brain of the subject are stimulated to elicit neuromodulation. In some embodiments, a montage that targets the prefrontal cortex can be used in a method to treat depression. In some embodiments, the montage targets the prefrontal cortex of the subject stimulates the prefrontal cortex to elicit neuromodulation. In some embodiments, a montage that targets the dorsolateral prefrontal cortex (DLPFC) can be used in a method to treat depression. In some embodiments, the montage targets the DLPFC of the subject stimulates the DLPFC to elicit neuromodulation. In some embodiments, neural activity in the DLPFC increases at a time point following the one or more of non-invasive brain stimulation sessions. In some embodiments, functional connectivity is increased between the DLPFC and the orbitofrontal cortex, the thalamus, the dorsal caudate nucleus, the hippocampus, one or more primary association areas of the neocortex, or one or more secondary association areas of the neocortex, or any combination thereof. In some embodiments, neuroplasticity in the brain of the subject increases. In some embodiments, administering to the subject a pharmacologic antidepressant agent and delivering to the subject a tDCS leads to an improvement in one or more symptoms of depression or a depression-related condition in the subject.

When applying a current in tDCS, negatively charged ions travel from a cathode to an anode. In some embodiments described herein, neural cell bodies and axons below an anodal electrode used in tDCS tend to become depolarized. In some embodiments described herein, neural cell bodies and axons below an cathodal electrode used in tDCS tend to become hyper-polarized. These results in depolarization and hyper-polarized rely in part on the orientation of the neurons. As many pyramidal neurons near a surface to which a tDCS anode is applied may be oriented parallel to a direction of current, these pyramidal neurons may become depolarized following a tDCS session. As many pyramidal neurons near a surface to which a tDCS cathode is applied may be oriented parallel to a direction of current, these pyramidal neurons may become hyper-polarized following a tDCS session. As such, neurons near an anode or a cathode of a tDCS session will be exposed to different directions of current flow. It should be noted that due to the gyri and sulci of the cerebral cortex, columnar-oriented pyramidal neurons in different cortical areas will vary in their respective orientations toward any directional flow of current in tDCS depending on the particular location within a gyrus or sulcus. In some embodiments, anodal tDCS leads to the soma of nearby neurons becoming depolarized and the apical dendrite becoming hyper-polarized which generally increases excitability. In some embodiments, cathodal tDCS leads to the soma of nearby neurons becoming hyper-polarized and the apical dendrite becoming depolarized which generally decreases excitability. In some embodiments, anodal tDCS leads to nearby interneurons becomes depolarized. In some embodiments, cathodal tDCS leads to nearby interneurons becomes hyper-polarized. In some embodiments, pyramidal cells of the cerebral cortex exhibit cell bodies and axons which become depolarized. In some embodiments, pyramidal cells of the cerebral cortex exhibit cell bodies and axons which become hyper-polarized. In some embodiments, pyramidal cells of the cerebral cortex exhibit apical dendrites which become depolarized. In some embodiments, pyramidal cells of the cerebral cortex exhibit apical dendrites which become hyper-polarized. In some embodiments, conventional tDCS uses larger conducting pads to produce a diffuse flow through the brain and thereby not stimulating a particular gyrus of the cerebral cortex. In some embodiments, at the level of a single gyrus of the cerebral cortex, tDCS current will flow in and out of the various orientation of cells within the gyrus creating a striped pattern of neurostimulation. In some embodiments, high definition tDCS (hd tDCS) may be used to focus neurostimulation in particular cortical areas. In some embodiments, a multi-electrode array may be used to focus neurostimulation in a plurality of cortical areas. In some embodiments, in conventional tDCS, a goal of neuromodulation is termed circuit therapeutics. In circuit therapeutics, multiple nodes in the brain are stimulated in aggregate and the outcome seen in the subject is the effect of stimulating different brain regions. When applying the same tDCS across a population, aggregate response reflect individual variability (e.g., differences of anatomy such as brain and skull size and shape). In some embodiments, tDCS may make the brain of the subject more responsive to TMS. In some embodiments, the effects of tDCS are specific to particular neural network pathways. In some embodiments, the effects of tDCS depend on the particular size of the electrodes used, the exact placement of the electrodes on the surface of the scalp, the electrical intensity of the tDCS session, the duration of the tDCS session, the frequency of tDCS sessions delivered to the subject, the state of connectivity within various neural networks of the subject at the time of tDCS, and the overall state of depolarization and hyperpolarization of cortical cells in the subject.

tACS operates by applying a low-intensity sinusoidal electrical current to the brain of the subject through electrodes on the scalp. In several aspects, tACS operates as a neuromodulatory technique in a similar manner as tDCS, but instead of applying a direct electrical current, tACS oscillates a sinusoidal current as a selected frequency. In some embodiments, tACS interacts with the natural cortical oscillations in the brain of the subject. In some embodiments, a large electrode is placed over an area of interest in the brain of the subject and the large electrode applies stimulation while a reference electrode is place in a neural location in the subject. In some embodiments, when a single low frequency tACS stimulation is applied, this exogenous oscillation may synchronize with the endogenous frequency of the brain of the subject. In some embodiments, when several oscillations of tACS are pulsated, desynchronization of cortical oscillations may occur. In some embodiments, tACS effects depend on the frequency, amplitude, and phase of the electrical stimulation applied. In some embodiments, tACS is applied in the EEG frequency range of 0.1 to 80 Hz and may entrain neural oscillations and enhance neural oscillations. In some embodiments, higher frequency oscillations of tACS in the range of 1 to 5 kHz are less likely to induce oscillation interactions but may induce cortical excitability. In some embodiments, administering to the subject a pharmacologic antidepressant agent and delivering to the subject a tACS leads to an improvement in one or more symptoms of depression or a depression-related condition in the subject.

tRNS is a non-invasive electrical stimulation of the brain whereby a weak alternating current oscillating at random frequencies is delivered through the scalp of the subject using two or more electrodes. In some embodiments, a frequency band used in tRNS encompasses a range of 0.1 to 640 Hz. In some embodiments, tRNS can be delivered to the subject at a low frequency range of between about 0.1 to 100 Hz. In some embodiments, tRNS can be delivered to the subject at a high frequency range of between about 101 to 640 Hz. In some embodiments, delivery of tRNS to the subject improves motor tasks. In some embodiments, delivery of tRNS to the subject improves sensory tasks. In some embodiments, delivery of tRNS to the subject improves cognitive tasks. In some embodiments, the improvement in sensory tasks comprises an improvement in sensory or perceptual processing. In some embodiments, delivery of tRNS to the subject improves pain associated with a co-morbid condition. In some embodiments, the co-morbid condition is multiple sclerosis. In some embodiments, delivery of tRNS to the subject improves depressive symptoms in schizophrenia. In some embodiments, delivery of tRNS to the subject improves perceptual and motor learning. In some embodiments, administering to the subject a pharmacologic antidepressant agent and delivering to the subject a tRNS leads to an improvement in one or more symptoms of depression or a depression-related condition in the subject.

tES in a single session can be delivered to a subject for an amount of time sufficient to elicit neuromodulation. The length of time sufficient to elicit neuromodulation may depend on a number of factors including the type of tES utilized, the electrical intensity, the size and positioning and conductivity of electrodes used, the neurological condition of the subject, the psychological condition of the subject, the pathological condition of the subject, distinct features of the neural networks of the subject being stimulation, the time of day of the session, the latency since the previous tES session, the sum of the number of tES sessions recently delivered to the subject, the sum of the lengths of time of tES sessions recently delivered to the subject, and synergistic effects with a pharmacologic antidepressant agent administered to the subject. In some embodiments, each non-invasive brain stimulation sessions delivers tES to the subject for a duration of between about 1-50 minutes. In some embodiments, each of the one or more of non-invasive brain stimulation sessions deliver tES to the subject for a duration of at least about 1 minute, 2 minutes, 3 minutes, 4 minutes, 5 minutes, 6 minutes, 7 minutes, 8 minutes, 9 minutes, 10 minutes, 11 minutes, 12 minutes, 13 minutes, 14 minutes, 15 minutes, 16 minutes, 17 minutes, 18 minutes, 19 minutes, 20 minutes, 21 minutes, 22 minutes, 23 minutes, 24 minutes, 25 minutes, 26 minutes, 28 minutes, 29 minutes, 30 minutes, 31 minutes, 32 minutes, 33 minutes, 34 minutes, 35 minutes, 40 minutes, 45 minutes, or 50 minutes. In some embodiments, each of the one or more of non-invasive brain stimulation sessions deliver tES to the subject for a duration of less than about 1 minute, 2 minutes, 3 minutes, 4 minutes, 5 minutes, 6 minutes, 7 minutes, 8 minutes, 9 minutes, 10 minutes, 11 minutes, 12 minutes, 13 minutes, 14 minutes, 15 minutes, 16 minutes, 17 minutes, 18 minutes, 19 minutes, 20 minutes, 21 minutes, 22 minutes, 23 minutes, 24 minutes, 25 minutes, 26 minutes, 28 minutes, 29 minutes, 30 minutes, 31 minutes, 32 minutes, 33 minutes, 34 minutes, 35 minutes, 40 minutes, 45 minutes, or 50 minutes. In some embodiments, a duration of tES sessions delivered to the subject in a strengthening phase is less than a duration of tES sessions delivered to the subject in an activation phase. In some embodiments, a duration of tES sessions delivered to the subject in a strengthening phase is 1, 2, 3, 4, 5, 6, 7, 8, 9, 10, 11, 12, 13, 14, 15, 16, 17, 18, 19, 20, 21, 22, 23, 24, 25, 26, 27, 28, 29, or 30 minutes less than a duration of tES sessions delivered to the subject in an activation phase. In some embodiments, current is delivered continuously during a duration of the one or more of non-invasive brain stimulation sessions.

tES sessions can be delivered to a subject with a frequency sufficient to elicit neuromodulation. The frequency of tES sufficient to elicit neuromodulation may depend on a number of factors including the type of tES utilized, the electrical intensity, the size and positioning and conductivity of electrodes used, the neurological condition of the subject, the psychological condition of the subject, the pathological condition of the subject, distinct features of the neural networks of the subject being stimulation, the time of day of sessions, the latency since the previous tES session, the sum of the number of tES sessions recently delivered to the subject, the sum of the lengths of time of tES sessions recently delivered to the subject, and synergistic effects with a pharmacologic antidepressant agent administered to the subject. In some embodiments, the methods comprise an activation phase. In some embodiments, the activation phase will last for a duration of between 1 to 3 weeks. In some embodiments, the activation phase will last for a duration of between 1 to 6 weeks. In some embodiments, the methods comprise a strengthening phase. In some embodiments, the strengthening phase will begin at week 2 of treatment In some embodiments, the strengthening phase will begin at week 3 of treatment In some embodiments, the strengthening phase will begin at week 4 of treatment. In some embodiments, the strengthening phase will begin at week 5 of treatment In some embodiments, the strengthening phase will begin at week 6 of treatment In some embodiments, the strengthening phase will begin at week 7 of treatment. In some embodiments, the strengthening phase will last from between about week 2 to 7 of treatment until the subject has achieved a desired treatment outcome. In some embodiments, the strengthening phase will last from about week 2 to 7 of treatment until one or more symptoms of depression have shown improvement. In some embodiments, the strengthening phase will last from about week 2 to 7 of treatment until one or more symptoms of depression have shown remission. In some embodiments, the subject undergoes the one or more of non-invasive brain stimulation sessions with a frequency of twice every day, once every 18 hours, once every day, once every 36 hours, once every other day, 6 times per week, 5 times per week, 4 times per week, 3 times per week, 2 times per week, 1 time per week, or 1 time every two weeks. In some embodiments, the activation phase comprises delivery of at least 3 tES sessions to the subject per week. In some embodiments, the activation phase comprises delivery of at least 4 tES sessions to the subject per week. In some embodiments, the activation phase comprises delivery of at least 5 tES sessions to the subject per week. In some embodiments, the activation phase comprises delivery of at least 6 tES sessions to the subject per week. In some embodiments, the activation phase comprises delivery of at least 7 tES sessions to the subject per week. In some embodiments, the activation phase comprises delivery of at least 8 tES sessions to the subject per week. In some embodiments, the activation phase comprises delivery of at least 9 tES sessions to the subject per week. In some embodiments, the activation phase comprises delivery of at least 10 tES sessions to the subject per week. In some embodiments, the strengthening phase comprises delivery of at least 1 tES session to the subject every other week. In some embodiments, the strengthening phase comprises delivery of at least 1 tES session to the subject per week. In some embodiments, the strengthening phase comprises delivery of at least 3 tES sessions to the subject every other week. In some embodiments, the strengthening phase comprises delivery of at least 2 tES sessions to the subject per week. In some embodiments, the strengthening phase comprises delivery of at least 3 tES sessions to the subject per week. In some embodiments, the strengthening phase comprises delivery of at least 4 tES sessions to the subject per week. In some embodiments, the strengthening phase comprises delivery of at least 5 tES sessions to the subject per week. In some embodiments, the strengthening phase comprises delivery of at least 6 tES sessions to the subject per week. In some embodiments, the strengthening phase comprises delivery of at least 7 tES sessions to the subject per week. In some embodiments, the activation phase comprises delivery of at least between 1-10 tES sessions to the subject through three weeks of treatment. In some embodiments, the activation phase comprises delivery of at least between 11-14 tES sessions to the subject through three weeks of treatment. In some embodiments, the activation phase comprises delivery of at least between 15-16 tES sessions to the subject through three weeks of treatment. In some embodiments, the activation phase comprises delivery of more than 16 tES sessions to the subject through three weeks of treatment. In some embodiments, the methods comprise delivery of at least between 1-10 tES sessions to the subject through six weeks of treatment. In some embodiments, the methods comprise delivery of at least between 11-15 tES sessions to the subject through six weeks of treatment. In some embodiments, the methods comprise delivery of at least between 16-20 tES sessions to the subject through six weeks of treatment. In some embodiments, the methods comprise delivery of 21 or more tES sessions to the subject through six weeks of treatment. In some embodiments, the methods comprise delivery of 20 tES sessions or fewer to the subject through ten weeks of treatment. In some embodiments, the methods comprise delivery of between 21-24 tES sessions to the subject through ten weeks of treatment. In some embodiments, the methods comprise delivery of between 25-28 tES sessions to the subject through ten weeks of treatment. In some embodiments, the methods comprise delivery of 29 or more tES sessions to the subject through ten weeks of treatment. In some embodiments, the methods comprise delivery of 30 tES sessions or fewer to the subject through 25 weeks of treatment. In some embodiments, the methods comprise delivery of between 31-58 tES sessions to the subject through 25 weeks of treatment. In some embodiments, the methods comprise delivery of 59 or more tES sessions to the subject through 25 weeks of treatment. In some embodiments, the methods comprise delivery of between 1-6 tES sessions to the subject through 8 weeks of treatment. In some embodiments, the methods comprise delivery of between 7-8 tES sessions to the subject through 8 weeks of treatment. In some embodiments, the methods comprise delivery of between 9-10 tES sessions to the subject through 8 weeks of treatment. In some embodiments, the methods comprise delivery of between 11-12 tES sessions to the subject through 8 weeks of treatment. In some embodiments, the methods comprise delivery of between 13-14 tES sessions to the subject through 8 weeks of treatment. In some embodiments, the methods comprise delivery of between 15-16 tES sessions to the subject through 8 weeks of treatment.

In some embodiments, the methods comprise delivery of tES to the subject about 5 times per week. In some embodiments, the methods comprise delivery of tES to the subject about 5 times per week for at least 3 weeks. In some embodiments, the methods comprise delivery of tES to the subject about 5 times per week for at least 3 weeks, after which the tES is delivered to the subject about 3 times per week for at least 7 weeks. In some embodiments, the methods comprise delivery of tES to the subject about 5 times per week for at least 3 weeks, after which the tES is delivered to the subject about 3 times per week for at least 7 weeks, wherein the tES is not delivered to the subject more than 36 times in a 10-week period and/or the tES is not delivered to the subject more than 5 times per week. In some embodiments, the methods comprise delivery of tES to the subject about 5 times per week for at least 3 weeks, after which the tES is delivered to the subject about 3 times per week for at least 7 weeks, wherein the tES is not delivered to the subject more than 36 times in a 10-week period and the tES is not delivered to the subject more than 5 times per week. In some embodiments, the methods comprise delivery of tES to the subject about 5 times per week for at least 3 weeks, after which the tES is delivered to the subject about 3 times per week for at least 7 weeks, wherein the tES is not delivered to the subject more than 36 times in a 10-week period or the tES is not delivered to the subject more than 5 times per week. In some embodiments, the methods comprise delivery of tES to the subject about 5 times per week for at least 3 weeks, after which the tES is delivered to the subject about 3 times per week for at least 7 weeks, wherein the tES is not delivered to the subject more than 36 times in a 10-week period. In some embodiments, the methods comprise delivery of tES to the subject about 5 times per week for at least 3 weeks, after which the tES is delivered to the subject about 3 times per week for at least 7 weeks, wherein the tES is not delivered to the subject more than 5 times per week.

In some embodiments, the methods comprise delivery of tES to the subject no more than 1 time per day. In some embodiments, the methods comprise delivery of tES to a subject no more than 5 times per week. In some embodiments, the methods comprise delivery of tES to the subject no more than 5 times per week and tES is no more than 1 time per day. In some embodiments, the methods comprise delivery of tES to a subject no more than 36 times in a 10-week period. In some embodiments, the methods comprise delivery of tES to the subject no more than 36 times in a 10-week period and no more than 5 times per week. In some embodiments, the methods comprise delivery of tES to the subject no more than 36 times in a 10-week period or no more than 5 times per week. In some embodiments, the methods comprise delivery of tES to the subject no more than 36 times in a 10-week period and tES is not delivered to the subject more than 5 times per week and tES is not delivered to the subject more than 1 time per day. In some embodiments, the methods comprise delivery of tES to the subject about 5 times per week for at least 3 weeks, after which the tES is delivered to the subject about 3 times per week for at least 7 weeks, wherein the tES is not delivered to the subject more than 5 times per week and the tES is not delivered to the subject more than 1 time per day. In some embodiments, the methods comprise delivery of tES to the subject about 5 times per week for at least 3 weeks, after which the tES is delivered to the subject about 3 times per week for at least 7 weeks, wherein the tES is not delivered to the subject more than 36 times in a 10-week period and the tES is not delivered to the subject more than 5 times per week and the tES is not delivered to the subject more than 1 time per day.

In some embodiments, adherence to delivery of a number of tES sessions to the subject in the activation phase results in a greater improvement in one or more symptoms of depression. In some embodiments, the number of tES sessions in the activation phase required for greater improvement in one or more symptoms of depression is at least 3, 4, 5, 6, 7, 8, 9 or 10 sessions per week. In some embodiments, adherence to delivery of a number of tES sessions to the subject in the strengthening phase results in a greater improvement in one or more symptoms of depression. In some embodiments, the number of tES sessions in the strengthening phase required for greater improvement in one or more symptoms of depression is at least 0, 1, 2, 3, 4, 5, 6 or 7 sessions per week. In some embodiments, the subject undergoes the one or more of non-invasive brain stimulation sessions according to a schedule of an initial activation phase with a frequency of twice every day, once every 18 hours, once every day, once every 36 hours, once every other day, 6 times per week, 5 times per week, 4 times per week, 3 times per week, 2 times per week, 1 time per week, or 1 time every two weeks. In some embodiments, the subject undergoes the one or more of non-invasive brain stimulation sessions according to a schedule of a secondary strengthening phase with a frequency of twice every day, once every 18 hours, once every day, once every 36 hours, once every other day, 6 times per week, 5 times per week, 4 times per week, 3 times per week, 2 times per week, 1 time per week, or 1 time every two weeks. In some embodiments, the initial activation phase lasts for a period of time about 3 days, 4 days, 5 days, 6 days, 7 days, 8 days, 9 days, 10 days, 11 days, 12 days, 13 days, 2 weeks, 3 weeks, 4 weeks, 5 weeks, 6 weeks, 7 weeks, 8 weeks, 9 weeks, 10 weeks, 11 weeks, 12 weeks, 13 weeks, 14 weeks, 15 weeks, 16 weeks, 17 weeks, 18 weeks, 19 weeks, or 20 weeks. In some embodiments, secondary strengthen phase begins a period of time about 3 days, 4 days, 5 days, 6 days, 7 days, 8 days, 9 days, 10 days, 11 days, 12 days, 13 days, 2 weeks, 3 weeks, 4 weeks, 5 weeks, 6 weeks, 7 weeks, 8 weeks, 9 weeks, 10 weeks, 11 weeks, 12 weeks, 13 weeks, 14 weeks, 15 weeks, 16 weeks, 17 weeks, 18 weeks, 19 weeks, 20 weeks, 21 weeks, 22 weeks, 23 weeks, 24 weeks, or 25 weeks after completion of the initial activation phase. In some embodiments, the subject completes at least 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, or 70 of the one or more of non-invasive brain stimulation sessions. In some embodiments, a subject having moderate depression shows a significant decrease in MADRS-s following at least 6 weeks of tDCS treatment comprising at least 21 of the non-invasive brain stimulation sessions. In some embodiments, a subject having moderate depression shows a significant decrease in MADRS-S following at least 10 weeks of tDCS treatment comprising at least 21 of the non-invasive brain stimulation sessions. In some embodiments, a subject having severe depression shows a significant decrease in MADRS-S following at least 6 weeks of tDCS treatment comprising at least 21 of the non-invasive brain stimulation sessions. In some embodiments, a subject having severe depression shows a significant decrease in MADRS-s following at least 10 weeks of tDCS treatment comprising at least 21 of the non-invasive brain stimulation sessions. In some embodiments, a subject having depression being administered sertraline as part of a treatment regimen and following at least 6 weeks of tDCS treatment comprising at least 21 of the non-invasive brain stimulation sessions shows a significant decrease in MADRS-S. In some embodiments, the significant decrease in MADRS-s in the subject administered sertraline is greater than a decrease in MADRS-s in a second subject being administered fluoxetine as part of a treatment regimen and following at least 6 weeks of tES treatment comprising at least 21 of the non-invasive brain stimulation sessions. In some embodiments, administering to the subject a pharmacologic antidepressant agent and delivering to the subject a plurality of tDCS sessions in an activation phase and continue deliver to the subject a plurality of tDCS sessions in a strengthening phase provides a sufficient improvement in one or more symptoms of depression to achieve a desired treatment outcome of the subject. In some embodiments, administering to the subject a pharmacologic antidepressant agent and delivering to the subject a plurality of tDCS sessions in an activation phase and continue deliver to the subject a plurality of tDCS sessions in a strengthening phase provides a remission in one or more symptoms of depression to achieve a desired treatment outcome of the subject. In some embodiments, administering to the subject a pharmacologic antidepressant agent and delivering to the subject a plurality of tDCS sessions in an activation phase and continue deliver to the subject a plurality of tDCS sessions in a strengthening phase allows for an assessment of a response of the subject to a treatment regimen and enables an ability to adjust parameters of administering of the pharmacologic antidepressant agent and of delivering of the plurality of tDCS sessions to the subject to achieve to a desired treatment outcome.

tES can be delivered to the subject by a variety of neurostimulation devices. In some embodiments, the tES device comprises a transcranial direct current stimulation (tDCS) device. In some embodiments, the tES device comprises a transcranial alternating current stimulation (tACS) device. In some embodiments, the tES device comprises a transcranial random noise stimulation (tRNS) device. In some embodiments, the tES device is configurated as a headset comprising a circuit comprising a first electrode, a second electrode, and a power source configured to provide power to the circuit. In some embodiments, the tES device further comprises a wireless transceiver configured to wirelessly communicate with an electronic device having processing capabilities and a controller being configured to control powering of the circuit according to a control signal for the headset such that transcranial brain stimulation is performed according to a schedule for performing the transcranial brain stimulation. In some embodiments, the headset further comprises a memory configured to store the schedule for performing the transcranial brain stimulation. In some embodiments, the electronic device having processing capabilities comprises a non-transitory computer-readable recording medium having recorded thereon a program which is executable on the electronic device wherein the program comprises program code portions which when executed on the electronic device is configured to: store, in a computer memory, a schedule for performing the transcranial brain stimulation, generate and maintain the control signal according to the schedule for performing the transcranial brain stimulation, and display information on a display of the electronic device in accordance with a schedule for displaying information, wherein the schedule for displaying information is related to the schedule for performing the transcranial brain stimulation. In some embodiments, the headset further comprises a forehead frame, the forehead frame defining an elongated arch; the first electrode arranged at a first end portion of the elongated arched forehead frame; the second electrode arranged at a second end portion of the elongated arched forehead frame; and a bracket fixedly fastened at a center portion of the elongated arched forehead frame, the elongated arched forehead frame is configured to support the bracket. In some embodiments, wherein upon use of the headset in delivering concurrently to the subject one or more of non-invasive brain stimulation sessions, the elongated arched forehead frame is configured such that the first electrode is located at a left side of a forehead of the subject, and such that the second electrode is located at a right side of the forehead of the subject, and the bracket is configured to extend from the elongated arched forehead frame over the skull of the subject towards a neck portion of the subject. In some embodiments, the program further comprises program code portions which when executed on the electronic device is configured to prompt the subject to input information pertaining to status of the subject wherein the information pertaining to status of the subject comprises information pertaining to information about the subject's current health. In some embodiments, the program further comprises program code portions which when executed on the electronic device is configured to store information pertaining to performed transcranial brain stimulation on a computer memory. In some embodiments, the program further comprises program code portions which when executed on the electronic device is configured to remind the subject to use the headset according to the schedule for performing the transcranial brain stimulation. In some embodiments, the program further comprises program code portions which when executed on the electronic device is configured to update the schedule for performing the transcranial brain stimulation. In some embodiments, the headset further comprises the first and second electrodes being pivotable such that they can adapt to a shape of the forehead of the subject. In some embodiments, the headset further comprises the first and second electrodes having an adhesive layer configured such that the adhesive layer adheres to the forehead of the subject. In some embodiments, the bracket has a longitudinal extension which, when the headset is used, extends from the forehead of the subject towards the back of the subject's head and wherein the bracket has a variable extension from the forehead frame. In some embodiments, the bracket further comprises a support cushion arranged at an end portion of the bracket being opposite to where the bracket is fastened at the forehead frame and wherein the forehead frame is a single member shaped as an elongated arch. In some embodiments, the prompt of the subject to input information pertaining to information about the subject's current health comprises displaying a self-assessment MADRS-S questionnaire to the subject and the subject completing the questionnaire and having results from the completed questionnaire stored in a computer memory of the electronic device. In some embodiments, the electronic device is a handheld device.

Figure 9:
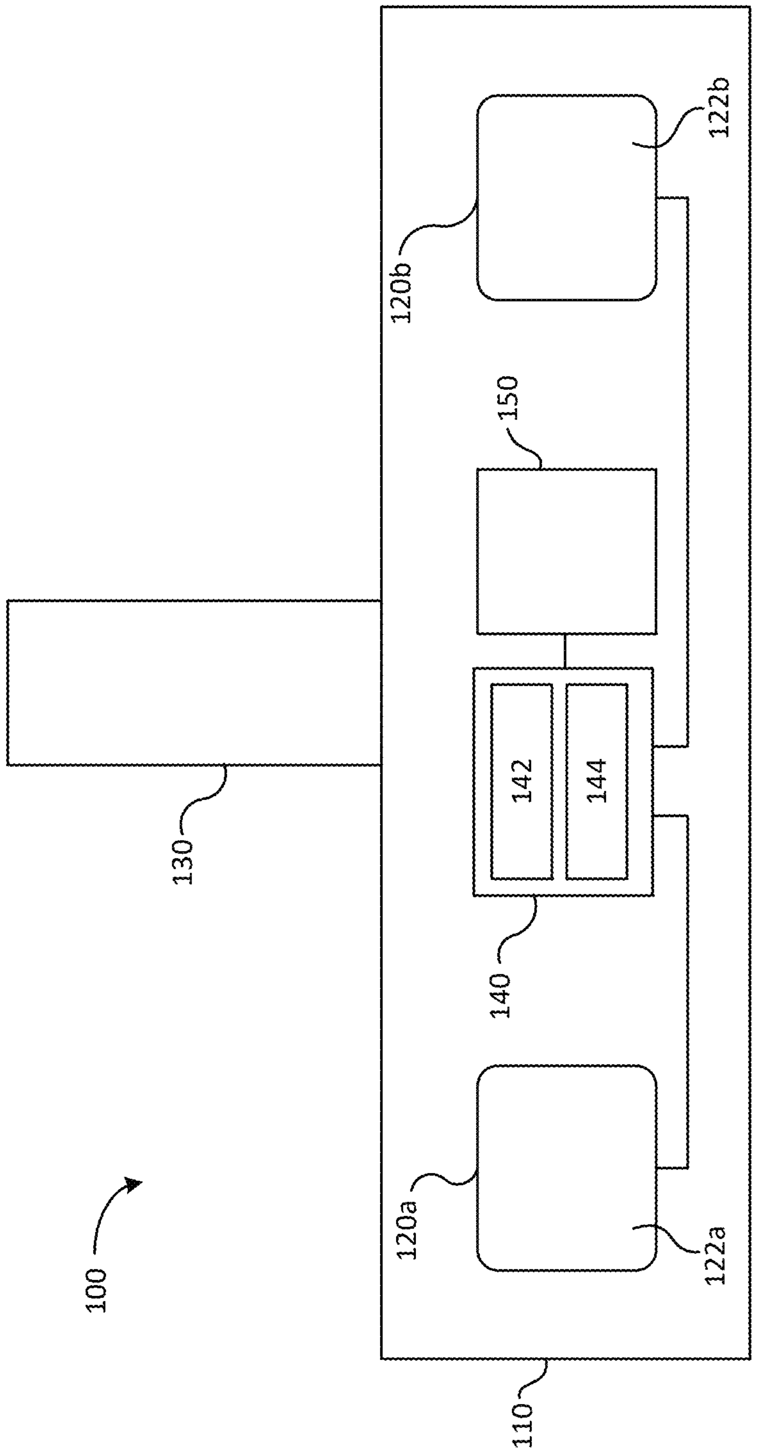
FIG. 9 schematically depicts a device 100 for delivering tES, according to embodiments.

FIG. 9 is a schematic block diagram depicting an example of a transcranial stimulation device 100 for delivering tES such as, for example, tDCS according to any of the methods described herein. The device 100 can be configured to implement protocols for delivering tES, as described in the studies below. As shown, the device 100 may include a pair of electrodes 120*a*, 120*b* coupled to a frame 110 configured to fit across a forehead of a user. In some embodiments a first electrode 120*a* from the pair of electrodes may be coupled to an inner surface of the frame 110 on a first end of the frame 110 such that the electrode 120*a* is configured to be disposed on a first side of the forehead. The second electrode 120*b* from the pair of electrodes may be coupled to an inner surface of the frame 110 on a second end of the frame 110 such that the second electrode 120*b* is configured to be disposed on a second side of the forehead.

In some embodiments, the device 100 includes a support member (e.g., a bracket) 130 coupled to the frame 110 and configured to secure the frame 110 across the forehead of the user. In some embodiments, the bracket 130 may extend longitudinally from the frame 110, over a top of the head of the user, toward a back of the head of the user to support the frame when fitted across the forehead to ensure that the first electrode 120*a* and the second electrode 120*b* are disposed on the first and second sides of the forehead. In some embodiments, the bracket 130 may prevent a user from wearing the device 100 incorrectly. For example, the bracket 130 may prevent the user from wearing the device 100 in an incorrect orientation (e.g., upside down). In other words, the bracket 130 can be configured to extend over a head of the subject to ensure that the frame is worn in a predefined orientation by the subject. The bracket 130 may prevent the user from wearing the device 100 with the electrodes 120*a*, 120*b* positioned over incorrect cortical targets. In some embodiments, the bracket 130 may ensure that the user positions the electrodes 120*a*, 120*b* over a desired neurostimulation target (DLPFC) in a home setting. In some embodiments, a portion of the support member 130 may include a cushion configured to rest on the back of the head of the user. In some embodiments, the support member 130 may be adjustable such that the device 100 may be worn by users with different head sizes.

In some embodiments, the support member 130 may alternatively be a band that extends around the head of the user to secure the frame 110 across the forehead of the user. In some embodiments, the band may be a stretchable material such that the electrodes 120*a*, 120*b* are secured to the surface of the forehead when the device 100 is worn by the user and the band is placed around the back of the head of the user. In some embodiments, the device 100 may include an electronics subsystem 140 and a power supply 150 configured to power the electronics subsystem 140.

In some embodiments, the device 100 is configured such that when worn by the user, the pair of electrodes 120*a*, 120*b* are secured on the forehead of the user to target the prefrontal cortex of the user. In some embodiments, the pair of electrodes 120*a*, 120*b* are secured on the forehead of the user to target the DLPFC. In some embodiments, the pair of electrodes 120*a*, 120*b* are secure on the forehead of the user to target the left DLPFC. In some embodiments, the pair of electrodes 120*a*, 120*b* are secured on the forehead of the user according to an F3/F4 electrode montage to target the DLPFC. For example, the first electrode 120*a* may be positioned over an F3 electrode region and the second electrode 120*b* may be positioned over an F4 electrode region. In some embodiments, the first electrode 120*a* may be configured as an anode and positioned over the F3 region (e.g., the left side of the forehead), and the second electrode 120*b* may be configured as a cathode and positioned over the F4 region (e.g., the right side of the forehead). In some embodiments, each electrode 120*a*, 120*b* may include an adhesive material that is configured to improve contact between the electrodes 120*a*, 120*b* and a surface of the forehead of the user.

In some embodiments, each electrode from the pair of electrodes 120*a*, 120*b* includes a conducting surface 122*a*, 122*b* configured to contact the forehead of the user. In some embodiments, each electrode 120*a*, 120*b* may be pivotable such that the conducting surface 122*a*, 122*b* lay parallel to the surface of the forehead when the device 100 is worn by the user to improve contact between the conducting surface 122*a*, 122*b* and the forehead of the user. In some embodiments, the conducting surface 122*a*, 122*b* of each electrode 120*a*, 120*b* may have a length of about 3.0 cm to about 5.0 cm and a width of about 5.0 cm to about 7.0 cm, inclusive of all ranges and subranges therebetween. In some embodiments, the conducting surface 122*a*, 122*b* may have a surface area between about 15 $cm^2$ to about 35 $cm^2$, inclusive of all ranges and subranges therebetween. In some embodiments, the surface area of the conducting surface 122*a*, 122*b* may be between about 20 $cm^2$ to about 25 $cm^2$. In some embodiments, the surface area of the conducting surface 122*a*, 122*b* may be at least 15 $cm^2$ and less than 25 $cm^2$. In some embodiments, the surface area of the conducting surface 122*a*, 122*b* may be at least 20 $cm^2$ and less than 25 $cm^2$. In some embodiments, the surface area of the conducting surface 122*a*, 122*b* may be about 23 $cm^2$.

The pair of electrodes 120*a*, 120*b* may be configured to provide neurostimulation (e.g., tDCS) to the user. In some embodiments, the conducting surface 122*a*, 122*b* having a surface area of about 23 $cm^2$ may help focus the neurostimulation to a target cortical area (e.g., the DLPFC). In some embodiments, the conducting surface 122*a*, 122*b* having a surface area of about 23 $cm^2$ may contribute to an improvement in at least one of a remission rate and a response rate by delivering a more focused neurostimulation to the target cortical area. The surface area of the conducting surface 122*a*, 122*b* is inversely proportional to a current density (or a charge density, or a field density) of the stimulation delivered by the electrodes 120*a*, 120*b*. As the surface area of the conducting surface 122*a*, 122*b* decreases, the current density increases and therefore the delivered stimulation can be more focused. If the current density (or charge density, or field density) delivered by the electrodes 120*a*, 120*b* is above a threshold, the conducting surface 122*a*, 122*b* thermal effects may start to occur (e.g., the conducting surface 122*a*, 122*b* may increase in temperature), which may put the user at risk of experiencing pain and/or burns on the skin in contact with and/or around the conducting surface 122*a*, 122*b*. Therefore, the surface conducting surface 122*a*, 122*b* must be large enough such that the current density does not surpass the threshold to ensure safety of the user.

In some embodiments, the conducting surface 122*a*, 122*b* may include a hydrophilic material (e.g., an electrolyte) configured to conduct an electrical output (e.g., current) to the brain of the user. In some embodiments, the conducting surface 122*a*, 122*b* includes a hydrophilic pad. In some embodiments, the hydrophilic pad may be disposable such that a new hydrophilic pad is placed on each electrode 120*a*, 120*b* before each use of the device 100. In some embodiments, the hydrophilic layer may be coupled to a conductive substrate (e.g., a conductive polymer), and the conductive substrate may electrically connect the hydrophilic material to the electronics subsystem 140.

In some embodiments, the electronics subsystem 140 and the power supply 150 are integrated into the device 100. The electronics subsystem 140 may be configured to cause the pair of electrodes 120*a*, 120*b* to stimulate the user according to the methods described herein. For example, the electronics subsystem 140 may be configured to cause the pair of electrodes 120*a*, 120*b* to deliver a current of 2 mA over the DLPFC of the user for a predetermined amount of time (e.g., 30 minutes). In some embodiments, the electronics subsystem 140 may include a processor 142 and a memory 144. In some embodiments, the processor 142 may be configured to periodically power a circuit including the electrodes 120*a*, 120*b* to deliver tES according to a predetermined schedule. In some embodiments, the memory 144 may store instructions and/or code that when executed by the processor 144, cause the device 144 to deliver tES according to the predetermined schedule. In some embodiments, the processor 142 may be configured to receive instructions and/or code relating to the predetermined schedule from a remote server. In some embodiments, the memory 144 may be configured to store code and/or instructions for delivering tES sessions according to any of the methods described herein. For example, the memory 144 and/or processor 142 may be configured to cause the device 100 to deliver 36 tES sessions over the course of 10 weeks. In some embodiments, the memory 144 and/or processor 142 may be configured to cause the device 100 to deliver tES sessions 5 times a week for 3 weeks and then 3 times a week for 7 weeks. In some embodiments, the memory 144 and/or processor 142 may be configured to prevent the device 100 from delivering more than 1 tES a day. In some embodiments, the memory 144 and/or processor 142 may be configured to prevent the device 100 from delivering more than 5 tES a week. In some embodiments, the memory 144 and/or processor 142 may be configured to prevent the user from delivering an excess of tES sessions to ensure safety of the user. In some embodiments, the memory 144 and/or processor 142 are fully integrated into the hardware of the device 100 such that the user may receive tES at home without supervision of a practitioner.

In some embodiments, the memory 144 and/or processor 142 may be configured to deliver tES (or tDCS) sessions according to the following instructions: (1) the user begins with 6 reserve stimulation sessions at the beginning of a treatment plan. (2) The processor 142 does not allow the device 100 to deliver tES sessions more than 5 times per week and more than 1 per day. (3) If the device 100 delivers more than 3 sessions in a week, one of the reserve stimulation sessions is used for each session over 3 times that week. The user may be instructed (e.g., via a user device and/or a third party such as a physician or researcher) to stimulate for 5 sessions per week for the first 3 weeks, meaning that if the user adheres and the device delivers 5 sessions per week for the first 3 weeks, 2 reserve stimulation sessions per week for the 3 first weeks are used. Therefore, when the user adheres to the instructions, all 6 reserve stimulation sessions are used by the end of the first 3 weeks such that the processor 142 only allows the device 100 to deliver 3 sessions per week for the rest of the treatment period (e.g., 10 weeks). (4) If a user has remaining reserve stimulation sessions, the processor 142 allows the device to deliver a session (so long as the weekly session are less than 5 times per week). In some embodiments, the memory 144 and/or processor 142 may implement all of the instructions 1-4. In some embodiments, the memory 144 and/or processor 142 may implement a subset of the instructions 1-4.

In some embodiments, the device 100 can include a communications interface, e.g., for communicating with one of more external devices, e.g., via a wired and/or wireless connection. For example, the device 100 can include a wireless transceiver and be configured to wirelessly communicate with an electronic device. In some embodiments, the device 100 can be configured to communicate with a user device, such as, for example, a mobile device, a phone, a tablet, a personal computer, a laptop, and the like. In some embodiments, the device 100 can be configured to communicate with one or more remote devices, such as, for example, a server, via a user device. In some embodiments, the external device can have a processor configured to send signals and/or instructions to the device 100 including a schedule for performing transcranial brain stimulation. The schedule can include or be based on any one of the protocols and/or methods described herein. In some embodiments, the schedule can be stored in the onboard memory 144 of the device 100, and the processor 142 can be configured to implement the schedule, e.g., by delivering transcranial brain stimulation (e.g., tDCS) according to the schedule.

Further examples of systems and devices for delivering tDCS are described in U.S. patent application Ser. No. 14/470,683, filed Aug. 27, 2014, now U.S. Pat. No. 9,889,290, U.S. patent application Ser. No. 14/878,647, filed Oct. 8, 2015, now U.S. Pat. No. 9,486,618, U.S. patent application Ser. No. 15/916,170, filed Mar. 8, 2018, now U.S. Pat. No. 10,525,255, U.S. patent application Ser. No. 16/480,679, filed Jul. 25, 2019, now U.S. Pat. No. 11,351,362, U.S. Patent Publication No. 2021/0275801, filed Jul. 25, 2019, and U.S. Patent Publication No. 2021/0299434, filed Jan. 29, 2021, the disclosures of each of which are incorporated herein by reference.

Psychosocial Interventions

Additional methods of intervention may be combined with the methods of administering to the subject a pharmacologic antidepressant agent and delivering to the subject a tES described herein for treatment of depression or a depression-related condition. In some embodiments, regular psychotherapy sessions are completed between the subject and a licensed profession psychotherapist. In some embodiments, the regular psychotherapy sessions are psychoanalysis or psychodynamic therapy sessions. In some embodiments, the subject undergoes psychotherapy sessions 3 times a week, 2 times a week, 1 weeks, about once every 10 days, or bi-weekly. In some embodiments, the subject undergoes cognitive behavioral therapy sessions. In some embodiments, the subject undergoes behavioral therapy sessions. In some embodiments, the subject undergoes Humanistic therapy. In some embodiments, the subject completes 0 to 2, 3 to 4, or more than 4 sessions of psychoanalysis or psychodynamic therapy, cognitive behavioral therapy, behavioral therapy, and/or the Humanistic therapy within the past month of treatment. In some embodiments, subjects add regular meditation sessions to a treatment regimen. In some embodiments, the subject undergoes meditation sessions at least 8, 7, 6, 5, 4, 3, 2, or 1 times a day, or once every 2, 3, 4, 5, 6, or 7 days. In some embodiments, the meditation session is conducted simultaneously with the tES session. In some embodiments, subjects add regular relaxation sessions to a treatment regimen. In some embodiments, the subject undergoes relaxation sessions at least 8, 7, 6, 5, 4, 3, 2, or 1 times a day, or once every 2, 3, 4, 5, 6, or 7 days. In some embodiments, the relaxation session is conducted simultaneously with the tES session.

II. DEFINITIONS

Unless defined otherwise, all terms of art, notations and other technical and scientific terms or terminology used herein are intended to have the same meaning as is commonly understood by one of ordinary skill in the art to which the claimed subject matter pertains. In some cases, terms with commonly understood meanings are defined herein for clarity and/or for ready reference, and the inclusion of such definitions herein should not necessarily be construed to represent a substantial difference over what is generally understood in the art.

Throughout this application, various embodiments may be presented in a range format. It should be understood that the description in range format is merely for convenience and brevity and should not be construed as an inflexible limitation on the scope of the disclosure. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

As used in the specification and claims, the singular forms “a”, “an” and “the” include plural references unless the context clearly dictates otherwise. For example, the term “a sample” includes a plurality of samples, including mixtures thereof.

The terms “determining,” “measuring,” “evaluating,” “assessing,” “assaying,” and “analyzing” are often used interchangeably herein to refer to forms of measurement. The terms include determining if an element is present or not (for example, detection). These terms can include quantitative, qualitative or quantitative and qualitative determinations. Assessing can be relative or absolute. “Detecting the presence of” can include determining the amount of something present in addition to determining whether it is present or absent depending on the context.

The terms “subject,” “individual,” or “patient” are often used interchangeably herein. A “subject” can be a biological entity containing expressed genetic materials. The biological entity can be a plant, animal, or microorganism, including, for example, bacteria, viruses, fungi, and protozoa. The subject can be tissues, cells and their progeny of a biological entity obtained in vivo or cultured in vitro. The subject can be a mammal. The mammal can be a human. The subject may be diagnosed or suspected of being at high risk for a disease. In some cases, the subject is not necessarily diagnosed or suspected of being at high risk for the disease.

As used herein, the term "about" a number refers to that number plus or minus 10% of that number. The term "about" a range refers to that range minus 10% of its lowest value and plus 10% of its greatest value.

As used herein, the terms "treatment" or "treating" are used in reference to a pharmaceutical or other intervention regimen for obtaining beneficial or desired results in the recipient. Beneficial or desired results include but are not limited to a therapeutic benefit and/or a prophylactic benefit. A therapeutic benefit may refer to eradication or amelioration of symptoms or of an underlying disorder being treated. Also, a therapeutic benefit can be achieved with the eradication or amelioration of one or more of the physiological symptoms associated with the underlying disorder such that an improvement is observed in the subject, notwithstanding that the subject may still be afflicted with the underlying disorder. A prophylactic effect includes delaying, preventing, or eliminating the appearance of a disease or condition, delaying or eliminating the onset of symptoms of a disease or condition, slowing, halting, or reversing the progression of a disease or condition, or any combination thereof. For prophylactic benefit, a subject at risk of developing a particular disease, or to a subject reporting one or more of the physiological symptoms of a disease may undergo treatment, even though a diagnosis of this disease may not have been made.

As used herein, the term "treatment effective amount" (and grammatical variants thereof) refers to an amount that is sufficient to provide some improvement or benefit to the subject. For example, a "treatment effective amount" can be an amount that provides some alleviation, mitigation, decrease, or stabilization in at least one symptom (e.g., clinical symptom) or condition associated with a disorder in the subject. Those skilled in the art can appreciate that the therapeutic effects need not be complete or curative, as long as some benefit is provided to the subject.

The section headings used herein are for organizational purposes only and are not to be construed as limiting the subject matter described.

III. EXAMPLES

The following examples are included for illustrative purposes only and are not intended to limit the scope of the invention.

Example 1: Completion of a MADRS-s Questionnaire

In this example, a subject completed a MADRS-s questionnaire at baseline (defined as a time preceding initiation of neurostimulation) to determine a starting measurement to be used in an assessment of treatment efficacy. Ideally, baseline measures were made close to the period of time in which the first neurostimulation session began. The subject completed the same MADRS-s questionnaire weekly during a period of ongoing treatment comprising administering of a prescribed pharmacologic antidepressant agent and delivery to the subject of plurality tDCS sessions. The number of and date completed of each tDCS session was recording in order to analyze subjects according to how often they successfully completed tDCS sessions as part of their treatment regimens. Subjects were parcellated into groups of 1) depression symptoms absent, 2) mild depression, 3) moderate depression, or 4) severe depression to further enable analysis of changes in MADRS-s score according to severity of depression and adherence to the recommended tDCS session schedule. Groups were analyzed by ANOVA to determine statistically significant differences present between them. Below is a replication of the questionnaire that subjects completed at baseline and weekly during treatment.

MADRS-s has 9 questions. Each question has 7 response options with score 0-6. Note that only even-numbered options have a description.

Instructions to the Subject:

Try to answer the following 9 questions as accurately as possible based on how you have been feeling the last 3 days Mood Here you should try to indicate your mood, whether you have felt sad or gloomy. Try to recall how you have felt during the past 3 days, whether your mood has been changeable or much the same all the time. In particular, try to recall whether you have felt more cheerful if something good happened.

0. I can be either cheerful or sad, depending on the circumstances.
2. I feel a bit low for the most part, though sometimes it eases up a little.
4. I feel thoroughly low and gloomy. Even things that normally cheer me up give me no.
6. I feel so utterly low and miserable, that I can imagine nothing worse.

Feelings of Unease

Here you should indicate to what extent you have had feelings of inner tension, uneasiness, anxiety, or vague fear, during the past 3 days. Pay particular attention to how intense any such feelings have been, whether they have come and gone or persisted almost all the time.

0. I feel calm for the most part.
2. I sometimes have unpleasant feelings of unease.
4. I am constantly plagued by feelings of uneasiness that can be very strong, and which I must make an effort to overcome.
6. I have dreadful, persistent or unbearable feelings of anxiety.

Sleep

NOTE: This section is not the same as MADRS.

Here you should indicate how well you sleep, how long you sleep, and how good your sleep has been for the past 3 nights. Your assessment should reflect how you have actually slept, regardless of whether you have used sleeping pills. If you have slept more than usual, you should mark the scale at zero (0).

0. I have no sleeping problems, and get as much sleep as I need. I have no difficulty in falling asleep.
2. I have some sleeping problems. Sometimes it is hard to get off to sleep, or I sleep more lightly or restlessly than usual.
4. I sleep at least 2 h a night less than usual. I wake often during the night, even if nothing has disturbed me.
6. I sleep very badly, no more than 2-3 hours a night.

Appetite

Here you should indicate how your appetite has been, and try to recall whether it has differed in any way from normal. If your appetite has been better than usual, you should mark the scale at zero (0).

0. My appetite has been much the same as usual.
2. My appetite has been poorer than usual.
4. I have had almost no appetite at all. Food seems tasteless and I have to make myself eat.
6. I haven't felt like eating at all. I need persuading if I am to get anything down.

Ability to Concentrate

Here you should try to indicate your ability to collect your thoughts, to concentrate on what you are doing. Try to recall how well you have been able to cope with tasks requiring different degrees of concentration—for instance, compare your ability to read a more complex text and an easy passage in the newspaper, or to pay attention to the TV.

0. I have no difficulty in concentrating.
2. Occasionally I find it hard to concentrate on things that I would usually find interesting (e.g., reading, or watching TV).
4. I find it particularly hard to concentrate on things that usually require no effort (e.g., reading, or talking with other people).
6. I am quite unable to concentrate on anything at all.

Initiative

Here you should try to assess your ability to get things done. This item concerns how hard or how easy it is for you to get started on things you think should be done, and to what extent you feel you must overcome inner resistance (inertia) in order to get started on anything.

0. I have no difficulties starting new tasks.
2. When I have to get on with something, I find it more difficult than usual.
4. It requires great effort for me to get started on simple tasks that I normally perform more or less without thinking.
6. I cannot get started with the simplest everyday tasks.

Emotional Involvement

NOTE: This section is not the same as MADRS

Here you should assess your interest in your surroundings, in other people, and in activities that normally give you pleasure.

0. I am interested and involved in my surroundings, and this gives me pleasure.
2. I feel less strongly about things that normally arouse my interest; it is harder than usual to be cheerful, or to be angry when there is cause.
4. I feel no interest in my surroundings, not even for friends and acquaintances.
6. I no longer have any feelings. I feel painfully indifferent, even toward those closest to me.

Pessimism

Here you should consider how you view your future, and how you feel about yourself. Consider to what extent you may feel self-critical, whether you are plagued with guilty feelings, and whether you have been worrying more than usual—for example, about your finances or your health.

0. I view the future with confidence. On the whole I am quite satisfied with life.
2. Sometimes I am self-critical and think I am less worthy than others.
4. I brood over my failures and feel inferior or worthless, even if others may not agree.
6. Everything seems black to me, and I can see no glimmering of hope. I feel I am thoroughly useless, and that there is no chance of forgiveness for the awful things I have done.

Zest for Life

This item concerns your appetite for life, and whether you have felt listless and weary of life. Have you had thoughts of suicide, and if so to what extent do you consider it a realistic escape?

0. My appetite for life is normal.
2. Life doesn't seem particularly meaningful, though I don't wish I were dead.
4. I often think it would be better to be dead, and though I don't really want to commit suicide it does seem a possible solution.
6. I am quite convinced that my only solution is to die, and I give a lot of thought to the best way to take my own life.

Example 2: Depression Severity in Outcome of Combining Neurostimulation and Pharmacologic Treatment In this example, subjects were identified which had undergone a clinical evaluation by a psychiatrist and been diagnosed with Major depressive disorder (MDD). Subjects currently undergoing a depressive episode were enrolled to test parameters of these methods of treatment. The subjects were categorized in an extent severity of depression by the diagnosing psychiatrist applying one of several clinically validated standard scales available for the assessment of the severity of depressive symptoms. In this example, subjects were classified for an extent of depression or depressive symptoms by the diagnosing psychiatrist conducting a HAM-D or MADRS assessment. Based on the cut-offs from the scales of these assessment, subjects were classified according to the severity of MDD of the subject as mild depression, moderate depression, or severe depression. A control group with depression symptoms absent was also examined.

Subjects were provided with a tDCS neurostimulation device, instructions of use, and an program capable of being run on a handheld electronic device which provided instructions, recorded responses to various questionnaires completed by the subject, and recorded information regarding the tDCS stimulation sessions completed by the user. Amongst the tDCS stimulation session information recorded was the date of each session completed, the time of day of each completed session, the duration of each completed session, the intensity of electrical stimulation in each session, the latency from the most recently completed session to the previous session.

Subjects completed a MADSR-s assessment at baseline prior to their first tDCS session. Subjects completed a TAQ assessment at baseline to record expectations for desired treatment outcomes. Subjects were prompted weekly to complete additional MADRS-s assessments. Subjects completed AEQ forms throughout treatment when necessary to record any potential adverse effects of the treatment protocol. Subjects completed a treatment tracking questionnaire monthly to record the specific antidepressant agent, dosage, and frequency of administration of the pharmacologic antidepressant agent there were being administered. In this treatment tracking questionnaire, subjects recorded if their specific antidepressant agent or category of antidepressant had changed. If taking a new antidepressant medication, the new antidepressant agent was indicated. Subjects also recorded if the dosage administered of the antidepressant medication had changed in the past month. If the dosage had changed, the subject recorded the extent of the change. If the subject stopped taking an antidepressant medication during the past month, that was recorded. Subjects recorded any benzodiazepine medication they have been taking in the past month, indicating any change in the specific benzodiazepine agent being taking, any change in dosage, any change in frequency of administration, and the nature of any of those changes. Subjects also listed the specific benzodiazepine agent they were taking, dosage, and frequency of administration taken as part of their treatment regimens. Additionally in the monthly treatment tracking questionnaire completed by the subject, it was recorded if the subject was still undergoing any kind of additional therapy. Responses were recorded to indicate which kind of ongoing therapy was completed on the past month (e.g., psychoanalysis or psychodynamic, cognitive behavioral therapy, behavioral therapy, Humanistic therapy, or other), how many sessions were completed, if the subject had changed to replace or include a number therapy and if so what kind and how many sessions were completed. In the monthly treatment tracking questionnaire completed by the subject, it was also recorded if the subject was on sick leave from their occupation. The extent and any change in extent of sick leave was recorded. In the monthly treatment tracking questionnaire completed by the subject, depression symptoms were recorded. An assessment of depression symptoms increasing, decreasing, or staying the same was recorded. If the subject had a recent diagnosis other than depression that was recorded. Choices for additional diagnoses apart from depression were listed as Long-term stress/exhaustion, insomnia, PTSD, Anxiety syndrome, ADHD, Autism, Chronic pain, Eating disorder, Alcohol or drug addiction, or Other. The subject was asked if they were currently being treated for this new condition. If the subject had a recent change in diagnosis from depression to a different diagnosis, this was recorded. Choices for alternative diagnoses instead of depression were listed as Long-term stress/exhaustion, insomnia, Anxiety syndrome, ADHD, Borderline disorder, Bipolar disorder, Chronic pain, Eating Disorder or other. If the subject was female, they were asked to record if they were currently pregnant.

To assess if depression severity was a factor in predicting outcome of a treatment, the groups to be examined were mild depression in MDD, moderate depression in MDD, severe depression in MDD, and a control group of depression symptoms absent. A precondition for inclusion in this analysis was that the subjects adhere to the treatment. Initially, subjects were analyzed at timepoints of 3 weeks, 6 weeks, 10 weeks, and 25 weeks after initiation of treatment.

As seen in FIG. 1, groups of subjects were divided by depression severity and amount of tDCS stimulation sessions. Subjects were administered a prescribed pharmacologic antidepressant agent either that they had already been taking as part of a treatment regimen or were newly prescribed. A MADRS-s score was taken at baseline before initiation of any tDCS sessions. Subjects were instructed to complete an activation phase of neurostimulation by following instructions for delivering tDCS via a tDCS headset programmed to stimulate an intensity of 2.0 mA for a period of up to 30 minutes per session. Subjects were instructed to complete at least 5 tDCS sessions during the activation phase per week for the first 3 weeks. Subjects were instructed that each tDCS session should last at least 20 minutes. Information regarding completion of tDCS sessions was recorded by the program. Subjects were asked to complete weekly MADRD-s assessments the results of which were recorded by the program. In FIG. 1, four graphs segregated by depression severity were generated graphing change in MADRS-s score by week. Groups of subjects completing 1-10 tDCS sessions, 11-14 tDCS sessions, and 15-16 tDCS sessions were graphed separated by stimulation group to determine if extent of stimulation had a noticeable effect. A clear signal is indicated for mild, moderate, and severe depression that group having 15-16 tDCS sessions had a greater reduction in MADRS-s score compared to the less adherent 1-10 tDCS session group. For this analysis, the 1-10 tDCS session group contained 824 subjects, the 11-14 tDCS session group contained 1293 subjects, and the 15-16 tDCS session group contained 1063 subjects.

Figure 2:
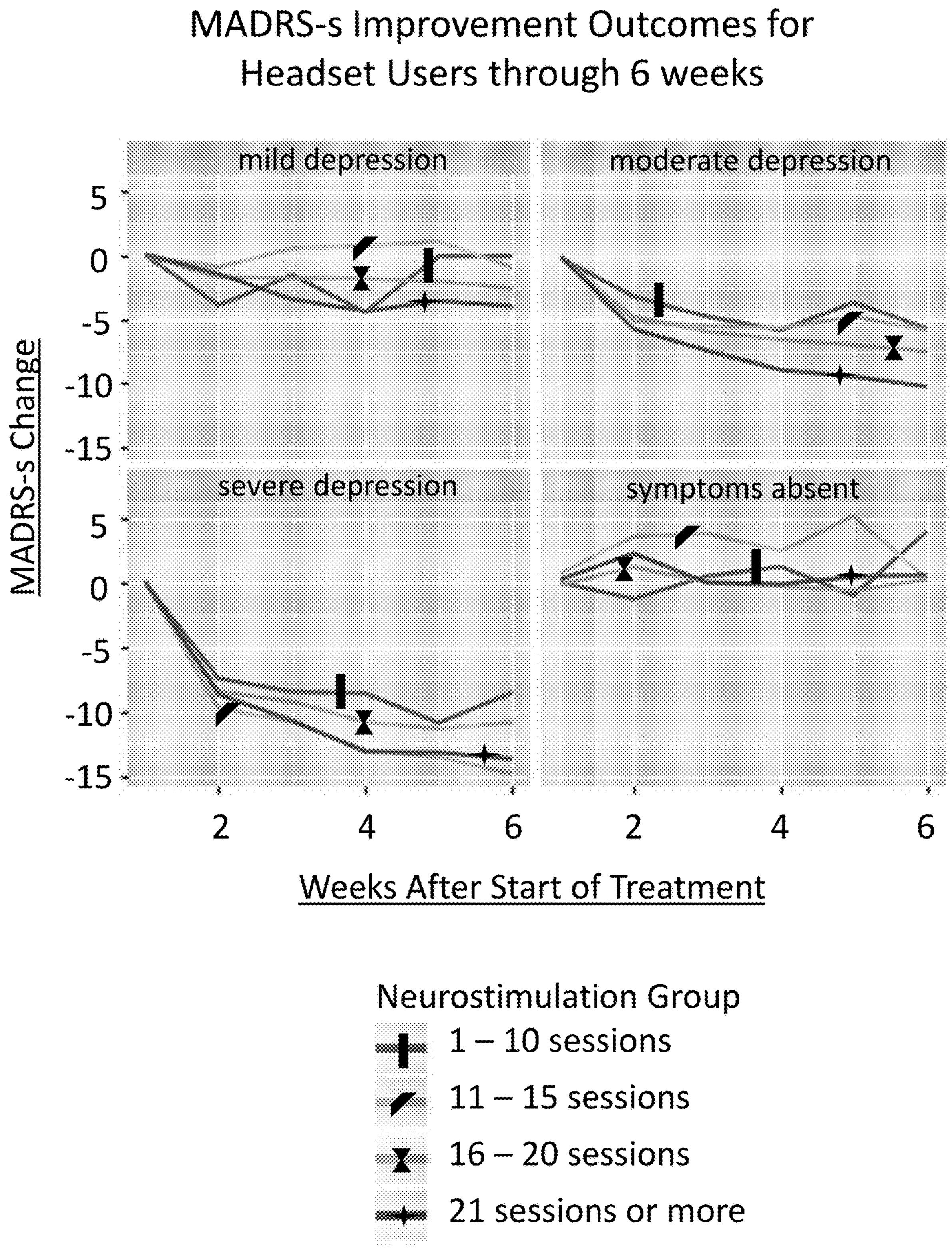
FIG. 2 shows graphs of depression score improvement outcomes through six weeks following initiation of neurostimulation. Subjects were grouped by symptom severity and graphed according to number of neurostimulation sessions.

As seen in FIG. 2, groups of subjects were divided by depression severity and amount of tDCS stimulation sessions. Subjects were instructed the follow the same treatment and assessment recordation protocols as in FIG. 1. Subjects were analyzed for up to 6 weeks following initiation of treatment. In FIG. 2, four graphs segregated by depression severity were generated graphing change in MADRS-s score by week. Groups of subjects completing 1-10 tDCS sessions, 11-15 tDCS sessions, 16-20 tDCS sessions, and 21 or more sessions were graphed separated by stimulation group to determine if extent of stimulation had a noticeable effect. In moderate depression, the 16-20 tDCS sessions group, and 21 or more sessions group had a larger improvement in depression symptoms as evidence by a greater reduction in MADRS-s score compared to the 1-10 tDCS group. In severe depression, the 11-15, the 16-20, and the 21 or more tDCS sessions group had a greater improvement depression symptoms compared to the 1-10 tDCS group. For this analysis, the 1-10 tDCS session group contained 188 subjects, the 11-15 tDCS session group contained 300 subjects, the 16-20 tDCS session group contained 907 subjects, and the 21 or more tDCS session group contained 855 subjects.

Figure 3:
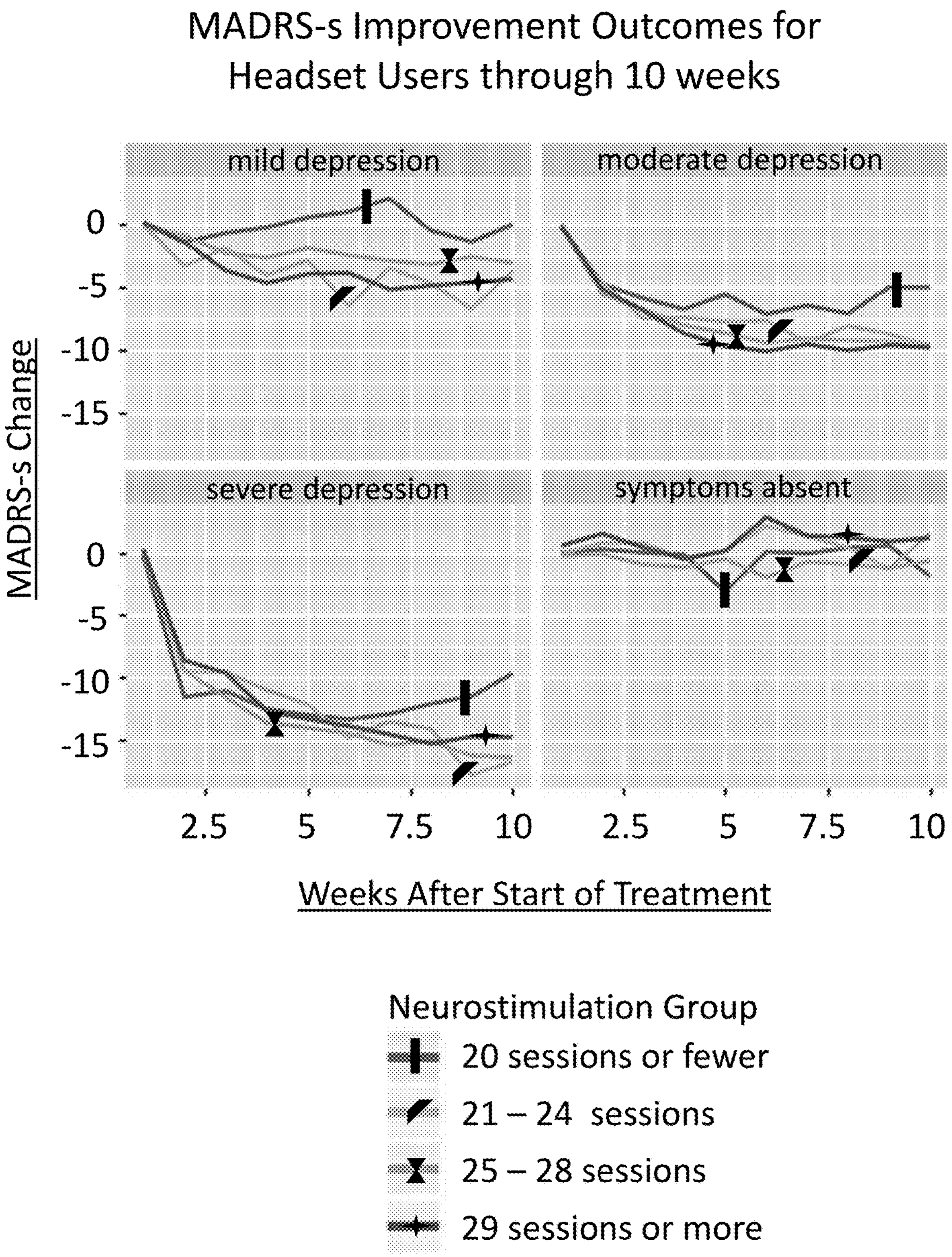
FIG. 3 shows graphs of depression score improvement outcomes through ten weeks following initiation of neurostimulation. Subjects were grouped by symptom severity and graphed according to number of neurostimulation sessions.

As seen in FIG. 3, groups of subjects were divided by depression severity and amount of tDCS stimulation sessions. Subjects were instructed the follow the same treatment and assessment recordation protocols as in FIG. 1. Subjects were analyzed for up to 10 weeks following initiation of treatment. After week 6, subjects were instructed to follow tDCS stimulation according to the strengthening phase comprising delivery of at least 2 tDCS sessions per week to the subject. In FIG. 3, four graphs segregated by depression severity were generated graphing change in MADRS-s score by week. Groups of subjects completing fewer than 20 tDCS sessions, 20-24 tDCS sessions, 25-28 tDCS sessions, and 29 or more sessions were graphed separated by stimulation group to determine if extent of stimulation had a noticeable effect. In the mild, moderate, and severe depression group, stimulation by completion of 20 or more tDCS sessions provided a clear benefit over completion of fewer than 20 tDCS sessions by showing significantly lower MADRS-s scores. It should be noted that when comparing large groups of subjects, an average difference of 2 points in MADRS-s score is often considered clinically relevant to represent between group effects. For this analysis, the fewer than 20 tDCS session group contained 327 subjects, the 20-24 tDCS session group contained 263 subjects, the 25-28 tDCS session group contained 554 subjects, and the 29 or more tDCS session group contained 413 subjects.

Figure 4:
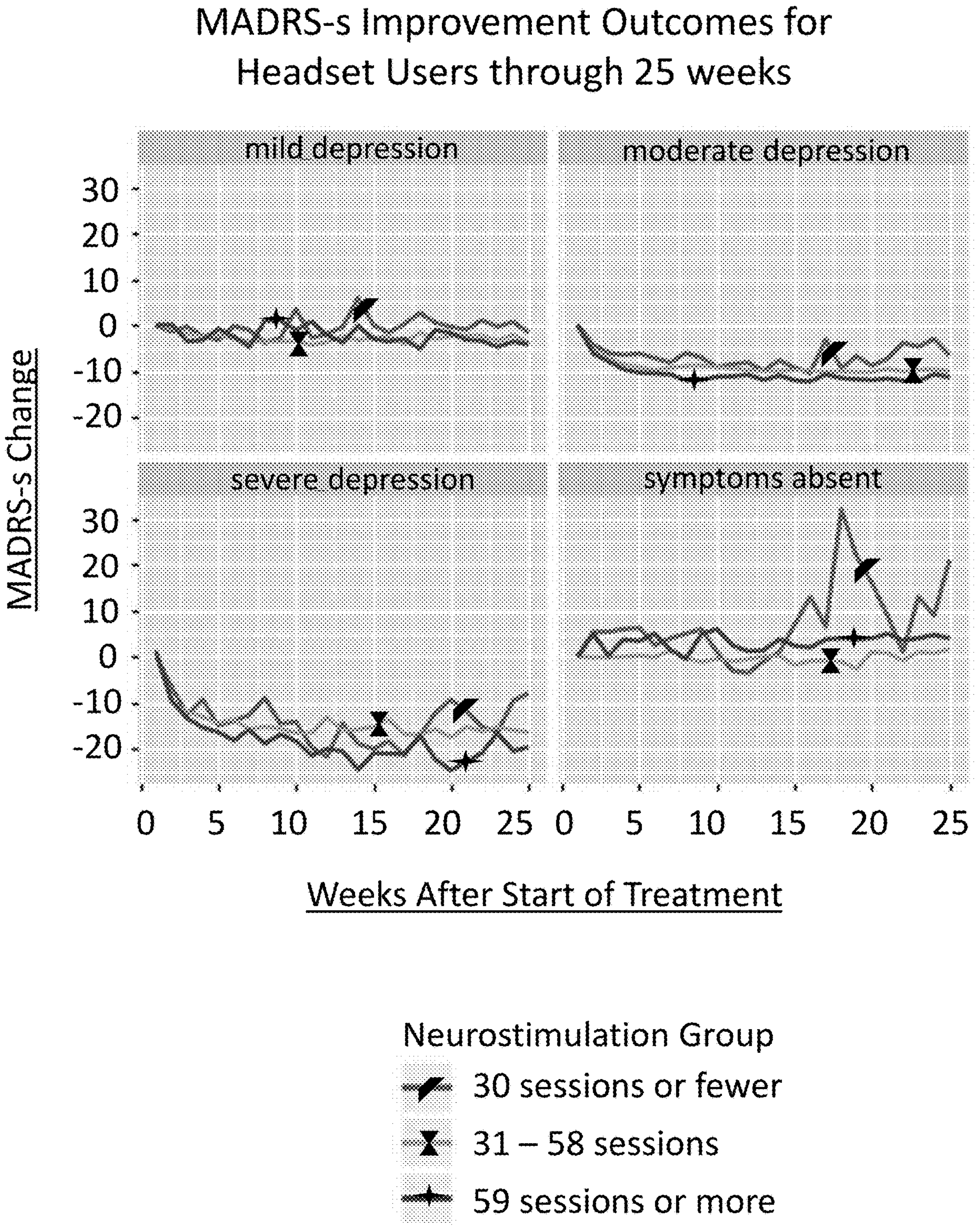
FIG. 4 shows graphs of depression score improvement outcomes through twenty-five weeks following initiation of neurostimulation. Subjects were grouped by symptom severity and graphed according to number of neurostimulation sessions.

As seen in FIG. 4, groups of subjects were divided by depression severity and amount of tDCS stimulation sessions. Subjects were instructed the follow the same treatment and assessment recordation protocols as in FIG. 1. Subjects were analyzed for up to 25 weeks following initiation of treatment. After week 6, subjects were instructed to follow tDCS stimulation according to the strengthening phase comprising delivery of at least 2 tDCS sessions per week to the subject. In FIG. 4, four graphs segregated by depression severity were generated graphing change in MADRS-s score by week. Groups of subjects completing fewer than 30 tDCS sessions, 31-58 tDCS sessions, and 59 or more sessions were graphed separated by stimulation group to determine if extent of stimulation had a noticeable effect. A tend is present in the subjects with severe depression to indicate a stronger response to treatment in subjects completing 59 or mores tDCS sessions compared to those completing fewer tDCS sessions. However, too few subjects were analyzed at this time point to provide sufficient statistical power. For this analysis, the fewer than 30 tDCS session group contained 105 subjects, the 31-58 tDCS session group contained 465 subjects, and the 59 or more tDCS session group contained 78 subjects.

From FIG. 1-FIG. 4, it was determined that the groups are strongly powered so these comparisons are highly significant. Under similarly designed experiments, a clinically significant change in extent of depression would be a drop of 3 or more points on average in MADSR-s score. At 3 weeks there are no clinically significant differences between the severity groups. At week 6 and 10 there is a significant difference between the people that have stimulated 20 sessions or less vs they who have stimulated 21 sessions or more, but only for users that are suffering from moderate or severe depression. At week 25 there is not enough data to allow for a meaningful statistical comparison of subject having completed 59 or more tDCS sessions.

To determine if there is a difference in the type of antidepressant/medication that is used in combination with the tDCS treatment in respect of outcome, an analysis was conducted comparing subjects being administered different categories of antidepressants. Subjects were instructed the follow the same treatment and assessment recordation protocols as in FIG. 1. Subjects were analyzed irrespective of adherence to a certain number of tDCS sessions indicated in the treatment protocol. Groups of antidepressant analyzed are listed in Table 1. Statistical analysis by groups of antidepressant is listed in Table 2.

TABLE 1

Groups tested by antidepressant type

| Groups of antidepressants | Subjects analyzed |
|---|---|
| MAOIs | 1 |
| NaSSAs | 15 |
| SNRIs | 45 |
| SSRIs | 152 |
| TCAs | 13 |

TABLE 2

Statistical analysis by antidepressant category

| Antidepressant Category | Mean Starting MADRS-s score | Subjects analyzed |
|---|---|---|
| NaSSAs | 32.2 | 10 |
| SNRIs | 27.4 | 34 |
| SSRIs | 26.7 | 112 |
| TCAs | 27.6 | 11 |

Figure 5:
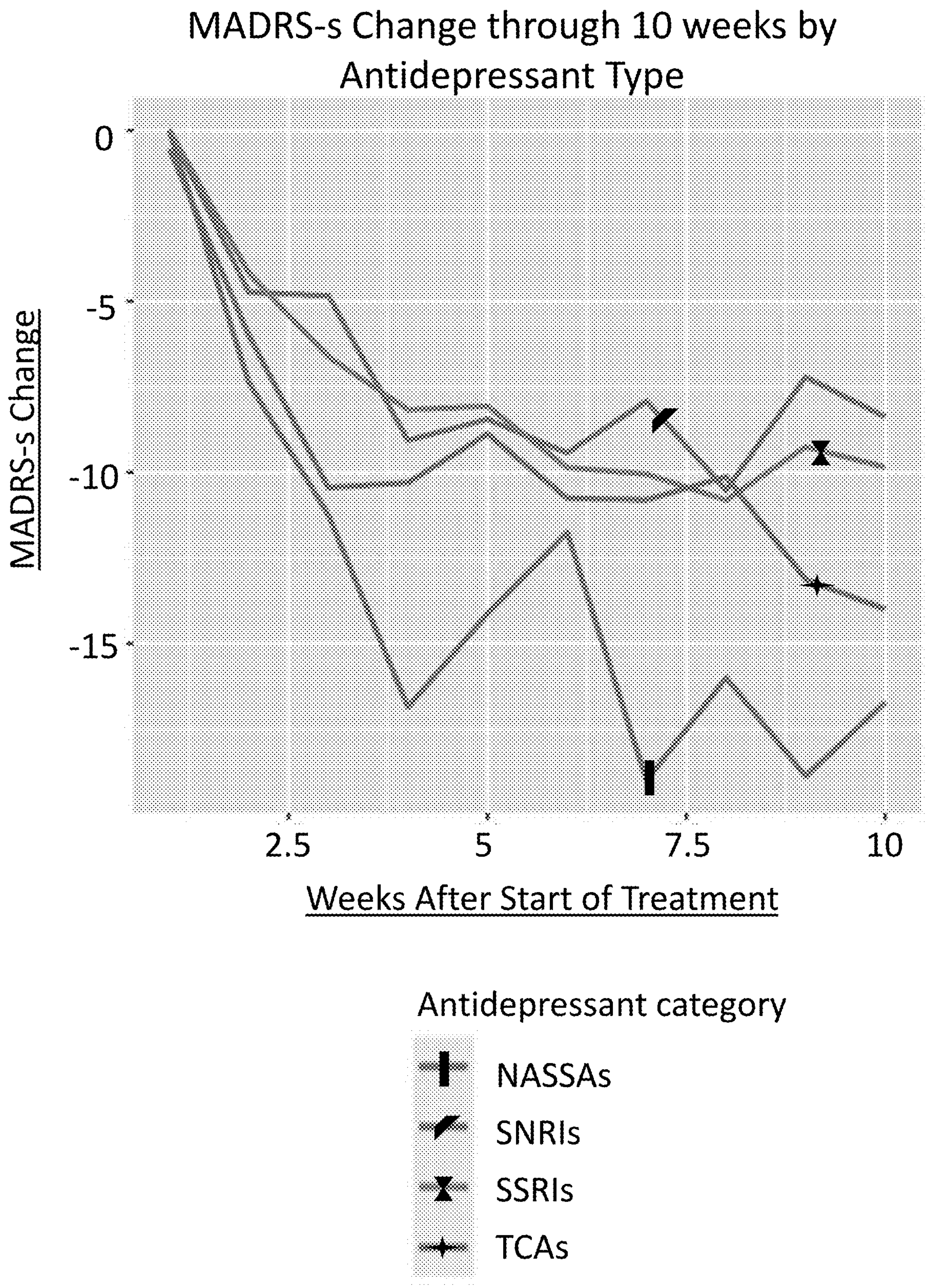
FIG. 5 shows a graph of depression score improvement outcomes through ten weeks following initiation of neurostimulation. Subjects were not segregated by depression symptom severity nor by adherence to a neurostimulation protocol. Subjects were graphed according to category of antidepressant used during treatment.

As seen in FIG. 5, change in MADRS-s score was graphed according to antidepressant category administered to the subjects irrespective of adherence to any particular number of tDCS sessions. As can be seen here, NaSSAs appear to yield more improvement in depression symptoms compared to other categories of antidepressants.

Figure 6:
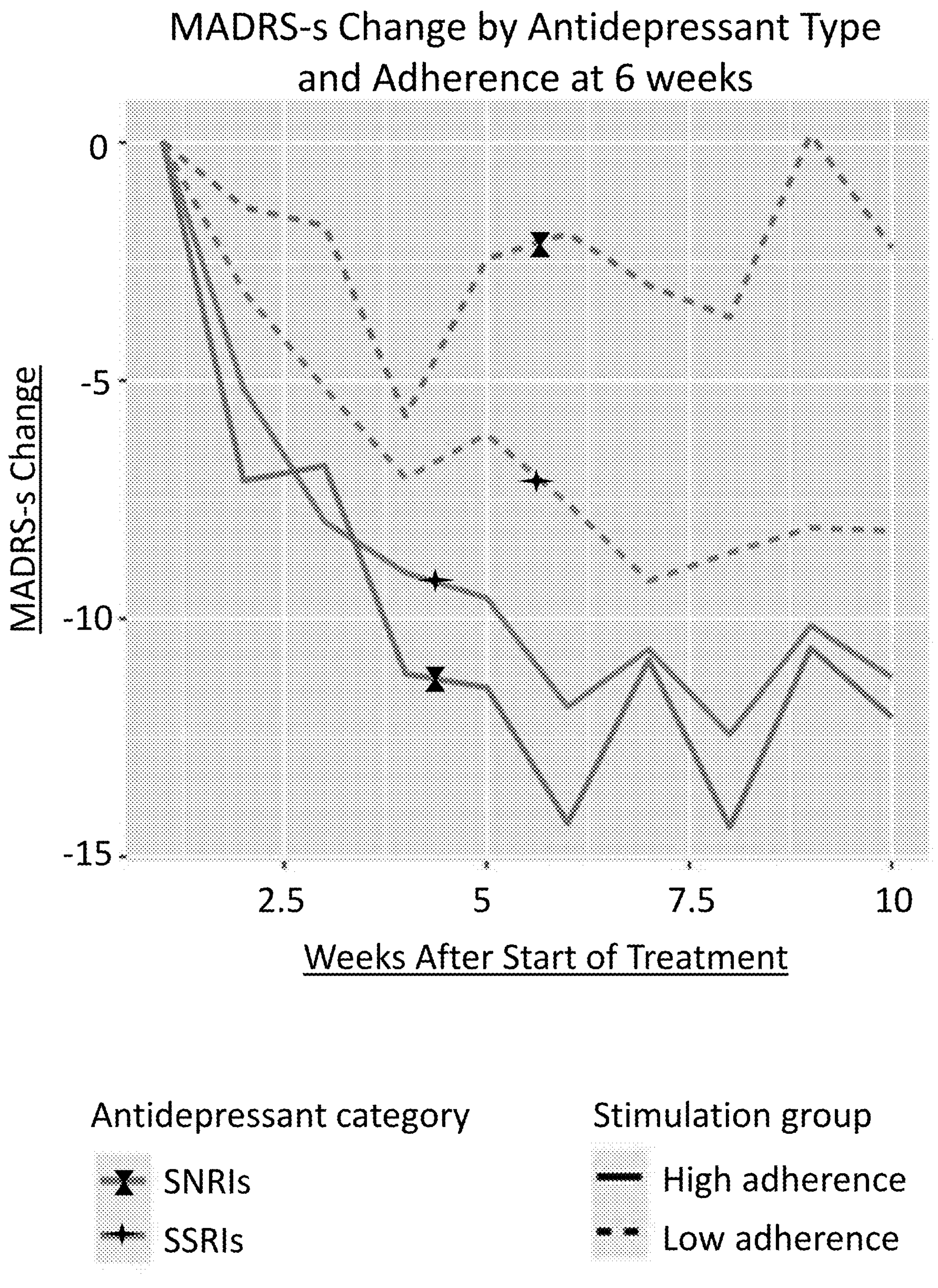
FIG. 6 shows a graph of depression score improvement outcomes through ten weeks following initiation of neurostimulation. Subjects were not segregated by depression symptom severity but subjects were segregated based on extent of adherence to a neurostimulation protocol. Subjects were graphed according to category of antidepressant used during treatment.

As seen in FIG. 6, change in MADRS-s score was graphed according to antidepressant category administered to the subjects further distinguishing antidepressant category administered to user by those subjects adhering to the recommended tDCS schedule of sessions at 6 weeks of treatment and those with low adherence who had completed fewer tDCS sessions. As can be seen, the high adherence group for both SNRIs and SSRI achieved a significantly larger improvement in MADRS-s decrease compared to the lower adherence group for both SNRIs and SSRI. When comparing differences in tDCS adherence, both SNRI and SSRI administration worked significantly better with the high adherence group and this effect was especially pronounced in the SNRI comparison.

To determine if there is a difference in the specific antidepressant agent within a group, MADRS-s changes was analyzed by SSRI irrespective of adherence to the recommended tDCS schedule. In this analysis, citalopram, fluoxetine, and sertraline were compared to each other to determine if administration of one specific SSRI agent provides different results when paired with delivery of tDCS to the subject. Venlafaxine was included in this analysis to examine differences between SSRI agents to an exemplary SNRI. Specific antidepressant agents analyzed are listed in Table 3. Statistical analysis by antidepressant agent is listed in Table 4.

TABLE 3

Starting MADRS-s score by antidepressant agent

| Antidepressant Agent | Mean Starting MADRS-s score |
|---|---|
| Citalopram | 25.1 |
| Fluoxetine | 26.7 |
| Sertraline | 28.5 |
| Venlafaxine | 27.0 |

TABLE 4

Statistical analysis by antidepressant agent

| Comparison | DF | Sum of squares | Mean square | F-value | Pr(>F) | Result |
|---|---|---|---|---|---|---|
| Fluoxetine vs. Sertraline | 1 | 1.0189 | 1.01888 | 4.3531 | 0.04127 | Significant |
| Fluoxetine vs. Venlafaxine | 1 | 0.8386 | 0.83861 | 3.7708 | 0.05858 | Approaching significance |
| Fluoxetine vs. Citalopram | 1 | 0.5003 | 0.50031 | 1.7177 | 0.19649 | Not significant |

Figure 7:
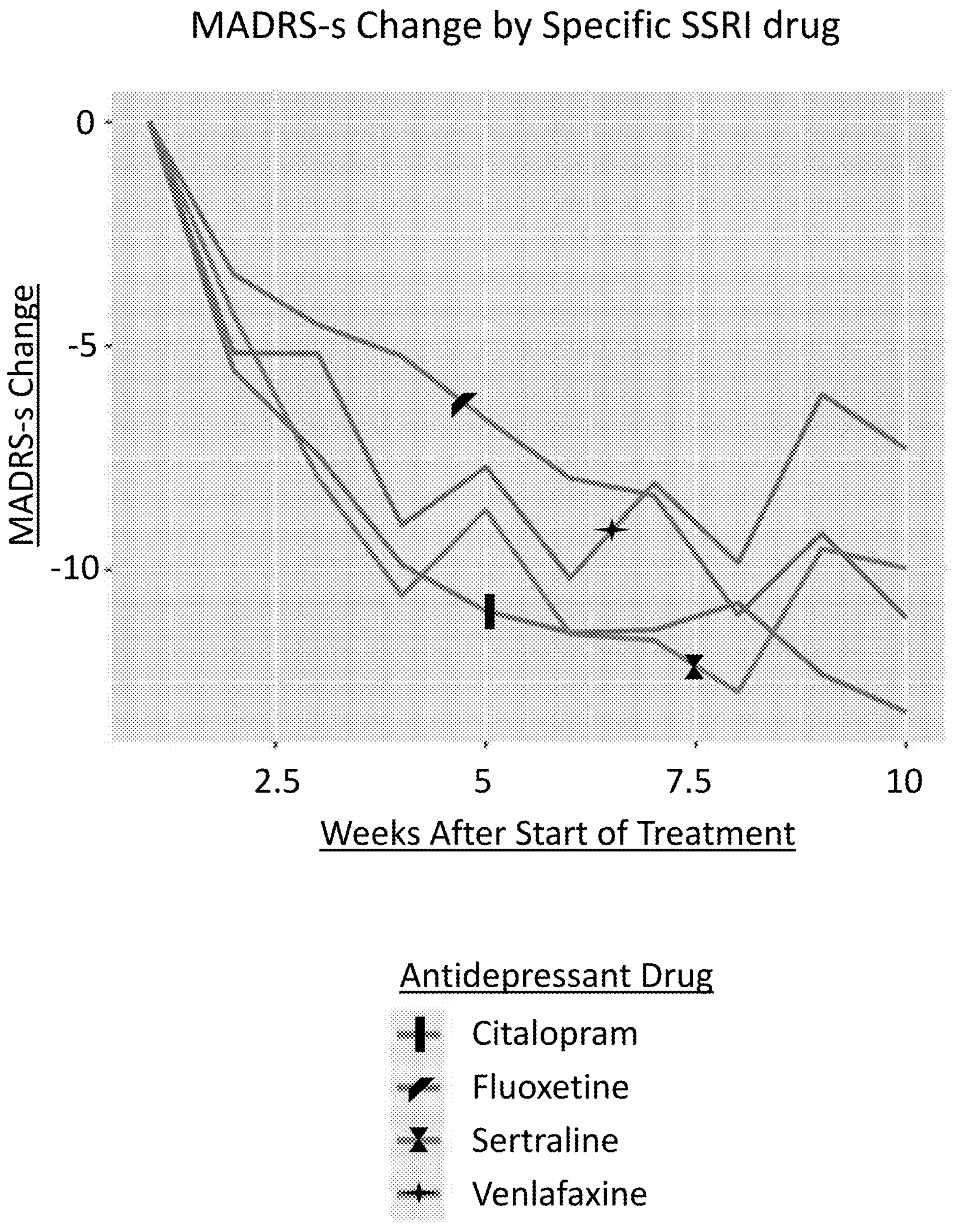
FIG. 7 shows a graph of depression score improvement outcomes through ten weeks following initiation of neurostimulation. Subjects were not segregated by depression symptom severity nor by adherence to a neurostimulation protocol. Subjects were graphed according to selective serotonin reuptake inhibitor (SSRI) drug agent used during treatment.

As seen in FIG. 7, change in MADRS-s score was graphed according to specific antidepressant agent administered to the subjects, irrespective of adherence to the recommendation tDCS number of sessions. As seen in the graph, there are differences evidence on the effectiveness of particular antidepressant agents when combined with tDCS to reduce symptoms of depression. ANOVA statistical analysis was carried out using data from Week 6 after initiation of treatment and presented in Table 4. As can be seen, there is a significant difference in the effectiveness of sertraline compared to fluoxetine at Week 6 and the difference between fluoxetine and venlafaxine although not significant, is approaching significance.

Figure 8:
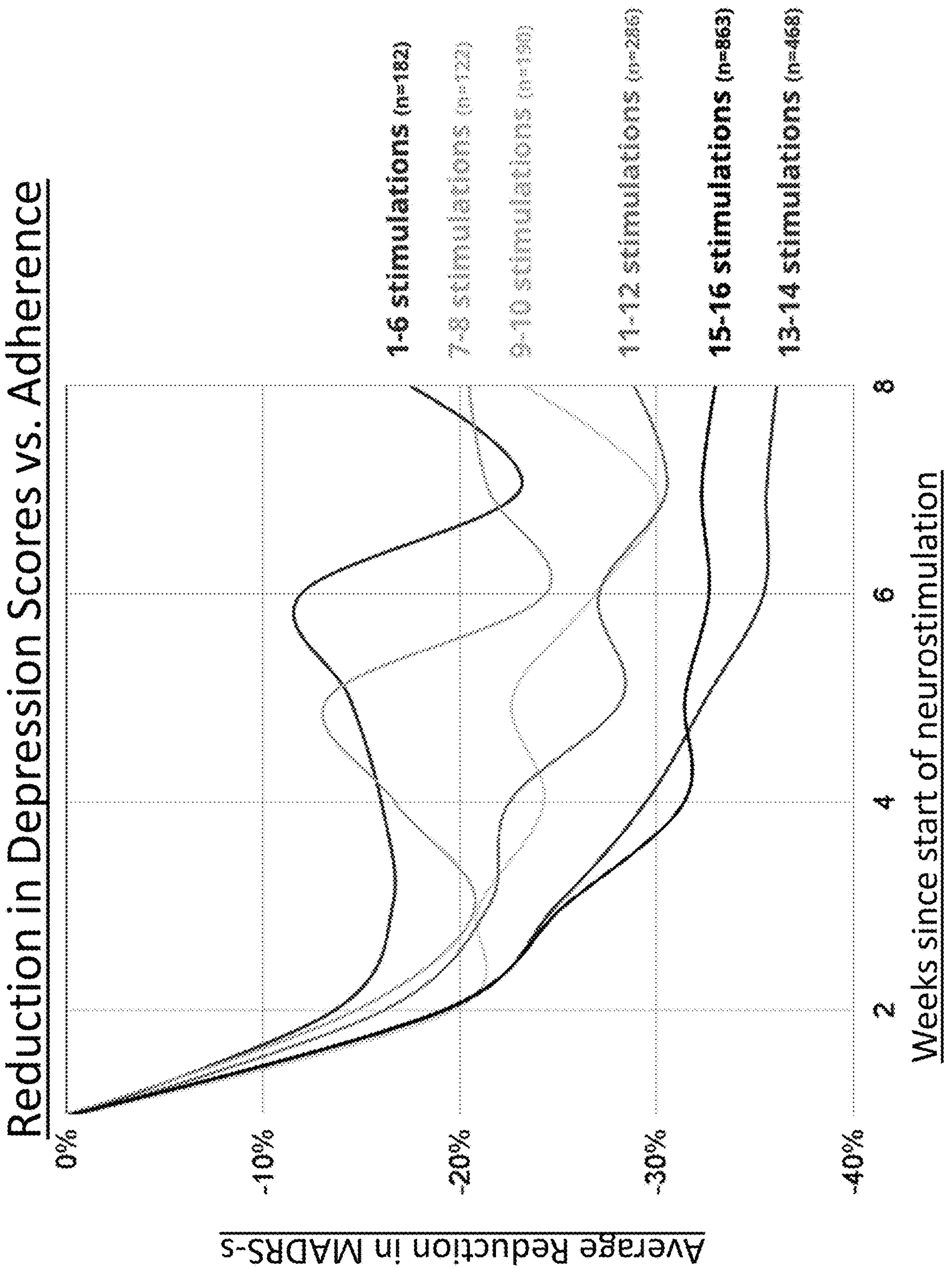
FIG. 8 shows a graph of depression score improvement outcomes through eight weeks following initiation of neurostimulation. Subjects were graphed according to neurostimulation adherence during the first three weeks.

As seen in FIG. 8, change in MADRS-s score was graphed according adherence to tDCS session number through 8 weeks of treatment. As is clearly seen according to stimulation group, those subjects with a greater number of tDCS sessions exhibited a larger reduction in MADRS-s indicating a larger extent of improvement in one or more symptoms of depression.

FIG. 1 to FIG. 8 indicated that NaSSAs appear to be more effective at reducing depression in combination with tDCS than SSRIs and SNRIs. Additionally, stronger adherence to the protocol of tDCS session number per week of treatment created better results in reducing depression symptoms than low adherence to the protocol of tDCS session number.

Surprisingly, combining tDCS with sertraline administration improved symptoms of depression significantly better than combining tDCS with fluoxetine administration. As the mechanism of actions of sertraline and fluoxetine are highly related this is a non-obvious result as one would expect their efficacy when combined with tDCS to be equivalent. However, this was demonstrated not to be the case.

Example 3: Clinical Trials Involving Non-Invasive Brain Stimulation for Treatment of Depression Clinical trials were conducted to test the efficacy of the tDCS device for providing active stimulation for treating unipolar major depressive disorder (MDD) compared to sham stimulation. A tDCS device, the Flow Neuroscience FL-100 device, was used to administer at-home, active or sham stimulation, and clinician-administered and self-reported questionnaires were used to track patient symptoms and progress.

A total of 270 participants were to be recruited to participate in the study, including participants in the United States and in the U.K. The study participants were screened based on predefined eligibility and ineligibility criteria. Of the 2234 participants who completed a telephone screen, 368 were screened and a total of 173 participants were enrolled and underwent randomisation. The final mITT population included 173 participants (86 in the active tDCS group and 87 in the sham tDCS group); 120 (69.3%) of these participants were female and 53 (30.6%) were male.

For example, participants were required to be older than 18 years of age, have a diagnosis of unipolar MDD with a current depressive episode, have a Hamilton Depression Rating Score (HDRS-17)≥16, have a stable antidepressant regimen or not take antidepressants, be in psychotherapy for at least 6 weeks prior to enrollment, and be under the care of a psychiatrist or primary care physician and agree to be evaluated at regular intervals by this care provider. Additional criteria such as access to internet connection, access to a smartphone or similar device, and agreement to the terms of the study procedures were also evaluated. Certain individuals were excluded from the study, e.g., if they exhibited conditions that would impact their ability to complete the study, had a history of illness or conditions that may impact participant safety, etc. More particularly, Exclusion criteria included: 1) have treatment resistant depression as defined by inadequate clinical response to 2 or more trials of antidepressants at an adequate dose and duration; 2) answering yes to Questions 4, 5 or 6 on the Columbia Suicide Severity Rating Scale (C-SSRS) Triage and Risk Identification Screener (ref), indicating high suicide risk; 3) previous hospitalization for depression or suicidal behaviour; 4) Have a history of electroconvulsive therapy (ECT), transcranial magnetic stimulation (TMS), electrotherapy stimulation (CES), transcranial direct current stimulation (tDCS), deep brain stimulation (DBS), or other brain stimulation; 5) history of treatment with esketamine or ketamine for depression; 6) comorbid psychiatric disorder, including an active primary anxiety disorder, panic disorder, post-traumatic stress disorder, obsessive compulsive disorder, bipolar disorder, anorexia, bulimia, personality disorder; 7) vitamin or hormonal deficiencies which could mimic a mood disorder; 8) using any medications that affect cortical excitability (e.g., benzodiazepines, epileptics); 9) history of intractable migraines; 10) history of epilepsy or seizures; 11) history of myocardial infarction or history of other cardiac issues; 12) movement disorders or Parkinsonism; 13) currently pregnant or breastfeeding or any plans during the study; 13) contraindications to tDCS (e.g., metal in the head, implanted devices).

Based on an interim analysis to assess futility and trial sample size, enrolment was ended early.

Of the 2234 participants who completed a telephone screen, 368 were screened and a total of 173 participants were enrolled and underwent randomisation. The final mITT population included 173 participants (86 in the active tDCS group and 87 in the sham tDCS group); 120 (69.3%) of these participants were female and 53 (30.6%) were male, with a mean age of 37.7 years (active group) and 38/8 years (sham group).

At week 10, 53 participants received all of the 36 planned tDCS sessions, 153 completed the minimum number of 22 sessions. 20 participants (11.6%) withdrew before week 10 (n=11 in active group (12.7%), n=9 in sham group (10.3%)). One participant in each group was withdrawn due to treatment failure.

Study Design & Protocol

The trial was designed as a double-blind, placebo-controlled, randomized trial for the treatment of MDD. The study spanned a 10-month period, with the treatment period lasting 5 months. The treatment period comprised three phases including the pre-treatment phase (week −3 to −1), the blinded phase (0 to 10 weeks), and the open-label phase (10 to 20 weeks). In the pre-treatment phase, participants completed informed consent and HIPAA forms and underwent a screening video call to confirm patient eligibility and collect baseline evaluation measurements. After screening and baseline evaluation, participants were trained to use the tDCS device and then randomly assigned to active treatment and sham treatment groups with both study coordinators and participants blind to group assignment. Block randomization was used to assign participants, with permuted block sizes of 4 and 6 and. Participants were randomized 1:1 active vs. sham and randomization for each site was entirely independent.

The tDCS device included a headset that is placed over the forehead with two pre-positioned conductive rubber electrodes, each having a conducting surface area of 23 $cm^2$. One electrode can function as the anode electrode, and one electrode can function as the cathode electrode. The anode and cathode electrodes were placed over the left and right dorsolateral prefrontal cortices, respectively, based on the international 10/20 EEG system. The device included a frame (e.g., similar to frame 110) that extends across the forehead such that the electrodes were positioned according to an F3/F4 electrode montage when the tDCS device was worn. The tDCS further included a bracket (e.g., similar to the bracket 130) coupled to the frame and configured to extend over the head of the user to ensure that the anode and the cathode were disposed over the left and right DLPFC, respectively. The tDCS device further included an electronics subsystem (e.g., similar to subsystem 140 described herein) integrated into the device and pre-programmed to deliver the tDCS sessions according to the protocol described below. The active tDCS stimulation consisted of 2 mA direct current stimulation for 30 minutes with a gradual ramp up over 30 seconds at the start and gradual ramp down over 30 seconds at the end of the session. The sham tDCS stimulation consisted of a gradual ramp up from 0 mA to 1 mA over 30 seconds then a gradual ramp down to 0 mA over 15 seconds. At the end of the session, this is repeated with a gradual ramp up from 0 mA to 1 mA over 30 seconds and then ramp down to 0 mA over 15 seconds. The 1 mA current allowed participants to feel the tingling sensation while minimizing the amount of current. If stimulation was paused, the same ramping procedure is followed upon resumption.

In the blinded phase, at-home stimulation and sham treatments were administered. For the active group, the device was configured to provide 2 mA of direct current to a region of the prefrontal cortex, including the left dorsolateral prefrontal cortex, for a 30-minute session with a 2-minute ramp-up to the maximum amplitude at the beginning of the session and a 1 second ramp-down at the end of the session. The left dorsolateral prefrontal cortex is an area of the brain associated with depression. For the sham group, the device was configured such that at the beginning of the 30-minute session, the device ramps up the current to a maximum amplitude of 1 mA over 30s, then immediately ramp down the current to 0 mA over 15s and holds the current at 0 mA throughout the session. At the end of the 30 minutes, the device ramps up the current again to 1 mA over 30s, and ramps back down to 0 mA over 15s. The sham protocol was designed such that the user feels the tingling of the stimulation while significantly minimizing the participant's exposure to current.

Both active and sham groups received 5 sessions per week for the first 3 weeks of the blinded phase (week 1-3) and then 3 sessions per week for the last 7 weeks of the blinded phase (week 4-10)

In the open-label phase, members of the sham group were notified of their assignment and offered the option to begin active stimulation treatment for the following 10 weeks (week 11-20). The sham group began active treatment at a rate of 5 sessions per week for the first 3 weeks of the open-label phase (week 11-13) and then received the reduced rate of 3 sessions per week for the final 7 weeks of the open-label phase (14-20). Members of the active group were also notified of their assignment and offered the option to continue active stimulation treatment for the open-label phase, receiving 3 sessions per week for the entire open-label phase (week 11-20).

Participants underwent evaluations to track treatment acceptability and progress at week −3, week −2, week −1, week 0, week 1, week 4, week 7, week 10, and week 20. All evaluations were conducted remotely by real-time video conferencing. Evaluations consisted of Clinician Reported Outcome (ClinRO) assessments, Patient Reported Outcome (PRO) Questionnaires, review of concomitant medications, and record of any adverse events and device deficiencies if applicable. The following ClinRO assessments were used: the Hamilton Depression Rating Score (HDRS-17), the Montgomery-Åsberg Depression Rating Scale (MADRS) and self report-rated Montgomery-Åsberg Depression Rating Scale-self report (MADRS-s), the Mini International Neuropsychiatric Interview (MINI), the Hamilton Anxiety Rating Scale (HAM-A), the Young Mania Rating Scale (YMRS), and the Rey Auditory Verbal Learning Test (RAVLT). In conjunction with the ClinRO assessments, the following PRO questionnaires were used: EQ-5D-3L, the Symbol-Digit Modalities Test (SDMT), the Treatment Acceptability Questionnaire (TAQ), the tDCS Adverse Events Questionnaire (AEQ), and the Columbia Suicide Severity Rating Scale (C-SSRS). During the pre-treatment phase, one or more of these assessments were administered and used as baselines to track treatment progress.

At the week 0 evaluation, investigators collected SDMT, reviewed concomitant medications, and recorded any adverse events and device deficiencies for each participant. At the week 1, 4, and 7 evaluations, investigators administered HDRS-17, MADRS, YMRS, and C-SSRS; reviewed concomitant medications; and recorded any adverse events and device deficiencies. On the last week of the blinded phase (week 10), investigators administered HDRS-17, MADRS, HAM-A, YMRS, and RAVLT; reviewed concomitant medications; and completed a final review of inclusion and exclusion criteria. Participants also completed scales including the EQ-5D-3L, SDMT, TAQ, AEQ, and C-SSRS. On the last week of the open-label phase (week 20), the same evaluation as week 10 was conducted. Participants were able to be seen for unscheduled visits as needed. At unscheduled visits, investigators performed HDRS-17, MADRS, YMRS, and C-SSRS, as well as reviewed concomitant medications and recorded any adverse events or device deficiencies.

Statistical Analysis

To quantify outcomes of the study, primary endpoints, secondary endpoints, and exploratory endpoints were considered.

The primary endpoint was defined as the adjusted mean group difference in the HDRS-17 scores at week 10 compared to baseline (e.g., based on data collected during pre-treatment week(s)) for subjects in the active device and sham device groups.

There were four secondary endpoints including: (1) mean change in points for the MADRS score from baseline to week 10 for sham and active groups; (2) clinical response (greater than 50% reduction in scores) from baseline to week 10 on the HDRS-17, MADRS, and MADRS-s scales; (3) remission on the HDRS-17 and MADRS scales; and (4) quality of life improvement as measured by EQ-5D-3L in active vs. sham groups at week 10 compared to baseline.

There were ten exploratory endpoints including: (1) MADRS response rate at all follow-up time points; (2) MADRS-s scores of the two treatment groups (response and remission rates) at all time points; (3) HAM-A) at all time points; (4) YMRS at all time points; (5) tDCS Adverse Events Questionnaire (AEQ) at 10 and 20 weeks; (6) HDRS-17, MADRS, MADRS-s mean decrease, remission, and response rate at 6 weeks comparison between groups; (7) HDRS-17, MADRS, MADRS-s at 20 weeks (after open-label); (8) Correlation between MADRS and MADRS-s; (9) Correlation between the percent of sessions using the FLOW FL-100 and HDRS-17/MADRS decrease in the active group at 10 weeks; and (10) within-patient clinically meaningful improvement as defined as at least-3 points on the HDRS-17 scale. In other words, the percentage of subjects for each treatment group that reaches-3 points or more improvement and also the Cumulative Distribution Function Curves of Change in HDRS-17 Score from Baseline to Primary endpoint by treatment group.

Adjustments to the sample population were made during analysis to account for events such as randomization error, participant drop-out, or device failure.

The formal statistical hypothesis for the primary endpoint was as follows:

$$\text{The Null Hypothesis } (H_0) = d_{flow} - d_{sham} \leq 0$$

$$\text{The Alternative Hypothesis } (H_a) = d_{flow} - d_{sham} > 0$$

Where dflow and dsham are the adjusted mean group difference in HDRS-17 scores in subjects randomized to the active and sham groups, respectively. An analysis population that included randomized participants who received at least one treatment (active or sham) was used to analyze the primary endpoint. The primary endpoint was analyzed when all randomized subjects completed their week 10 visit, had been withdrawn from the trial, or passed the end of their week 10 follow-up visit window. The difference in the group means were assessed using a mixed model for repeated measures (MMRM). The use of the MMRM allows for inclusion of participants with missing 10-week values. The trial was declared a success if the difference in group mean difference in HDRS-17 scores has a p-value≤0.025, using a one-sided t-test. The secondary endpoints were then tested if the primary endpoint demonstrated superiority (e.g., the active group had a significantly higher group mean difference in HDRS-17 than the sham group). Should the first of the four secondary endpoints (i.e., mean change in points for the MADRS score from baseline to week 10 for sham and active groups) show significance, the remaining endpoints were then tested using Hochberg correction for multiplicity.

The sample size calculation for the original protocol was based on data from Brunoni et al (2017). The calculation is based on a two-sample t-test for mean difference with 80% power and one-sided Type 1 error of 0.025. The resulting sample was 176 participants. To obtain an increase in statistical power (87.6%), the sample size was increased to 216. Assuming a 20% attrition rate, the overall sample size for the original protocol was estimated to be 270 participants.

An interim analysis was performed when 90 participants have week 10 data, which included both a futility assessment and sample size re-estimation. The futility assessment was based on stochastic curtailing approach by Lachin, J. M. (2005), A review of methods for futility stopping based on conditional power. Statist. Med., 24:2747-2764. The sample size re-estimation was based on a Promising Zone methodology by Mehta, C. R. and Pocock, S. J. (2011), Adaptive increase in sample size when interim results are promising: A practical guide with examples. Statist. Med., 30:3267-3284 with a Fuzzy design approach introduced by Keenan and Maislin (2014), The Use of "Fuzzy Promising Zones" to Mitigate Against Operational Bias in Adaptive Sample Size Re-estimation Designs. JSM 2014:1493-1506. Separate sample size assessments were performed for evaluating the secondary endpoint of clinical response. Adjustments to the trial for the secondary endpoint were only to be performed if the primary endpoint met criteria as dictated by the promising zone criteria. Sample size assessments for the primary and secondary were provided with extensive details including simulation analyses and methods for controlling operational bias were provided in the adaptive design report. At a high level, the Interim analysis may modify the trial in two ways for the primary endpoint: declare the trial futile and stop enrolment or specify a number of subjects between 100 and 270 needed for powering the trial.

The intent to treat (ITT) analysis consisted of all randomized participants that were included and classified according to their intended treatment regardless of failure to complete the required follow-up examinations. Subjects excluded prior to randomization were considered as screen failures.

The modified intent-to-treat (mITT) analysis set included ITT participants who receive at least 1 tDCS treatment session (active or sham) and excluded participants who were randomized in error. Only one participant, who was randomized but never received any treatment sessions, was excluded from the mITT analysis set. Participants in the mITT population were analyzed in the group to which they were randomized.

The completers per protocol (PP) analysis consisted of participants who completed a minimum of 60% of tDCS sessions (22 sessions) and excluded participants who had met any of the exclusion criteria during the initial 10-week blinded treatment phase, for example, if they had started a new treatment during the trial.

Results

In total, 173 patients were taken through the treatment program over the entire 10-week period. No major side effects were reported from the treatment group.

The primary endpoint was statistically significant. In particular, the p-value was below 0.025.

An initial analysis of the clinical response endpoint (greater than 50% reduction in HDRS-17 or MADRS score from baseline) indicated that a significantly higher percentage of participants in the active group had showed a clinical response according to both the HDRS-17 assessment and the MADRS questionnaire. For the HDRS-17 assessment, 56%±2% of participants in the active group showed a clinical response, whereas only 28%±2% of participants in the sham group showed this trend. Additionally, 62%±2% of participants in the active group showed a clinical response on the MADRS questionnaire, whereas only 33.3%±2% of sham participants showed this reduction.

Analysis of remission (depression score falling below a threshold score, the threshold score being unique to a given depression scale) also demonstrated significant improvements. For the HDRS-17 assessment, a score of 7 and below is considered clinical remission, and for the MADRS scale, a score of 10 and below is considered clinical remission. The results of the trial showed that 43.7%±2% of participants in the active group reached remission as defined by HDRS-17, whereas only 22.7%±2% of the sham group reached remission as defined by HDRS-17. Furthermore, 56.3%±2% of participants in the active group reached remission as defined by the MADRS scale, whereas only 33.3%±2% of participants in the sham group reached remission as defined by the MADRS scale.

Lastly, the odds ratio (OR) was calculated to determine the association between active tDCS stimulation and reduction in depression symptoms. The odds ratio was found to be 3.11±0.4, showing that the odds individuals who received tDCS treatment following the specified protocol experience a 50% or more reduction in depression symptoms are roughly 3 times that of individuals who do not receive the treatment. In other words, the difference in effect between the placebo (sham) and treatment response for the trial was 3.23±0.4. Therefore, the tDCS device provided significant relief in depression symptoms as well as increased rates of remission in the active group compared to the sham group. These findings highlight the use of the disclosed tDCS device as a convenient, cost-effective, and accessible treatment option for individuals diagnosed with MDD.

As shown by the study data, almost 60%±2% of participants using the tDCS headset were relieved of all depressive symptoms within 10 weeks without any severe side effects. The difference in effect between treatment and placebo (sham) was twice as large as witnessed in other antidepressant trials. Since the tDCS device can target the DLPFC via delivery of relatively low current using electrodes placed externally on the forehead, the device causes users to experience little to no side effects compared to antidepressants.

Further Analysis of mITT Results

Data presented below represents results calculated as of Oct. 3, 2023. Further analysis of the underlying data may yield slightly different values. Unless otherwise indicated, significance was assessed with a threshold of p<0.025.

Further analysis of the mITT results suggests that active tDCS was superior to sham tDCS as measured by the HDRS-17 change score at week 10 compared to baseline. HDRS-17 score decreased (greater decrease indicates less depression) by −10.2±5.3 in the active tDCS group and by −7.8±5 in the sham tDCS group. The mean difference between the active tDCS group and the sham tDCS group was-2.2 points (95% confidence interval [CI], −4.0 to −0.5; p=0.013) indicating a greater decrease in the active tDCS group.

HDRS-17 scores were significantly smaller in the active tDCS group (difference in mean score, 2.2 points; 95% confidence interval [CI], −4.0 to −0.5; p=0.012) at 10 weeks.

Response rates (defined as a reduction of >50% in baseline HDRS-17, MADRS or MADRS-s score) and remission rates (defined as a HDRS-17 score ≤7, a MADRS score ≤10 or a MADRS-s score ≤12) in the active group were significantly higher than the sham group at 10 weeks (Table 5). A similar pattern of significant results was found for week 10 change scores on MADRS and MADRS-s (Table 5), and for the per-protocol analyses. There was no difference between groups in change scores on the EQ5D3L at 10 weeks (Table 5):

TABLE 5

Primary and secondary outcomes at 10 weeks

| Outcome | Active tDCS (N = 86) | Sham tDCS (N = 87) | Difference or OR (95% CI) | P Value |
|---|---|---|---|---|
| Primary outcome | | | | |
| HDRS-17 change score | −10.2 ± 5.3 | −7.8 ± 5.0 | −2.2 (−3.9 to −0.5) | 0.013 |
| Secondary outcomes | | | | |
| MADRS change score | −12.8 ± 7.7 | −8.9 ± 7.4 | −3.6 (−6.1 to −1.1) | 0.006 |
| MADRS-s change score | −11.6 ± 8.4 | −6.3 ± 8.3 | −3.6 (−6.4 to −0.9) | 0.010 |
| HDRS-17 - n (%) | | | | |
| response | 41 (55.4) | 21 (28.0) | 3.05 (1.49 to 6.26) | 0.002 |
| remission | 34 (45.9) | 17 (22.7) | 2.88 (1.38 to 5.99) | 0.004 |
| MADRS - n (%) | | | | |
| response | 46 (62.2) | 25 (33.3) | 3.56 (1.73 to 7.31) | <0.001 |
| remission | 42 (56.8) | 25 (33.3) | 3.20 (1.49 to 6.84) | 0.002 |
| MADRS-s - n (%) | | | | |
| response | 30 (47.6) | 14 (20.3) | 3.10 (1.42 to 6.72) | 0.004 |
| remission | 32 (55.8) | 18 (26.1) | 3.80 (1.88 to 8.99) | 0.002 |
| EQ-5D-3L change score | 0.07 ± 0.15 | 0.07 ± 0.17 | 0.02 (−0.02 to 0.05) | 0.380 |

OR = Odds Ratio; Plus-minus values are means ± standard deviation.

Change score were calculated as the score at baseline minus the score at 10 weeks, with greater decreases indicating less depression. Between-group differences are shown for the outcomes regarding decreases in scores from baseline to week 10, and odds ratios are shown for the outcomes regarding response and remission. Percentages for response and remission outcomes are adjusted based on odds ratios. Response was defined as a decrease in the score (indicating less depression) of 50% or more from baseline to week 10. Remission was defined as a score of 7 or fewer points on the HDRS-17 or as 10 or fewer points on the MADRS or as 12 or fewer points of the MADRS-s at 10 weeks. Fully Conditional Specification (FCS) approach was used to produce 20 multiply imputed completed data sets. The FCS approach accommodates monotonicity in the pattern of missing data and requires regression models to be specified for each variable with missing values needing imputation. All models included age, sex, in psychotherapy at baseline, use of any antidepressants at baseline and treatment group. The resulting completed datasets were combined using Rubin's Rules. HDRS-17, Hamilton Depression Rating Scale; MADRS, Montgomery-Åsberg Depression Rating Scale; MADRS-s, Montgomery-Åsberg Depression Rating Scale-self report While the study was not powered to prove statistical significance within the subpopulation of patients receiving concomitant pharmacological antidepressants, the data indicates that the HDRS-17 mean change score, the mean change score MADRS score and the MADRS-s change score was better for the active group (i.e., the group receiving the tDCS treatment) than for the sham group (see Tables 6-8 below).

TABLE 6

HDRS-17 Change Over Time Analysis; mITT Analysis Set; patients receiving concomitant AD (N = 90)

| | Active | | | Sham | | | Group Diff. [1] | | | |
|---|---|---|---|---|---|---|---|---|---|---|
| Week | N | Est | SE | N | Est | SE | Δ | LB | UB | p |
| 1 | 46 | −3.9 | 0.8 | 42 | −5.5 | 0.8 | 1.6 | −0.2 | 3.5 | 0.083 |
| 4 | 40 | −7.3 | 1.0 | 34 | −6.8 | 0.9 | −0.5 | −3.0 | 1.9 | 0.652 |
| 7 | 40 | −8.9 | 1.0 | 35 | −7.9 | 0.9 | −0.9 | −3.3 | 1.5 | 0.446 |
| 10 | 38 | −10.5 | 1.0 | 34 | −7.8 | 1.0 | −2.7 | −5.2 | −0.2 | 0.038 |

[1] Fully Conditional Specification (FCS) approach was used to produce 20 multiply imputed completed data sets. The FCS approach accommodates nonmonotonicity in the pattern of missing data and requires regression models to be specified for each variable with missing values needing imputation. All models included age, sex, in psychotherapy at baseline, use of any antidepressants at baseline and treatment group. The resulting completed datasets were combined using Rubin's Rules.

TABLE 7

MADRS Change Over Time Analysis; mITT Analysis Set; patients receiving concomitant AD (N = 90)

| | Active | | | Sham | | | Group Diff. [1] | | | |
|---|---|---|---|---|---|---|---|---|---|---|
| Week | N | Est | SE | N | Est | SE | Δ | LB | UB | p |
| 1 | 46 | −3.2 | 1.0 | 42 | −4.4 | 1.0 | 1.1 | −1.2 | 3.4 | 0.332 |
| 4 | 40 | −8.1 | 1.2 | 34 | −5.9 | 1.2 | −2.1 | −5.3 | 1.0 | 0.178 |
| 7 | 40 | −10.2 | 1.4 | 35 | −6.5 | 1.4 | −3.8 | −7.3 | −0.2 | 0.037 |
| 10 | 38 | −12.5 | 1.4 | 34 | −7.9 | 1.4 | −4.6 | −8.3 | −0.9 | 0.015 |

[1] Fully Conditional Specification (FCS) approach was used to produce 20 multiply imputed completed data sets. The FCS approach accommodates nonmonotonicity in the pattern of missing data and requires regression models to be specified for each variable with missing values needing imputation. All models included age, sex, in psychotherapy at baseline, use of any antidepressants at baseline and treatment group. The resulting completed datasets were combined using Rubin's Rules.

TABLE 8

MADRS-s Change Over Time Analysis; mITT Analysis Set; patients receiving concomitant AD (N = 90)

| | Active | | | Sham | | | Group Diff. [1] | | | |
|---|---|---|---|---|---|---|---|---|---|---|
| Week | N | Est | SE | N | Est | SE | Δ | LB | UB | p |
| 1 | 43 | −4.0 | 1.2 | 42 | −3.2 | 1.2 | −0.8 | −3.7 | 2.2 | 0.613 |
| 4 | 42 | −6.4 | 1.4 | 37 | −4.5 | 1.3 | −2.0 | −5.5 | 1.5 | 0.264 |
| 7 | 41 | −7.6 | 1.5 | 36 | −6.1 | 1.4 | −1.6 | −5.3 | 2.2 | 0.408 |
| 10 | 34 | −9.8 | 1.7 | 33 | −6.4 | 1.8 | −3.4 | −8.0 | 1.1 | 0.140 |

[1] Fully Conditional Specification (FCS) approach was used to produce 20 multiply imputed completed data sets. The FCS approach accommodates nonmonotonicity in the pattern of missing data and requires regression models to be specified for each variable with missing values needing imputation. All models included age, sex, in psychotherapy at baseline, use of any antidepressants at baseline and treatment group. The resulting completed datasets were combined using Rubin's Rules.

In the subgroup that was taking antidepressant medication, the response and remission rates, as measured by HDRS-17, MADRS, MADRS-s improved more for the active group (i.e., the group receiving the tDCS treatment) than for the sham group (see Tables 9-14 below).

TABLE 9

HDRS-17 Clinical Response Analysis; mITT Analysis Set; patients receiving concomitant AD (N = 90)

| | Active | | | | Sham | | | | Group Diff. [1] | | | | Odds Ratio | | |
|---|---|---|---|---|---|---|---|---|---|---|---|---|---|---|---|
| Week | N | n | % | Adj % | N | n | % | Adj % | Δ | LB | UB | p | OR | LB | UB |
| 1 | 46 | 4 | 8.7% | 7.6% | 42 | 9 | 21.4% | 20.6% | −12.9% | −29.3% | 3.4% | 0.120 | 0.32 | 0.09 | 1.17 |
| 4 | 40 | 12 | 30.0% | 35.1% | 34 | 8 | 23.5% | 25.0% | 10.0% | −13.0% | 33.1% | 0.390 | 1.62 | 0.55 | 4.81 |
| 7 | 40 | 21 | 52.5% | 57.8% | 35 | 13 | 37.1% | 39.4% | 18.4% | −6.5% | 43.3% | 0.146 | 2.11 | 0.79 | 5.66 |
| 10 | 38 | 23 | 60.5% | 61.6% | 34 | 13 | 38.2% | 38.8% | 22.7% | −2.1% | 47.5% | 0.072 | 2.53 | 0.93 | 6.90 |

[1] Fully Conditional Specification (FCS) approach was used to produce 20 multiply imputed completed data sets. The FCS approach accommodates nonmonotonicity in the pattern of missing data and requires regression models to be specified for each variable with missing values needing imputation. All models included age, sex, in psychotherapy at baseline, use of any antidepressants at baseline and treatment group. The resulting completed datasets were combined using Rubin's Rules.

TABLE 10

MADRS Clinical Response Analysis; mITT Analysis Set; patients receiving concomitant AD (N = 90)

| | Active | | | | Sham | | | | Group Diff. [1] | | | | Odds Ratio | | |
|---|---|---|---|---|---|---|---|---|---|---|---|---|---|---|---|
| Week | N | n | % | Adj % | N | n | % | Adj % | Δ | LB | UB | p | OR | LB | UB |
| 1 | 46 | 4 | 8.7% | 6.0% | 42 | 6 | 14.3% | 9.6% | −3.5% | −16.3% | 9.3% | 0.587 | 0.61 | 0.15 | 2.50 |
| 4 | 40 | 14 | 35.0% | 35.9% | 34 | 8 | 23.5% | 23.9% | 12.0% | −10.5% | 34.4% | 0.293 | 1.79 | 0.63 | 5.11 |
| 7 | 40 | 19 | 47.5% | 50.9% | 35 | 12 | 34.3% | 34.6% | 16.3% | −8.8% | 41.4% | 0.201 | 1.97 | 0.71 | 5.42 |
| 10 | 38 | 26 | 68.4% | 69.4% | 34 | 14 | 41.2% | 44.8% | 24.6% | −1.0% | 50.2% | 0.060 | 2.81 | 0.97 | 8.16 |

[1] Fully Conditional Specification (FCS) approach was used to produce 20 multiply imputed completed data sets. The FCS approach accommodates nonmonotonicity in the pattern of missing data and requires regression models to be specified for each variable with missing values needing imputation. All models included age, sex, in psychotherapy at baseline, use of any antidepressants at baseline and treatment group. The resulting completed datasets were combined using Rubin's Rules.

TABLE 11

MADRS-s Clinical Response Analysis; mITT Analysis Set; patients receiving concomitant AD (N = 90)

| | Active | | | | Sham | | | | Group Diff. [1] | | | | Odds Ratio | | |
|---|---|---|---|---|---|---|---|---|---|---|---|---|---|---|---|
| Week | N | n | % | Adj % | N | n | % | Adj % | Δ | LB | UB | p | OR | LB | UB |
| 1 | 43 | 4 | 9.3% | 9.3% | 42 | 5 | 11.9% | 15.7% | −6.4% | −22.6% | 9.8% | 0.439 | 0.56 | 0.13 | 2.43 |
| 4 | 42 | 9 | 21.4% | 15.9% | 37 | 5 | 13.5% | 13.4% | 2.5% | −14.9% | 19.9% | 0.775 | 1.24 | 0.36 | 4.30 |
| 7 | 41 | 13 | 31.7% | 33.2% | 36 | 9 | 25.0% | 29.4% | 3.7% | −20.1% | 27.5% | 0.756 | 1.20 | 0.41 | 3.54 |
| 10 | 34 | 17 | 50.0% | 55.1% | 33 | 8 | 24.2% | 27.8% | 27.4% | 2.4% | 52.3% | 0.032 | 3.23 | 1.06 | 9.85 |

[1] Fully Conditional Specification (FCS) approach was used to produce 20 multiply imputed completed data sets. The FCS approach accommodates nonmonotonicity in the pattern of missing data and requires regression models to be specified for each variable with missing values needing imputation. All models included age, sex, in psychotherapy at baseline, use of any antidepressants at baseline and treatment group. The resulting completed datasets were combined using Rubin's Rules.

TABLE 12

HDRS-17 Remission Analysis; mITT Analysis Set; patients receiving concomitant AD (N = 90)

| | Active | | | | Sham | | | | Group Diff. [1] | | | | Odds Ratio | | |
|---|---|---|---|---|---|---|---|---|---|---|---|---|---|---|---|
| Week | N | n | % | Adj % | N | n | % | Adj % | Δ | LB | UB | p | OR | LB | UB |
| 1 | 46 | 2 | 4.3% | 3.3% | 42 | 4 | 9.5% | 8.1% | −4.8% | −16.7% | 7.0% | 0.419 | 0.39 | 0.06 | 2.53 |
| 4 | 40 | 8 | 20.0% | 21.2% | 34 | 8 | 23.5% | 24.9% | −3.6% | −25.5% | 18.2% | 0.742 | 0.81 | 0.25 | 2.65 |
| 7 | 40 | 15 | 37.5% | 43.9% | 35 | 9 | 25.7% | 29.5% | 14.4% | −9.7% | 38.5% | 0.240 | 1.88 | 0.66 | 5.31 |
| 10 | 38 | 19 | 50.0% | 50.3% | 34 | 9 | 26.5% | 26.7% | 23.7% | −1.1% | 48.4% | 0.061 | 2.81 | 0.94 | 8.44 |

[1] Fully Conditional Specification (FCS) approach was used to produce 20 multiply imputed completed data sets. The FCS approach accommodates nonmonotonicity in the pattern of missing data and requires regression models to be specified for each variable with missing values needing imputation. All models included age, sex, in psychotherapy at baseline, use of any antidepressants at baseline and treatment group. The resulting completed datasets were combined using Rubin's Rules.

TABLE 13

MADRS Remission Analysis; mITT Analysis Set; patients receiving concomitant AD (N = 90)

| | Active | | | | Sham | | | | Group Diff. [1] | | | | Odds Ratio | | |
|---|---|---|---|---|---|---|---|---|---|---|---|---|---|---|---|
| Week | N | n | % | Adj % | N | n | % | Adj % | Δ | LB | UB | p | OR | LB | UB |
| 1 | 46 | 4 | 8.7% | 2.0% | 42 | 8 | 19.0% | 7.1% | −5.1% | −16.9% | 6.8% | 0.397 | 0.27 | 0.05 | 1.65 |
| 4 | 40 | 12 | 30.0% | 30.2% | 34 | 9 | 26.5% | 24.7% | 5.4% | −17.0% | 27.8% | 0.633 | 1.32 | 0.46 | 3.81 |
| 7 | 40 | 21 | 52.5% | 58.1% | 35 | 13 | 37.1% | 38.6% | 19.5% | −5.9% | 45.0% | 0.132 | 2.22 | 0.81 | 6.09 |
| 10 | 38 | 24 | 63.2% | 69.2% | 34 | 14 | 41.2% | 47.5% | 21.7% | −4.8% | 48.2% | 0.107 | 2.50 | 0.85 | 7.40 |

[1] Fully Conditional Specification (FCS) approach was used to produce 20 multiply imputed completed data sets. The FCS approach accommodates nonmonotonicity in the pattern of missing data and requires regression models to be specified for each variable with missing values needing imputation. All models included age, sex, in psychotherapy at baseline, use of any antidepressants at baseline and treatment group. The resulting completed datasets were combined using Rubin's Rules.

TABLE 14

MADRS-s Remission Analysis; mITT Analysis Set; patients receiving concomitant AD (N = 90)

| | Active | | | | Sham | | | | Group Diff. [1] | | | | Odds Ratio | | |
|---|---|---|---|---|---|---|---|---|---|---|---|---|---|---|---|
| Week | N | n | % | Adj % | N | n | % | Adj % | Δ | LB | UB | p | OR | LB | UB |
| 1 | 43 | 5 | 11.6% | 9.1% | 42 | 6 | 14.3% | 11.9% | −2.9% | −19.1% | 13.4% | 0.730 | 0.75 | 0.16 | 3.51 |
| 4 | 42 | 13 | 31.0% | 32.7% | 37 | 7 | 18.9% | 21.2% | 11.5% | −10.7% | 33.7% | 0.307 | 1.82 | 0.59 | 5.64 |
| 7 | 41 | 15 | 36.6% | 41.7% | 36 | 11 | 30.6% | 32.4% | 9.4% | −14.8% | 33.5% | 0.444 | 1.50 | 0.55 | 4.12 |
| 10 | 34 | 19 | 55.9% | 67.3% | 33 | 12 | 36.4% | 31.4% | 35.8% | 8.9% | 62.7% | 0.009 | 4.52 | 1.32 | 15.48 |

[1] Fully Conditional Specification (FCS) approach was used to produce 20 multiply imputed completed data sets. The FCS approach accommodates nonmonotonicity in the pattern of missing data and requires regression models to be specified for each variable with missing values needing imputation. All models included age, sex, in psychotherapy at baseline, use of any antidepressants at baseline and treatment group. The resulting completed datasets were combined using Rubin's Rules.

For patients that were not taking antidepressant medication, response and remission rates were higher, and the mean change over time was better, for all three scales in the active tDCS group than in the sham group (see Tables 15-23 below).

TABLE 15

HDRS-17 Change Over Time Analysis; mITT Analysis Set; patients NOT receiving concomitant AD (N = 83)

| | Active | | | Sham | | | Group Diff. [1] | | | |
|---|---|---|---|---|---|---|---|---|---|---|
| Week | N | Est | SE | N | Est | SE | Δ | LB | UB | p |
| 1 | 37 | −3.5 | 0.9 | 42 | −2.7 | 0.9 | −0.8 | −2.8 | 1.2 | 0.431 |
| 4 | 37 | −7.5 | 1.0 | 42 | −3.9 | 1.0 | −3.6 | −6.0 | −1.2 | 0.004 |

TABLE 15-continued

HDRS-17 Change Over Time Analysis; mITT Analysis Set; patients NOT receiving concomitant AD (N = 83)

| | Active | | | Sham | | | Group Diff. [1] | | | |
|---|---|---|---|---|---|---|---|---|---|---|
| Week | N | Est | SE | N | Est | SE | Δ | LB | UB | p |
| 7 | 35 | −7.7 | 1.0 | 40 | −5.1 | 1.1 | −2.6 | −5.2 | 0.0 | 0.047 |
| 10 | 36 | −8.3 | 1.0 | 41 | −6.1 | 1.0 | −2.2 | −4.7 | 0.2 | 0.075 |

[1] Fully Conditional Specification (FCS) approach was used to produce 20 multiply imputed completed data sets. The FCS approach accommodates nonmonotonicity in the pattern of missing data and requires regression models to be specified for each variable with missing values needing imputation. All models included age, sex, in psychotherapy at baseline, use of any antidepressants at baseline and treatment group. The resulting completed datasets were combined using Rubin's Rules.

TABLE 16

MADRS Change Over Time Analysis; mITT Analysis Set; patients NOT receiving concomitant AD (N = 83)

| | Active | | | Sham | | | Group Diff. [1] | | | |
|---|---|---|---|---|---|---|---|---|---|---|
| Week | N | Est | SE | N | Est | SE | Δ | LB | UB | p |
| 1 | 37 | −3.4 | 1.1 | 42 | −2.2 | 1.2 | −1.2 | −3.8 | 1.3 | 0.344 |
| 4 | 37 | −9.1 | 1.4 | 42 | −4.1 | 1.4 | −5.0 | −8.4 | −1.6 | 0.004 |
| 7 | 35 | −9.6 | 1.4 | 40 | −5.8 | 1.4 | −3.9 | −7.3 | −0.4 | 0.028 |
| 10 | 36 | −10.0 | 1.5 | 41 | −6.7 | 1.5 | −3.3 | −6.9 | 0.3 | 0.074 |

[1] Fully Conditional Specification (FCS) approach was used to produce 20 multiply imputed completed data sets. The FCS approach accommodates nonmonotonicity in the pattern of missing data and requires regression models to be specified for each variable with missing values needing imputation. All models included age, sex, in psychotherapy at baseline, use of any antidepressants at baseline and treatment group. The resulting completed datasets were combined using Rubin's Rules.

TABLE 17

MADRS-s Change Over Time Analysis; mITT Analysis Set; patients NOT receiving concomitant AD (N = 83)

| | Active | | | Sham | | | Group Diff. [1] | | | |
|---|---|---|---|---|---|---|---|---|---|---|
| Week | N | Est | SE | N | Est | SE | Δ | LB | UB | p |
| 1 | 36 | −3.7 | 1.4 | 42 | −2.5 | 1.4 | −1.2 | −4.2 | 1.8 | 0.424 |
| 4 | 35 | −8.7 | 1.6 | 42 | −5.3 | 1.6 | −3.4 | −7.2 | 0.3 | 0.072 |
| 7 | 33 | −7.1 | 1.7 | 40 | −5.7 | 1.6 | −1.5 | −5.5 | 2.6 | 0.479 |
| 10 | 29 | −9.9 | 1.8 | 36 | −6.1 | 1.7 | −3.8 | −8.0 | 0.4 | 0.078 |

[1] Fully Conditional Specification (FCS) approach was used to produce 20 multiply imputed completed data sets. The FCS approach accommodates nonmonotonicity in the pattern of missing data and requires regression models to be specified for each variable with missing values needing imputation. All models included age, sex, in psychotherapy at baseline, use of any antidepressants at baseline and treatment group. The resulting completed datasets were combined using Rubin's Rules.

TABLE 18

HDRS-17 Clinical Response Analysis; mITT Analysis Set; patients NOT receiving concomitant AD (N = 83)

| | Active | | | | Sham | | | | Group Diff. [1] | | | | Odds Ratio | | |
|---|---|---|---|---|---|---|---|---|---|---|---|---|---|---|---|
| Week | N | n | % | Adj % | N | n | % | Adj % | Δ | LB | UB | p | OR | LB | UB |
| 1 | 37 | 5 | 13.5% | 14.3% | 42 | 3 | 7.1% | 6.1% | 8.2% | −6.0% | 22.3% | 0.255 | 2.55 | 0.48 | 13.47 |
| 4 | 37 | 15 | 40.5% | 38.4% | 42 | 5 | 11.9% | 10.5% | 27.9% | 8.6% | 47.2% | 0.005 | 5.32 | 1.52 | 18.58 |
| 7 | 35 | 14 | 40.0% | 41.1% | 40 | 9 | 22.5% | 17.1% | 24.0% | 2.7% | 45.3% | 0.027 | 3.39 | 1.08 | 10.70 |
| 10 | 36 | 18 | 50.0% | 52.1% | 41 | 8 | 19.5% | 14.1% | 38.0% | 17.4% | 58.6% | <.001 | 6.65 | 1.95 | 22.63 |

[1] Fully Conditional Specification (FCS) approach was used to produce 20 multiply imputed completed data sets. The FCS approach accommodates nonmonotonicity in the pattern of missing data and requires regression models to be specified for each variable with missing values needing imputation. All models included age, sex, in psychotherapy at baseline, use of any antidepressants at baseline and treatment group. The resulting completed datasets were combined using Rubin's Rules.

TABLE 19

MADRS Clinical Response Analysis; mITT Analysis Set; patients NOT receiving concomitant AD (N = 83)

| | Active | | | | Sham | | | | Group Diff. [1] | | | | Odds Ratio | | |
|---|---|---|---|---|---|---|---|---|---|---|---|---|---|---|---|
| Week | N | n | % | Adj % | N | n | % | Adj % | Δ | LB | UB | p | OR | LB | UB |
| 1 | 37 | 6 | 16.2% | 13.4% | 42 | 1 | 2.4% | 2.6% | 10.8% | −2.2% | 23.9% | 0.104 | 5.89 | 0.62 | 55.80 |
| 4 | 37 | 16 | 43.2% | 43.3% | 42 | 5 | 11.9% | 10.5% | 32.8% | 13.6% | 52.0% | <.001 | 6.50 | 1.91 | 22.06 |
| 7 | 35 | 16 | 45.7% | 45.0% | 40 | 11 | 27.5% | 24.2% | 20.8% | −1.3% | 43.0% | 0.065 | 2.57 | 0.92 | 7.20 |
| 10 | 36 | 20 | 55.6% | 57.1% | 41 | 11 | 26.8% | 21.8% | 35.3% | 13.7% | 56.9% | 0.002 | 4.79 | 1.63 | 14.07 |

[1] Fully Conditional Specification (FCS) approach was used to produce 20 multiply imputed completed data sets. The FCS approach accommodates nonmonotonicity in the pattern of missing data and requires regression models to be specified for each variable with missing values needing imputation. All models included age, sex, in psychotherapy at baseline, use of any antidepressants at baseline and treatment group. The resulting completed datasets were combined using Rubin's Rules.

TABLE 20

MADRS-s Clinical Response Analysis; mITT Analysis Set; patients NOT receiving concomitant AD (N = 83)

| | Active | | | | Sham | | | | Group Diff. [1] | | | | Odds Ratio | | |
|---|---|---|---|---|---|---|---|---|---|---|---|---|---|---|---|
| Week | N | n | % | Adj % | N | n | % | Adj % | Δ | LB | UB | p | OR | LB | UB |
| 1 | 36 | 4 | 11.1% | 4.8% | 42 | 1 | 2.4% | 1.0% | 3.8% | −4.8% | 12.5% | 0.385 | 4.99 | 0.45 | 55.84 |
| 4 | 35 | 13 | 37.1% | 37.1% | 42 | 0 | 14.3% | 14.0% | 23.2% | 3.4% | 42.9% | 0.022 | 3.63 | 1.13 | 11.69 |
| 7 | 33 | 12 | 36.4% | 35.2% | 40 | 0 | 15.0% | 17.3% | 17.9% | −3.3% | 39.1% | 0.097 | 2.60 | 0.80 | 8.40 |
| 10 | 29 | 13 | 44.8% | 45.9% | 36 | 6 | 16.7% | 15.7% | 30.1% | 7.6% | 52.7% | 0.009 | 4.54 | 1.35 | 15.25 |

[1] Fully Conditional Specification (FCS) approach was used to produce 20 multiply imputed completed data sets. The FCS approach accommodates nonmonotonicity in the pattern of missing data and requires regression models to be specified for each variable with missing values needing imputation. All models included age, sex, in psychotherapy at baseline, use of any antidepressants at baseline and treatment group. The resulting completed datasets were combined using Rubin's Rules.

TABLE 21

HDRS-17 Remission Analysis; mITT Analysis Set; patients NOT receiving concomitant AD (N = 83)

| | Active | | | | Sham | | | | Group Diff. [1] | | | | Odds Ratio | | |
|---|---|---|---|---|---|---|---|---|---|---|---|---|---|---|---|
| Week | N | n | % | Adj % | N | n | % | Adj % | Δ | LB | UB | p | OR | LB | UB |
| 1 | 37 | 2 | 5.4% | 5.3% | 42 | 2 | 4.8% | 2.9% | 2.4% | −7.3% | 12.2% | 0.625 | 1.83 | 0.19 | 17.50 |
| 4 | 37 | 10 | 27.0% | 27.9% | 42 | 3 | 7.1% | 4.1% | 23.8% | 6.8% | 40.8% | 0.006 | 9.07 | 1.85 | 44.57 |
| 7 | 35 | 12 | 34.3% | 35.9% | 40 | 6 | 15.0% | 12.5% | 23.4% | 3.5% | 43.2% | 0.021 | 3.93 | 1.12 | 13.79 |
| 10 | 36 | 15 | 41.7% | 44.1% | 41 | 8 | 19.5% | 14.2% | 30.0% | 9.3% | 50.6% | 0.005 | 4.79 | 1.42 | 16.11 |

[1] Fully Conditional Specification (FCS) approach was used to produce 20 multiply imputed completed data sets. The FCS approach accommodates nonmonotonicity in the pattern of missing data and requires regression models to be specified for each variable with missing values needing imputation. All models included age, sex, in psychotherapy at baseline, use of any antidepressants at baseline and treatment group. The resulting completed datasets were combined using Rubin's Rules.

TABLE 22

MADRS Remission Analysis; mITT Analysis Set; patients NOT receiving concomitant AD (N = 83)

| | Active | | | | Sham | | | | Group Diff. [1] | | | | Odds Ratio | | |
|---|---|---|---|---|---|---|---|---|---|---|---|---|---|---|---|
| Week | N | n | % | Adj % | N | n | % | Adj % | Δ | LB | UB | p | OR | LB | UB |
| 1 | 37 | 3 | 8.1% | 7.1% | 42 | 1 | 2.4% | 0.9% | 6.3% | −3.2% | 15.8% | 0.192 | 8.97 | 0.55 | 146.88 |
| 4 | 37 | 13 | 35.1% | 35.5% | 42 | 2 | 4.8% | 3.1% | 32.4% | 15.1% | 49.7% | <.001 | 17.05 | 2.80 | 103.90 |
| 7 | 35 | 13 | 37.1% | 38.4% | 40 | 6 | 15.0% | 11.8% | 26.6% | 6.7% | 46.6% | 0.009 | 4.68 | 1.34 | 16.31 |
| 10 | 36 | 18 | 50.0% | 51.6% | 41 | 11 | 26.8% | 17.4% | 34.2% | 12.5% | 55.8% | 0.002 | 5.06 | 1.59 | 16.14 |

[1] Fully Conditional Specification (FCS) approach was used to produce 20 multiply imputed completed data sets. The FCS approach accommodates nonmonotonicity in the pattern of missing data and requires regression models to be specified for each variable with missing values needing imputation. All models included age, sex, in psychotherapy at baseline, use of any antidepressants at baseline and treatment group. The resulting completed datasets were combined using Rubin's Rules.

TABLE 23

MADRS-s Remission Analysis; mITT Analysis Set; patients NOT receiving concomitant AD (N = 83)

| | Active | | | | Sham | | | | Group Diff. [1] | | | | Odds Ratio | | |
|---|---|---|---|---|---|---|---|---|---|---|---|---|---|---|---|
| Week | N | n | % | Adj % | N | n | % | Adj % | Δ | LB | UB | p | OR | LB | UB |
| 1 | 36 | 6 | 16.7% | 5.1% | 42 | 3 | 7.1% | 1.6% | 3.5% | −5.6% | 12.6% | 0.452 | 3.27 | 0.39 | 27.76 |
| 4 | 35 | 10 | 28.6% | 26.9% | 42 | 6 | 14.3% | 12.7% | 14.2% | −5.0% | 33.5% | 0.146 | 2.52 | 0.72 | 8.83 |
| 7 | 33 | 9 | 27.3% | 27.0% | 40 | 5 | 12.5% | 12.2% | 14.8% | −4.3% | 33.9% | 0.128 | 2.66 | 0.73 | 9.68 |
| 10 | 29 | 13 | 44.8% | 46.0% | 36 | 6 | 16.7% | 14.0% | 32.0% | 9.1% | 54.9% | 0.006 | 5.26 | 1.47 | 18.84 |

[1] Fully Conditional Specification (FCS) approach was used to produce 20 multiply imputed completed data sets. The FCS approach accommodates nonmonotonicity in the pattern of missing data and requires regression models to be specified for each variable with missing values needing imputation. All models included age, sex, in psychotherapy at baseline, use of any antidepressants at baseline and treatment group. The resulting completed datasets were combined using Rubin's Rules.

Other studies have investigated the clinical effect of using tDCS to treat depression but have yielded less successful results. For example, one study delivered tDCS with a current of 2 mA for 21 sessions using electrodes arranged in an OLE montage (Brunoni, Andre R, et al. "Trial of Electrical Direct-Current Therapy versus Escitalopram for Depression." New England Journal of Medicine 376, no. 26 (2017): 2523-33.). While the Brunoni et al. study demonstrated that the tDCS group showed statistically significant improvement in remission rates and response rates compared to placebo, the remission and response rates were lower than those of the current trial. Additionally, a different study delivered tDCS with a current of 2 mA for 24 sessions using electrodes arranged in an F3/F4 montage and having a conducting surface area of 30 $cm^2$ (Burkhardt et al. 2023. "Transcranial Direct Current Stimulation as an Additional Treatment to Selective Serotonin Reuptake Inhibitors in Adults with Major Depressive Disorder in Germany (DepressionDC): A Triple-Blind, Randomised, Sham-Controlled, Multicentre Trial." The Lancet 402 (10401): 545-554). However, the findings of Burkhardt et al. showed no statistically significant improvement in remission rates and response rates compared to placebo. In contrast, the current trial delivered tDCS with a current of 2 mA for 36 sessions using electrodes arranged in a F3/F4 montage and having a surface area of 23 $cm^2$. The higher remission and response rates observed in the current trial compared to previous studies highlights the importance of delivering tDCS for about 36 sessions using electrodes arranged in a F3/F4 montage and having a surface area of 23 $cm^2$ for achieving superior clinical outcomes.

Figure 10:
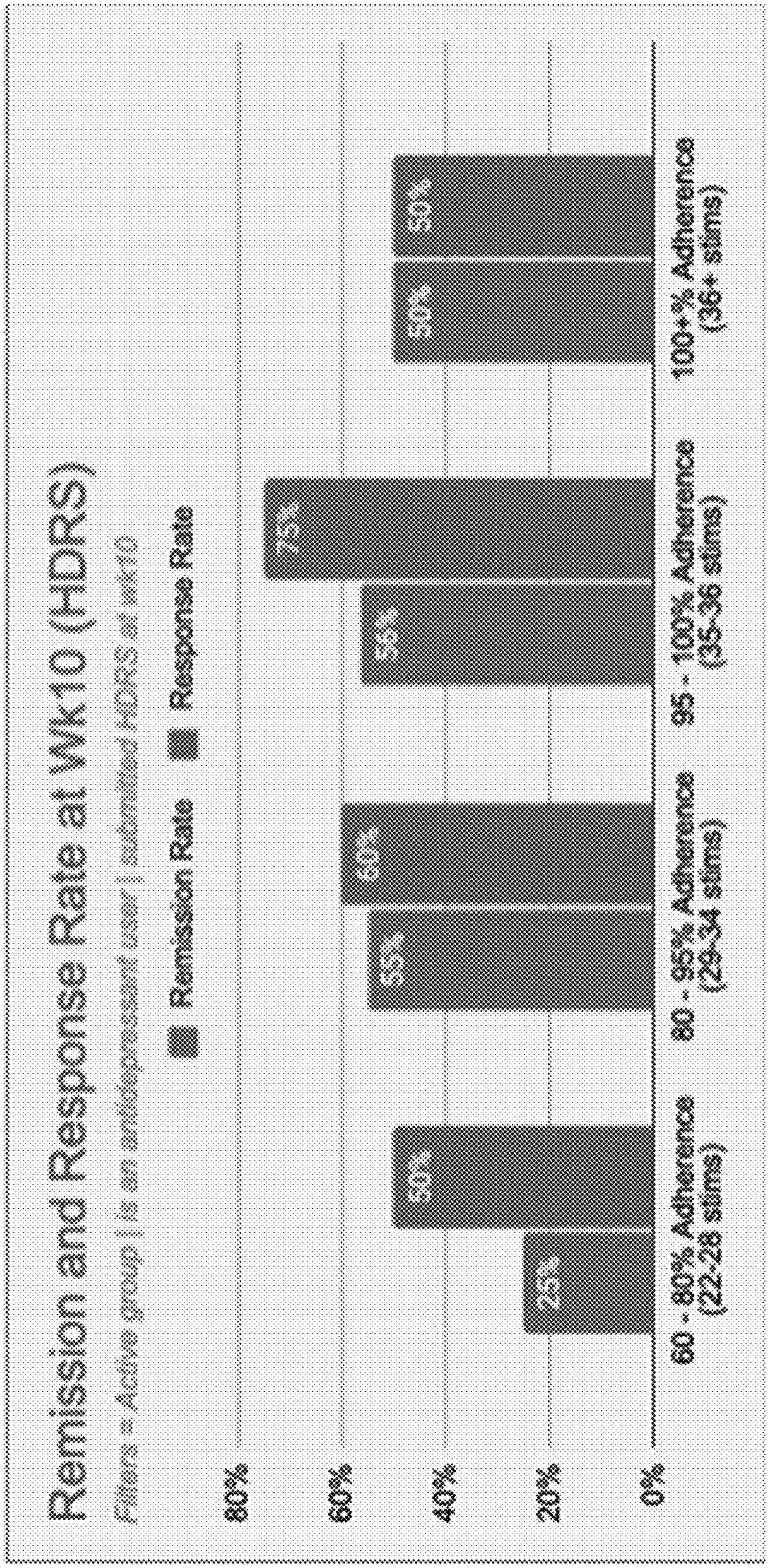
FIG. 10 depicts the difference in remission and response rates, as measured by HDRS-17 scores, among patients with different levels of adherence to the prescribed dosing protocol for the clinical trial described in Example 3. The number of stims in parentheses indicates the number of tCDS stimulation sessions administered to the patient over the course of the 10 week blinded portion of the trial. Data is shown for patients in the active group who were also receiving concomitant administration of an antidepressant. For each group, remission rates are shown on the left bar, and response rates are shown on the right bars.
Figure 11:
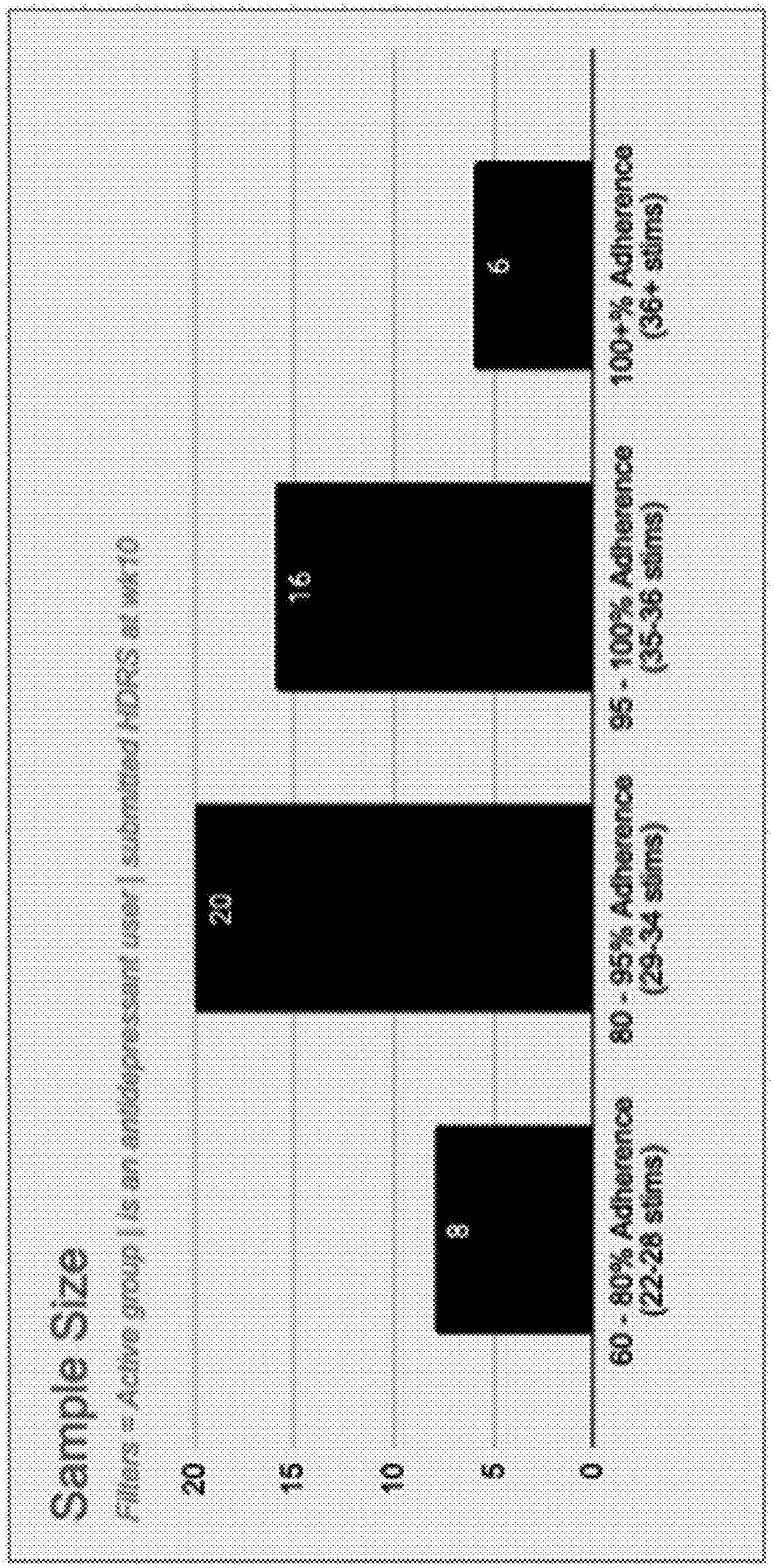
FIG. 11 depicts the number of patients in each subgroup group depicted in FIG. 10.
Figure 12A:
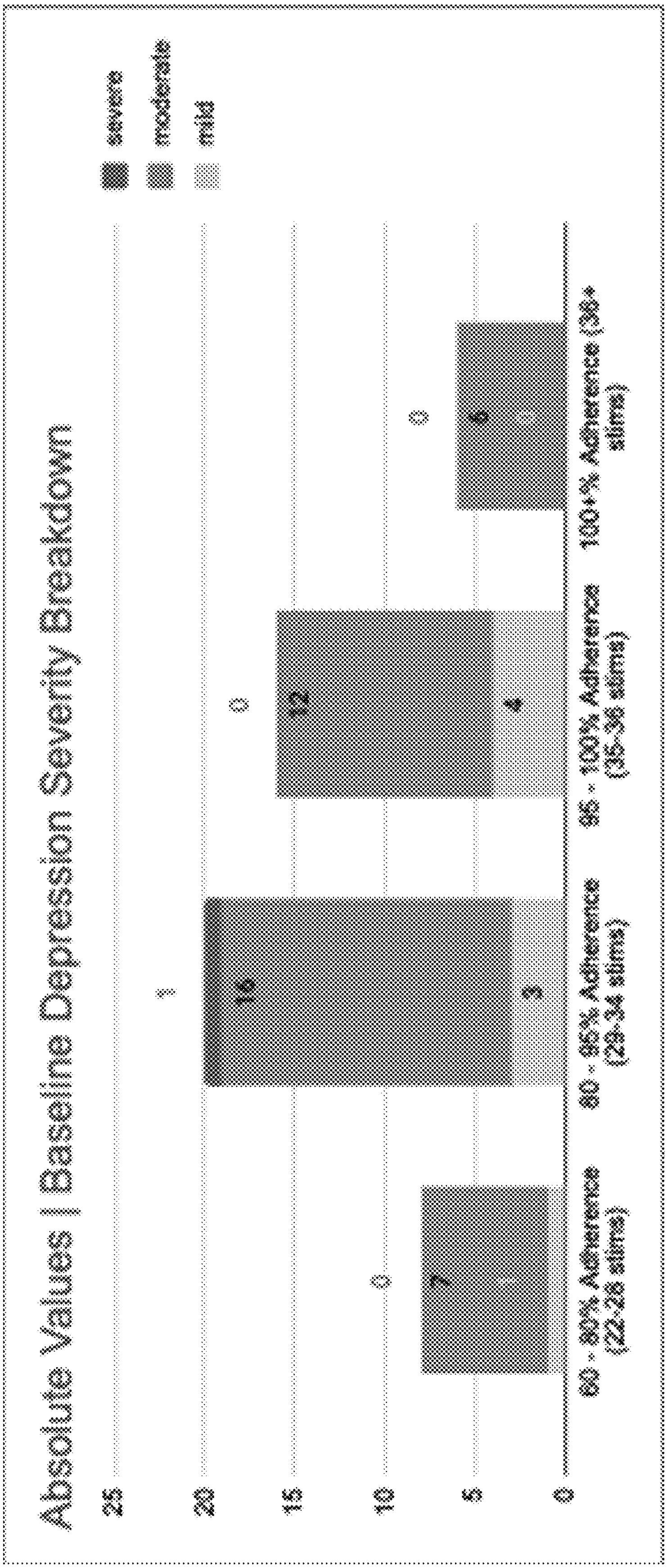
FIGS. 12A and 12B depict the number of patients in each subgroup group depicted in FIG. 10, further categorized by depression severity at baseline, as measured by HDRS-17.
Figure 12B:
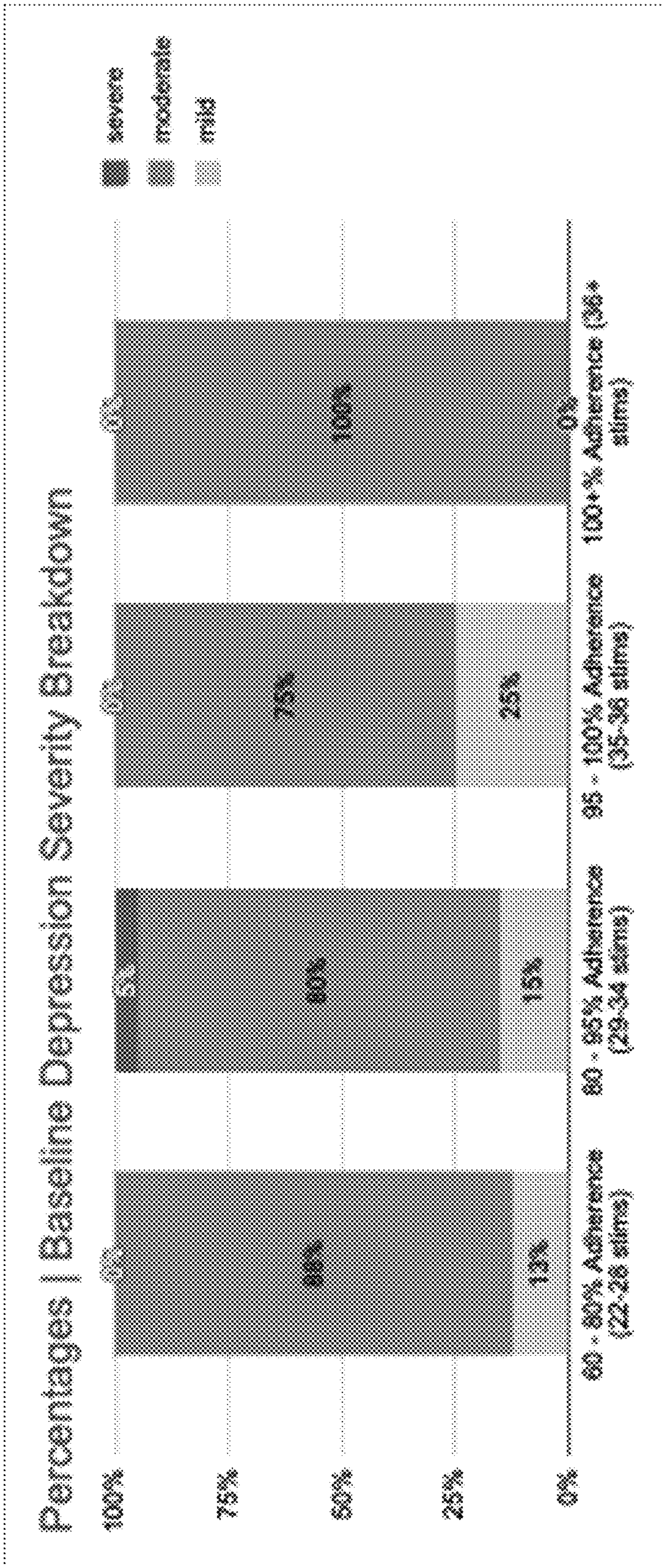

Although the trial protocol specified 36 total doses of tDCS during the 10-week blinded phase, not all patients completed all prescribed stimulation sessions, and some patients completed more sessions than prescribed. An analysis was conducted of the dosing trends for the patients receiving concomitant antidepressants. The results are shown in FIGS. 10-12B. There is a trend in increased remission/response for increasing number of stimulation sessions up to 36 during the 10 week blinded study period (FIGS. 10 and 11). Patient adherence was not correlated with disease severity, (FIGS. 12A and 12B), suggesting that the trend identified in FIGS. 10 and 11 is attributable to the number of stimulation sessions received, rather than the underlying severity of the patient's disease.

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

ENUMERATED EMBODIMENTS

A1. A method of treatment for depression in a subject comprising delivering to the subject a transcranial electrical stimulation (tES), optionally wherein the tES is tDCS, by a tES device, wherein the tES device includes first and second electrodes each having a conducting surface area of between about 20 $cm^2$ and 25 $cm^2$.

A2. A method of treatment for depression in a subject comprising delivering to the subject a transcranial electrical stimulation (tES), optionally wherein the tES is tDCS, by a tES device, wherein the tES device includes first and second electrodes each having a conducting surface area of about 23 $cm^2$.

A3. The method of embodiment A1 or A2, wherein the tES device further includes:
- i) a frame supporting the first and second electrodes; and
- ii) a bracket coupled to the frame, the bracket being configured to extend over a head of the subject to ensure that the frame is worn in a predefined orientation by the subject.

B1. A method of treatment for depression in a subject comprising delivering to the subject a transcranial electrical stimulation (tES), optionally wherein the tES is tDCS, wherein the tES is delivered to the subject about 5 times per week.

B2. A method of treatment for depression in a subject comprising delivering to the subject a transcranial electrical stimulation (tES), optionally wherein the tES is tDCS, wherein the tES is delivered to the subject about 5 times per week for at least 3 weeks.

B3. A method of treatment for depression in a subject comprising delivering to the subject a transcranial electrical stimulation (tES), optionally wherein the tES is tDCS, wherein the tES is delivered to the subject about 5 times per week for at least 3 weeks, after which the tES is delivered to the subject about 3 times per week for at least 7 weeks.

B4. A method of treatment for depression in a subject comprising delivering to the subject a transcranial electrical stimulation (tES), optionally wherein the tES is tDCS, wherein the tES is delivered to the subject about 5 times per week for at least 3 weeks, after which the tES is delivered to the subject about 3 times per week for at least 7 weeks; further wherein:
- i) the tES is not delivered to the subject more than 36 times in a 10-week period; and/or
- ii) the tES is not delivered to the subject more than 5 times per week.

B5. A method of treatment for depression in a subject comprising delivering to the subject a transcranial electrical stimulation (tES), optionally wherein the tES is tDCS, wherein the tES is delivered to the subject about 5 times per week for at least 3 weeks, after which the tES is delivered to the subject about 3 times per week for at least 7 weeks; further wherein:
- i) the tES is not delivered to the subject more than 36 times in a 10-week period; and
- ii) the tES is not delivered to the subject more than 5 times per week.

B6. The method of any one of embodiments B1-B5, wherein the tES is delivered using a tES device, the tES device including:
- i) a frame supporting first and second electrodes configured deliver the tES; and
- ii) a bracket coupled to the frame, the bracket being configured to extend over a head of the subject to ensure that the frame is worn in a predefined orientation by the subject.

C1. A method of treatment for depression in a subject comprising delivering to the subject a transcranial electrical stimulation (tES), optionally wherein the tES is tDCS, wherein the patient is also being administered at least one pharmacologic antidepressant agent.

C2. The method of embodiment C1, wherein the pharmacologic antidepressant agent comprises a selective serotonin reuptake inhibitor (SSRI).

C3. The method of embodiment C1, wherein the pharmacologic antidepressant agent comprises fluoxetine, citalopram, escitalopram, paroxetine, sertraline, dapoxetine, fluvoxamine, or vortioxetine.

D1. A method of treatment for depression in a subject comprising delivering to the subject a transcranial electrical stimulation (tES), optionally wherein the tES is tDCS, and wherein tES is delivered using a tES device having first electrode positioned over a F3 electrode region and a second electrode positioned over a F4 electrode region.

D2. A method of treatment for depression in a subject comprising delivering to the subject a transcranial electrical stimulation (tES), optionally wherein the tES is tDCS, and wherein tES is delivered using a tES device having first electrode positioned over a left dorsolateral prefrontal cortex and a second electrode positioned over a right dorsolateral prefrontal cortex.

E1. A method comprising the features described in Embodiment C1, and Embodiment D1.

E2. A method comprising the features described in Embodiment C1, and Embodiment D2.

E3. A method comprising the features described in Embodiment C2, and Embodiment D1.

E4. A method comprising the features described in Embodiment C2, and Embodiment D2.

E5. A method comprising the features described in Embodiment C3, and Embodiment D1.

E6. A method comprising the features described in Embodiment C3, and Embodiment D2.

E7. A method comprising the features described in Embodiment B1, and Embodiment D1.

E8. A method comprising the features described in Embodiment B1, and Embodiment D2.

E9. A method comprising the features described in Embodiment B1, and Embodiment C1.

E10. A method comprising the features described in Embodiment B1, Embodiment C1, and Embodiment D1.

E11. A method comprising the features described in Embodiment B1, Embodiment C1, and Embodiment D2.

E12. A method comprising the features described in Embodiment B1, and Embodiment C2.

E13. A method comprising the features described in Embodiment B1, Embodiment C2, and Embodiment D1.

E14. A method comprising the features described in Embodiment B1, Embodiment C2, and Embodiment D2.

E15. A method comprising the features described in Embodiment B1, and Embodiment C3.

E16. A method comprising the features described in Embodiment B1, Embodiment C3, and Embodiment D1.

E17. A method comprising the features described in Embodiment B1, Embodiment C3, and Embodiment D2.

E18. A method comprising the features described in Embodiment B2, and Embodiment D1.

E19. A method comprising the features described in Embodiment B2, and Embodiment D2.

E20. A method comprising the features described in Embodiment B2, and Embodiment C1.

E21. A method comprising the features described in Embodiment B2, Embodiment C1, and Embodiment D1.

E22. A method comprising the features described in Embodiment B2, Embodiment C1, and Embodiment D2.

E23. A method comprising the features described in Embodiment B2, and Embodiment C2.

E24. A method comprising the features described in Embodiment B2, Embodiment C2, and Embodiment D1.

E25. A method comprising the features described in Embodiment B2, Embodiment C2, and Embodiment D2.

E26. A method comprising the features described in Embodiment B2, and Embodiment C3.

E27. A method comprising the features described in Embodiment B2, Embodiment C3, and Embodiment D1.

E28. A method comprising the features described in Embodiment B2, Embodiment C3, and Embodiment D2.

E29. A method comprising the features described in Embodiment B3, and Embodiment D1.

E30. A method comprising the features described in Embodiment B3, and Embodiment D2.

E31. A method comprising the features described in Embodiment B3, and Embodiment C1.

E32. A method comprising the features described in Embodiment B3, Embodiment C1, and Embodiment D1.

E33. A method comprising the features described in Embodiment B3, Embodiment C1, and Embodiment D2.

E34. A method comprising the features described in Embodiment B3, and Embodiment C2.

E35. A method comprising the features described in Embodiment B3, Embodiment C2, and Embodiment D1.

E36. A method comprising the features described in Embodiment B3, Embodiment C2, and Embodiment D2.

E37. A method comprising the features described in Embodiment B3, and Embodiment C3.

E38. A method comprising the features described in Embodiment B3, Embodiment C3, and Embodiment D1.

E39. A method comprising the features described in Embodiment B3, Embodiment C3, and Embodiment D2.

E40. A method comprising the features described in Embodiment B4, and Embodiment D1.

E41. A method comprising the features described in Embodiment B4, and Embodiment D2.

E42. A method comprising the features described in Embodiment B4, and Embodiment C1.

E43. A method comprising the features described in Embodiment B4, Embodiment C1, and Embodiment D1.

E44. A method comprising the features described in Embodiment B4, Embodiment C1, and Embodiment D2.

E45. A method comprising the features described in Embodiment B4, and Embodiment C2.

E46. A method comprising the features described in Embodiment B4, Embodiment C2, and Embodiment D1.

E47. A method comprising the features described in Embodiment B4, Embodiment C2, and Embodiment D2.

E48. A method comprising the features described in Embodiment B4, and Embodiment C3.

E49. A method comprising the features described in Embodiment B4, Embodiment C3, and Embodiment D1.

E50. A method comprising the features described in Embodiment B4, Embodiment C3, and Embodiment D2.

E51. A method comprising the features described in Embodiment B5, and Embodiment D1.

E52. A method comprising the features described in Embodiment B5, and Embodiment D2.

E53. A method comprising the features described in Embodiment B5, and Embodiment C1.

E54. A method comprising the features described in Embodiment B5, Embodiment C1, and Embodiment D1.

E55. A method comprising the features described in Embodiment B5, Embodiment C1, and Embodiment D2.

E56. A method comprising the features described in Embodiment B5, and Embodiment C2.

E57. A method comprising the features described in Embodiment B5, Embodiment C2, and Embodiment D1.

E58. A method comprising the features described in Embodiment B5, Embodiment C2, and Embodiment D2.

E59. A method comprising the features described in Embodiment B5, and Embodiment C3.

E60. A method comprising the features described in Embodiment B5, Embodiment C3, and Embodiment D1.

E61. A method comprising the features described in Embodiment B5, Embodiment C3, and Embodiment D2.

E62. A method comprising the features described in Embodiment B6, and Embodiment D1.

E63. A method comprising the features described in Embodiment B6, and Embodiment D2.

E64. A method comprising the features described in Embodiment B6, and Embodiment C1.

E65. A method comprising the features described in Embodiment B6, Embodiment C1, and Embodiment D1.

E66. A method comprising the features described in Embodiment B6, Embodiment C1, and Embodiment D2.

E67. A method comprising the features described in Embodiment B6, and Embodiment C2.

E68. A method comprising the features described in Embodiment B6, Embodiment C2, and Embodiment D1.

E69. A method comprising the features described in Embodiment B6, Embodiment C2, and Embodiment D2.

E70. A method comprising the features described in Embodiment B6, and Embodiment C3.

E71. A method comprising the features described in Embodiment B6, Embodiment C3, and Embodiment D1.

E72. A method comprising the features described in Embodiment B6, Embodiment C3, and Embodiment D2.

E73. A method comprising the features described in Embodiment A1, and Embodiment D1.

E74. A method comprising the features described in Embodiment A1, and Embodiment D2.

E75. A method comprising the features described in Embodiment A1, and Embodiment C1.

E76. A method comprising the features described in Embodiment A1, Embodiment C1, and Embodiment D1.

E77. A method comprising the features described in Embodiment A1, Embodiment C1, and Embodiment D2.

E78. A method comprising the features described in Embodiment A1, and Embodiment C2.

E79. A method comprising the features described in Embodiment A1, Embodiment C2, and Embodiment D1.

E80. A method comprising the features described in Embodiment A1, Embodiment C2, and Embodiment D2.

E81. A method comprising the features described in Embodiment A1, and Embodiment C3.

E82. A method comprising the features described in Embodiment A1, Embodiment C3, and Embodiment D1.

E83. A method comprising the features described in Embodiment A1, Embodiment C3, and Embodiment D2.

E84. A method comprising the features described in Embodiment A1, and Embodiment B1.

E85. A method comprising the features described in Embodiment A1, Embodiment B1, and Embodiment D1.

E86. A method comprising the features described in Embodiment A1, Embodiment B1, and Embodiment D2.

E87. A method comprising the features described in Embodiment A1, Embodiment B1, and Embodiment C1.

E88. A method comprising the features described in Embodiment A1, Embodiment B1, Embodiment C1, and Embodiment D1.

E89. A method comprising the features described in Embodiment A1, Embodiment B1, Embodiment C1, and Embodiment D2.

E90. A method comprising the features described in Embodiment A1, Embodiment B1, and Embodiment C2.

E91. A method comprising the features described in Embodiment A1, Embodiment B1, Embodiment C2, and Embodiment D1.

E92. A method comprising the features described in Embodiment A1, Embodiment B1, Embodiment C2, and Embodiment D2.

E93. A method comprising the features described in Embodiment A1, Embodiment B1, and Embodiment C3.

E94. A method comprising the features described in Embodiment A1, Embodiment B1, Embodiment C3, and Embodiment D1.

E95. A method comprising the features described in Embodiment A1, Embodiment B1, Embodiment C3, and Embodiment D2.

E96. A method comprising the features described in Embodiment A1, and Embodiment B2.

E97. A method comprising the features described in Embodiment A1, Embodiment B2, and Embodiment D1.

E98. A method comprising the features described in Embodiment A1, Embodiment B2, and Embodiment D2.

E99. A method comprising the features described in Embodiment A1, Embodiment B2, and Embodiment C1.

E100. A method comprising the features described in Embodiment A1, Embodiment B2, Embodiment C1, and Embodiment D1.

E101. A method comprising the features described in Embodiment A1, Embodiment B2, Embodiment C1, and Embodiment D2.

E102. A method comprising the features described in Embodiment A1, Embodiment B2, and Embodiment C2.

E103. A method comprising the features described in Embodiment A1, Embodiment B2, Embodiment C2, and Embodiment D1.

E104. A method comprising the features described in Embodiment A1, Embodiment B2, Embodiment C2, and Embodiment D2.

E105. A method comprising the features described in Embodiment A1, Embodiment B2, and Embodiment C3.

E106. A method comprising the features described in Embodiment A1, Embodiment B2, Embodiment C3, and Embodiment D1.

E107. A method comprising the features described in Embodiment A1, Embodiment B2, Embodiment C3, and Embodiment D2.

E108. A method comprising the features described in Embodiment A1, and Embodiment B3.

E109. A method comprising the features described in Embodiment A1, Embodiment B3, and Embodiment D1.

E110. A method comprising the features described in Embodiment A1, Embodiment B3, and Embodiment D2.

E111. A method comprising the features described in Embodiment A1, Embodiment B3, and Embodiment C1.

E112. A method comprising the features described in Embodiment A1, Embodiment B3, Embodiment C1, and Embodiment D1.

E113. A method comprising the features described in Embodiment A1, Embodiment B3, Embodiment C1, and Embodiment D2.

E114. A method comprising the features described in Embodiment A1, Embodiment B3, and Embodiment C2.

E115. A method comprising the features described in Embodiment A1, Embodiment B3, Embodiment C2, and Embodiment D1.

E116. A method comprising the features described in Embodiment A1, Embodiment B3, Embodiment C2, and Embodiment D2.

E117. A method comprising the features described in Embodiment A1, Embodiment B3, and Embodiment C3.

E118. A method comprising the features described in Embodiment A1, Embodiment B3, Embodiment C3, and Embodiment D1.

E119. A method comprising the features described in Embodiment A1, Embodiment B3, Embodiment C3, and Embodiment D2.

E120. A method comprising the features described in Embodiment A1, and Embodiment B4.

E121. A method comprising the features described in Embodiment A1, Embodiment B4, and Embodiment D1.

E122. A method comprising the features described in Embodiment A1, Embodiment B4, and Embodiment D2.

E123. A method comprising the features described in Embodiment A1, Embodiment B4, and Embodiment C1.

E124. A method comprising the features described in Embodiment A1, Embodiment B4, Embodiment C1, and Embodiment D1.

E125. A method comprising the features described in Embodiment A1, Embodiment B4, Embodiment C1, and Embodiment D2.

E126. A method comprising the features described in Embodiment A1, Embodiment B4, and Embodiment C2.

E127. A method comprising the features described in Embodiment A1, Embodiment B4, Embodiment C2, and Embodiment D1.

E128. A method comprising the features described in Embodiment A1, Embodiment B4, Embodiment C2, and Embodiment D2.

E129. A method comprising the features described in Embodiment A1, Embodiment B4, and Embodiment C3.

E130. A method comprising the features described in Embodiment A1, Embodiment B4, Embodiment C3, and Embodiment D1.

E131. A method comprising the features described in Embodiment A1, Embodiment B4, Embodiment C3, and Embodiment D2.

E132. A method comprising the features described in Embodiment A1, and Embodiment B5.

E133. A method comprising the features described in Embodiment A1, Embodiment B5, and Embodiment D1.

E134. A method comprising the features described in Embodiment A1, Embodiment B5, and Embodiment D2.

E135. A method comprising the features described in Embodiment A1, Embodiment B5, and Embodiment C1.

E136. A method comprising the features described in Embodiment A1, Embodiment B5, Embodiment C1, and Embodiment D1.

E137. A method comprising the features described in Embodiment A1, Embodiment B5, Embodiment C1, and Embodiment D2.

E138. A method comprising the features described in Embodiment A1, Embodiment B5, and Embodiment C2.

E139. A method comprising the features described in Embodiment A1, Embodiment B5, Embodiment C2, and Embodiment D1.

E140. A method comprising the features described in Embodiment A1, Embodiment B5, Embodiment C2, and Embodiment D2.

E141. A method comprising the features described in Embodiment A1, Embodiment B5, and Embodiment C3.

E142. A method comprising the features described in Embodiment A1, Embodiment B5, Embodiment C3, and Embodiment D1.

E143. A method comprising the features described in Embodiment A1, Embodiment B5, Embodiment C3, and Embodiment D2.

E144. A method comprising the features described in Embodiment A1, and Embodiment B6.

E145. A method comprising the features described in Embodiment A1, Embodiment B6, and Embodiment D1.

E146. A method comprising the features described in Embodiment A1, Embodiment B6, and Embodiment D2.

E147. A method comprising the features described in Embodiment A1, Embodiment B6, and Embodiment C1.

E148. A method comprising the features described in Embodiment A1, Embodiment B6, Embodiment C1, and Embodiment D1.

E149. A method comprising the features described in Embodiment A1, Embodiment B6, Embodiment C1, and Embodiment D2.

E150. A method comprising the features described in Embodiment A1, Embodiment B6, and Embodiment C2.

E151. A method comprising the features described in Embodiment A1, Embodiment B6, Embodiment C2, and Embodiment D1.

E152. A method comprising the features described in Embodiment A1, Embodiment B6, Embodiment C2, and Embodiment D2.

E153. A method comprising the features described in Embodiment A1, Embodiment B6, and Embodiment C3.

E154. A method comprising the features described in Embodiment A1, Embodiment B6, Embodiment C3, and Embodiment D1.

E155. A method comprising the features described in Embodiment A1, Embodiment B6, Embodiment C3, and Embodiment D2.

E156. A method comprising the features described in Embodiment A2, and Embodiment D1.

E157. A method comprising the features described in Embodiment A2, and Embodiment D2.

E158. A method comprising the features described in Embodiment A2, and Embodiment C1.

E159. A method comprising the features described in Embodiment A2, Embodiment C1, and Embodiment D1.

E160. A method comprising the features described in Embodiment A2, Embodiment C1, and Embodiment D2.

E161. A method comprising the features described in Embodiment A2, and Embodiment C2

E162. A method comprising the features described in Embodiment A2, Embodiment C2, and Embodiment D1.

E163. A method comprising the features described in Embodiment A2, Embodiment C2, and Embodiment D2.

E164. A method comprising the features described in Embodiment A2, and Embodiment C3.

E165. A method comprising the features described in Embodiment A2, Embodiment C3, and Embodiment D1.

E166. A method comprising the features described in Embodiment A2, Embodiment C3, and Embodiment D2.

E167. A method comprising the features described in Embodiment A2, and Embodiment B1.

E168. A method comprising the features described in Embodiment A2, Embodiment B1, and Embodiment D1.

E169. A method comprising the features described in Embodiment A2, Embodiment B1, and Embodiment D2.

E170. A method comprising the features described in Embodiment A2, Embodiment B1, and Embodiment C1.

E171. A method comprising the features described in Embodiment A2, Embodiment B1, Embodiment C1, and Embodiment D1.

E172. A method comprising the features described in Embodiment A2, Embodiment B1, Embodiment C1, and Embodiment D2.

E173. A method comprising the features described in Embodiment A2, Embodiment B1, and Embodiment C2.

E174. A method comprising the features described in Embodiment A2, Embodiment B1, Embodiment C2, and Embodiment D1.

E175. A method comprising the features described in Embodiment A2, Embodiment B1, Embodiment C2, and Embodiment D2.

E176. A method comprising the features described in Embodiment A2, Embodiment B1, and Embodiment C3.

E177. A method comprising the features described in Embodiment A2, Embodiment B1, Embodiment C3, and Embodiment D1.

E178. A method comprising the features described in Embodiment A2, Embodiment B1, Embodiment C3, and Embodiment D2.

E179. A method comprising the features described in Embodiment A2, and Embodiment B2.

E180. A method comprising the features described in Embodiment A2, Embodiment B2, and Embodiment D1.

E181. A method comprising the features described in Embodiment A2, Embodiment B2, and Embodiment D2.

E182. A method comprising the features described in Embodiment A2, Embodiment B2, and Embodiment C1.

E183. A method comprising the features described in Embodiment A2, Embodiment B2, Embodiment C1, and Embodiment D1.

E184. A method comprising the features described in Embodiment A2, Embodiment B2, Embodiment C1, and Embodiment D2.

E185. A method comprising the features described in Embodiment A2, Embodiment B2, and Embodiment C2.

E186. A method comprising the features described in Embodiment A2, Embodiment B2, Embodiment C2, and Embodiment D1.

E187. A method comprising the features described in Embodiment A2, Embodiment B2, Embodiment C2, and Embodiment D2.

E188. A method comprising the features described in Embodiment A2, Embodiment B2, and Embodiment C3.

E189. A method comprising the features described in Embodiment A2, Embodiment B2, Embodiment C3, and Embodiment D1.

E190. A method comprising the features described in Embodiment A2, Embodiment B2, Embodiment C3, and Embodiment D2.

E191. A method comprising the features described in Embodiment A2, and Embodiment B3.

E192. A method comprising the features described in Embodiment A2, Embodiment B3, and Embodiment D1.

E193. A method comprising the features described in Embodiment A2, Embodiment B3, and Embodiment D2.

E194. A method comprising the features described in Embodiment A2, Embodiment B3, and Embodiment C1.

E195. A method comprising the features described in Embodiment A2, Embodiment B3, Embodiment C1, and Embodiment D1.

E196. A method comprising the features described in Embodiment A2, Embodiment B3, Embodiment C1, and Embodiment D2.

E197. A method comprising the features described in Embodiment A2, Embodiment B3, and Embodiment C2.

E198. A method comprising the features described in Embodiment A2, Embodiment B3, Embodiment C2, and Embodiment D1.

E199. A method comprising the features described in Embodiment A2, Embodiment B3, Embodiment C2, and Embodiment D2.

E200. A method comprising the features described in Embodiment A2, Embodiment B3, and Embodiment C3.

E201. A method comprising the features described in Embodiment A2, Embodiment B3, Embodiment C3, and Embodiment D1.

E202. A method comprising the features described in Embodiment A2, Embodiment B3, Embodiment C3, and Embodiment D2.

E203. A method comprising the features described in Embodiment A2, and Embodiment B4.

E204. A method comprising the features described in Embodiment A2, Embodiment B4, and Embodiment D1.

E205. A method comprising the features described in Embodiment A2, Embodiment B4, and Embodiment D2.

E206. A method comprising the features described in Embodiment A2, Embodiment B4, and Embodiment C1.

E207. A method comprising the features described in Embodiment A2, Embodiment B4, Embodiment C1, and Embodiment D1.

E208. A method comprising the features described in Embodiment A2, Embodiment B4, Embodiment C1, and Embodiment D2.

E209. A method comprising the features described in Embodiment A2, Embodiment B4, and Embodiment C2.

E210. A method comprising the features described in Embodiment A2, Embodiment B4, Embodiment C2, and Embodiment D1.

E211. A method comprising the features described in Embodiment A2, Embodiment B4, Embodiment C2, and Embodiment D2.

E212. A method comprising the features described in Embodiment A2, Embodiment B4, and Embodiment C3.

E213. A method comprising the features described in Embodiment A2, Embodiment B4, Embodiment C3, and Embodiment D1.

E214. A method comprising the features described in Embodiment A2, Embodiment B4, Embodiment C3, and Embodiment D2.

E215. A method comprising the features described in Embodiment A2, and Embodiment B5.

E216. A method comprising the features described in Embodiment A2, Embodiment B5, and Embodiment D1.

E217. A method comprising the features described in Embodiment A2, Embodiment B5, and Embodiment D2.

E218. A method comprising the features described in Embodiment A2, Embodiment B5, and Embodiment C1.

E219. A method comprising the features described in Embodiment A2, Embodiment B5, Embodiment C1, and Embodiment D1.

E220. A method comprising the features described in Embodiment A2, Embodiment B5, Embodiment C1, and Embodiment D2.

E221. A method comprising the features described in Embodiment A2, Embodiment B5, and Embodiment C2.

E222. A method comprising the features described in Embodiment A2, Embodiment B5, Embodiment C2, and Embodiment D1.

E223. A method comprising the features described in Embodiment A2, Embodiment B5, Embodiment C2, and Embodiment D2.

E224. A method comprising the features described in Embodiment A2, Embodiment B5, and Embodiment C3.

E225. A method comprising the features described in Embodiment A2, Embodiment B5, Embodiment C3, and Embodiment D1.

E226. A method comprising the features described in Embodiment A2, Embodiment B5, Embodiment C3, and Embodiment D2.

E227. A method comprising the features described in Embodiment A2, and Embodiment B6.

E228. A method comprising the features described in Embodiment A2, Embodiment B6, and Embodiment D1.

E229. A method comprising the features described in Embodiment A2, Embodiment B6, and Embodiment D2.

E230. A method comprising the features described in Embodiment A2, Embodiment B6, and Embodiment C1.

E231. A method comprising the features described in Embodiment A2, Embodiment B6, Embodiment C1, and Embodiment D1.

E232. A method comprising the features described in Embodiment A2, Embodiment B6, Embodiment C1, and Embodiment D2.

E233. A method comprising the features described in Embodiment A2, Embodiment B6, and Embodiment C2.

E234. A method comprising the features described in Embodiment A2, Embodiment B6, Embodiment C2, and Embodiment D1.

E235. A method comprising the features described in Embodiment A2, Embodiment B6, Embodiment C2, and Embodiment D2.

E236. A method comprising the features described in Embodiment A2, Embodiment B6, and Embodiment C3.

E237. A method comprising the features described in Embodiment A2, Embodiment B6, Embodiment C3, and Embodiment D1.

E238. A method comprising the features described in Embodiment A2, Embodiment B6, Embodiment C3, and Embodiment D2.

E239. A method comprising the features described in Embodiment A3, and Embodiment D1.

E240. A method comprising the features described in Embodiment A3, and Embodiment D2.

E241. A method comprising the features described in Embodiment A3, and Embodiment C1.

E242. A method comprising the features described in Embodiment A3, Embodiment C1, and Embodiment D1.

E243. A method comprising the features described in Embodiment A3, Embodiment C1, and Embodiment D2.

E244. A method comprising the features described in Embodiment A3, and Embodiment C2.

E245. A method comprising the features described in Embodiment A3, Embodiment C2, and Embodiment D1.

E246. A method comprising the features described in Embodiment A3, Embodiment C2, and Embodiment D2.

E247. A method comprising the features described in Embodiment A3, and Embodiment C3

E248. A method comprising the features described in Embodiment A3, Embodiment C3, and Embodiment D1.

E249. A method comprising the features described in Embodiment A3, Embodiment C3, and Embodiment D2.

E250. A method comprising the features described in Embodiment A3, and Embodiment B1.

E251. A method comprising the features described in Embodiment A3, Embodiment B1, and Embodiment D1.

E252. A method comprising the features described in Embodiment A3, Embodiment B1, and Embodiment D2.

E253. A method comprising the features described in Embodiment A3, Embodiment B1, and Embodiment C1.

E254. A method comprising the features described in Embodiment A3, Embodiment B1, Embodiment C1, and Embodiment D1.

E255. A method comprising the features described in Embodiment A3, Embodiment B1, Embodiment C1, and Embodiment D2.

E256. A method comprising the features described in Embodiment A3, Embodiment B1, and Embodiment C2.

E257. A method comprising the features described in Embodiment A3, Embodiment B1, Embodiment C2, and Embodiment D1.

E258. A method comprising the features described in Embodiment A3, Embodiment B1, Embodiment C2, and Embodiment D2.

E259. A method comprising the features described in Embodiment A3, Embodiment B1, and Embodiment C3.

E260. A method comprising the features described in Embodiment A3, Embodiment B1, Embodiment C3, and Embodiment D1.

E261. A method comprising the features described in Embodiment A3, Embodiment B1, Embodiment C3, and Embodiment D2.

E262. A method comprising the features described in Embodiment A3, and Embodiment B2.

E263. A method comprising the features described in Embodiment A3, Embodiment B2, and Embodiment D1.

E264. A method comprising the features described in Embodiment A3, Embodiment B2, and Embodiment D2.

E265. A method comprising the features described in Embodiment A3, Embodiment B2, and Embodiment C1.

E266. A method comprising the features described in Embodiment A3, Embodiment B2, Embodiment C1, and Embodiment D1.

E267. A method comprising the features described in Embodiment A3, Embodiment B2, Embodiment C1, and Embodiment D2.

E268. A method comprising the features described in Embodiment A3, Embodiment B2, and Embodiment C2.

E269. A method comprising the features described in Embodiment A3, Embodiment B2, Embodiment C2, and Embodiment D1.

E270. A method comprising the features described in Embodiment A3, Embodiment B2, Embodiment C2, and Embodiment D2.

E271. A method comprising the features described in Embodiment A3, Embodiment B2, and Embodiment C3.

E272. A method comprising the features described in Embodiment A3, Embodiment B2, Embodiment C3, and Embodiment D1.

E273. A method comprising the features described in Embodiment A3, Embodiment B2, Embodiment C3, and Embodiment D2.

E274. A method comprising the features described in Embodiment A3, and Embodiment B3.

E275. A method comprising the features described in Embodiment A3, Embodiment B3, and Embodiment D1.

E276. A method comprising the features described in Embodiment A3, Embodiment B3, and Embodiment D2.

E277. A method comprising the features described in Embodiment A3, Embodiment B3, and Embodiment C1.

E278. A method comprising the features described in Embodiment A3, Embodiment B3, Embodiment C1, and Embodiment D1.

E279. A method comprising the features described in Embodiment A3, Embodiment B3, Embodiment C1, and Embodiment D2.

E280. A method comprising the features described in Embodiment A3, Embodiment B3, and Embodiment C2.

E281. A method comprising the features described in Embodiment A3, Embodiment B3, Embodiment C2, and Embodiment D1.

E282. A method comprising the features described in Embodiment A3, Embodiment B3, Embodiment C2, and Embodiment D2.

E283. A method comprising the features described in Embodiment A3, Embodiment B3, and Embodiment C3.

E284. A method comprising the features described in Embodiment A3, Embodiment B3, Embodiment C3, and Embodiment D1.

E285. A method comprising the features described in Embodiment A3, Embodiment B3, Embodiment C3, and Embodiment D2.

E286. A method comprising the features described in Embodiment A3, and Embodiment B4.

E287. A method comprising the features described in Embodiment A3, Embodiment B4, and Embodiment D1.

E288. A method comprising the features described in Embodiment A3, Embodiment B4, and Embodiment D2.

E289. A method comprising the features described in Embodiment A3, Embodiment B4, and Embodiment C1.

E290. A method comprising the features described in Embodiment A3, Embodiment B4, Embodiment C1, and Embodiment D1.

E291. A method comprising the features described in Embodiment A3, Embodiment B4, Embodiment C1, and Embodiment D2.

E292. A method comprising the features described in Embodiment A3, Embodiment B4, and Embodiment C2.

E293. A method comprising the features described in Embodiment A3, Embodiment B4, Embodiment C2, and Embodiment D1.

E294. A method comprising the features described in Embodiment A3, Embodiment B4, Embodiment C2, and Embodiment D2.

E295. A method comprising the features described in Embodiment A3, Embodiment B4, and Embodiment C3.

E296. A method comprising the features described in Embodiment A3, Embodiment B4, Embodiment C3, and Embodiment D1.

E297. A method comprising the features described in Embodiment A3, Embodiment B4, Embodiment C3, and Embodiment D2.

E298. A method comprising the features described in Embodiment A3, and Embodiment B5.

E299. A method comprising the features described in Embodiment A3, Embodiment B5, and Embodiment D1.

E300. A method comprising the features described in Embodiment A3, Embodiment B5, and Embodiment D2.

E301. A method comprising the features described in Embodiment A3, Embodiment B5, and Embodiment C1.

E302. A method comprising the features described in Embodiment A3, Embodiment B5, Embodiment C1, and Embodiment D1.

E303. A method comprising the features described in Embodiment A3, Embodiment B5, Embodiment C1, and Embodiment D2.

E304. A method comprising the features described in Embodiment A3, Embodiment B5, and Embodiment C2.

E305. A method comprising the features described in Embodiment A3, Embodiment B5, Embodiment C2, and Embodiment D1.

E306. A method comprising the features described in Embodiment A3, Embodiment B5, Embodiment C2, and Embodiment D2.

E307. A method comprising the features described in Embodiment A3, Embodiment B5, and Embodiment C3.

E308. A method comprising the features described in Embodiment A3, Embodiment B5, Embodiment C3, and Embodiment D1.

E309. A method comprising the features described in Embodiment A3, Embodiment B5, Embodiment C3, and Embodiment D2.

E310. A method comprising the features described in Embodiment A3, and Embodiment B6.

E311. A method comprising the features described in Embodiment A3, Embodiment B6, and Embodiment D1.

E312. A method comprising the features described in Embodiment A3, Embodiment B6, and Embodiment D2.

E313. A method comprising the features described in Embodiment A3, Embodiment B6, and Embodiment C1.

E314. A method comprising the features described in Embodiment A3, Embodiment B6, Embodiment C1, and Embodiment D1.

E315. A method comprising the features described in Embodiment A3, Embodiment B6, Embodiment C1, and Embodiment D2.

E316. A method comprising the features described in Embodiment A3, Embodiment B6, and Embodiment C2.

E317. A method comprising the features described in Embodiment A3, Embodiment B6, Embodiment C2, and Embodiment D1.

E318. A method comprising the features described in Embodiment A3, Embodiment B6, Embodiment C2, and Embodiment D2.

E319. A method comprising the features described in Embodiment A3, Embodiment B6, and Embodiment C3.

E320. A method comprising the features described in Embodiment A3, Embodiment B6, Embodiment C3, and Embodiment D1.

E321. A method comprising the features described in Embodiment A3, Embodiment B6, Embodiment C3, and Embodiment D2.

F1. A method of treatment for depression in a subject comprising:
(a) administering to the subject a pharmacologic antidepressant agent; and
(b) delivering to the subject a transcranial electrical stimulation (tES).

F2. The method of embodiment F1, wherein the pharmacologic antidepressant agent comprises one or more pharmacologic antidepressant agents.

F3. The method of embodiment F1 or F2, wherein the pharmacologic antidepressant agent is administered as part of a treatment regimen.

F4. The method of any one of embodiments F1-F3, wherein the pharmacologic antidepressant agent is administered in a treatment effective amount.

F5. The method of any one of embodiments F1-F4, wherein the delivering to the subject the tES comprises a delivery of tES prior to the administering, a delivery of tES concurrently to the administering as part of a treatment regimen, a delivery of tES subsequent to the administering, a delivery of tES concurrently with or following a change in a dosage of the pharmacologic antidepressant agent of the administering, or a delivery of tES following a completion of a schedule of the administering.

F6. The method of embodiment F5, wherein the delivery comprises one or more of non-invasive brain stimulation sessions.

F7. The method of any one of embodiments F1-F6, wherein the delivering in (b) comprises delivering tES via a tES device.

F8. The method of embodiment 7, wherein delivering tES via the tES device elicits neuromodulation in the subject.

F9 The method of any one of embodiments F3-F8, further comprising assessing a response of the subject to the treatment regimen.

F10. The method of any one of embodiments F6-F9, further comprising assessing a response of the subject to the one or more of non-invasive brain stimulation sessions.

F11. The method of embodiment F9 or F10, wherein the assessing the response of the subject comprises determining a treatment effectiveness.

F12. The method of any one of embodiments F1-F11, further comprising adjusting parameters in (a) and (b) to achieve to a desired treatment outcome.

F13. A method of treatment for depression in a subject comprising:
(a) administering to the subject a pharmacologic antidepressant agent in a treatment effective amount as part of a treatment regimen;
(b) delivering concurrently to the subject one or more of non-invasive brain stimulation sessions via a transcranial electrical stimulation (tES) device to elicit neuromodulation;
(c) assessing a response of the subject to the treatment regimen and to the one or more of non-invasive brain stimulation sessions in order to determine treatment effectiveness; and (d) adjusting parameters in (a) and (b) to achieve to a desired treatment outcome.

F14. The method of any one of embodiments F1-F13, wherein the pharmacologic antidepressant agent comprises a selective serotonin reuptake inhibitor (SSRI), a serotonin-norepinephrine reuptake inhibitor (SNRI), a noradrenergic and specific serotonergic antidepressant (NaSSA), a serotonin modulator and stimulator (SMS), a serotonin antagonist and reuptake inhibitor (SARI), a serotonin-norepinephrine-dopamine reuptake inhibitor (SNDRI), a norepinephrine reuptake inhibitor (NRI), a norepinephrine-dopamine reuptake inhibitor (NDRI), a norepinephrine-dopamine releasing agent (NDRA), a serotonin-norepinephrine-dopamine releasing agent (SNDRA), a tricyclic antidepressant (TCA), a tetracyclic antidepressant (TeCA), a monoamine oxidase inhibitor (MAOI), an NMDA receptor modulator, an atypical antipsychotic, an atypical antidepressant, a benzodiazepine, or any combination thereof.

F15. The method of embodiment F14, wherein the SSRI comprises fluoxetine, citalopram, escitalopram, paroxetine, sertraline, dapoxetine, fluvoxamine, or vortioxetine.

F16. The method of embodiment F14, wherein the SNRI comprises desvenlafaxine, duloxetine, levomilnacipran, milnacipran, venlafaxine immediate release (venlafaxine IR), or venlafaxine extended release (venlafaxine XR).

F17. The method of embodiment F14, wherein the NaSSA comprises aptazapine, esmirtazapine, mianserin, mirtazapine, or setiptiline.

F18. The method of embodiment F14, wherein the SMS comprises vilazodone or vortioxetine.

F19. The method of embodiment F14, wherein the SARI comprises nefazodone or trazodone.

F20. The method of embodiment F14, wherein the SNDRI comprises toludesvenlafaxine, OPC-64005, or ansofaxine.

F21. The method of embodiment F14, wherein the NRI comprises atomoxetine, reboxetine, teniloxazine, or viloxazine.

F22. The method of embodiment F14, wherein the NDRI comprises bupropion, amineptine, methylphenidate, or AXS-05.

F23. The method of embodiment F14, wherein the NDRA comprises lisdexamfetamine, phenethylamine, tyramine, amphetamine, methamphetamine, cathinone, methcathinone, propylhexedrine, phenmetrazine, pemoline, 4-methylaminorex, or benzylpiperazine.

F24. The method of embodiment F14, wherein the SNDRA comprises midomafetamine, 3,4-Methyl enedioxymethamphetamine, 3,4-Methylenedioxyamphetamine, naphthylisopropylamine, mephedrone, methylone, α-methyltryptamine, or α-ethyltryptamine.

F25. The method of embodiment F14, wherein the TCA comprises amitriptyline, clomipramine, desipramine, dosulepin, doxepin, imipramine, lofepramine, nortriptyline, protriptyline, or trimipramine.

F26. The method of embodiment F14, wherein the TeCA comprises amoxapine, maprotiline, mianserin, mirtazapine, or setiptiline.

F27. The method of embodiment F14, wherein the MAOI comprises selegiline, tranylcypromine, phenelzine, or isocarboxazid.

F28. The method of embodiment F14, wherein the NMDA receptor modulator comprises 4-chlorokynurenine, apimostinel, arketamine, esketamine, esmethadone, ketamine, rislenemdaz, or rapastinel.

F29. The method of embodiment F14, wherein the atypical antipsychotic comprises brilaroxazine, cariprazine, lumateperone, lurasidone, pimavanserin, aripiprazole, brexpiprazole, olanzapine, quetiapine, ziprasidone, SEP-4199, or NRX-101.

F30. The method of embodiment F14, wherein the atypical antidepressant comprises allopregnanolone, agomelatine, trazodone, mirtazapine, vortioxetine, vilazodone, psilocybin, DMT, zuranolone, seltorexant, XEN1101, erteberel, NV-5138, TS-121, or ALKS 5461.

F31. The method of embodiment F14, wherein the benzodiazepine comprises diazepam, alprazolam, triazolam, clonazepam, chlordiazepoxide, nitrazepam, or loprazolam.

F32. The method of any one of embodiments F1-F31, wherein the pharmacologic antidepressant agent is administered in a formulation comprising a tablet, a capsule, a delayed-release capsule, or a liquid.

F33. The method of any one of embodiments F1-F32, wherein the pharmacologic antidepressant agent is administered orally, sublingually, buccally, nasally, rectally, vaginally, intravenously, intramuscularly, subcutaneously, or through inhalation.

F34. The method of any one of embodiments F4-F33, wherein the treatment effective amount comprises a dose of the pharmacologic antidepressant agent of at least about 0.01 mg, 0.02 mg, 0.03 mg, 0.04 mg, 0.05 mg, 0.06 mg, 0.07 mg, 0.08 mg, 0.09 mg, 0.1 mg, 0.15 mg, 0.2 mg, 0.25 mg, 0.30 mg, 0.35 mg, 0.4 mg, 0.45 mg, 0.50 mg, 0.55 mg, 0.6 mg, 0.7 mg, 0.8 mg, 0.9 mg, 1 mg, 1.25 mg, 1.5 mg, 1.75 mg, 2 mg, 2.5 mg, 3 mg, 3.5 mg, 4 mg, 4.5 mg, 5 mg, 5.5 mg, 6 mg, 6.5 mg, 7 mg, 7.5 mg, 8 mg, 8.5 mg, 9 mg, 9.5 mg, 10 mg, 11 mg, 12 mg, 13 mg, 14 mg, 15 mg, 16 mg, 17 mg, 18 mg, 19 mg, 20 mg, 21 mg, 22 mg, 23 mg, 24 mg, 25 mg, 26 mg, 27 mg, 28 mg, 29 mg, 30 mg, 32 mg, 34 mg, 35 mg, 36 mg, 37.5 mg, 38 mg, 40 mg, 42 mg, 44 mg, 46 mg, 48 mg, 50 mg, 52 mg, 54 mg, 56 mg, 58 mg, 60 mg, 65 mg, 70 mg, 75 mg, 80 mg, 85 mg, 90 mg, 95 mg, 100 mg, 105 mg, 110 mg, 115 mg, 120 mg, 125 mg, 130 mg, 140 mg, 150 mg, 160 mg, 170 mg, 180 mg, 190 mg, 200 mg, 250 mg, 300 mg, or 400 mg.

F35. The method of any one of embodiments F4-F34, wherein the treatment effective amount comprises a dose of the pharmacologic antidepressant agent of less than about 0.01 mg, 0.02 mg, 0.03 mg, 0.04 mg, 0.05 mg, 0.06 mg, 0.07 mg, 0.08 mg, 0.09 mg, 0.1 mg, 0.15 mg, 0.2 mg, 0.25 mg, 0.30 mg, 0.35 mg, 0.4 mg, 0.45 mg, 0.50 mg, 0.55 mg, 0.6 mg, 0.7 mg, 0.8 mg, 0.9 mg, 1 mg, 1.25 mg, 1.5 mg, 1.75 mg, 2 mg, 2.5 mg, 3 mg, 3.5 mg, 4 mg, 4.5 mg, 5 mg, 5.5 mg, 6 mg, 6.5 mg, 7 mg, 7.5 mg, 8 mg, 8.5 mg, 9 mg, 9.5 mg, 10 mg, 11 mg, 12 mg, 13 mg, 14 mg, 15 mg, 16 mg, 17 mg, 18 mg, 19 mg, 20 mg, 21 mg, 22 mg, 23 mg, 24 mg, 25 mg, 26 mg, 27 mg, 28 mg, 29 mg, 30 mg, 32 mg, 34 mg, 35 mg, 36 mg, 37.5 mg, 38 mg, 40 mg, 42 mg, 44 mg, 46 mg, 48 mg, 50 mg, 52 mg, 54 mg, 56 mg, 58 mg, 60 mg, 65 mg, 70 mg, 75 mg, 80 mg, 85 mg, 90 mg, 95 mg, 100 mg, 105 mg, 110 mg, 115 mg, 120 mg, 125 mg, 130 mg, 140 mg, 150 mg, 160 mg, 170 mg, 180 mg, 190 mg, 200 mg, 250 mg, 300 mg, 400 mg, or 600 mg.

F36. The method of any one of embodiments F3-F35, wherein the treatment regimen comprises a drug administration regime wherein the dose of the pharmacologic antidepressant agent is administered at most about every 1 hour, every 2 hours, every 3 hours, every 4 hours, every 5 hours, every 6 hours, every 7 hours, every 8 hours, every 9 hours, every 10 hours, every 11 hours, every 12 hours, every 13 hours, every 14 hours, every 15 hours, every 16 hours, every 17 hours, every 18 hours, every 19 hours, every 20 hours, every 21 hours, every 22 hours, every 23 hours, every 24 hours, every 28 hours, every 32 hours, every 36 hours, every 40 hours, every 44 hours, every 2 days, every 3 days, every 4 days, every 5 days, every 6 days, every 7 days, every 10 days, every 14 days, every 21 days, or every 28 days.

F37. The method of any one of embodiments F3-F36, wherein the treatment regimen comprises a drug administration regime wherein the dose of the pharmacologic antidepressant agent is administered about once a month, once every three weeks, once every two weeks, once every 10 days, once every week, once every 6 days, once every 5 days, once every 4 days, once every 3 days, once every 2 days, once every day, twice every day, three times every day, four times every day, five times every day, six times every day, seven times every day, eight times every day, nine times every day, ten times every day, eleven times every day, or twelve times every day.

F38. The method of embodiment F36 or F37, wherein the drug administration regime continues for a period of time of at least 1 week, 2 weeks, 3 weeks, 4 weeks, 5 weeks, 6 weeks, 7 weeks, 8 weeks, 9 weeks, 10 weeks, 11 weeks, 12 weeks, 13 weeks, 14 weeks, 15 weeks, 16 weeks, 17 weeks, 18 weeks, 19 weeks, 20 weeks, 21 weeks, 22 weeks, 23 weeks, 24 weeks, 25 weeks, 26 weeks, 7 months, 8 months, 9 months, 10 months, 11 months, 12 months, 13 months, 14 months, 15 months, 16 months, 17 months, 18 months, or 2 years.

F39. The method of any one of embodiments F3-F38, wherein the treatment regimen comprises a multi-dose drug administration regime.

F40. The method of any one of embodiments F7-F39, wherein the tES device comprises a transcranial direct current stimulation (tDCS) device, a transcranial alternating current stimulation (tACS) device, or a transcranial random noise stimulation (tRNS) device.

F41. The method of any one of embodiments F7-F39, wherein the tES device comprises a transcranial direct current stimulation (tDCS) device.

F42. The method of any one of embodiments F7-F41, wherein the tES device is configurated as a headset comprising a circuit comprising a first electrode, a second electrode, and a power source configured to provide power to the circuit.

F43. The method of embodiment F41, wherein the tES device further comprises a wireless transceiver configured to wirelessly communicate with an electronic device having processing capabilities and a controller being configured to control powering of the circuit according to a control signal for the headset such that transcranial brain stimulation is performed according to a schedule for performing the transcranial brain stimulation.

F44. The method of embodiment F42 or F43, wherein the headset further comprises a memory configured to store the schedule for performing the transcranial brain stimulation.

F45. The method of embodiment F43 or F44, wherein the electronic device having processing capabilities comprises a non-transitory computer-readable recording medium having recorded thereon a program which is executable on the electronic device wherein the program comprises program code portions which when executed on the electronic device is configured to: store, in a computer memory, a schedule for performing the transcranial brain stimulation, generate and maintain the control signal according to the schedule for performing the transcranial brain stimulation, and display information on a display of the electronic device in accordance with a schedule for displaying information, wherein the schedule for displaying information is related to the schedule for performing the transcranial brain stimulation.

F46. The method of any one of embodiments F42-F45, wherein the headset further comprises a forehead frame, the forehead frame defining an elongated arch; the first electrode arranged at a first end portion of the elongated arched forehead frame; the second electrode arranged at a second end portion of the elongated arched forehead frame; and a bracket fixedly fastened at a center portion of the elongated arched forehead frame, the elongated arched forehead frame is configured to support the bracket.

F47. The method of embodiment F46, wherein upon use of the headset in delivering concurrently to the subject one or more of non-invasive brain stimulation sessions, the elongated arched forehead frame is configured such that the first electrode is located at a left side of a forehead of the subject, and such that the second electrode is located at a right side of the forehead of the subject, and the bracket is configured to extend from the elongated arched forehead frame over the skull of the subject towards a neck portion of the subject.

F48. The method of any one of embodiments F45-F47, wherein the program further comprises program code portions which when executed on the electronic device is configured to prompt the subject to input information pertaining to status of the subject wherein the information pertaining to status of the subject comprises information pertaining to information about the subject's current health.

F49. The method of any one of embodiments F45-F48, wherein the program further comprises program code portions which when executed on the electronic device is configured to store information pertaining to performed transcranial brain stimulation on a computer memory.

F50. The method of any one of embodiments F45-F49, wherein the program further comprises program code portions which when executed on the electronic device is configured to remind the subject to use the headset according to the schedule for performing the transcranial brain stimulation.

F51. The method of any one of embodiments F45-F50, wherein the program further comprises program code portions which when executed on the electronic device is configured to update the schedule for performing the transcranial brain stimulation.

F52. The method of any one of embodiments F42-F51, wherein the headset further comprises the first and second electrodes being pivotable such that they can adapt to a shape of the forehead of the subject.

F53. The method of embodiment F52, wherein the headset further comprises the first and second electrodes having an adhesive layer configured such that the adhesive layer adheres to the forehead of the subject.

F54. The method of any one of embodiments F46-F53, wherein the bracket has a longitudinal extension which, when the headset is used, extends from the forehead of the subject towards the back of the subject's head and wherein the bracket has a variable extension from the forehead frame.

F55. The method of any one of embodiments F46-F54, wherein the bracket further comprises a support cushion arranged at an end portion of the bracket being opposite to where the bracket is fastened at the forehead frame and wherein the forehead frame is a single member shaped as an elongated arch.

F56. The method of any one of embodiments F1-F55, wherein the subject has been diagnosed with one or more conditions or disorders selected from the group consisting of: depression, mild depression, moderate depression, severe depression, major depression, major depressive disorder, anxious distress, melancholy, melancholic depression, agitation, persistent depressive disorder, bipolar disorder type 1, bipolar disorder type 2, bipolar disorder not otherwise specified, cyclothymia, season affective disorder, psychotic depression, psychotic major depression, postpartum depression, premenstrual dysphoric disorder, situational depression, breakthrough depression, atypical depression, treatment resistant depression, catatonic depression, dysthymia, double depression, unspecified depressive disorder, depressive personality disorder, recurrent brief depression, minor depressive disorder, alcohol-induced depression, substance-induced depression, benzodiazepine-induced depression, and mixed anxiety-depressive disorder.

F57. The method of any one of embodiments F1-F56, wherein the subject is at risk for developing a condition or disorder selected from the group consisting of: depression, mild depression, moderate depression, severe depression, major depression, major depressive disorder, anxious distress, melancholy, melancholic depression, agitation, persistent depressive disorder, bipolar disorder type 1, bipolar disorder type 2, bipolar disorder not otherwise specified, cyclothymia, season affective disorder, psychotic depression, psychotic major depression, postpartum depression, premenstrual dysphoric disorder, situational depression, breakthrough depression, atypical depression, treatment resistant depression, catatonic depression, dysthymia, double depression, unspecified depressive disorder, depressive personality disorder, recurrent brief depression, minor depressive disorder, alcohol-induced depression, substance-induced depression, benzodiazepine-induced depression, and mixed anxiety-depressive disorder.

F58. The method of any one of embodiments F1-F57, wherein the subject has achieved remission from symptoms related to a condition or disorder selected from the group consisting of: depression, mild depression, moderate depression, severe depression, major depression, major depressive disorder, anxious distress, melancholy, melancholic depression, agitation, persistent depressive disorder, bipolar disorder type 1, bipolar disorder type 2, bipolar disorder not otherwise specified, cyclothymia, season affective disorder, psychotic depression, psychotic major depression, postpartum depression, premenstrual dysphoric disorder, situational depression, breakthrough depression, atypical depression, treatment resistant depression, catatonic depression, dysthymia, double depression, unspecified depressive disorder, depressive personality disorder, recurrent brief depression, minor depressive disorder, alcohol-induced depression, substance-induced depression, benzodiazepine-induced depression, and mixed anxiety-depressive disorder.

F59. The method of any one of embodiments F1-F58, wherein the subject has demonstrated improvement of one or more symptoms related to a condition or disorder selected from the group consisting of: depression, mild depression, moderate depression, severe depression, major depression, major depressive disorder, anxious distress, melancholy, melancholic depression, agitation, persistent depressive disorder, bipolar disorder type 1, bipolar disorder type 2, bipolar disorder not otherwise specified, cyclothymia, season affective disorder, psychotic depression, psychotic major depression, postpartum depression, premenstrual dysphoric disorder, situational depression, breakthrough depression, atypical depression, treatment resistant depression, catatonic depression, dysthymia, double depression, unspecified depressive disorder, depressive personality disorder, recurrent brief depression, minor depressive disorder, alcohol-induced depression, substance-induced depression, benzodiazepine-induced depression, and mixed anxiety-depressive disorder.

F60. The method of any one of embodiments F1-F59, wherein the subject has been diagnosed with one or more conditions or disorders that carry a risk of depression as a co-morbidity selected from the group consisting of: Alzheimer's disease, a cancer, coronary heart disease, acute coronary syndrome, diabetes, epilepsy, HIV/AIDS, hypothyroidism, multiple sclerosis, Parkinson's disease, stroke, systemic lupus erythematosus, rheumatoid arthritis, psoriasis, panic disorder, generalized anxiety disorder, obsessive-compulsive disorder, post-traumatic stress disorder, dementia, substance-abuse disorder, a psychotic disorder, anorexia nervosa, bulimia nervosa, muscle dysmorphia, binge eating disorder, compulsive over eating, polycystic ovary syndrome, Prader Willi syndrome, diabulimia, an autoimmune disorder, and an inflammatory disorder.

F61. The method of any one of embodiments F6-F60, wherein the one or more of non-invasive brain stimulation sessions comprises using the tES device with the first electrode and the second in close proximity to or touching the forehead of the subject.

F62. The method of embodiment F61, wherein the frontal lobes of the brain of the subject are stimulated to elicit neuromodulation.

F63. The method of embodiments F61 or F62, wherein the parietal lobes of the brain of the subject are stimulated to elicit neuromodulation.

F64. The method of any one of embodiments F61-F63, wherein the temporal lobes of the brain of the subject are stimulated to elicit neuromodulation.

F65. The method of any one of embodiments F61-F64, wherein the prefrontal cortex of the subject is stimulated to elicit neuromodulation.

F66. The method of any one of embodiments F61-F65, wherein the dorsolateral prefrontal cortex (DLPFC) of the subject is stimulated to elicit neuromodulation.

F67. The method of any one of embodiments F61-F66, wherein pyramidal cells of the cerebral cortex exhibit cell bodies and axons which become depolarized.

F68. The method of any one of embodiments F61-F67, wherein pyramidal cells of the cerebral cortex exhibit cell bodies and axons which become hyper-polarized.

F69. The method of any one of embodiments F61-F68, wherein pyramidal cells of the cerebral cortex exhibit apical dendrites which become depolarized.

F70. The method of any one of embodiments F61-F69, wherein pyramidal cells of the cerebral cortex exhibit apical dendrites which become hyper-polarized.

F71. The method of any one of embodiments F61-F70, wherein interneurons of the cerebral cortex become depolarized.

F72. The method of any one of embodiments F61-F71, wherein interneurons of the cerebral cortex become hyper-polarized.

F73. The method of any one of embodiments F61-F72, wherein neural activity in the DLPFC increases at a time point following the one or more of non-invasive brain stimulation sessions.

F74. The method of any one of embodiments F61-F73, wherein functional connectivity is increased between the DLPFC and the orbitofrontal cortex, the thalamus, the dorsal caudate nucleus, the hippocampus, one or more primary association areas of the neocortex, or one or more secondary association areas of the neocortex, or any combination thereof.

F75. The method of any one of embodiments F61-F74, wherein neuroplasticity in the brain of the subject increases.

F76. The method of any one of embodiments F1-F75, wherein cognitive function is significantly improved in the subject.

F77. The method of any one of embodiments F1-F76, wherein one or more executive functions of the brain is significantly improved in the subject.

F78. The method of any one of embodiments F1-F77, wherein attention is significantly improved in the subject.

F79. The method of any one of embodiments F1-F78, wherein cognitive inhibition is significantly improved in the subject.

F80. The method of any one of embodiments F1-F79, wherein inhibitory control is significantly improved in the subject.

F81. The method of any one of embodiments F1-F80, wherein cognitive planning is significantly improved in the subject.

F82. The method of any one of embodiments F1-F81, wherein working memory is significantly improved in the subject.

F83. The method of any one of embodiments F1-F82, wherein depressive mood is significantly improved in the subject.

F84. The method of any one of embodiments F1-F83, wherein one or more symptoms of depressive are significantly improved in the subject.

F85. The method of any one of embodiments F1-F84, wherein a feeling of wellness is significantly restored in the subject.

F86. The method of any one of embodiments F6-F85, wherein each of the one or more of non-invasive brain stimulation sessions deliver tES to the subject for a duration of at least about 1 minute, 2 minutes, 3 minutes, 4 minutes, 5 minutes, 6 minutes, 7 minutes, 8 minutes, 9 minutes, 10 minutes, 11 minutes, 12 minutes, 13 minutes, 14 minutes, 15 minutes, 16 minutes, 17 minutes, 18 minutes, 19 minutes, 20 minutes, 21 minutes, 22 minutes, 23 minutes, 24 minutes, 25 minutes, 26 minutes, 28 minutes, 29 minutes, 30 minutes, 31 minutes, 32 minutes, 33 minutes, 34 minutes, 35 minutes, 40 minutes, 45 minutes, or 50 minutes.

F87. The method of any one of embodiments F6-F86, wherein each of the one or more of non-invasive brain stimulation sessions deliver tES to the subject for a duration of less than about 1 minute, 2 minutes, 3 minutes, 4 minutes, 5 minutes, 6 minutes, 7 minutes, 8 minutes, 9 minutes, 10 minutes, 11 minutes, 12 minutes, 13 minutes, 14 minutes, 15 minutes, 16 minutes, 17 minutes, 18 minutes, 19 minutes, 20 minutes, 21 minutes, 22 minutes, 23 minutes, 24 minutes, 25 minutes, 26 minutes, 28 minutes, 29 minutes, 30 minutes, 31 minutes, 32 minutes, 33 minutes, 34 minutes, 35 minutes, 40 minutes, 45 minutes, or 50 minutes.

F88. The method of any one of embodiments F6-F87, wherein the subject undergoes the one or more of non-invasive brain stimulation sessions with a frequency of about twice every day, once every 18 hours, once every day, once every 36 hours, once every other day, 6 times per week, 5 times per week, 4 times per week, 3 times per week, 2 times per week, 1 time per week, or 1 time every two weeks.

F89. The method of any one of embodiments F6-F88, wherein the subject undergoes the one or more of non-invasive brain stimulation sessions according to a schedule of an initial activation phase with a frequency of about twice every day, once every 18 hours, once every day, once every 36 hours, once every other day, 6 times per week, 5 times per week, 4 times per week, 3 times per week, 2 times per week, 1 time per week, or 1 time every two weeks.

F90. The method of any one of embodiments F6-F89, wherein the subject undergoes the one or more of non-invasive brain stimulation sessions according to a schedule of a secondary strengthening phase with a frequency of about twice every day, once every 18 hours, once every day, once every 36 hours, once every other day, 6 times per week, 5 times per week, 4 times per week, 3 times per week, 2 times per week, 1 time per week, or 1 time every two weeks.

F91. The method of embodiment F88 or F89, wherein the initial activation phase lasts for a period of time about 3 days, 4 days, 5 days, 6 days, 7 days, 8 days, 9 days, 10 days, 11 days, 12 days, 13 days, 2 weeks, 3 weeks, 4 weeks, 5 weeks, 6 weeks, 7 weeks, 8 weeks, 9 weeks, 10 weeks, 11 weeks, 12 weeks, 13 weeks, 14 weeks, 15 weeks, 16 weeks, 17 weeks, 18 weeks, 19 weeks, or 20 weeks.

F92. The method of embodiment F90 or F91, wherein the secondary strengthen phase begins a period of time about 3 days, 4 days, 5 days, 6 days, 7 days, 8 days, 9 days, 10 days, 11 days, 12 days, 13 days, 2 weeks, 3 weeks, 4 weeks, 5 weeks, 6 weeks, 7 weeks, 8 weeks, 9 weeks, 10 weeks, 11 weeks, 12 weeks, 13 weeks, 14 weeks, 15 weeks, 16 weeks, 17 weeks, 18 weeks, 19 weeks, 20 weeks, 21 weeks, 22 weeks, 23 weeks, 24 weeks, or 25 weeks after completion of the initial activation phase.

F93. The method of any one of embodiments F1-F92, wherein tDCS delivers a current of about +/−0.5 mA, +/−0.6 mA, +/−0.7 mA, +/−0.8 mA, +/−0.9 mA, +/−1.0 mA, +/−1.1 mA, +/−1.2 mA, +/−1.3 mA, +/−1.4 mA, +/−1.5 mA, +/−1.6 mA, +/−1.7 mA, +/−1.8 mA, +/−1.9 mA, +/−2.0 mA, +/−2.1 mA, +/−2.2 mA, +/−2.3 mA, +/−2.4 mA, +/−2.5 mA, +/−2.6 mA, +/−2.7 mA, +/−2.8 mA, +/−2.9 mA, +/−3.0 mA, +/−3.1 mA, +/−3.2 mA, +/−3.3 mA, +/−3.4 mA, +/−3.5 mA, +/−3.6 mA, +/−3.7 mA, +/−3.8 mA, +/−3.9 mA, +/−4.0 mA, +/−4.5 mA, or +/−5.0 mA to the subject during the one or more of non-invasive brain stimulation sessions.

F94. The method of embodiment F93, wherein the current is delivered continuously during a duration of the one or more of non-invasive brain stimulation sessions.

F95. The method of any one of embodiments F6-F94, wherein the subject completes at least 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, or 70 of the one or more of non-invasive brain stimulation sessions.

F96. The method of any one of embodiments F1-F95, wherein the subject shows an decrease in Montgomery-Asberg Depression Rating Scale Score (MADRS-S) during treatment or after treatment completion compared to a MADRS-S taken prior to treatment initiation or taken at an earlier time point in treatment of at least 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, or 54 points.

F97. The method of embodiment F96 wherein one or more MADRS-S measurements are determined via a self-assessment questionnaire.

F98. The method of embodiment F96 or F97, wherein MADRS-S measurements are used in part for assessing the response of the subject to the treatment regimen and to the one or more stimulation sessions in order to determine treatment effectiveness in (c).

F99. The method of any one of embodiments F48-F98, wherein the prompt of the subject to input information pertaining to information about the subject's current health comprises displaying a self-assessment MADRS-S questionnaire to the subject and the subject completing the questionnaire and having results from the completed questionnaire stored in a computer memory of the electronic device.

F100. The method of any one of embodiments F43-F99, wherein the electronic device is a handheld device.

F101. The method of any one of embodiments F12-F100, wherein the desired treatment outcome is an improvement in a symptom of the subject.

F102. The method of embodiment F101, wherein the symptom of the subject is a symptom of depression.

F103. The method of embodiment F101 or F102, wherein the improvement comprises decrease in MADRS-S of the subject.

F104. The method of embodiment F103, wherein the decrease in MADRS-S of the subject is sustained for a period of at least 1 week, 2 weeks, 3 weeks, 4 weeks, 5 weeks, 6 weeks, 7 weeks, 8 weeks, 9 weeks, 10 weeks, 11 weeks, 12 weeks, 13 weeks, 14 weeks, 15 weeks, 16 weeks, 17 weeks, 18 weeks, 19 weeks, 20 weeks, 21 weeks, 22 weeks, 23 weeks, 24 weeks, or 25 weeks.

F105. The method of any one of embodiments F1-F104, wherein a subject having moderate depression shows a significant decrease in MADRS-S following at least 6 weeks of tES treatment comprising at least 21 of the non-invasive brain stimulation sessions.

F106. The method of any one of embodiments F1-F105, wherein a subject having moderate depression shows a significant decrease in MADRS-S following at least 10 weeks of tES treatment comprising at least 21 of the non-invasive brain stimulation sessions.

F107. The method of any one of embodiments F1-F106, wherein a subject having severe depression shows a significant decrease in MADRS-S following at least 6 weeks of tES treatment comprising at least 21 of the non-invasive brain stimulation sessions.

F108. The method of any one of embodiments F1-F104 and F107, wherein a subject having severe depression shows a significant decrease in MADRS-S following at least 10 weeks of tES treatment comprising at least 21 of the non-invasive brain stimulation sessions.

F109. The method of any one of embodiments F1-F108, wherein a subject having depression being administered sertraline as part of a treatment regimen and following at least 6 weeks of tES treatment comprising at least 21 of the non-invasive brain stimulation sessions shows a significant decrease in MADRS-S.

FF110. The method of embodiment F109, wherein the significant decrease in MADRS-S is greater than a decrease in MADRS-S in a second subject being administered fluoxetine as part of a treatment regimen and following at least 6 weeks of tES treatment comprising at least 21 of the non-invasive brain stimulation sessions.

F111. The method of any one of embodiments F12-F110, wherein the adjusting parameters in (a) and (b) to achieve to a desired treatment outcome comprises decreasing an ongoing dosage of the administered pharmacologic antidepressant agent to the subject necessary to maintain an improvement in one of more symptoms of depression.

F112. The method of any one of embodiments F12-F111, wherein the adjusting parameters in (a) and (b) to achieve to a desired treatment outcome comprises decreasing an ongoing administration frequency of the pharmacologic antidepressant agent to the subject necessary to maintain an improvement in one of more symptoms of depression.

F113. The method of any one of embodiments F12-F112, wherein the adjusting parameters in (a) and (b) to achieve to a desired treatment outcome comprises decreasing a frequency of tES sessions the subject requires to maintain an improvement in one of more symptoms of depression.

F114. The method of any one of embodiments F12-F113, wherein the adjusting parameters in (a) and (b) to achieve to a desired treatment outcome comprises decreasing a duration of tES sessions the subject requires to maintain an improvement in one of more symptoms of depression.

F115. The method of any one of embodiments F12-F114, wherein the adjusting parameters in (a) and (b) to achieve to a desired treatment outcome comprises decreasing a current administered to the subject in ongoing tES sessions required to maintain an improvement in one of more symptoms of depression.

F116. The method of any one of embodiments F6-F115, further comprising the subject undergoing a focused meditation exercise or a focused relaxation exercise during the one or more of non-invasive brain stimulation sessions.

F117. A method of neuromodulatory intervention in a subject comprising:

(a) administering to the subject a pharmacological antidepressant agent in a treatment effective amount as part of a treatment regimen;

(b) delivering concurrently to the subject one or more of non-invasive brain stimulation sessions via a transcranial electrical stimulation (tES) device;

(c) assessing a response of the subject to the treatment regimen and the one or more of non-invasive brain stimulation sessions in order to determine treatment effectiveness; and (d) adjusting parameters in (a) and (b) to achieve to a desired treatment outcome.

F118. A method of preventing breakthrough depression in a subject comprising:

(a) administering to the subject a pharmacological antidepressant agent in a treatment effective amount as part of a treatment regimen;

(b) delivering concurrently to the subject one or more of non-invasive brain stimulation sessions via a transcranial electrical stimulation (tES) device;

(c) assessing a response of the subject to the treatment regimen and the one or more of non-invasive brain stimulation sessions in order to determine treatment effectiveness; and (d) adjusting parameters in (a) and (b) to achieve to a desired treatment outcome.

F119. A method of maintaining depression remission in a subject comprising:

(a) administering to the subject a pharmacological antidepressant agent in a treatment effective amount as part of a treatment regimen;

(b) delivering concurrently to the subject one or more of non-invasive brain stimulation sessions via a transcranial electrical stimulation (tES) device;

(c) assessing a response of the subject to the treatment regimen and the one or more of non-invasive brain stimulation sessions in order to determine treatment effectiveness; and (d) adjusting parameters in (a) and (b) to achieve to a desired treatment outcome.

F120. Use of a pharmaceutical composition comprising a pharmacologic antidepressant agent, for manufacture of a medicament for treating depression in subject in need thereof, wherein the pharmaceutical composition is administered to the subject and wherein a transcranial electrical stimulation (tES) is administered to the subject.

What is claimed is:

1. A method of treatment comprising administering to a patient with treatment resistant depression as part of a treatment regimen lasting at least 3 weeks:

(a) trans-cranial electrical stimulation (tES) and (b) a selective serotonin reuptake inhibitor (SSRI).

2. The method of claim 1, wherein the SSRI comprises fluoxetine.

3. The method of claim 1, wherein the SSRI comprises citalopram.

4. The method of claim 1, wherein the SSRI comprises escitalopram.

5. The method of claim 1, wherein the SSRI comprises paroxetine.

6. The method of claim 1, wherein the SSRI comprises sertraline.

7. The method of claim 1, wherein the SSRI comprises dapoxetine.

8. The method of claim 1, wherein the SSRI comprises fluvoxamine.

9. The method of claim 1, wherein the SSRI comprises vortioxetine.

10. The method of claim 1, wherein the treatment resistant depression comprises inadequate clinical response to at least two antidepressants administered separately.

* * * * *